US012807593B2

(12) United States Patent
Tan et al.

(10) Patent No.: US 12,807,593 B2
(45) Date of Patent: Nov. 24, 2026

(54) PROGRAMMED CELL NECROSIS INHIBITOR, PREPARATION METHOD THEREFOR, AND USE THEREOF

(71) Applicant: Shanghai Institute of Organic Chemistry, Chinese Academy of Sciences, Shanghai (CN)

(72) Inventors: Li Tan, Shanghai (CN); Ying Li, Shanghai (CN); Ying Qin, Shanghai (CN); Chunting Qi, Shanghai (CN); Huaijiang Xiang, Shanghai (CN)

(73) Assignee: Shanghai Institute of Organic Chemistry, Chinese Academy of Sciences, Shanghai (CN)

( * ) Notice: Subject to any disclaimer, the term of this patent is extended or adjusted under 35 U.S.C. 154(b) by 693 days.

(21) Appl. No.: 18/245,676

(22) PCT Filed: Sep. 14, 2021

(86) PCT No.: PCT/CN2021/118212

§ 371 (c)(1),
(2) Date: Mar. 16, 2023

(87) PCT Pub. No.: WO2022/057787

PCT Pub. Date: Mar. 24, 2022

(65) Prior Publication Data

US 2023/0331707 A1 Oct. 19, 2023

(30) Foreign Application Priority Data

Sep. 16, 2020 (CN) ......................... 202010974345.2

(51) Int. Cl.

| | |
|---|---|
| ***C07D 487/04*** | (2006.01) |
| ***A61K 31/519*** | (2006.01) |
| ***A61P 29/00*** | (2006.01) |
| ***A61P 35/00*** | (2006.01) |
| ***C07D 235/06*** | (2006.01) |
| ***C07D 401/02*** | (2006.01) |
| ***C07D 403/12*** | (2006.01) |
| ***C07D 413/12*** | (2006.01) |
| ***C07D 471/04*** | (2006.01) |
| ***C07D 473/34*** | (2006.01) |
| ***C07D 487/14*** | (2006.01) |

(52) U.S. Cl.

CPC ......... *C07D 403/12* (2013.01); *C07D 235/06* (2013.01); *C07D 413/12* (2013.01); *C07D 471/04* (2013.01); *C07D 473/34* (2013.01); *C07D 487/04* (2013.01)

(58) Field of Classification Search

CPC .. C07D 487/04; C07D 487/14; C07D 401/02; C07D 471/04; A61K 31/519; A61P 35/00; A61P 29/00

See application file for complete search history.

(56) References Cited

U.S. PATENT DOCUMENTS

| | | | |
|---|---|---|---|
| 2004/0220169 | A1 | 11/2004 | Gillard et al. |
| 2005/0239820 | A1 | 10/2005 | Borzilleri et al. |
| 2019/0330226 | A1 | 10/2019 | Lindsley et al. |

FOREIGN PATENT DOCUMENTS

| | | | |
|---|---|---|---|
| CN | 101910133 | A | 12/2010 |
| CN | 102781940 | A | 11/2012 |
| CN | 103929961 | A | 7/2014 |
| CN | 109678845 | A | 4/2019 |
| CN | 110520423 | A | 11/2019 |
| CN | 111100130 | A | 5/2020 |
| JP | H05505199 | A | 8/1993 |
| JP | 2002161084 | A | 6/2002 |
| JP | 2006514987 | A | 5/2006 |
| JP | 2011500809 | A | 1/2011 |
| JP | 2013516419 | A | 5/2013 |
| JP | 2014518223 | A | 7/2014 |
| JP | 2017524026 | A | 8/2017 |
| JP | 2018529739 | A | 10/2018 |
| JP | 2020507582 | A | 3/2020 |
| JP | 2022528251 | A | 6/2022 |
| PT | 97587 | A | 2/1992 |
| WO | 2006066937 | A2 | 6/2006 |
| WO | 2011050245 | A1 | 4/2011 |
| WO | 2016202898 | A1 | 12/2016 |
| WO | 2018148626 | A1 | 8/2018 |
| WO | 2019089442 | A1 | 5/2019 |
| WO | 2021055621 | A1 | 3/2021 |

OTHER PUBLICATIONS

Office Action and Search Report issued in Chinese Application No. 202010974345.2, dated Jun. 27, 2024, with English translation.
Office Action and Search Report issued in Chinese Application No. 202010974345.2, dated Mar. 20, 2025, with English translation.
Office Action and Search Report issued in Chinese Application No. 202180063390.5, dated Dec. 5, 2024, with English translation.
RN 1293853-03-8 Registry Entered STN: May 12, 2011, Cited in Office Action in Chinese counterpart.
RN 1293853-10-7 Registry Entered STN: May 12, 2011, Cited in Office Action in Chinese counterpart.
RN 1296007-52-7 Registry Entered STN: May 17, 2011, Cited in Office Action in Chinese counterpart.
RN 1316430-63-3 Registry Entered STN: Aug. 12, 2011, Cited in Office Action in Chinese counterpart.

(Continued)

*Primary Examiner* — Bruck Kifle
(74) *Attorney, Agent, or Firm* — HSML P.C.

(57) ABSTRACT

The present invention provides a programmed cell necrosis inhibitor, a preparation method therefor, and a use thereof. Specifically, the present invention provides a compound, or a pharmaceutically acceptable salt, hydrate, or solvent thereof, wherein the compound is as represented by formula I. The present invention further provides a preparation method for the compound and a pharmaceutical composition containing same, or a use of the compound in treatment or prevention of diseases or disorders related to programmed cell necrosis and/or human receptor interacting protein kinase 1 (RIPK1).

12 Claims, 5 Drawing Sheets

(56) References Cited

OTHER PUBLICATIONS

RN 1318014-90-2 Registry Entered STN: Aug. 15, 2011, Cited in Office Action in Chinese counterpart.
Office Action issued in Japanese Application No. 20230517810, date May 16, 2024, with machine translation, 27 pages provided.
Registry(STN)[online], Feb. 15, 2015[Search date: Mar. 18, 2024] CAS registration No. 1647437-78-2.
International Search Report and Written Opinion issued in PCT/CN2021/118212, dated Dec. 10, 2021, 15 pages provided, with English translation.
STN Registry1647437-78-2, dated Feb. 15, 2015, cited in PCT International Search Report.
The extended European search report issued in European Application No. 21868610.3, dated Mar. 18, 2025.

| PK parameter(IV) | | PK parameter(PO) | |
|---|---|---|---|
| Cl (ml/min/kg) | 70.1 | $T_{max}$ (hr) | 0.2 |
| Vss (l/kg) | 3.1 | $C_{max}$ (nM) | 2274.7 |
| $T_{1/2}$ (hr) | 1.5 | $T_{1/2}$ (hr) | 3.3 |
| $MRT_{INF}$ (hr) | 0.7 | $AUC_{last}$ (hr*nM) | 2276.2 |
| $AUC_{last}$ (hr*nM) | 541.5 | $AUC_{INF}$ (hr*nM) | 2410.9 |
| $AUC_{INF}$ (hr*nM) | 552.0 | F (%)* | 43.7 |

PROGRAMMED CELL NECROSIS INHIBITOR, PREPARATION METHOD THEREFOR, AND USE THEREOF

TECHNICAL FIELD

The invention belongs to the field of small molecule compounds, and specifically relates to programmed cell necrosis inhibitors, preparation method therefor, and use thereof.

BACKGROUND

In the process of development and aging, the human body is always accompanied by dynamic regulation of cell proliferation and cell death. Active cell death is indispensable in normal development, the invasion resistance of pathogenic microorganisms, maintaining the internal environment homeostasis and other physiological activities, and its imbalance often leads to developmental malformation, immune system diseases, neurodegenerative diseases, cancer and other diseases, and even death of the individual. Therefore, intervention on programmed cell death is of great significance for disease treatment research. Apoptosis is the first elucidated mechanism of programmed cell death. In recent years, programmed cell necrosis has become a new hot spot in the field of cell death. It has been reported in many studies that it is accompanied by the important pathological feature of programmed cell necrosis in various diseases such as various degenerative diseases (such as Alzheimer's disease (AD), multiple sclerosis (MS), amyotrophic lateral sclerosis (ALS), retinal degenerative diseases, etc.), inflammation (enteritis, rheumatoid arthritis, psoriasis, etc.), ischemia-reperfusion injury (cerebral infarction, myocardial infarction, etc.), and pathogen infection and the like. In addition, programmed cell necrosis is also involved in the regulation of the tumor microenvironment: lung cancer cells can induce programmed necrosis of specific cells in the blood vessel wall in order to pass through the circulatory system and metastasize; high expression of the main component of necrosomes in pancreatic cancer can induce the expression of chemokine CXCL1 and inhibit the immune response of the body. Therefore, inhibiting the occurrence of programmed cell necrosis is recognized as helpful for the treatment and alleviation of various diseases.

Studies have shown that tumor necrosis factor α (TNF-α) is one of the main ways to stimulate programmed necrosis of cells in vivo, and its downstream signaling pathway is also the necrosis signaling pathway with the most clear mechanism. In the classical TNF-α-induced cell necrosis process, TNF-α first binds to the receptor TNFR1, induces its trimerization and recruits a series of intracellular factors including multiple proteins such as TRADD, TRAF2, RIPK1, cIAP1/2 and the like, thereby forming signaling complex I. Complex 1 can recruit and activate the IKKα/IKKβ/IKKγ complex and the NF-1B pathway, and partially enter the cytoplasm after dissociation to form a new protein complex IIa, then recruit procaspase-8 and other proteins through FADD or TRADD to activate the downstream caspases including caspase-3 and caspase-7 and mediate the occurrence of apoptosis. In the absence of FADD or the administration of caspase inhibitors, the kinase protein RIPK1 induced and activated by TNF-α binds to RIPK3 to form a new complex IIb and induces phosphorylation activation of the latter, which phosphorylates the downstream substrate MLKL to promote its oligomerization, and eventually disrupts the structure of the cell membrane and leads to necrosis.

Multiple adaptor proteins, ubiquitin ligases, deubiquitinases and kinase proteins are involved in regulating the downstream signaling pathways of TNF-α-induced programmed cell necrosis. For example, the K63 ubiquitination of RIPK1 by the E3 ubiquitin ligase cIAP can inhibit the activation of latter and the process of necrosis; the deubiquitinase CYLD can cleave the K63 ubiquitin chain of RIPK1, thereby activating RIPK1 kinase activity and promoting the formation of necrosome, and eventually achieving positive regulation of cell necrosis; the adaptor protein SPATA2 promotes the activity of CYLD deubiquitinase and inhibits the NF-κB and MAPK signaling pathways, thereby positively regulating programmed necrosis; the kinase protein TAK1 inhibits the kinase activity of RIPK1 by phosphorylating Ser321 site of RIPK1, thereby negatively regulating programmed necrosis, while deubiquitinating enzyme A20 (TNF-α induced protein 3), adaptor protein TAB2 (TAK1 binding protein 2) and other regulation factors are also involved in this regulatory process; the kinase protein TBK1 inhibits the activation of the RIPK1 by phosphorylating the Thr189 site of RIPK1, and the inactivating mutation of TBK1 during aging is also an important pathogenic risk for neurodegenerative diseases such as ALS and FTD; the adaptor protein Optineurin (OPTN) negatively regulates programmed necrosis by inhibiting RIPK1 kinase activity, and loss of OPTN in ALS may contribute to progressive dysmyelination and axonal degeneration. It can be seen that in the signaling pathway network of TNF-α-induced programmed cell necrosis, the functional abnormalities of multiple regulatory components mediate the occurrence of programmed necrosis through the activation of RIPK1 kinase (the core regulatory factor).

Therefore, RIPK1 kinase is recognized as a potential therapeutic target for diseases related to programmed cell necrosis. The first-in-class RIPK1 inhibitor Necrostatin-1 (Nec-1) and analogs thereof have demonstrated clear curative effects on a variety of degenerative diseases, inflammation, cancer and other diseases in preclinical studies. For example, it has relieving effect on AD, ALS, MS, Parkinson's disease (PD), Huntington's disease (PD), inflammatory bowel disease, age-related macular degeneration, etc.; it has protective effect on psoriasis, retinitis pigmentosa, inflammatory bowel disease, autoimmune diseases, bombesin-induced acute pancreatitis and sepsis/systemic inflammatory response syndrome (SIRS); it can effectively alleviate ischemic brain injury, ischemic myocardial injury, retinal ischemia/reperfusion injury, retinal detachment-induced photoreceptor cell necrosis, glaucoma, renal ischemia-reperfusion injury, cisplatin-induced renal injury, and traumatic brain injury; relieves at least partially other diseases associated with RIPK1-dependent apoptosis, necrosis, or cytokine production, including hematological malignancies and solid organ malignancies, bacterial infections and viral infections (including tuberculosis, influenza, etc.), and lysosomal storage disorders (especially Gaucher disease). Currently, Nec-1 derivatives have entered clinical trials for the treatment of ALS and AD; another class of RIPK1 inhibitor GSK2982772 is also in clinical trials for the treatment of various autoimmune diseases. However, all the existing programmed necrosis inhibitors have different degrees of defects, such as unsatisfactory in vivo inhibitory activity, poor pharmacokinetic properties, low oral bioavailability and the like, and some cannot enter the central nervous system through the blood-brain barrier, or some are difficult to carry out preclinical animal trials because some cannot effectively inhibit murine RIPK1. These shortcomings limit their further research and clinical application.

Therefore, it is difficult and a hot spot in the current research on the treatment of programmed cell necrosis-related diseases to develop small molecule inhibitors of RIPK1 kinase activity with high specificity, high activity and blood-brain barrier penetration that have clinical application value. Summing up, there is still an urgent need in the art for novel RIPK1 inhibitors and/or programmed cell necrosis inhibitors with novel chemical structures and more outstanding pharmacokinetic and pharmacodynamic properties, which can be used as drug candidates for the prevention and treatment of diseases involving cell death and/or inflammatory diseases.

SUMMARY OF THE INVENTION

The purpose of the present invention is to provide inhibitors of RIPK1 inhibitors and/or programmed cell necrosis inhibitors with novel structures.

In the first aspect of the present invention, provided is a compound, or pharmaceutically acceptable salts, hydrates or solvates thereof, characterized in that the compound is as shown in Formula I;

(I)

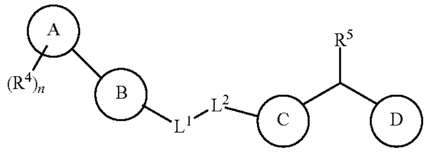

wherein, ring A is a substituted or unsubstituted 9-10 membered nitrogen-containing heteroaryl, wherein the 9-10 membered nitrogen-containing heteroaryl contains 1, 2, 3 or 4 nitrogen heteroatoms as ring atoms;

n=0, 1 or 2.

$R^4$ is each independently selected from the group consisting of: H, —CN, halogen, substituted or unsubstituted $C_{1-6}$alkyl, —O—$R^b$, —S—$R^b$, —N($R^b$)$_2$, —C(O)—NR$^6$—$R^b$, —C(O)—NR$^6$—$C_{1-4}$alkylene-N($R^b$)$_2$, —NR$^6$—C(O)—$R^b$;

each $R^b$ is each independently selected from the group consisting of: H, substituted or unsubstituted $C_{1-6}$alkyl; or two $R^b$ together with the nitrogen atom to which they are attached form a substituted or unsubstituted 5, 6 or 7 membered heterocycloalkyl, wherein, in addition to the nitrogen atom attached to $R^b$, the heterocycloalkyl further contains 0, 1 or 2 additional heteroatoms as ring atoms;

$R^6$ is selected from the group consisting of: H, OH, substituted or unsubstituted $C_{1-4}$alkyl, substituted or unsubstituted $C_{1-4}$alkoxy;

ring B is selected from the group consisting of: substituted or unsubstituted $C_{6-10}$aryl, substituted or unsubstituted 5-10 membered heteroaryl;

$L^1$ and $L^2$ are each independently a divalent group selected from the group consisting of: null,

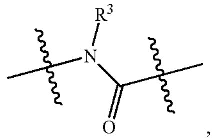

,

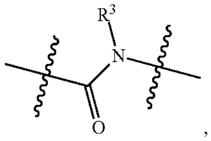

,

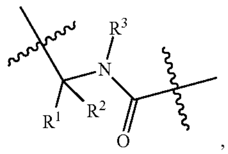

,

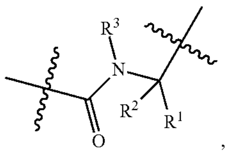

,

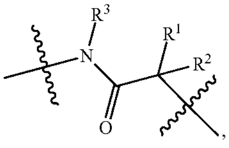

,

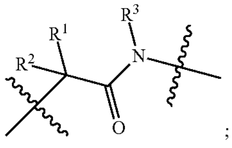

;

and $L^1$ and $L^2$ are not null at the same time;

$R^1$ and $R^2$ are each independently selected from the group consisting of: H, substituted or unsubstituted $C_{1-4}$alkyl;

$R^3$ is selected from the group consisting of: H, OH, substituted or unsubstituted $C_{1-4}$alkyl, substituted or unsubstituted $C_{1-4}$alkoxy;

ring C is null or

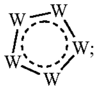

;

wherein, W are each independently selected from the group consisting of: O, S, C, N, C($R^c$), and N($R^d$); $R^c$ is each independently selected from the group consisting of: H, CN, halogen, substituted or unsubstituted $C_{1-6}$alkyl, $R^d$ is each independently selected from the group consisting of: H, CN, substituted or unsubstituted $C_{1-6}$alkyl (preferably, $R^d$ is substituted or unsubstituted $C_{1-6}$alkyl, more preferably, $R^d$ is selected from the group consisting of: methyl, ethyl, propyl and butyl);

or, when ring C is

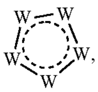

, $L^1$ is

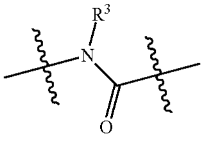

or

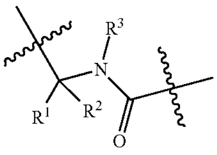

(the carbonyl moiety in $L^1$ is attached to ring C) and $L^2$ is null, $R^3$ together with the ring atom W, that is located at the ortho position of attachment position of $L^1$ and ring C, and —C(O)— in $L^1$ forms a substituted or unsubstituted 5, 6 or 7-membered saturated heterocyclic ring (preferably, 6-membered saturated heterocyclic ring); wherein, in addition to the nitrogen atom attached to $R^3$, the saturated heterocyclic ring further contains 0, 1 or 2 additional heteroatoms as ring atoms;

$R^5$ is selected from the group consisting of: H, OH, substituted or unsubstituted $C_{1-4}$alkyl, substituted or unsubstituted $C_{1-4}$alkoxy;

or when ring C is null and $L^2$ is

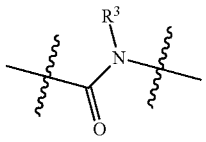

or

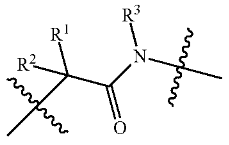

(the $N(R^3)$ moiety in $L^1$ is attached to ring C), $R^3$ and $R^5$ together with the atom to which they are attached form a substituted or unsubstituted 5, 6 or 7-membered saturated heterocyclic ring, wherein in addition to N that is attached to $R^3$, the saturated heterocyclic ring further contains 0, 1 or 2 additional heteroatoms as ring atoms;

ring D is selected from the group consisting of: substituted or unsubstituted $C_{6-10}$aryl ring, and substituted or unsubstituted 5-10-membered heteroaryl;

unless otherwise specified, the substituted refers to the hydrogen atom on the group being substituted with one or more (e. g., 1, 2, 3, or 4 and the like) substituents selected from the group consisting of: oxo (=O), —CN, halogen (such as F, Cl, Br or I), nitro, $C_{1-6}$alkyl, halogenated $C_{1-6}$alkyl, —OR, —SR, $—S(O)_2R$, $—S(=O)_2NR_2$, $—NR_2$, —COOR, $C_{6-10}$aryl that is optionally substituted with R, 5-10-membered heteroaryl containing 1-3 heteroatoms selected from N, S and O that is optionally substituted with R, $C_{3-8}$ cycloalkyl that is optionally substituted with R, 5-12-membered heterocycle containing 1-3 heteroatoms selected from N, S and O that is optionally substituted with R, —$C_{1-4}$alkylene —$C_{6-10}$aryl that is optionally substituted with R, —$C_{1-4}$alkylene-5-10 membered heteroaryl containing 1-3 heteroatoms selected from N, S and O that is optionally substituted with R, —$C_{1-4}$alkylene-$C_{3-8}$cycloalkyl that is optionally substituted with R, —$C_{1-4}$alkylene-5-12 membered heterocycloalkyl containing 1-3 heteroatoms selected from N, S and O that is optionally substituted with R;

R is each independently selected from the group consisting of: H, $C_{1-6}$alkyl, halogenated $C_{1-6}$alkyl, $C_{1-6}$hydroxyalkyl.

In another preferred embodiment, the heteroatoms are each independently selected from the group consisting of: O, N, S; preferably, each independently O or N.

In another preferred example, $R^4$ is each independently selected from the group consisting of: H, —CN, —O—$R^b$, —$N(R^b)_2$, —C(O)—$NR^6$—$R^b$, —C(O)—$NR^6$—$C_{1-4}$alkylene-$N(R^b)_2$; preferably, $R^4$ is each independently selected from the group consisting of: —CN, —O—$R^b$, —$N(R^b)_2$; more preferably, $R^4$ is each independently selected from the group consisting of: —CN, —O—$C_{1-6}$alkyl, $—NH_2$, —NH($C_{1-4}$alkyl), or —$N(C_{1-4}alkyl)_2$.

In another preferred example, $R^4$ is each independently selected from the group consisting of: H, substituted or unsubstituted $C_{1-6}$alkyl, —O—$R^b$, —S—$R^b$, —$N(R^b)_2$, —C(O)—$NR^6$—$R^b$, —C(O)—$NR^6$—$C_{1-4}$alkylene-$N(R^b)_2$, —$NR^6$—C(O)—$R^b$.

In another preferred example, ring A is shown in the structure selected from the group consisting of:

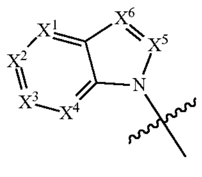

and

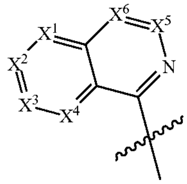

, wherein $X^1$, $X^2$, $X^3$, $X^4$, $X^5$ and $X^6$ are each independently selected from the group consisting of: N and $C(R^a)$; and at most 3 of $X^1$, $X^2$, $X^3$, $X^4$, $X^5$ and $X^6$ are N;

$R^a$ is each independently selected from the group consisting of: null, H, substituted or unsubstituted $C_{1-6}$alkyl.

In another preferred embodiment, $X^1$, $X^2$, $X^3$, $X^4$, $X^5$ and $X^6$ are each independently selected from the group consisting of: C, N and CH.

In another preferred embodiment, (III)

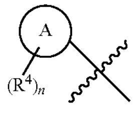

is

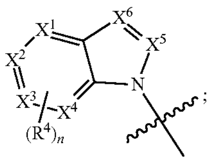

;

preferably, as shown in the structure selected from the group consisting of:

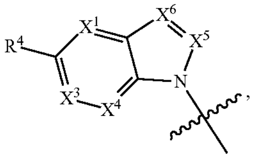

,

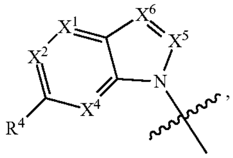

,

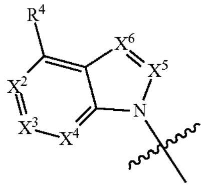

and

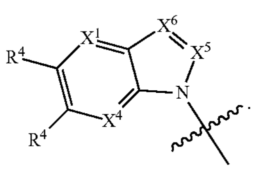

.

In another preferred embodiment,

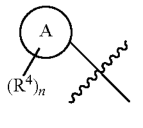

is

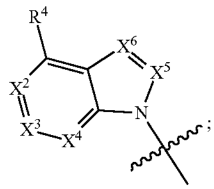

;

wherein, $X^3$ and $X^5$ are $C(R^a)$ (preferably, $X^3$ and $X^5$ are CH); $X^2$, $X^4$ and $X^6$ are N; and $R^4$ is selected from the group consisting of: —$N(R^b)_2$, —$NR^6$—C(O)—$R^b$ (preferably, $R^4$ is —$N(R^b)_2$; more preferably, $R^4$ is $—NH_2$, —NH($C_{1-4}$ alkyl), or —$N(C_{1-4}alkyl)_2$; or, In another preferred embodiment,

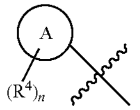

is

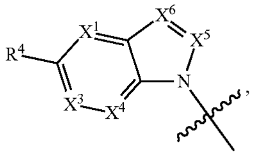

,

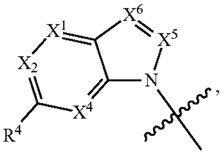

, or

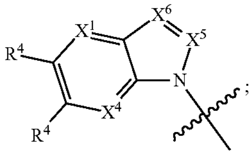

;

wherein, $X^6$ is N; $X^1$, $X^2$, $X^3$, and $X^5$ are $C(R^a)$ (preferably, $X^1$, $X^2$, $X^3$, and $X^5$ are CH); $X^4$ is N or $C(R^a)$ (preferably $X^4$ is N or CH); and $R^4$ is selected from the group consisting of: —CN, —O—$C_{1-6}$alkyl.

In another preferred embodiment, ring B is selected from the group consisting of: substituted or unsubstituted phenyl, substituted or unsubstituted 5 or 6 membered heteroaryl.

In another preferred embodiment, ring B is phenyl.

In another preferred embodiment, the $L^1$ is

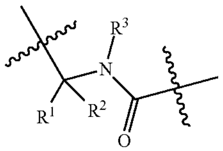

(the carbonyl moiety in the $L^1$ is attached to ring C) and the $L^2$ is null (i.e., -$L^1$-$L^2$- is

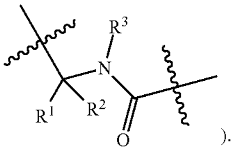

).

In another preferred embodiment, $R^1$ and $R^2$ are each independently selected from the group consisting of: H and methyl. In another preferred embodiment, one of $R^1$ and $R^2$ is H and the other is H or substituted or unsubstituted $C_{1-4}$alkyl (preferably, H or methyl).

In another preferred embodiment, ring C is

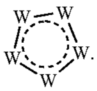

.

In another preferred embodiment, ring C is

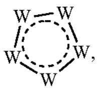

, $L^1$ is

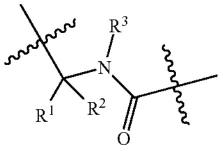

(the carbonyl moiety in the $L^1$ is attached to ring C) and $L^2$ is null, $R^3$ is H, or $R^3$ together with W, that is located at the ortho position of attachment position of $L^1$ and ring C, and —C(O)— in $L^1$ forms a substituted or unsubstituted 5 or 6 membered (preferably 6-membered) saturated heterocyclic ring.

In another preferred example, when $R^3$ together with W, that is located at the ortho position of attachment position of $L^1$ and ring C, and —C(O)— in $L^1$ forms a substituted or unsubstituted 5 or 6 membered saturated heterocyclic ring,

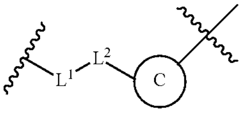

is

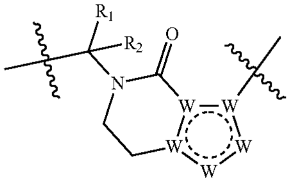

,

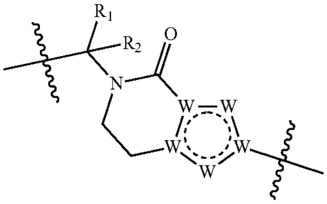

,

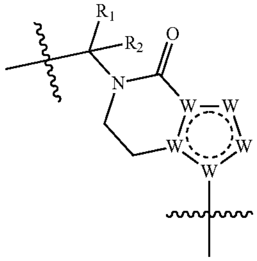

,

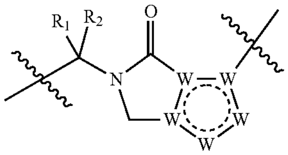

,

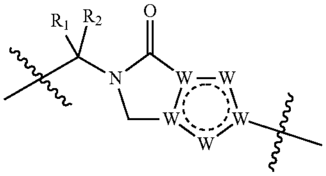

, or

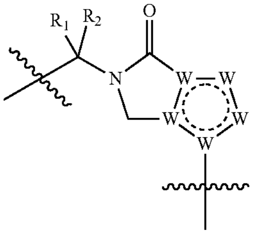

;

preferably, is

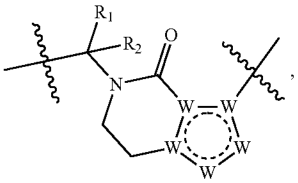
, or

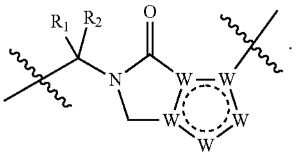

In another preferred embodiment, ring C is as shown in

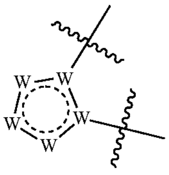
or
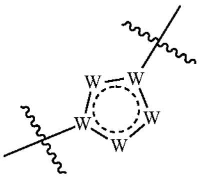
;

preferably, as shown in

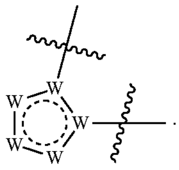

In another preferred embodiment, ring C is as shown in the structure selected from the group consisting of:

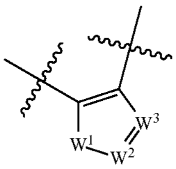
,
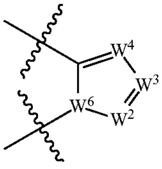
,
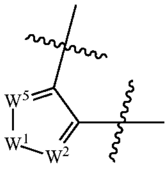
,
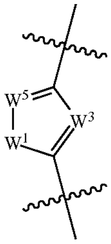
,
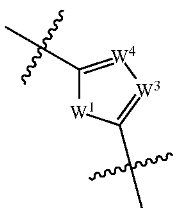
and
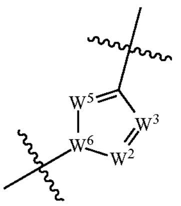
;

wherein $W^1$ is selected from the group consisting of: O, S, $N(R^d)$; $W^2$, $W^3$, $W^4$, $W^5$ and $W^6$ are each independently selected from the group consisting of: N and $C(R^c)$;

or, when $L^1$ is

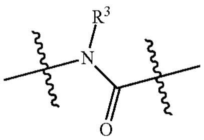
or
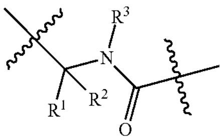

(the carbonyl moiety in $L^1$ is attached to ring C) and $L^2$ is null, $R^3$ together with $W^1$, $W^2$, $W^3$, $W^4$ or $W^5$, that is located at the ortho position of attachment position of $L^1$ and ring C, and the carbonyl group in $L^1$ forms a substituted or unsubstituted 5 or 6 membered saturated heterocyclic ring (preferably 6-membered saturated heterocyclic ring).

In another preferred embodiment, the ring C is as shown in the structure selected from the group consisting of:

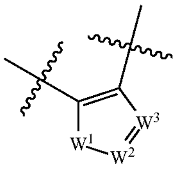
,
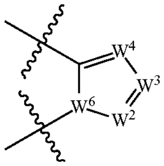
, and
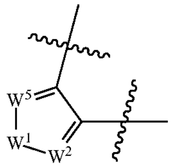
;

wherein $W^1$ is $N(R^a)$; $W^2$, $W^3$, $W^4$, and $W^5$ are each independently selected from the group consisting of: N and $C(R^c)$;

or, when $L^1$ is

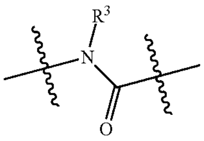
or
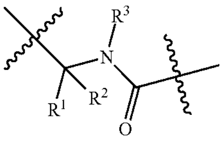

(the carbonyl moiety in $L^1$ is attached to ring C) and the $L^2$ is null, $R^3$ together with $W^1$, $W^2$, $W^3$, $W^4$ or $W^5$, that is located at the ortho position of attachment position of $L^1$ and ring C, and the carbonyl group in $L^1$ forms a substituted or unsubstituted 5 or 6 membered saturated heterocyclic ring (preferably 5-membered saturated heterocyclic ring).

In another preferred embodiment, ring C is selected from the group consisting of:

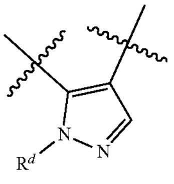
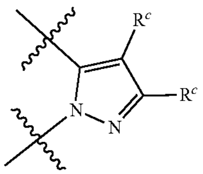
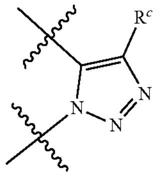

-continued

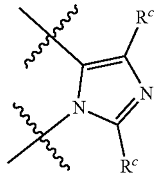
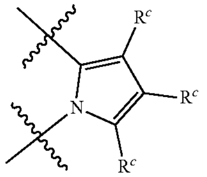
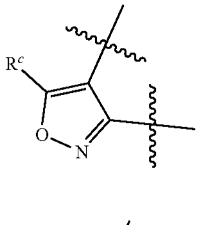
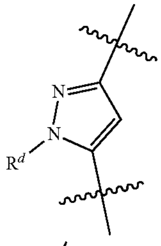
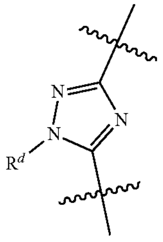
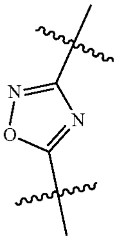
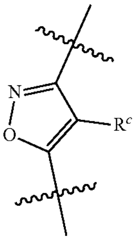
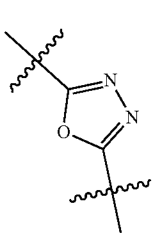
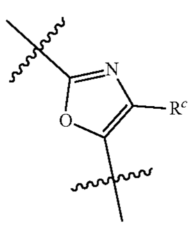
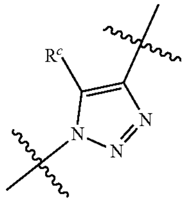
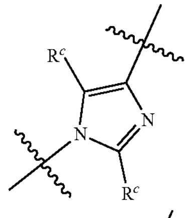
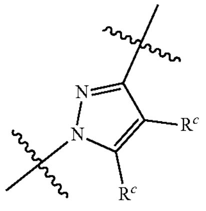
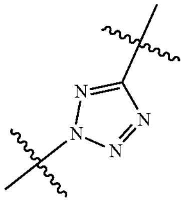
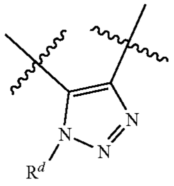
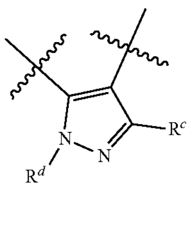
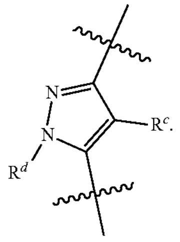

wherein $R^c$ is each independently selected from the group consisting of: H, CN, halogen (such as Cl), substituted or unsubstituted $C_{1-6}$alkyl, and $R^d$ is each independently selected from the group consisting of: H, substituted or unsubstituted $C_{1-6}$alkyl.

In another preferred embodiment, the ring C is selected from the group consisting of:

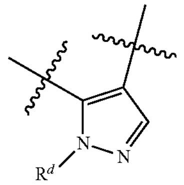
,
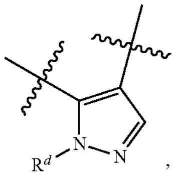
, and

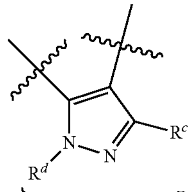
; or,

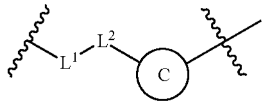
is

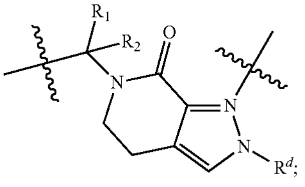

wherein $R^1$ and $R^2$ are defined as above (preferably, one of $R^1$ and $R^2$ is H and the other is H or $C_{1-4}$alkyl (such as methyl)).

In another preferred embodiment, $R^c$ is each independently selected from the group consisting of: H, CN, F, Cl, Br, $C_{1-4}$alkyl; and/or $R^d$ is selected from the group consisting of: H, $C_{1-4}$alkyl (preferably, $R^d$ is $C_{1-4}$alkyl).

In another preferred embodiment, ring D is phenyl.

In another preferred embodiment, ring A, ring B, ring C, ring D, $L^1$, $L^2$, $R^4$, $R^5$ and n are independently the corresponding groups in the specific compounds in Table A.

In another preferred embodiment, the compound is as shown in formula II;

(II)

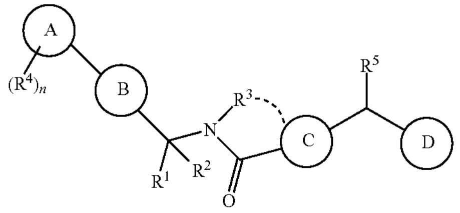

wherein, ring C is

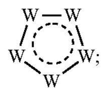

$R^3$ is selected from the group consisting of: H, OH, substituted or unsubstituted $C_{1-4}$alkyl, substituted or unsubstituted $C_{1-4}$alkoxy;

or, $R^3$ together with the ring atom W, that is located at the ortho position of attachment position of —C(O)— and ring C, and said —C(O)— forms a substituted or unsubstituted 5, 6 or 7 membered saturated heterocyclic ring (preferably 6-membered saturated heterocyclic ring); wherein in addition to N that is attached to $R^3$, the saturated heterocyclic ring further contains 0, 1 or 2 additional heteroatoms as ring atoms;

$R^5$ is selected from the group consisting of: H, OH, substituted or unsubstituted $C_{1-4}$alkyl, substituted or unsubstituted $C_{1-4}$alkoxy;

ring A, ring B, ring D, W, $R^1$, $R^2$, $R^4$, and n are as defined in Formula I.

In another preferred embodiment, ring A, ring B, ring C, ring D, $R^1$, $R^2$, $R^3$, $R^4$, $R^5$ and n are independently corresponding groups in the specific compounds in Table A.

In another preferred embodiment, the compound is as shown in formula III.

(III)

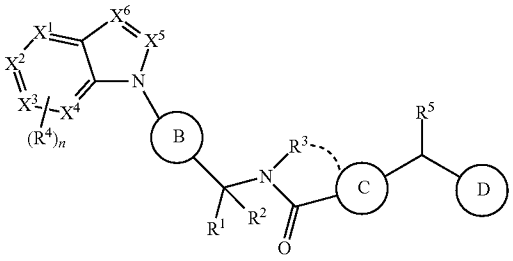

wherein, $X^1$, $X^2$, $X^3$, $X^4$, $X^5$ and $X^6$ are independently selected from the group consisting of: N and $C(R^a)$; and at most 3 of $X^1$, $X^2$, $X^3$, $X^4$, $X^5$ and $X^6$ are N;

$R^a$ is each independently selected from the group consisting of: null, H, substituted or unsubstituted $C_{1-6}$alkyl;

ring C is

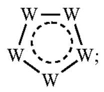

$R^3$ is selected from the group consisting of: H, OH, substituted or unsubstituted $C_{1-4}$alkyl, substituted or unsubstituted $C_{1-4}$alkoxy;

or, $R^3$ together with the ring W, that is located at the ortho position of attachment position of —C(O)— and ring C, and said —C(O)— forms a substituted or unsubstituted 5, 6 or 7 membered saturated heterocyclic ring (preferably 6-membered saturated heterocyclic ring); wherein in addition to N that is attached to $R^3$, the saturated heterocyclic ring further contains 0, 1 or 2 additional heteroatoms as ring atoms;

$R^5$ is selected from the group consisting of: H, OH, substituted or unsubstituted $C_{1-4}$alkyl, substituted or unsubstituted $C_{1-4}$alkoxy;

ring B, ring D, W, $R^1$, $R^2$, $R^4$, and n are as defined in Formula I.

In another preferred embodiment, $X^1$, $X^2$, $X^3$, $X^4$, $X^5$, $X^6$, ring B, ring C, ring D, $R^1$, $R^2$, $R^3$, $R^4$, $R^5$, and n are independently the corresponding groups in the specific compounds in Table A.

In another preferred embodiment, the compound is as shown in formula IV-1 or IV-2;

(IV-1)

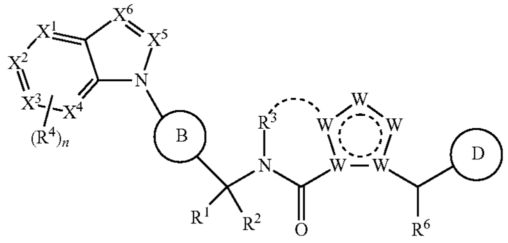

(IV-2)

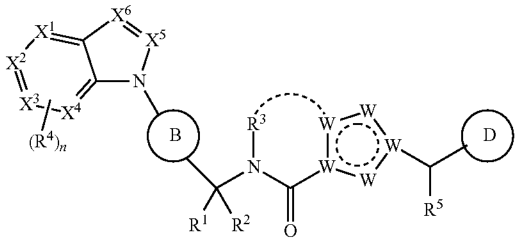

wherein, $X^1$, $X^2$, $X^3$, $X^4$, $X^5$ and $X^6$ are each independently selected from the group consisting of: N and $C(R^a)$; and at most 3 of $X^1$, $X^2$, $X^3$, $X^4$, $X^5$ and $X^6$ are N;

$R^3$ is selected from the group consisting of: H, OH, substituted or unsubstituted $C_{1-4}$alkyl;

or, $R^3$ together with the ring W and the —C(O)— forms a substituted or unsubstituted 5, 6 or 7 membered saturated heterocyclic ring (preferably 6-membered saturated heterocyclic ring), wherein in addition to N that is attached to $R^3$, the saturated heterocyclic ring further contains 0, 1 or 2 additional heteroatoms as ring atoms;

$R^5$ is selected from the group consisting of: H, OH, substituted or unsubstituted $C_{1-4}$alkyl;

ring B, ring D, W, $R^a$, $R^1$, $R^2$, $R^4$, and n are as defined in Formula I.

In another preferred embodiment, $X^1$, $X^2$, $X^3$, $X^4$, $X^5$, $X^6$, ring B, W, ring D, $R^1$, $R^2$, $R^3$, $R^4$, $R^5$, and n are independently the corresponding groups in the specific compounds in Table A.

In another preferred embodiment, ring B and ring D are each independently unsubstituted phenyl, or phenyl substituted with 1 or 2 substituents selected from the group consisting of: halogen, $C_{1-4}$alkyl, halogenated $C_{1-4}$alkyl.

In another preferred embodiment, the compound is selected from Table A.

In the second aspect of the present invention, provided is a preparation method of the compound according to the first aspect, wherein the compound is as shown in Formula II, wherein, i. the preparation method is Method-One, and the Method-One comprises a step of:

in an inert solvent, reacting a compound as shown in formula II-2A with a compound as shown in formula II-2B, thereby obtaining a compound as shown in formula II-2C;

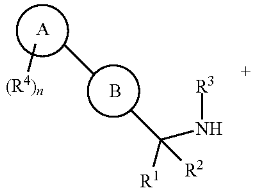

(II-1A)

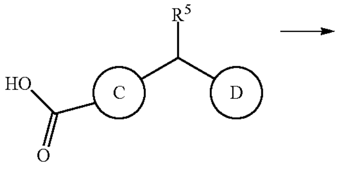

(II-1B)

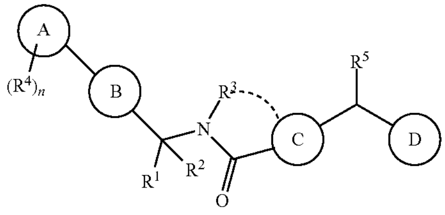

(II)

wherein, $R^3$ is selected from the group consisting of: H, OH, substituted or unsubstituted $C_{1-4}$alkyl, substituted or unsubstituted $C_{1-4}$alkoxy;

ring A, ring B, ring C, ring D, $R^c$, $R^1$, $R^2$, $R^4$, $R^5$ and n are as defined in formula II in the first aspect;

or, ii. the method is Method-Two, and the Method-Two comprises steps of:

a) in an inert solvent, reacting a compound as shown in formula II-2A with a compound as shown in formula II-2B, thereby obtaining a compound as shown in formula II-2C;

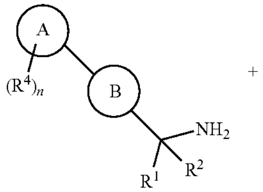

(II-2A)

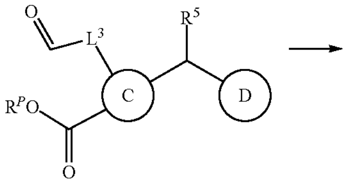

(II-2B)

-continued

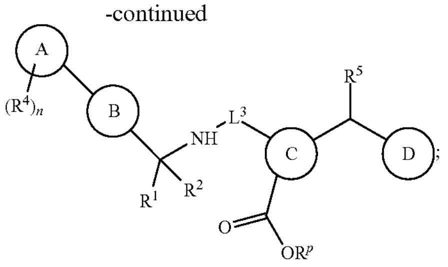

(II-2C)

b) in an inert solvent, reacting the compound as shown in formula II-2C, thereby forming a compound as shown in formula II,

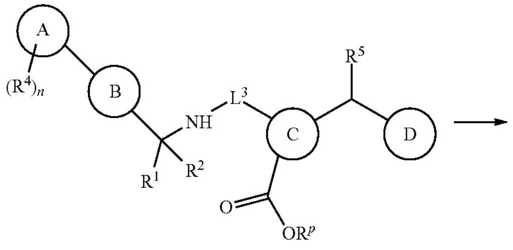

(II-2C)

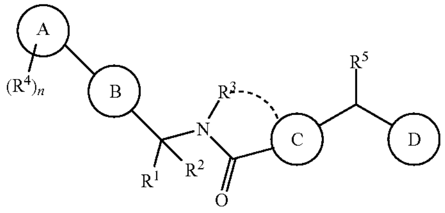

(II)

wherein, $R^3$ together with the ring atom W, that is located at the ortho position of the attachment position of —C(O)— and ring C, and the —C(O)— in $L^1$ forms a substituted or unsubstituted 5, 6 or 7 membered saturated heterocyclic ring;

$L^3$ is a single bond, substituted or unsubstituted $C_{1-2}$alkylene;

the saturated heterocyclic ring, ring A, ring B, ring D, $R^c$, $R^1$, $R^2$, $R^4$, $R^5$, and n are as defined in formula II in the first aspect.

In another preferred embodiment, the inert solvent is selected from the group consisting of dichloromethane.

In another preferred embodiment, the reaction is carried out in the presence of HATU and N,N-diisopropylethylamine.

In another preferred embodiment, the compound is as shown in formula III, wherein iii. the method is Method-Three, and the Method-Three comprises steps of:

a) in an inert solvent, reacting a compound as shown in formula III-A with a compound as shown in formula III-B, thereby obtaining a compound as shown in formula III;

(III-A)

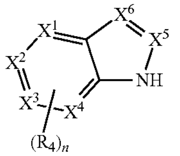

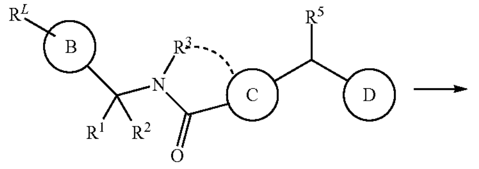

(III-B)

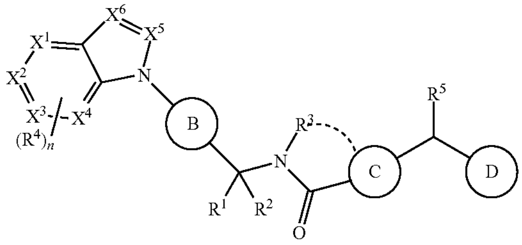

(III)

wherein $R^L$ is halogen; preferably is I;

$X^1$, $X^2$, $X^3$, $X^4$, $X^5$, $X^6$, ring B, ring C, ring D, $R^1$, $R^2$, $R^3$, $R^4$, $R^5$ and are as defined in the first aspect.

In the third aspect of the present invention, provided is a pharmaceutical composition comprising (a) a therapeutically effective amount of the compound according to the first aspect, or pharmaceutically acceptable salts, hydrates or solvates thereof; and (b) a pharmaceutically acceptable carrier.

In the fourth aspect of the invention, provided is a use of the compound according to the first aspect or the pharmaceutical composition according to the third aspect for the preparation of a medicament for treating or preventing diseases or disorders related to programmed cell necrosis and/or human receptor-interacting protein-1 kinase (RIPK1).

In another preferred embodiment, the compound or the pharmaceutical composition treats or prevents the diseases or disorders by the inhibition of the human receptor interacting protein 1 kinase (RIPK1).

In another preferred embodiment, the human receptor interacting protein 1 kinase (RIPK1) comprises RIPK1 in an inactivated (or inactive) state and RIPK1 in an activated state.

In another preferred embodiment, the compound or the pharmaceutical composition can further treat or prevent, especially treat, the diseases or disorders by the inhibition of the human receptor interacting protein 1 kinase (RIPK1) in the activated state.

In another preferred embodiment, the inhibition of the human receptor interacting protein 1 kinase (RIPK1) comprises one or more of the following: the inhibition of the activity of RIPK1, or the inhibition of the phosphorylation of RIPK1.

In another preferred embodiment, the compound or the pharmaceutical composition treats or prevents the diseases or disorders by the inhibition of the programmed cell necrosis pathway.

In another preferred embodiment, the inhibition of the programmed necrosis pathway comprises one or more of the following: the inhibition of the activity of RIPK1, the inhibition of the phosphorylation of RIPK1, or the inhibition of the phosphorylation of MLKL.

In another preferred example, the diseases or disorders are selected from one or more of the group consisting of: degenerative diseases, inflammation, ischemia-reperfusion injury, pathogen infection, Parkinson's disease (PD), age-related macular degeneration, autoimmune diseases, retinal detachment-induced photoreceptor cell necrosis, glaucoma, cisplatin-induced renal injury and traumatic brain injury, atherosclerosis caused by hyperlipidemia, other diseases related to RIPK1-dependent cell apoptosis, necrosis or cytokine production, bacterial infection, viral infection and lysosomal storage disease.

In another preferred embodiment, the degenerative disease comprises: such as Alzheimer's disease (AD), multiple sclerosis (MS), amyotrophic lateral sclerosis (ALS), retinal degenerative disease.

In another preferred embodiment, the inflammation comprises one or more of the following: enteritis, rheumatoid arthritis, psoriasis, retinitis pigmentosa, inflammatory bowel disease, Tynton's disease (PD) inflammatory bowel disease, bombesin-induced acute pancreatitis, sepsis/systemic inflammatory response syndrome (SIRS).

In another preferred embodiment, the ischemia-reperfusion injury comprises one or more of the following: cerebral infarction, myocardial infarction, ischemic brain injury, ischemic myocardial injury, retinal ischemia/reperfusion injury, renal ischemia-reperfusion injury.

In another preferred embodiment, the other diseases related to RIPK1-dependent cell apoptosis, necrosis or cytokine production comprises one or more of the following: blood and solid organ malignant tumor.

In another preferred embodiment, the viral infection comprises one or more of the following diseases or disorders: tuberculosis, influenza, coronavirus infection and the pneumonia caused by it.

In another preferred embodiment, the lysosomal storage disease comprises Gaucher's disease.

In the fifth aspect of the invention, provided is a method for treating or preventing a disease or disorder related to programmed cell necrosis and/or human receptor interacting protein 1 kinase (RIPK1), comprising administering to a subject in need thereof a therapeutically effective amount of the compound according to the first aspect or the pharmaceutical composition according to the third aspect.

In the sixth aspect of the present invention, provided is a method for inhibiting programmed cell necrosis, comprising a step of: culturing cells in the presence of the compound according to the first aspect, thereby inhibiting programmed cell necrosis.

In another preferred embodiment, the method is a non-therapeutic in vitro method.

In the seventh aspect of the present invention, provided is a method for inhibiting RIPK1 protein kinase activity, comprising a step of contacting the RIPK1 protein kinase with the compound according to the first aspect, thereby inhibiting RIPK1 protein kinase activity.

In another preferred embodiment, the method is a non-therapeutic in vitro method.

It should be understood that within the scope of the present invention, the above technical features of the present invention and the technical features specifically described in hereinafter (e.g., examples) can be combined with each other, thereby forming a new or preferred technical solution. Due to space limitation, it will not be repeated herein.

EMBODIMENTS FOR CARRYING OUT THE INVENTION

Figure 1:
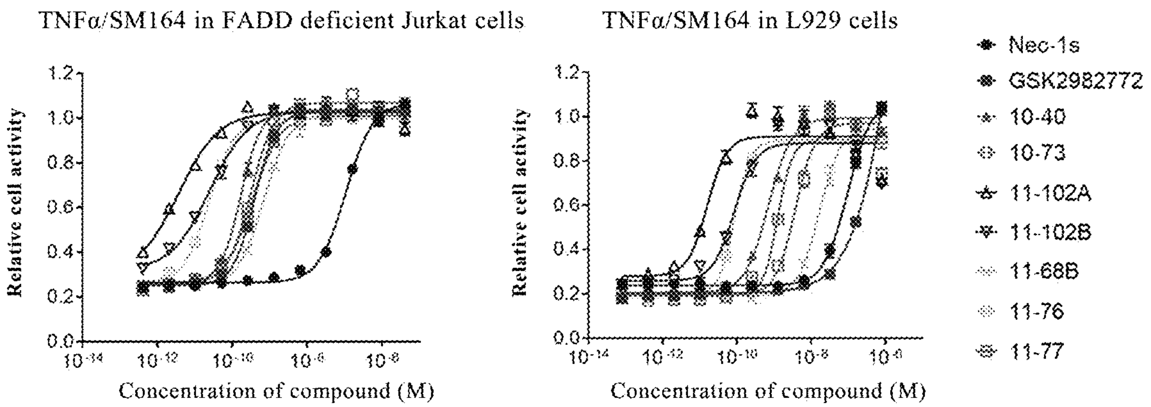
FIG. 1 shows the concentration-activity curves of representative compounds such as QY-10-40 and control compound inhibiting programmed necrosis of FADD-deficient Jurkat cells or L929 cells.

After a long and in-depth research, the present inventors unexpectedly discovered a class of programmed cell necrosis inhibitors with novel structure. The programmed cell necrosis inhibitor has excellent RIPK1 inhibitory activity. Therefore, it can be useful in preparing pharmaceutical compositions for the prevention and/or treatment of diseases involving cell death, RIPK1, and/or inflammation. In particular, the preferred compounds provided by the present invention also have excellent inhibitory activity on activated RIPK1 and thus they are able to improve or treat diseases or disorders involving cell death and/or inflammation of RIPK1 (e. g., inflammation) faster than existing RIPK1 inhibitors that only inhibit inactivated RIPK1. Based on the above, the present inventors have completed the present.

Terms

Unless otherwise defined, the terms used according to the present invention and herein have the following meanings:

As used herein, the term "alkyl" refers to a linear or branched alkyl group having a specified number of carbon atoms. For example, $C_{1-6}$alkyl refers to a linear or branched alkyl group having 1 to 6 carbon atoms. Preferably, alkyl refers to $C_{1-4}$alkyl. Examples of alkyl groups include, but are not limited to, methyl, ethyl, propyl, isopropyl, butyl, isobutyl, sec-butyl, tert-butyl, etc., or the like.

As used herein, the term "cycloalkyl" refers to a cyclic alkyl group having a specified number of carbon atoms. For example, "$C_{3-8}$cycloalkyl group" refers to a cycloalkyl group having 1 to 8 carbon atoms. Examples of cycloalkyl group include, but are not limited to: cyclopropyl, cyclobutyl, cyclopentyl, cyclohexyl, cycloheptyl, cyclooctyl, etc.

As used herein, the term "alkoxy" refers to an alkyl group as defined above that is attached to the rest of the molecule through oxygen atom. For example, $C_{1-6}$alkoxy refers to $C_{1-6}$alkyl-O—. Preferably, the alkoxy group may comprises methoxy, ethoxy and isopropoxy groups.

As used herein, the term "halogen" refers to F, Cl, Br and I.

As used herein, the term "haloalkyl" refers to an alkyl group substituted by a halogen (alkyl group is as defined above). Preferably, the haloalkyl group includes trifluoromethyl, difluoromethyl, trifluoromethoxy, perfluoroethyl, and the like.

As used herein, the term "cycloalkyl" refers to a hydrocarbon ring with a specified number of ring atoms (e. g., $C_{3-8}$cycloalkyl refers to a cyclic alkyl group containing 3, 4, 5, 6, 7, or 8 ring atoms) and is fully saturated or has no more than one double bond between ring vertices. "Cycloalkyl" also refers to bicyclic and polycyclic hydrocarbon rings such as, bicyclo[2.2.1]heptane, bicyclo[2.2.2]octane, etc. The term "heterocycloalkyl" or "heterocycloalkyl" refers to a cycloalkyl group having a specified number of ring atoms and containing one to five heteroatoms selected from N, O, and S, wherein nitrogen and sulfur atoms are optionally oxidized and nitrogen atoms are optionally quaternized. The heterocycloalkyl may be a monocyclic, a bicyclic or a polycylic ring system. Non-limiting examples of heterocycloalkyl include pyrrolidine, imidazolidine, pyrazolidine, butyrolactam, valerolactam, imidazolidinone, hydantoin, dioxolame, phthalimide, piperidine,1,4-dioxane, morpholine, thiomorpholine, thiomorpholine-S-oxide, thiomorpholine-S, S-oxide, piperazine, pyran, pyridone, 3-pyrroline, thiapyran, pyranone, tetrahydrofuran, thiophane, quinuclidine, etc. Heterocycloalkyl can be attached to the rest of the molecule via cyclic carbon or heteroatom.

The term "alkylene" itself or as part of another substituent refers to a divalent group derived from an alkane, such as $—CH_2—$, $—CH_2CH_2—$, $—CH_2CH_2CH_2—$, $—CH_2CH_2CH_2CH_2—$.

Unless otherwise stated, the term "aryl" refers to a polyunsaturated (usually aromatic) hydrocarbon group containing a specified number of ring atoms, which can be monocyclic or fused or covalently connected polycycle (such as dicyclic). The term "heteroaryl" refers to an aryl group (or ring) that has a specified number of ring atoms and contains 1 to 5 (such as 1, 2, 3, 4, or 5) heteroatoms selected from N, O, and S, where nitrogen and sulfur atoms are optionally oxidized, the nitrogen atom is optionally quaternized; for example, a 5-10 membered heteroaryl (or ring) refers to a heteroaryl (or ring) containing 5, 6, 7, 8, 9, or 10 ring atoms. As used herein, a nitrogen-containing heteroaryl means that at least one of the heteroatoms contained is a nitrogen heteroatom, and preferably all the heteroatoms contained are nitrogen heteroatoms. A heteroaryl group can be attached to the remainder of the molecule through a heteroatom. Non-limiting examples of aryl include phenyl, naphthyl, and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thiophenopyridyl, thiophenopyrimidinyl, pyrazolopyrimidinyl, imidazolopyridyl, benzothiazolyl, benzofuranyl, benzothiophenyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for above-stated aryl and heteroaryl ring systems are selected from the group of acceptable substituents described below.

For brevity, the term "aryl" when used in combination with other terms (e.g., aryloxy, arylthio, arylalkyl) includes aryl and heteroaryl rings as defined above.

The above terms (e.g., "alkyl," "aryl" and "heteroaryl"), in some embodiments, will include both substituted and unsubstituted forms of the indicated groups. Optional substituents in these groups include, for example, oxo (=O), —CN, halogen (such as F, Cl, Br or I), $C_{1-6}$alkyl, halogenated $C_{1-6}$alkyl, —OR, —SR, —$S(O)_2R$, —$S(=O)_2NR_2$, —$NR_2$, —COOR, or $C_{6-10}$aryl, 5-10 membered heteroaryl, $C_{3-8}$cycloalkyl, 5-12 membered heterocycloalkyl, aryl-alkyl (such as —$C_{1-4}$alkylene-$C_{6-10}$aryl), heteroaryl-alkyl such as —$C_{1-4}$alkylene-5-10 membered heteroaryl, cycloalkyl-alkyl such as —$C_{1-4}$alkylene-$C_{3-8}$cycloalkyl, heterocycloalkyl-alkyl such as —$C_{1-4}$alkylene-5-12 membered heterocycloalkyl that are optionally substituted with one or more R.

For the compound provided herein, a bond that is drawn from a substituent (typically an R group) to the center of an aromatic ring (e.g., benzene, pyridine, and the like) will be considered to refer to a bond providing a connection at any of the available vertices of the aromatic ring. In some embodiments, the depiction will also include connection at a ring which is fused to the aromatic ring. For example, a bond drawn to the center of the benzene portion of an indole, will indicate a bond to any available vertex of the six- or five-membered ring portions of the indole.

As used herein, the term "containing", "comprising" or "including" means that the various components can be used together in the mixture or composition of the present invention. Therefore, the terms "mainly consisting of . . . " and "consisting of . . . " are included in the term "comprising".

Active Ingredients

As used herein, the terms "compound of the present invention," "programmed cell necrosis inhibitor of the present invention", "RIPK1 inhibitor of the present invention" and "inhibitor of the present invention" may be used interchangeably and refer to the compound described in the first aspect of the present invention. The term also includes various crystalline forms, pharmaceutically acceptable salts, hydrates, or solvates of the compounds described in the first aspect of the present invention.

In another preferred embodiment, the compound of the present invention is as shown in Formula I;

(I)

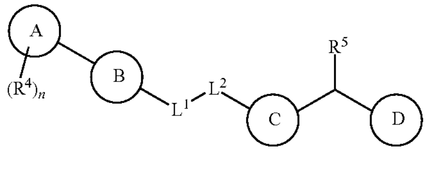

wherein each groups are as defined in the first aspect.

In another preferred embodiment, the compound of the present invention is as shown in formula II;

(II)

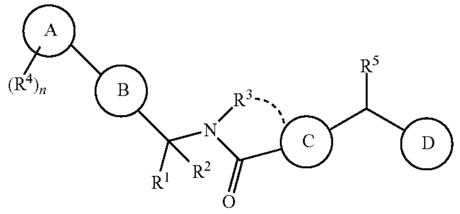

wherein each groups are as defined in the first aspect.

In another preferred embodiment, the compound of the present invention is as shown in formula III;

(III)

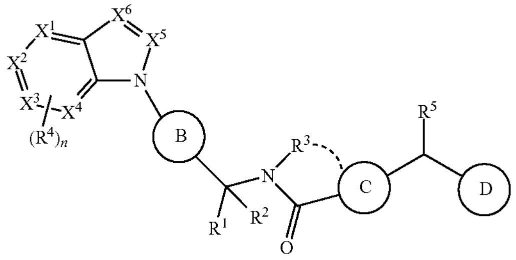

wherein each groups are as defined in the first aspect.

In another preferred embodiment, the compound of the present invention is as shown in formula IV-1 or IV-2

(IV-1)

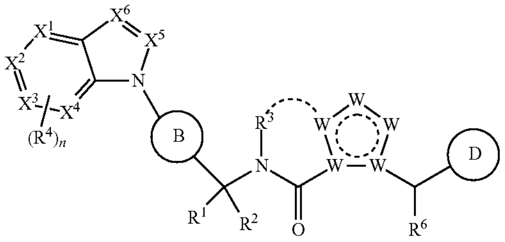

(IV-2)

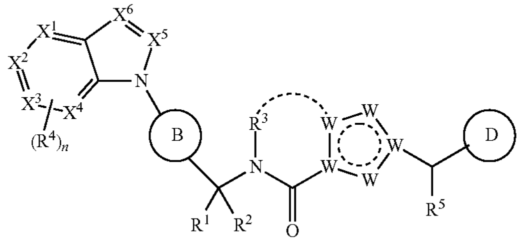

wherein each groups are as defined in the first aspect.

In another preferred embodiment, each groups of the compounds of formula I, formula II, formula III, formula IV-1 or formula IV-2 (e.g. ring A, ring B, ring C, ring D, $L^1$, $L^2$, n, $R^2$, $R^3$, $R^4$, $R^5$, $R^6$, $R^a$, $R^b$, $R^c$, $R^d$, W, $W^1$, $W^2$, $W^3$, $W^4$, $W^5$, $X^1$, $X^2$, $X^3$, $X^4$, $X^5$, and $X^6$) are each independently the corresponding groups in the specific compound in Table A.

In another preferred embodiment, the compound of the present invention are selected from the compounds in Table A, or pharmaceutically acceptable salts thereof.

Wherein, the term "pharmaceutically acceptable salts" refers to salts that are formed of the compound of the present invention and acids or bases, and suitable for use as a drug. Pharmaceutically acceptable salts include inorganic salts and organic salts. A group of preferred salts are salts formed of the compound of the present invention and the acids. Acids suitable for forming salts include, but are not limited to, inorganic acids such as hydrochloric acid, hydrobromic acid, hydrofluoric acid, sulfuric acid, nitric acid, phosphoric acid and the like; organic acids such as methanoic acid, acetic acid, trifluoroacetic acid, propionic acid, oxalic acid, malonic acid, succinic acid, fumanic acid, maleic acid, lactic acid, malic acid, tartaric acid, citric acid, bitter acid, benzoic acid, methanesulfonic acid, ethanesulfonic acid, p-toluenesulfonic acid, benzenesulfonic acid, naphthalene sulfonic acid, and the like; and amino acids such as proline, phenylalanine, aspartic acid, glutamic acid and the like. Another preferred type of salts are salts formed by compound of the present invention and bases, e.g., alkali metal salts (e.g. sodium or potassium salts), alkaline earth metal salts (e.g. magnesium or calcium salts), ammonium salts (e.g., lower alkanol ammonium salts or other pharmaceutically acceptable amine salts), for example, methylamine salt, ethylamine salt, propylamine salt, dimethylamine salt, trimethylamine salts, diethylamine salts, triethylamine salts, tert-butyl amine salts, ethylenediamine salts, hydroxyethylamine salts, bihydroxyethylamine salts, tri-hydroxyethylamine salts, and amine salts formed by morpholine, piperazine, and lysine.

The term "solvate" refers to complexes formed of the compound of the present invention and solvent molecules in any specific ratio. "Hydrate" refers to a complex formed by coordination of the compound of the present invention with water.

In addition, the compound of the present invention also includes prodrugs of the compound of the first aspect. The term "prodrug" include those are biologically active or non-active by themselves, when being administered with a suitable method, the prodrugs are a class of compounds that undergo metabolism or chemical reaction in the human body and converted to the compound of formula I or the salts thereof or solutions containing compound of formula I. The prodrugs include (but are not limited to) the carboxylic acid ester, carbonic ester, phosphate, nitrate, sulfate, sulfone ester, sulfoxide esters, amino compounds, carbamates, azo compounds, phosphoramides, glucoside, ether, acetal of the compound, and the like.

Preparation Method

The preparation methods of the compound of the present invention are described in more detail below, but these specific methods do not pose any restriction to the present invention. The compound of the present invention can also be conveniently prepared by optionally combining various synthesis methods described in this specification or known in the art. Such combinations can be easily carried out by those skilled in the art to which the present invention belongs.

In a specific embodiment, the preparation method for the compound of formula II provided by the present invention is Method One, and the Method One includes a step of: in an inert solvent, reacting the compound as shown in formula II-2A with the compound as shown in formula II-2B to obtain the compound as shown in formula II-2C;

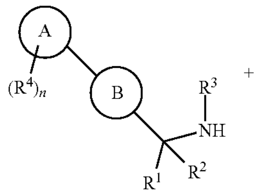

(II-1A)

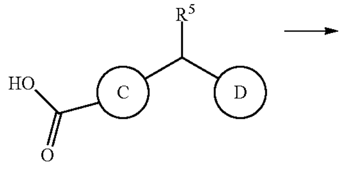

(II-1B)

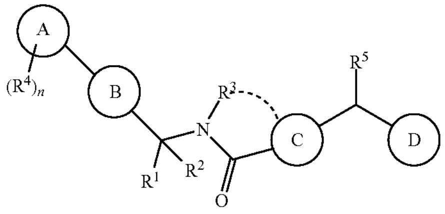

(II)

wherein $R^3$ is selected from the group consisting of: H, OH, substituted or unsubstituted $C_{1-4}$alkyl, substituted or unsubstituted $C_{1-4}$alkoxy;

ring A, ring B, ring C, ring D, $R^c$, $R^1$, $R^2$, $R^4$, $R^5$, and n are as defined in Formula II.

In a specific embodiment, the preparation method for the compound of formula II provided by the present invention is Method Two, and the Method Two includes steps of:

a) in an inert solvent, reacting the compound as shown in formula II-2A with the compound as shown in formula II-2B to obtain the compound as shown in formula II-2C;

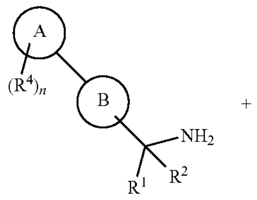

(II-2A)

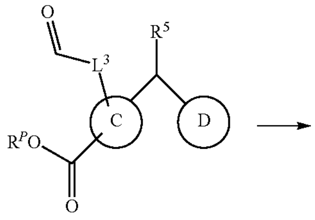

(II-2B)

-continued

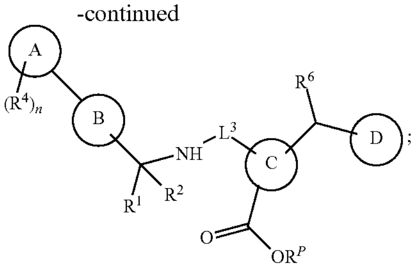

(II-2C)

b) in an inert solvent, reacting the compound as shown in formula II-2C to form a compound as shown in formula II,

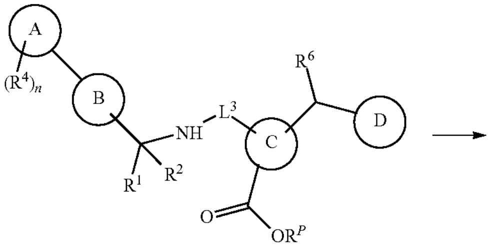

(II-2C)

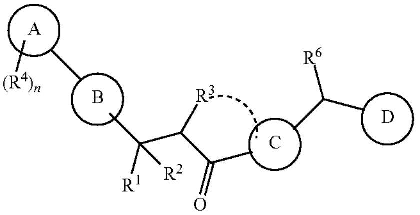

(II)

wherein, $R^3$ forms a substituted or unsubstituted 5, 6 or 7-membered saturated heterocyclic ring together with the ring atom W that is located at the ortho position of the connection position of —C(O)— to ring C and —C(O)— in $L^1$;

$L^3$ is a single bond, substituted or unsubstituted $C_{1-2}$alkylene;

the saturated heterocyclic ring, ring A, ring B, ring D, $R^c$, $R^1$, $R^2$, $R^4$, $R^5$, and n are as defined in formula II.

It should be understood that the active group (e. g., N—H, etc.) in the above-mentioned Method One or Method Two may be protected during the reaction, and then the compound of formula II of the present invention is obtained by removing the protecting group.

Pharmaceutical Compositions and Administration

Since the compound of the present invention have excellent inhibitory effects on RIPK1 activity and/or have inhibitory activity on programmed cell necrosis. Therefore, the compound of the present invention and various crystal forms, pharmaceutically acceptable inorganic or organic salts, hydrates or solvates thereof, and pharmaceutical compositions containing the compound of the present invention as main active ingredients can be used for preventing, treating and/or alleviating diseases and disorders related to programmed cell necrosis and/or human receptor interacting protein 1 kinase (RIPK1) (such as activity or expression thereof). In particular, the preferred compounds of the present invention not only have an inhibitory effect on RIPK1 in inactivated state thereby preventing the activation or activation of RIPK1 in related diseases or disorders (e. g., inflammation), but also can effectively inhibit the activated RIPK1 thereby achieving a therapeutic or intervention effect on related diseases/disorders (e. g., inflammation) faster. According to the prior art, the compound of the present invention can be used for treating the following diseases or disorders: degenerative diseases (such as Alzheimer's disease (AD), multiple sclerosis (MS), amyotrophic lateral sclerosis (ALS), retinal degenerative diseases and others), inflammation (enteritis, rheumatoid arthritis, psoriasis, and others), ischemia-reperfusion injury (cerebral infarction, myocardial infarction and others), and pathogen infection and others; or, Parkinson's disease (PD), Huntington's disease (PD), inflammatory bowel disease, age-related macular degeneration, psoriasis, retinitis pigmentosa, inflammatory bowel disease, autoimmune diseases, bombesin-induced acute pancreatitis and sepsis/systemic inflammatory response syndrome (SIRS), ischemic brain injury, ischemic myocardial injury, retinal ischemia/reperfusion injury, retinal detachment-induced photoreceptor cell necrosis, glaucoma, renal ischemia/reperfusion injury, cisplatin-induced kidney injury and traumatic brain injury, atherosclerosis caused by hyperlipidemia, other diseases related to RIPK1-dependent apoptosis, necrosis or cytokine production, including blood and solid organ malignant tumors, bacterial infections and viral infections (including tuberculosis, influenza, coronavirus infection and pneumonia caused by them and others) and lysosomal storage disease (especially, Gaucher's disease).

The pharmaceutical composition of the present invention comprises the compound of the present invention or pharmaceutically acceptable salts thereof in a safe and effective amount range and pharmaceutically acceptable excipients or carriers. Wherein the "safe and effective amount" means an amount of compound that is sufficient to significantly ameliorate the condition without causing significant side effects. Generally, the pharmaceutical composition contains 0.1-1000 mg of the invention per dose, preferably, 0.5-500 mg of the invention per dose. Preferably, the "one dose" is one capsule or one pill.

"Pharmaceutically acceptable carrier" means one or more compatible solid or liquid fillers, or gelatinous materials which are suitable for human use and should be of sufficient purity and sufficiently low toxicity. "Compatibility" herein means that each components in the composition can be admixed with the compound of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, and cellulose acetate, etc.), gelatin, talc, solid lubricants (such as stearic acid, and magnesium stearate), calcium sulfate, vegetable oils (such as soybean oil, sesame oil, peanut oil, and olive oil, etc.), polyols (such as propylene glycol, glycerol, mannitol, and sorbitol, etc.), emulsifiers (such as Tween), wetting agent (such as sodium dodecyl sulfate), coloring agents, flavoring agents, stabilizers, antioxidants, preservatives, and pyrogen-free water, etc.

There is no special limitation of administration mode for the compound or pharmaceutical composition of the present invention, and the representative administration mode includes (but is not limited to) oral, rectal, parenteral (intravenous, intramuscular or subcutaneous), and topical administration. A particularly preferred mode of administration is oral.

Solid dosage forms for oral administration include capsules, tablets, pills, powders and granules. In these solid dosage forms, the active compounds are mixed with at least one conventional inert excipient (or carrier), such as sodium citrate or dicalcium phosphate, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared with coatings and shells, such as enteric coatings and any other materials known in the art. Opaque agent may be contained. The active compound or compound in the composition may be released in a delayed mode in a given portion of the digestive tract. Examples of the embedding component that can be used include polymers and waxes. If necessary, the active compound can form microcapsules with one or more above excipients.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

In addition to these inert diluents, the composition may also contain additives such as wetting agents, emulsifiers, and suspending agents, sweeteners, flavoring agents and perfume.

In addition to the active compounds, the suspension may contain suspending agent, such as ethoxylated isooctadecanol, polyoxyethylene sorbitol and sorbitan esters, microcrystalline cellulose, methanol aluminum and agar, or the mixtures thereof.

The compositions for parenteral injection may comprise physiologically acceptable sterile aqueous or anhydrous solutions, dispersions, suspensions or emulsions, and sterile powders used for re-dissolution into sterile injectable solutions or dispersions. Suitable aqueous and non-aqueous carriers, diluents, solvents or excipients include water, ethanol, polyols and any suitable mixtures thereof.

Dosage forms for topical administration of the compound of the present invention include ointments, powders, patches, sprays and inhalants. The active ingredient is mixed with physiologically acceptable carriers and any preservatives, buffers, or propellants that may be required if necessary under sterile conditions.

The compound of the present invention can be administrated alone, or in combination with any other pharmaceutically acceptable compounds.

When the pharmaceutical compositions are used, a safe and effective amount of compound of the present invention is applied to a mammal (such as human) in need of treatment, wherein the dose of administration is a pharmaceutically effective dose. For a person weighed 60 kg, the daily dose is usually 0.2-1000 mg, preferably 0.5-500 mg. Of course, the particular dose should also take various factors, such as the route of administration, patient healthy status into consideration, which are all within the scope of an experienced physician's skill.

The main advantages of the present invention include:

(a) The compound of the present invention has excellent inhibitory activity on programmed cell necrosis.

(b) The compound of the present invention has excellent metabolic stability.

(c) The compound of the present invention has excellent inhibitory activity on RIPK1 kinase.

(d) The compound of the present invention is able to effectively inhibit the programmed cell necrosis pathway (such as phosphorylation of RIPK1 itself and phosphorylation of downstream protein MLKL).

(e) The bioavailability of the compound of the present invention is high, and within 24 hours after administration, the blood drug concentrations for most of the time are above the effective concentration.

(f) The compounds of the present invention is able to effectively reduce inflammatory reactions (especially those caused by TNFα).

(g) The compound of the present invention can alleviate the inflammatory reaction induced by the abnormal increase of TNF α level due to immune response during coronavirus infection.

(h) The compound of the present invention is able to effectively inhibit RIPK1 that is already in an activated state, therefore the intervention effect on related inflammation can be achieved more quickly.

(i) The compound of the present invention have very strong inhibitory activity on both human and mouse RIPK1, so there is no need to use expensive and limited primate models in preclinical trials, which is very conducive to its expanded application in different disease models.

The present invention was further described hereafter in combination with specific embodiments. It should be understood that these examples are only used to illustrate the and not to limit the scope of the invention. The experimental methods without specific conditions in the following examples generally follow the conventional conditions or the conditions suggested by the manufacturer. Unless otherwise stated, percentages and parts are percentages by weight and parts by weight.

Synthetic Example

Method 1:

Synthesis of Compound QY-5-23:

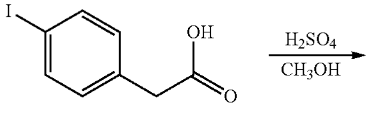

-continued

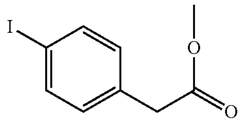

Methyl 2-(4-iodophenyl) acetate (QY-5-23): 4-iodophenyl acetic acid (500 mg, 1.91 mmol) was dissolved in 5 ml of methanol. The solution was added 5 drops of concentrated sulfuric acid at room temperature. The reaction solution was mixed and stirred evenly in a 15 ml pressure bottle, slowly heated to 65° C., and refluxed and stirred for 5 hours. After the completion of reaction, the reaction solution was quenched by adding saturated sodium bicarbonate solution dropwise in ice bat, the mixture was transferred to a separating funnel, and extracted with ethyl acetate (10 ml*3). The organic phases were combined, washed with saturated sodium chloride (5 ml*2). The resulting organic phase was dried over anhydrous sodium sulfate, filtered and spin-dried to remove the solvent to obtain 600 mg crude product as light yellow oily liquid, which was used in the next reaction without separation and purification. ESI-MS m/z 276.9 $(M+H)^+$.

Synthesis of Compound QY-5-14:

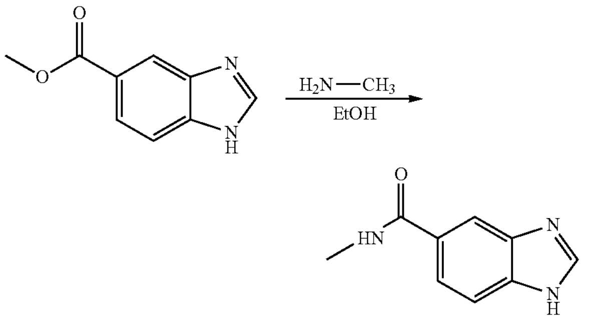

N-methyl-1H-benzo[d]imidazole-5-formamide (QY-5-14): methyl benzimidazole-5-formate (1.40 g, 7.94 mmol) was added to a 150 mL of sealed tube, and methylamine in ethanol (33% wt, 40 ml) was added. The reaction solution was heated and refluxed for 24 h. After the reaction was complete, ethanol was remove by spin-drying using a rotary evaporator to obtain yellowish brown massive solid, which was directly used in the next reaction without separation and purification. ESI-MS m/z 175.9 $(M+H)^+$.

Synthesis of Compound QY-5-25:

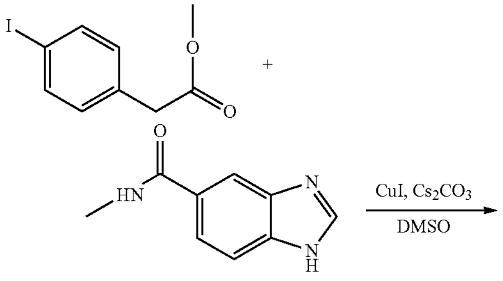

-continued

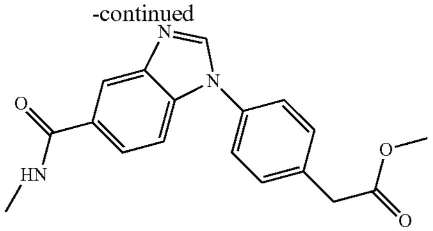

Methyl 2-(4-(5-(methylcarbamoyl)-1H-benzo[d]imidazol-1-yl)phenyl)acetate (QY-5-25): to a 15 ml pressure bottle, 5 ml dimethyl sulfoxide and QY-5-23 (600 mg, 2.17 mmol) were added sequentially. After stirring and dissolving evenly, QY-5-14 (314 mg, 1.81 mmol), cuprous iodide (172 mg, 0.91 mmol), cesium carbonate (1.18 g, 3.62 mmol), 4,7-dimethoxy-1,10 phenanthroline (87 mg, 0.36 mmol) were added, and After under nitrogen protection the mixture was heated to 100° C. and reacted overnight. After complete consumpt of the reactant, the mixture was filtered to remove solid insoluble substances via a filter membrane, then separated and purified by a C18 reversed-phase chromatographic column (water:acetonitrile=0-80%) to obtain 486 mg of dark brown oily liquid with a yield of 83%. ESI-MS m/z 324.1 $(M+H)^+$ Synthesis of Compound QY-5-34:

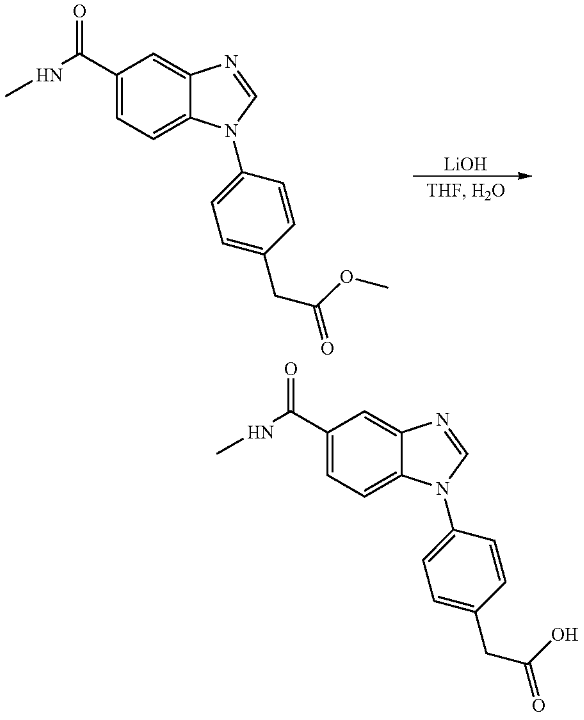

2-(4-(5-(methylaminoformyl)-1H-benzo[d]imidazol-1-yl)phenyl)acetic acid (QY-5-34)

QY-5-25 (486 mg, 1.50 mmol) was dissolved in 5 ml of tetrahydrofuran, and the solution was transferred to a 15 ml pressure bottle. Lithium hydroxide monohydrate (126 mg, 3.0 mmol) was dissolved in 5 ml of distilled water and then it was added into the reaction solution dropwise under ice bath condition. After mixing and stirring evenly, the reaction solution was allowed to gradually return to room temperature. The reaction was monitored in real time by LC-MS. The reaction was complete in 2 h, and then transferred to a 100 ml round bottom flask. After removing the organic solvent by evaporation, the reaction system was dissolved with methanol, separated and purified by C18 reversed-phase chromatographic column (water: acetonitrile=0 to 80%) to afford 292 mg dark green foam solid with a yield of 63%. ESI-MS m/z 308.0 $(M+H)^-$.

Synthesis of Compound QY-5-35:

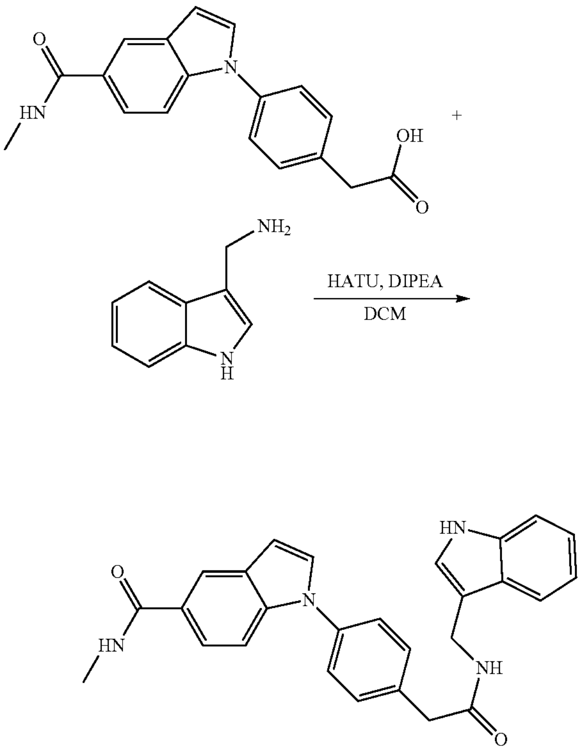

1-(4-(2-(((1H-indole-3-yl)methyl)amino)-2-oxoethyl) phenyl)-N-methyl-1H-benzo[d]imidazol-5-formamide (QY-5-35): In an 8 ml pressure bottle, QY-5-34 (38 mg, 0.12 mmol) was dissolved in 1.5 ml dichloromethane, and HATU (56 mg, 0.147 mmol) was added. Indole-3-methylamine (21 mg, 0.15 mmol) was dissolved in 1 ml of dichloromethane, and was added dropwise into the evenly mixed reaction solution. N,N-diisopropylethylamine (40 mg, 0.31 mmol) was added dropwise under ice bath condition, the mixture was stirred for 10 min, and after gradually returning to room temperature, the mixture was stirred for 4 hours. The reaction was monitored in real time by LC-MS. After the reaction was complete, the reaction solution was diluted with 5 ml of dichloromethane, transferred to a separating funnel, washed with 5 ml of distilled water, extracted with dichloromethane (5 ml*3). The organic phases were combined and washed with saturated sodium chloride (5 ml*2). The post-processing resulting organic phase was dried by anhydrous sodium sulfate, filtered and spin-dried to remove dichloromethane, and separated and purified by C18 reversed-phase chromatographic column (water:acetonitrile=0 to 80%) to obtain 29 mg of light yellow oily liquid with a yield of 55%. ESI-MS m/z 438.1 $(M+H)^+$.

Method 2:

Synthesis of Compound QY-5-30:

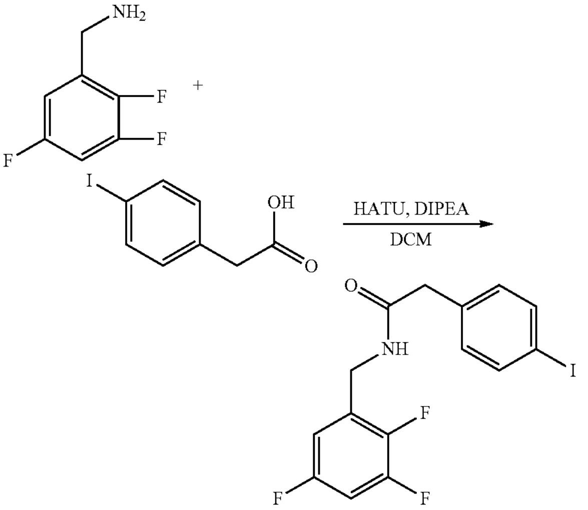

(4-iodophenyl)-N-(2,3,5-trifluorobenzyl)acetamide (QY-5-30): in a 15 ml pressure bottle, 2,3,5-trifluorobenzylamine (200 mg, 1.24 mmol) was dissolved in 7 ml of dichloromethane, HATU (566 mg, 1.49 mmol) was added. P-iodophenyl acetic acid (390 mg, 1.49 mmol) was dissolved in 1 ml of dichloromethane, and was added dropwise into the evenly mixed reaction solution. N,N-diisopropylethylamine (40 mg, 0.31 mmol) was added dropwise under ice bath condition, stirred for 10 min, and after gradually returning to room temperature, the mixture was stirred for 6 hours. The reaction was monitored in real time by LC-MS. After the consumption of the raw materials, the reaction solution was diluted by adding 15 ml of dichloromethane. The mixture was transferred to a separating funnel, washed with 15 ml of distilled water, and extracted with dichloromethane (15 ml*3). The organic phases were combined, washed with saturated sodium chloride (10 ml*2). The post-processing resulting organic phase was dried by anhydrous sodium sulfate, filtered and spin-dried to remove dichloromethane, and separated and purified by C18 reversed-phase column (water:acetonitrile=0-80%) to afford 400 mg white solid with a yield of 80%. ESI-MS m/z 406.0 $(M+H)^+$.

Synthesis of Compound QY-5-36:

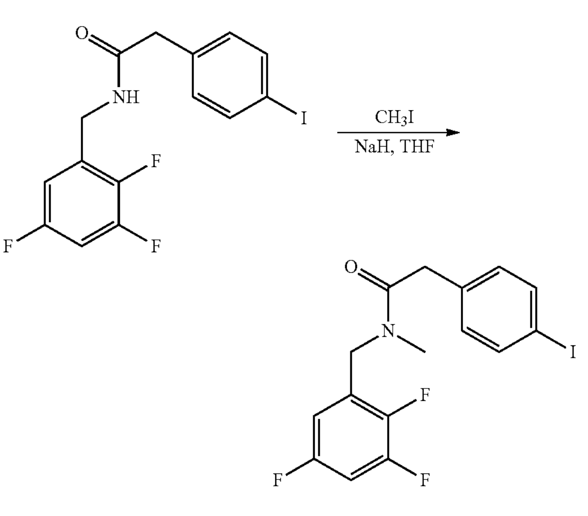

2-(4-iodophenyl)-N-methyl-N-(2,3, 5-trifluorobenzyl)acetamide (QY-5-36): pressure bottle QY-5-30 (300 mg, 0.74 mmol) and 6 ml tetrahydrofuran was added to a 15 ml pressure bottle, mixed and stirred evenly. with sodium hydride (30 mg, 0.74 mmol) was slowly added into the reaction solution under ice bath condition and stirred for 10 min. Methyl iodide (126 mg, 0.89 mmol) was added slowly into the reaction solution under the condition of ice salt bath. After gradually returning to room temperature, the reaction was continued to be stirred. The reaction was monitored in real time by LC-MS until complete consumption of the reactant. The reaction was quenched by adding distilled water, and then evaporated using a rotary evaporator to remove tetrahydrofuran, and the reaction system was dissolved with methanol. After the filtration via filter membrane, the mixture was separated and purified using C18 reversed-phase chromatographic column (water:acetonitrile=0 to 80%) to obtain 192 mg of light yellow oily liquid with a yield of 62%. ESI-MS m/z 419.9 $(M+H)^+$.

Synthesis of Compound QY-5-40:

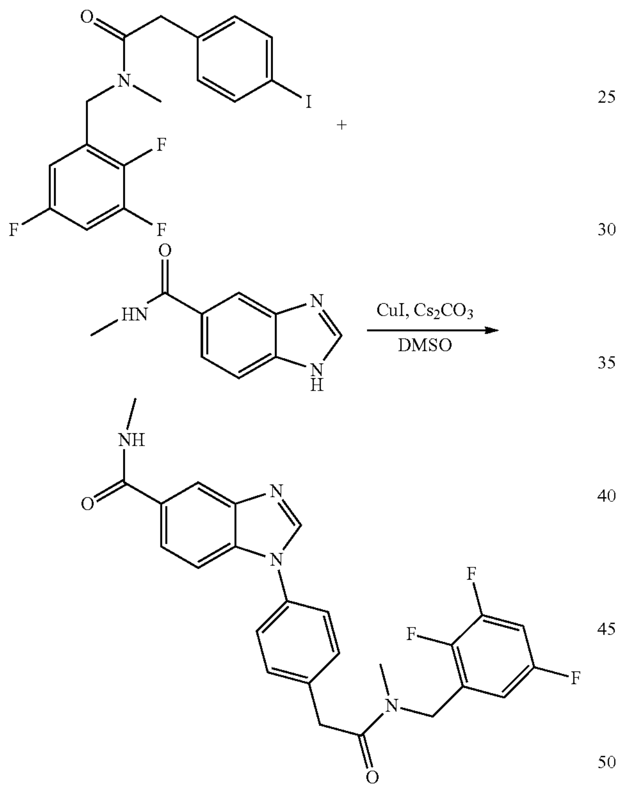

N-methyl-1-(4-(2-(methyl(2,3,5-trifluorobenzyl)amino)-2-oxoethyl) phenyl)-1H-benzo[d]imidazol-5-formamide (QY-5-40): QY-5-36 (192 mg, 0.46 mmol) was added to a 15 ml pressure bottle, and dissolved with 3 ml dimethyl sulfoxide. After stirring evenly QY-5-14 (88 mg, 0.51 mmol), cuprous iodide (44 mg, 0.23 mmol), cesium carbonate (298 mg, 0.92 mmol), and 4,7-dimethoxy-1,10 phenanthroline (33 mg, 0.14 mmol) were added, after nitrogen protection, the mixture was heated to 100° C. and reacted overnight. After complete consumption of the reactants, the reaction was filtered by filter membrane to remove the solid insoluble matter, and separated and purified by the C18 reversed-phase chromatographic column (water:acetonitrile=0-80%) to obtain 143 mg yellow-brown solid with a yield of 67%. ESI-MS m/z 467.1 $(M+H)^+$.

Method 3:

Synthesis of Compound QY-5-62:

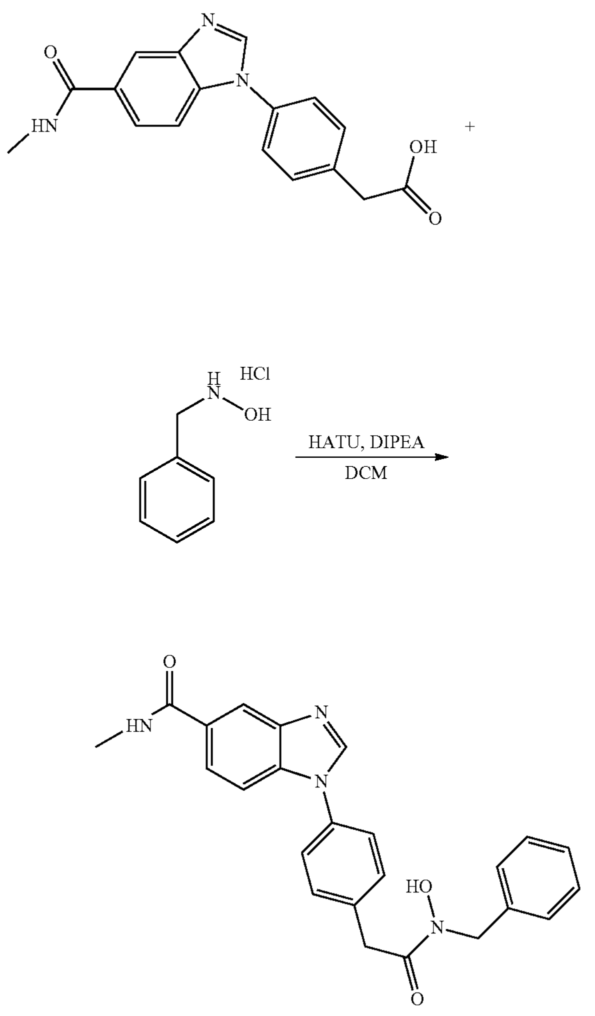

1-(4-(2-(benzyl(hydroxy)amino)-2-oxoethyl)phenyl)-N-methyl-1H-benzo[d]imidazol-5-formamide (QY-5-62): QY-5-34 (150 mg, 0.49 mmol) was dissolved in 4 ml dichloromethane and added to an 8 ml pressure resistant bottle was added, and HATU (221 mg, 0.58 mmol) was added. N-benzyl hydroxylamine hydrochloride (93 mg, 0.58 mmol) was added into the evenly-stirred reaction solution. N,N-diisopropylethylamine (250 mg, 1.94 mmol) was added dropwise under ice bath condition, and the reaction was stirred for 3 h after gradually returning to room temperature. The reaction was monitored in real time by LC-MS. After the reactant was completely consumed, the reaction solution was diluted with 5 ml of dichloromethane, transferred to a separating funnel, washed with 4 ml of distilled water, and extracted with dichloromethane extraction (5 ml*3). The organic phases were combined, washed with saturated sodium chloride (5 ml*2), dried over anhydrous sodium sulfate. The organic phase was filtered and evaporated to remove dichloromethane, separated and purified with C18 reversed-phase chromatographic column (water:acetonitrile=20%-90%) to obtain 85 mg white solid in a yield of 42%. ESI-MS m/z 415.1 $(M+H)^+$.

Method 4:

Synthesis of Compound QY-5-81:

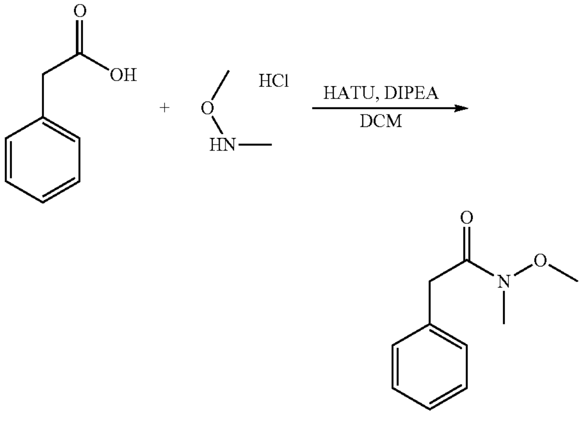

N-methoxy-N-methyl-2-phenylacetamide (QY-5-81): in a 30 ml pressure resistant bottle, phenylacetic acid (1.0 g, 7.34 mmol) was dissolved in 15 ml dichloromethane, and HATU (3.6 g, 9.54 mmol) was added. Dimethylhydroxylamine hydrochloride (787 mg, 8.07 mmol) was added to evenly-mixed reaction solution. N,N-diisopropylethylamine (2.84 g, 22.0 mmol) was added dropwise at room temperature, and continued to react under stirring for 5.5 h. The reaction was monitored in real time by LC-MS. After complete consumption of the reactant, the reaction solution was transferred to a separating funnel, washed with 25 ml distilled water, extracted with dichloromethane (20 ml*3). The organic phases were combined, washed with saturated sodium chloride (10 ml*2), dried over anhydrous sodium sulfate, filtered and evaporated to remove dichloromethane, separated and purified by silica gel column chromatography (petroleum ether:ethyl acetate=0-100%) to obtain 1.23 g of light yellow transparent liquid in a yield of 94%. ESI-MS m/z 180.1 $(M+H)^+$.

Synthesis of Compound QY-5-84:

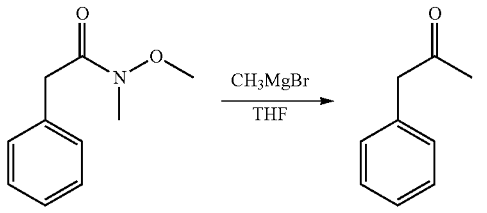

1-phenylpropane-2-one (QY-5-84): in a 30 ml pressure bottle, QY-5-81 (1.03 g, 5.75 mmol) was dissolved in 15 ml tetrahydrofuran. Methyl magnesium bromide (6.90 ml, 6.90 mmol) was added slowly at 0° C. under continuous stirring at 700 rp. Upon drop addition, the reaction solution was allowed gradually return to room temperature and continued to stir. the reaction was monitored in real time via LC-MS. The reaction was stopped after the reaction was complete. The reaction was quenched by adding 1N hydrochloric acid slowly into the reaction system, extracted with ethyl acetate (20 ml*3). The organic phases were combined, washed with saturated salt water (10 ml*1), and dried over anhydrous sodium sulfate. Organic solvent was removed using rotary evaporator, and the mixture was separated and purified using silica gel column chromatography (petroleum ether:ethyl acetate=0 to 60%) to afford 609 mg colorless transparent liquid with a yield of 79%.

Synthesis of Compound QY-5-87:

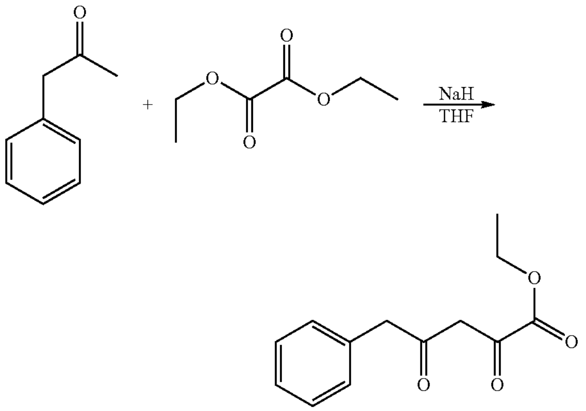

Ethyl 2,4-dioxo-5-phenylvalerate (QY-5-87): QY-5-84 (509 mg, 3.79 mmol) was mixed in 10 ml of ultra-dry tetrahydrofuran and added to a 30 ml of pressure flask was added. Sodium hydride (152 mg, 3.80 mmol) was dissolved in 5 ml of ultra-dry tetrahydrofuran and the mixture was added dropwise into the suspension at 0° C. After mixing, diethyl oxalate (665 mg, 4.55 mmol) was added to the reaction system at 0° C., and after gradually returning to room temperature, the reaction was continued to be stirred for 3 hours before stopping the reaction. The reaction was quenched by adding distilled water at 0° C. Super-dry tetrahydrofuran was removed by spin-drying, the reaction system was diluted with 10 ml ethyl acetate, transferred to a separating funnel, washed with 10 ml of distilled water, and then extracted with ethyl acetate (15 ml*3). The organic phases were combined, washed with saturated salt water (10 ml*2), dried over anhydrous sodium sulfate, filtered and spin-dried to remove ethyl acetate, separated and purified with C18 reversed-phase chromatographic column (water: acetonitrile=20% to 90%) to obtain 495 mg yellowish brown liquid with a yield of 56%. ESI-MS n/z 235.1 $(M+H)^+$.

Synthesis of Compound QY-5-90:

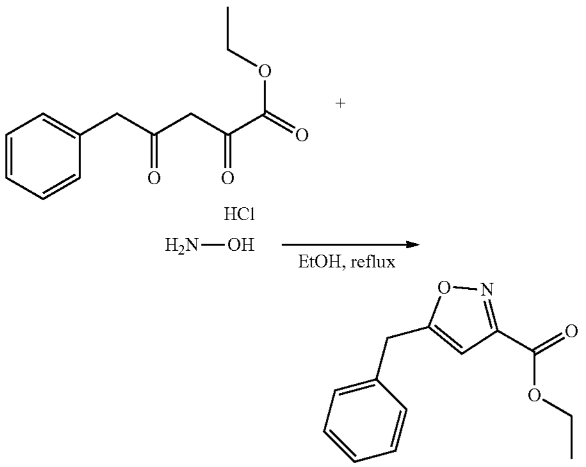

Ethyl 5-benzylisoxazole-3-carboxylate (QY-5-90): QY-5-87 (250 mg, 1.07 mmol) was added into 4 ml absolute ethanol, then transferred to a 15 ml of pressure flask, and the mixture was mixed and stirred evenly. Hydroxylamine hydrochloride (111 mg, 1.60 mmol) was slowly added into the reaction system at room temperature, the reaction system was heated to reflux and stirred continuously overnight. After complete consumption of the reactants, the organic solvent was removed by spin-drying and the residues were separated and purified by silica gel column chromatography (petroleum ether:ethyl acetate=0 to 35%) to afford 180 mg orange-yellow transparent liquid with a yield of 73%. ESI-MS n/z 232.1.1 $(M+H)^+$.

Synthesis of Compound QY-5-91:

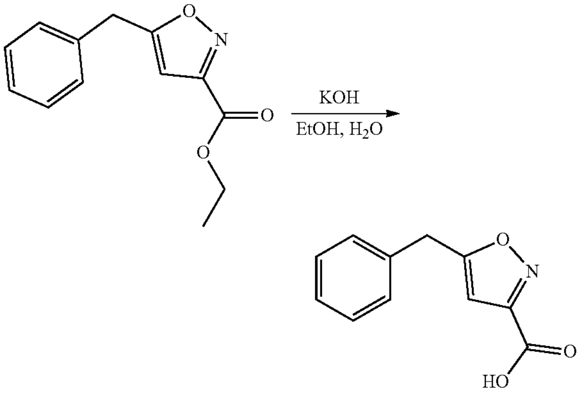

5-Benzylisoxazole-3-carboxylic acid (QY-5-91): QY-5-90 (360 mg, 1.56 mmol) was dissolved in 4 ml ethanol, and the mixture was transferred to a 15 ml pressure bottle. Potassium hydroxide (437 mg, 7.78 mmol) was dissolved in 3 ml distilled water, and added dropwise to the reaction solution under ice bath condition. After mixing and stirring well, the mixture was gradually warmed to room temperature and heated to 80° C. The reaction was monitored in real time by LC-MS. The reaction was finished in 4 h. Saturated potassium bisulfite was added to adjust PH to acidity. After spin-drying, the reaction system was dissolved by adding methanol. The mixture was filtered, and separated and purified by C18 reversed-phase chromatographic column (water:acetonitrile=0 to 80%) to obtain 258 mg white solid powder with a yield of 82%. ESI-MS n/z 202.1 $(M+H)^-$.

Synthesis of Compound QY-5-101:

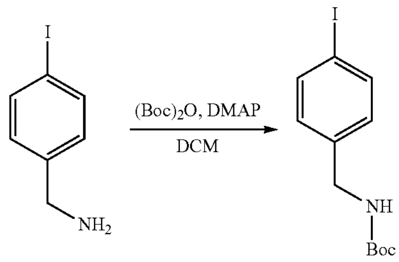 [SMILES: NCc1ccc(I)cc1 ; CC(C)(C)OC(=O)NCc1ccc(I)cc1]

Tert-butyl (4-iodobenzyl) carbamate (QY-5-101): p-iodobenzylamine (800 mg, 3.43 mmol) was dissolved in 10 ml dichloromethane, and the mixture was transferred to a 15 ml pressure bottle. Ditert-butyl dicarbonate (749 mg, 3.43 mmol) was slowly added dropwise into the reaction solution followed by the addition of 4-dimethylaminopyridine (126 mg, 1.03 mmol). The reaction was stirred at room temperature and monitored in real-time by LC-MS. The reaction was complete over 3.5 h. The reaction system was spin-dried together and separated and purified by silica gel column chromatography (petroleum ether:ethyl acetate=0 to 40%) to afford 925 mg white solid with a yield of 81%. ESI-MS m/z 277.0 $(M+H)^+$.

Synthesis of Compound QY-6-2:

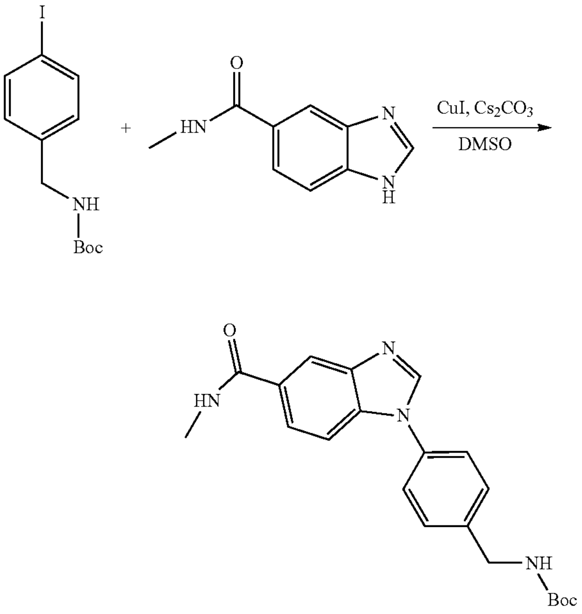

N-tert-butyl (4-(5-(methylcarbamoyl)-1H-benzo[d]imidazolyl)benzyl)carbamate (QY-6-2): QY-5-101 (200 mg, 0.60 mmol) was added to a 15 ml pressure bottle, and dissolved with 3 ml dimethyl sulfoxide. After mixing well, QY-5-14 (105 mg, 0.60 mmol), cuprous iodide (57 mg, 0.30 mmol), cesium carbonate (390 mg, 1.20 mmol) and 4,7-dimethoxy-1,10 phenanthroline (43 mg, 0.18 mmol) were added. The mixture was heated to 100° C. and reacted overnight under nitrogen protection. After complete complete consumption of the reactant, the reaction was filtered via filter membrane to remove solid insoluble matter, and then separated and purified by the C18 reversed-phase chromatographic column (water:acetonitrile=0 to 80%) to afford 203 mg yellow-brown oily liquid with a yield of 89%. ESI-MS m/z 381.1 $(M+H)^+$.

Synthesis of Compound QY-6-6:

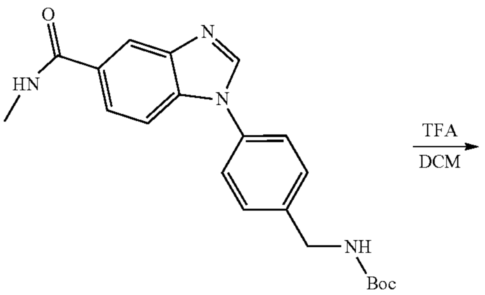

-continued

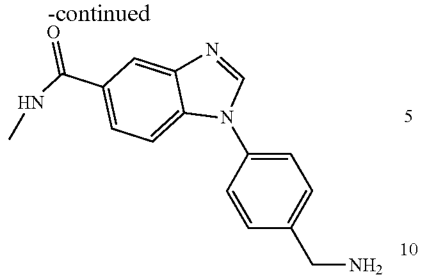

1-(4-(aminomethyl)phenyl)-N-methyl-1H-benzo[d]imidazol-5-formamide (QY-6-6): QY-6-2 (203 mg, 0.53 mmol) was mixed in 5 ml of dichloromethane, and the mixture was transferred to 8 ml-pressure bottle. Trifluoroacetic acid 0.1 ml was added dropwise to the reaction solution at room temperature and the mixture was mixed and stirred evenly. The reaction was monitored in real time by LC-MS and the material was completely consumed in 3.5 hours. The reaction was transferred to a round bottom flask. 20 ml of dichloromethane was added each time and the organic solvent mixture was removed by spin drying, repeating 4-6 times. The reaction product of this step was directly used in the next reaction without purification. ESI-MS m/z 281.0 $(M+H)^+$.

Synthesis of Compound QY-6-16:

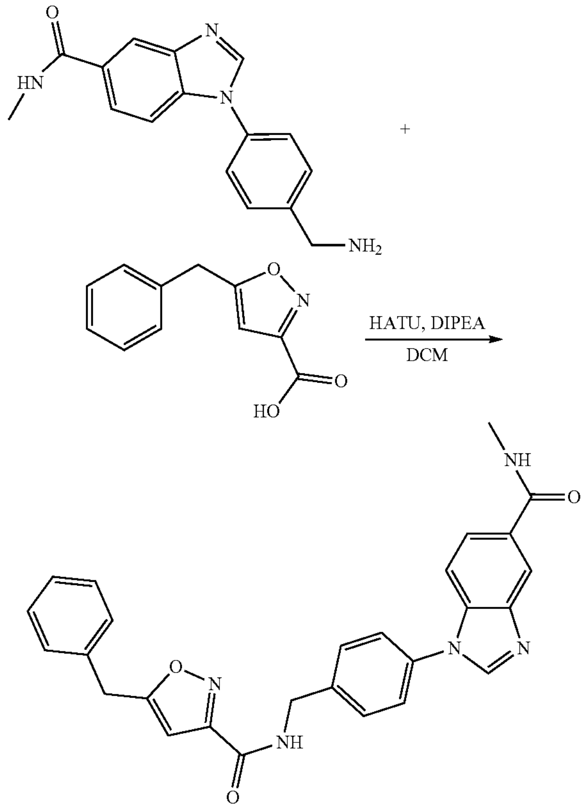

5-Benzyl-N-(4-(5-(methylcarbamoyl)-1H-benzo[d]imidazol-1-yl)benzyl) isoxazol-3-formamide (QY-6-16): in an 8 ml pressure flask, QY-6-6 (70 mg, 0.25 mmol) was dissolved in 2 ml dichloromethane, and HATU (114 g, 0.30 mmol) was added. QY-5-91 (50 mg, 0.25 mmol) was added into the well-mixed reaction solution. N,N-diisopropylethylamine (97 mg, 0.75 mmol) was added dropwise at room temperature, the mixture was continued to react under stirring for 4 hours. The reaction was monitored in real time by LC-MS. After the reactants were completely consumed, the reaction solution was transferred to a separatory funnel, washed with 5 ml of distilled water, extracted with dichloromethane (5 ml*3). The organic phases were combined, washed with saturated sodium chloride (5 ml*2), dried over anhydrous sodium sulfate, filtered and evaporated to remove dichloromethane, filtered by filter membrane and then separated and purified by C18 reversed-phase chromatographic column (water:acetonitrile=0 to 80%) to obtain 116 mg yellow brown oily liquid with a yield of 52%. ESI-MS m/z 466.1 $(M+H)^+$.

Method 5:

Synthesis of Compound QY-6-98:

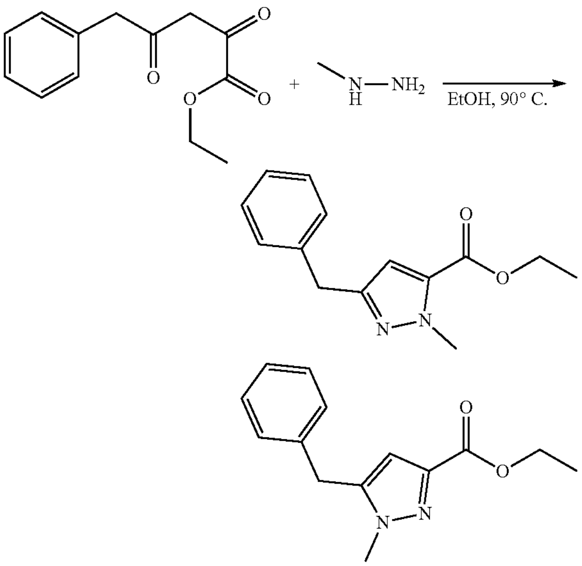

Ethyl 5-benzyl-1-ethylmethyl-1H-pyrazole-3-carboxylate (QY-6-98): in a 15 ml pressure bottle, QY-5-87 (250 mg, 1.07 mmol) was dissolved in 7 ml anhydrous ethanol, and methylhydrazine hydrochloride (101 mg, 1.21 mmol) was added at room temperature. The mixture was gradually heated to 90° C. The reaction was monitored by thin layer chromatography. The reaction was stopped after further stirring for 4 hours. The reaction solution was transferred to a rotary evaporator to remove organic solvent, and separated and purified by silica gel column chromatography (petroleum ether:ethyl acetate=0 to 60%) to afford products of two configurations, product A:104 mg orange yellow liquid, yield 40%; Product B: 62 mg orange yellow liquid, yield 24%. ESI-MS m/z 245.2 $(M+H)^+$.

Synthesis of Compound QY-6-103B:

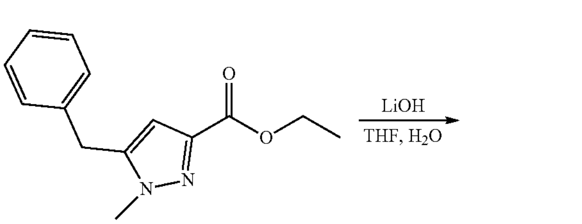

-continued

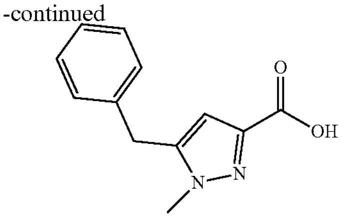

6-benzyl-1-methyl-1H-pyrazole-3-carboxylic acid (QY-6-103B): QY-6-98 (62 mg, 0.25 mmol) was dissolved in 2 ml of THF, and the mixture was transferred to 8 ml of pressure bottle. Lithium hydroxide monohydrate (27 mg, 0.63 mmol) was dissolved in 1 ml distilled water, and the resulting solution was added dropwise to the reaction solution under ice bath condition. The mixture was mixed and stirred evenly, and allowed to gradually return to room temperature. The reaction was monitored in real time by LC-MS. The reaction was stopped after stirring overnight. The organic solvent was removed by rotary evaporation, and the reaction system was dissolved with methanol, and then separated and purified by C18 reversed-phase chromatographic column (water:acetonitrile=0 to 80%) to afford 41 mg white solid with a yield of 76%. ESI-MS m/z 215.1 $(M+H)^-$.

Synthesis of Compound QY-7-2B:

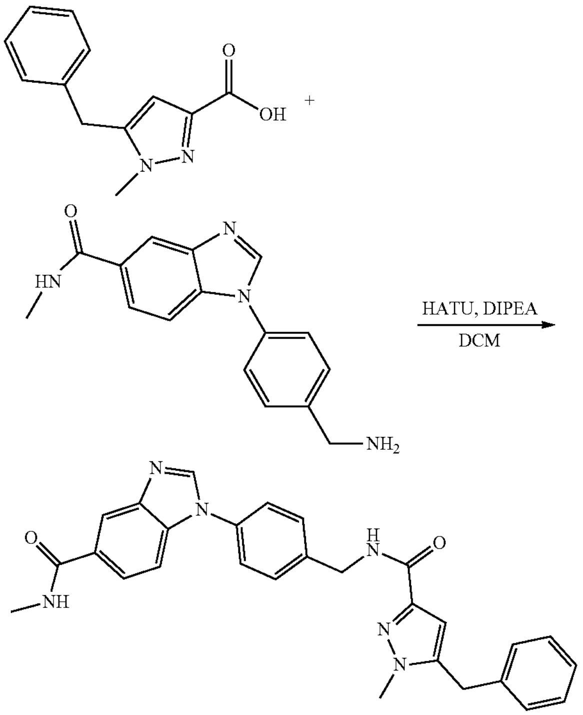

1-(4-((5-benzyl-1-methyl-1H-pyrazole-3-carboxamido)methyl)phenyl)-N-methyl-1H-benzo[d]imidazol-5-carboxamide (QY-7-2B): in an 8 ml pressure bottle, QY-6-103B (15 mg, 0.07 mmol) was dissolved in 1 ml dichloromethane, and HATU (32 mg, 0.09 mmol) was added. QY-6-6 (20 mg, 0.07 mmol) was added into well-mixed reaction solution. N,N-diisopropylethylamine (23 g, 0.18 mmol) was added dropwise at room temperature, the mixture was continued to react under stirring for 4 hours. The reaction was monitored in real time by LC-MS until the reactants were completely consumed. The reaction solution was transferred to a separatory funnel, washed with 2 ml of distilled water, extracted with dichloromethane (2 ml*3). The organic phases were combined, washed with saturated sodium chloride (2 ml*2), dried over anhydrous sodium sulfate, filtered and dichloromethane was removed by rotary evaporation. The residue was separated and purified by silica gel column chromatography (petroleum ether:ethyl acetate=0 to 100%) to obtain 19 mg light yellowish brown liquid with a yield of 59%. ESI-MS m/z 479.1 $(M+H)^+$.

Method 6:

Synthesis of Compound QY-6-97:

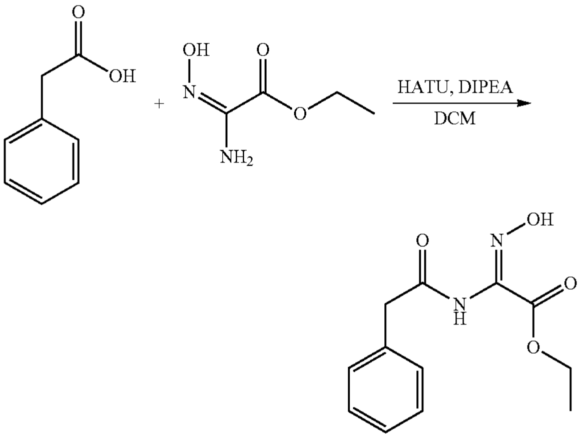

Ethyl (E)-2-(hydroxyimino)-2-(2-phenylacetamide) acetate (QY-6-97): in a 15 ml pressure bottle, phenylacetic acid (200 mg, 1.47 mmol) was dissolved in 7 ml dichloromethane, followed by the addition of HATU (669 mg, 1.76 mmol). Ethyl 2-hydroxyamino-2-iminoacetate (233 mg, 1.76 mmol) was dissolved in 2 ml of dichloromethane, and the resulting solution was added dropwise into the reaction solution. N,N-diisopropylethylamine (569 mg, 4.41 mmol) was added dropwise at room temperature. The mixture was stirred for 10 min and allowed to gradually return to room temperature and then reacted under stirring for 6 h. The reaction was monitored in real time by LC-MS. After the reaction was completed, the reaction solution was diluted with 10 ml of dichloromethane, transferred to a separatory funnel, washed with 5 ml of distilled water, extracted with dichloromethane (5 ml*3). The organic phases were combined, and washed with saturated sodium chloride (5 ml*2). The post-processed organic phase was dried over anhydrous sodium sulfate, filtered and spin-dried to remove dichloromethane, and separated and purified by silica gel column chromatography (petroleum ether:ethyl acetate=0 to 80%) to obtain 84 mg white solid powder with a yield of 23%. ESI-MS m/z 251.1 $(M+H)^+$.

Synthesis of Compound QY-7-4:

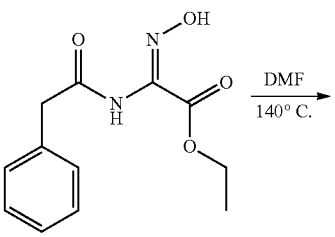

-continued

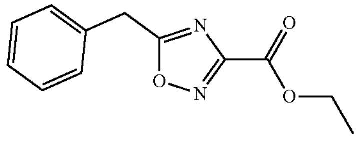

Ethyl 5-benzyl-1,2,4-oxadiazol-3-carboxylate (QY-7-4): QY-6-97 (84 mg, 0.34 mmol) was dissolved in 3 ml of N,N-dimethylformamide, and transferred to 8 ml pressure bottle. The mixture was mixed and stirred evenly and then gradually heated to 140° C. The reaction was monitored in real time by LC-MS. The reaction was complete in 2 hours and was separated and purified by C18 reversed-phase chromatographic column (water:acetonitrile=0 to 100%) to obtain 64 mg light yellow oily liquid with a yield of 81%. ESI-MS m/z 233.1 $(M+H)^+$.

Synthesis of Compound QY-7-13:

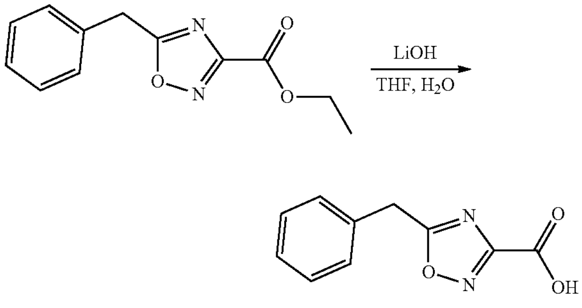

5-benzyl-1,2,4-oxadiazol-3-carboxylic acid (QY-7-13): QY-7-4 (51 mg, 0.22 mmol) was dissolved in 2 ml of tetrahydrofuran, and transferred to an 8 ml pressure bottle. Lithium hydroxide monohydrate (14 mg, 0.33 mmol) was dissolved in 1 ml distilled water, and the resulting solution was added dropwise to the reaction solution under ice bath condition. The mixture was mixed and stirred evenly, and allowed to gradually return to room temperature. The reaction was monitored in real time by LC-MS. The reaction stopped in 4 h. All solvents in the reaction system was removed by rotary evaporation, and the crude product was directly subjected to the subsequent synthesis. ESI-MS m/z 203.1 $(M+H)^-$.

Synthesis of Compound QY-7-14:

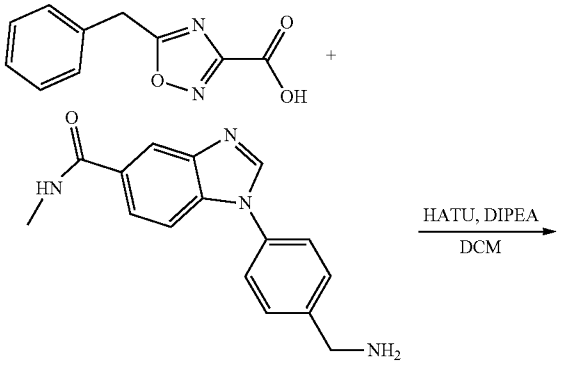

-continued

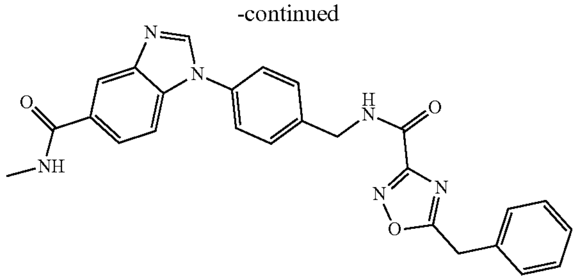

5-Benzyl-N-(4-(5-(methylcarbamoyl)-1H-benzo[d]imidazol-1-yl)benzyl)-1,2,4-oxadiazol-3-carboxamide (QY-7-14): in a 15 ml pressure bottle, QY-7-13 (0.22 mmol) was dissolved in 3 ml dichloromethane followed by the addition of HATU (83 mg, 0.22 mmol). QY-6-6 (51 mg, 0.18 mmol) was added into well-mixed reaction solution. N,N-diisopropylethylamine (59 mg, 0.46 mmol) was added dropwise at room temperature. The mixture was reacted under stirring for 4 h at room temperature. The reaction was monitored in real time by LC-MS. After the reaction was completed, the reaction solution was diluted by adding 10 ml of dichloromethane, transferred to a separatory funnel, washed with 5 ml of distilled water, extracted with dichloromethane (5 ml*3). The organic phases were combined, and washed with saturated sodium chloride (5 ml*2). The post-processed organic phase was dried over anhydrous sodium sulfate, filtered and spin-dried to remove dichloromethane, and separated and purified by C18 reversed-phase chromatography column (water:acetonitrile=0 to 90%) to afford 35 mg of yellow-brown oily liquid with a yield of 42%. ESI-MS m/z 467.1 $(M+H)^+$.

Method 7:

Synthesis of Compound QY-7-21:

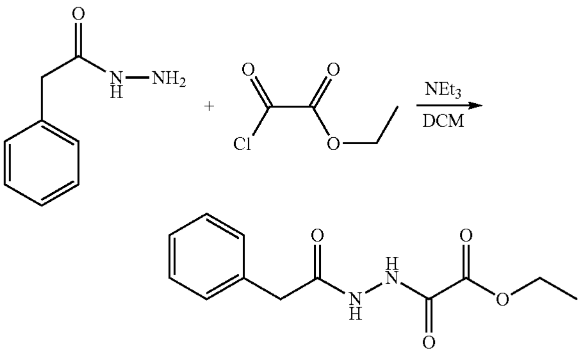

Ethyl 2-oxo-2-(2-(2-phenylacetyl)hydrazinyl)acetate (QY-7-21): in a 100 ml round bottom flask, phenylacetylhydrazine (600 mg, 3.99 mmol) was dissolved in 30 ml dichloromethane. Monoethyl oxalyl chloride (600 mg, 4.39 mmol) was slowly added dropwise under ice bath condition, and the reaction system was allowed to gradually return to room temperature and continued to stir. The reaction was monitored in real time by LC-MS. No raw material peak emerged after 3 hours, and the reaction was stopped. The reaction solution was quenched by adding distilled water, washed with 10 ml distilled water, and extracted with dichloromethane (15 ml*3). The organic phases were combined, washed with saturated salt water (10 ml*1), and dried over anhydrous sodium sulfate. The organic solvent was removed by a rotary evaporator to afford crude product as white solid, which was directly subjected to the next reaction. ESI-MS m/z 251.0 $(M+H)^+$.

Synthesis of Compound QY-7-23:

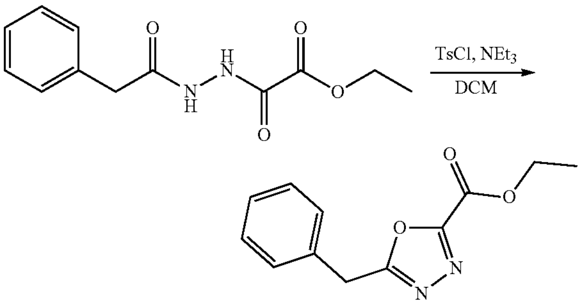

Ethyl 5-benzyl-1,3,4-oxadiazole-2-carboxylate (QY-7-23): in a 30 ml pressure bottle, QY-7-21 was well-mixed in 10 ml dichloromethane. P-methylbenzenesulfonyl chloride (760 mg, 3.99 mmol) was dissolved in 4 ml dichloromethane and then dropped into the reaction solution. The mixture was continued to stir at room temperature. The reaction was monitored by thin layer chromatography, and the reaction was stopped after stirring for another 6 hours. The reaction was transferred to a separatory funnel, washed with 10 ml of distilled water, and extracted with dichloromethane (10 ml*3). The organic phases were combined, washed with saturated ammonium chloride (5 ml*2), washed with saturated sodium chloride (5 ml*2). The post-processed organic phase was dried over anhydrous sodium sulfate, filtered and spin-dried to remove dichloromethane, separated and purified with silica gel column chromatography (petroleum ether:ethyl acetate=0 to 40%) to obtain 384 mg yellow brown liquid, with a yield of 41% for two steps. ESI-MS m/z 233.1 $(M+H)^+$.

Synthesis of Compound QY-7-28:

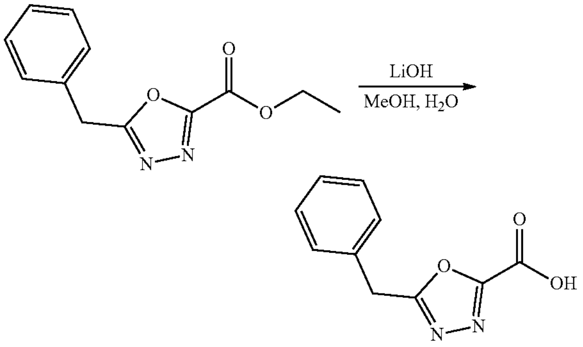

5-benzyl-1,3,4-oxadiazol-2-carboxylic acid (QY-7-28): QY-7-23 (56 mg, 0.24 mmol) was dissolved in 1 ml of methanol, and transferred to 8 ml pressure bottle. Lithium hydroxide monohydrate (10 mg, 0.24 mmol) was dissolved in 0.5 ml distilled water, and the resulting solution was added dropwise to the reaction solution under ice bath condition. After mixing and stirring evenly, the mixture was allowed to gradually return to room temperature. The reaction was monitored in real time by LC-MS and stopped after 1.5 h. All solvents in the reaction system were removed by rotary evaporation. After membrane filtration, the residue was separated and purified by C18 reversed-phase chromatographic column (water:acetonitrile=0 to 30%) to obtain 33 mg white solid with a yield of 67%. ESI-MS m/z 203.0 $(M+H)^-$.

Synthesis of Compound QY-7-32:

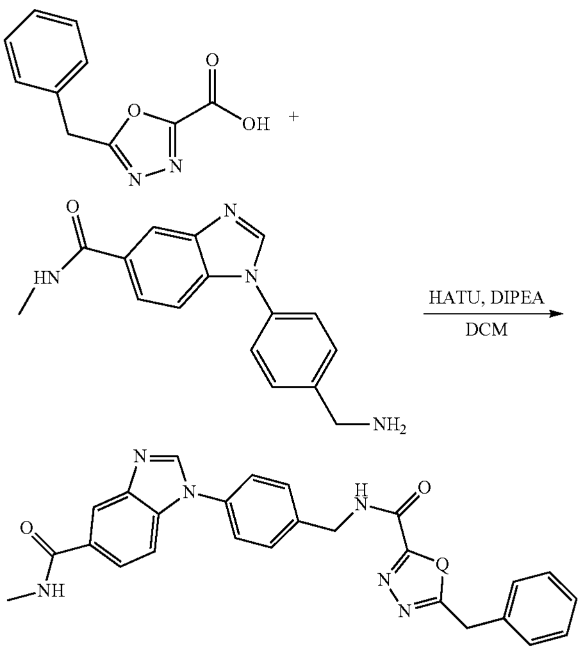

5-Benzyl-N-(4-(5-(methylcarbamoyl)-1H-benzo[d]imidazol-1-yl)benzyl)-1,3, 4-oxadiazol-2-carboxamide (QY-7-32): QY-7-28 (33 mg, 0.16 mmol) was dissolved in 2 ml dichloromethane contained in a 8 ml pressure bottle, followed by the addition of HATU (74 mg, 0.19 mmol). QY-6-6 (45 mg, 0.16 mmol) was added into the well-mixed reaction solution. N,N-diisopropylethylamine (52 mg, 0.40 mmol) was added dropwise at room temperature. The mixture was continued to react under stirring for 3.5 h at room temperature. The reaction was monitored in real time by LC-MS until the raw material was completely consumed. The reaction system was transferred to a separatory funnel, washed with 5 ml of distilled water, and extracted with dichloromethane (5 ml*3). The organic phases were combined, washed with saturated sodium chloride (5 ml*2), dried over anhydrous sodium sulfate, filtered and spin-dried to remove dichloromethane. The residue was filtered through filter membrane and then separated and purified with C18 reversed-phase chromatographic column (water:acetonitrile=0 to 80%) to obtain 15 mg white solid, yield 21%. ESI-MS n/z 467.0 $(M+H)^+$.

Method 8:

Synthesis of Compound QY-7-65:

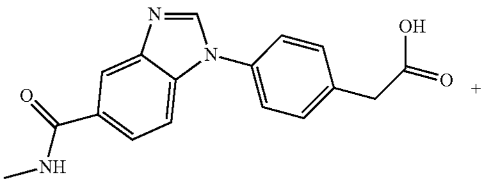

-continued

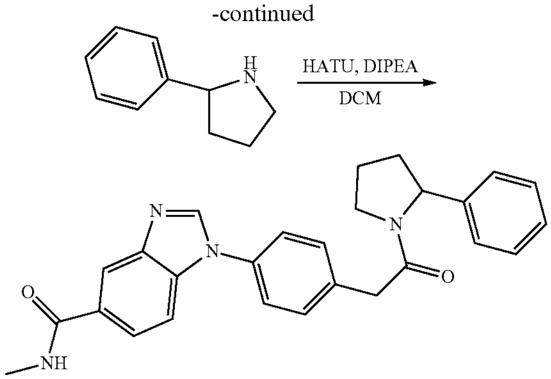

N-methyl-1-(4-(2-oxo-2-(2-phenylpyrrolidin-1-yl)ethyl)phenyl)-1H-benzo[d]imidazol-5-carboxamide (QY-7-65): QY-5-34 (49 mg, 0.16 mmol) was dissolved in 2 ml dichloromethane contained in an 8 ml pressure bottle, followed by the addition of HATU (69 mg, 0.18 mmol). QY-7-64 (20 mg, 0.14 mmol) was added into the well-mixed reaction solution. N,N-diisopropylethylamine (72 mg, 0.56 mmol) was added dropwise at room temperature and continued to react under stirring for 3 h. The reaction was monitored in real time by LC-MS. After the completion of the reaction, the reaction system was transferred to a separatory funnel, washed with 5 ml of distilled water, extracted with dichloromethane (5 ml*3). The organic phases were combined, washed with saturated sodium chloride (5 ml*2), dried over anhydrous sodium sulfate. Dichloromethane was removed by rotary evaporation. The residue was filtered by filter membrane and separated and purified by C18 reversed-phase chromatographic column (water:acetonitrile=0 to 80%) to obtain 19 mg yellow-brown solid with a yield of 31%. ESI-MS m/z 439.1 $(M+H)^+$.

Method 9:

Synthesis of Compound QY-9-15:

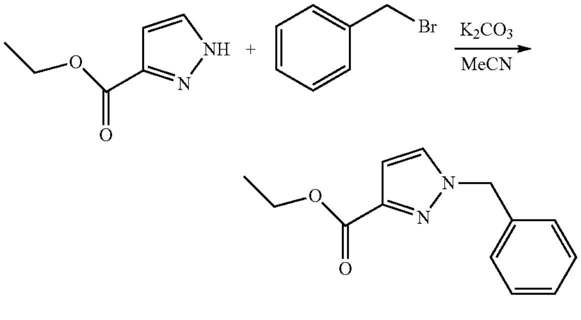

Ethyl 1-benzyl-1H-pyrazole-3-carboxylate (QY-9-15): in a 250 ml round bottom flask, 3-ethoxycarbonylpyrazole (6.0 g, 42.8 mmol) was dissolved in 90 ml acetonitrile. Potassium carbonate (17.8 g, 128.4 mmol) was added into the reaction solution, and benzyl bromide (8.8 g, 51.4 mmol) was added dropwise under vigorous stirring at room temperature. The reaction was monitored by LC-MS and continued to react under stirring for 8 h before the reaction was stopped. Inorganic salts was removed by suction filtration through celite, the organic solvent was removed by spin-drying. The residue was separated and purified by silica gel column chromatography (petroleum ether:ethyl acetate=0 to 50%) to afford 6.54 g white solid with a yield of 66%. ESI-MS m/z 231.1 $(M+H)^+$.

Synthesis of Compound QY-9-19:

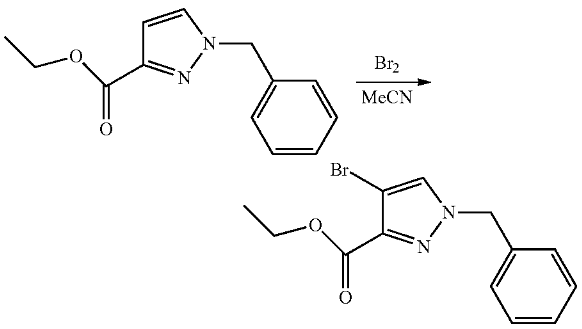

Ethyl 1-benzyl-4-bromo-1H-pyrazole-3-carboxylate (QY-9-19): in a 250 ml round bottom flask, QY-9-15 (6.4 g, 27.8 mmol) was dissolved in 100 ml acetonitrile. After well mixing, liquid bromine (6.7 g, 41.7 mmol) was added slowly dropwise into the reaction system at room temperature. The reaction was stopped after stirring overnight. The reaction solution was quench by slowly dropping 3M sodium thiosulfate solution and stirred for 15 min, evaporated to remove acetonitrile, extracted with ethyl acetate (20 ml*3). The organic phases were combined, washed with sodium thiosulfate solution (10 ml*1), washed with saturated brine solution (10 ml*1), dried over anhydrous sodium sulfate, spin-evaporated to remove ethyl acetate. The residue was separated and purified with silica gel column chromatography (petroleum ether:ethyl acetate=0 to 40%) to obtain 5.17 g white solid with a yield of 60%. ESI-MS m/z 309.0 $(M+H)^+$.

Synthesis of Compound QY-9-26:

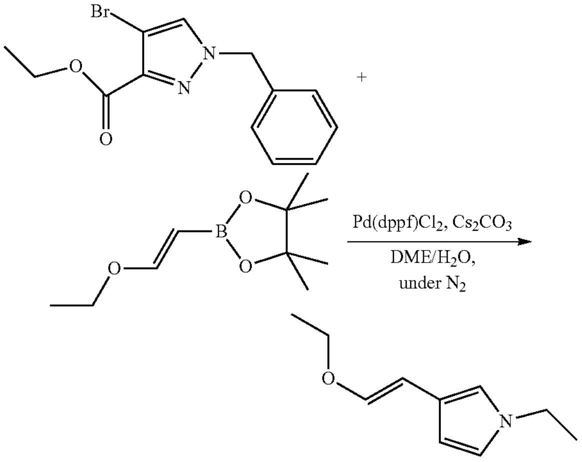

Ethyl (E)-1-benzyl-4-(2-ethoxyvinyl)-1H-pyrazole-3-carboxylate (QY-9-26): QY-9-19 (2.50 g, 8.1 mmol) was dissolved in 30 ml of ethylene glycol dimethyl ether and 5 ml of distilled water and added into a 150 ml sealed tube. $Pd(dppf)Cl_2$ (0.59 g, 0.81 mmol) and cesium carbonate (5.80 g, 17.8 mmol) was added. (E)-1-ethoxyvinyl-2-borate pinanol ester (3.20 g, 16.2 mmol) was dissolved in 10 ml of 1,2-dichloroethane, and then added dropwise into the vigorously stirred reaction solution. After nitrogen protection, the reaction solution was gradually heated to 90° C. and reacted overnight. After the Complete consumption of reactants, the reaction system was transferred to a separatory funnel, washed with 80 ml distilled water, and extracted with ethyl acetate (40 ml*3). The organic phases were combined, washed with saturated sodium chloride (15 ml*2), dried over anhydrous sodium sulfate, spin-evaporated to remove organic solvent. The residue was separated and purified by silica gel column chromatography (petroleum ether:ethyl acetate=0 to 60%) to afford 2.10 g white solid with a yield of 87%. ESI-MS n/z 301.1 (M+H)$^+$.

Synthesis of Compound QY-9-28:

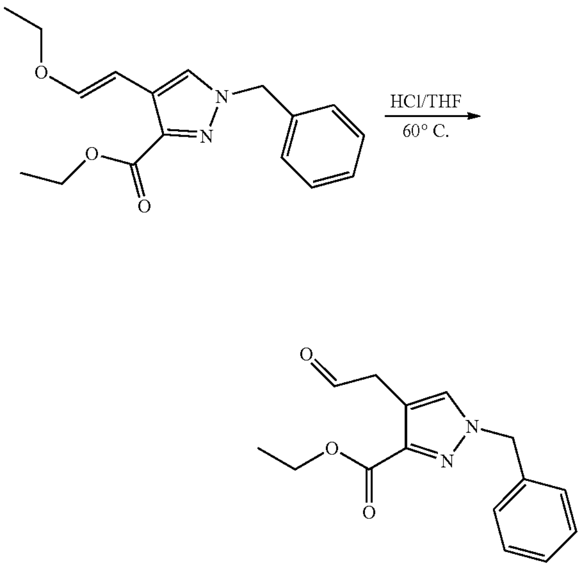

Ethyl 1-benzyl-4-(2-oxoethyl)-1H-pyrazole-3-carboxylate (QY-9-28): QY-9-26 (2.10 g, 7.0 mmol) was dissolved in 30 ml tetrahydrofuran and then added to a 100 ml round bottom flask. 6M hydrochloric acid aqueous solution was added slowly dropwise into the reaction solution under ice bath condition, after stirring for 2 h, another 15 ml of 6M hydrochloric acid aqueous solution was added. The reaction was monitored in real time by LC-MS. After the reactant was completely consumed, saturated sodium bicarbonate solution was added to adjust the PH to alkalescence, the reaction system was transferred to a separatory funnel, and extracted with ethyl acetate (20 ml*3). The organic phases were combined, washed with saturated sodium chloride (10 ml*2), dried over anhydrous sodium sulfate, spin-evaporated to remove ethyl acetate. The residue was separated and purified with silica gel column chromatography (petroleum ether:ethyl acetate=0 to −50%) to obtain 800 mg light yellow transparent liquid, yield 42%. ESI-MS n/z 273.1 (M+H)$^+$.

Synthesis of Compound QY-7-98:

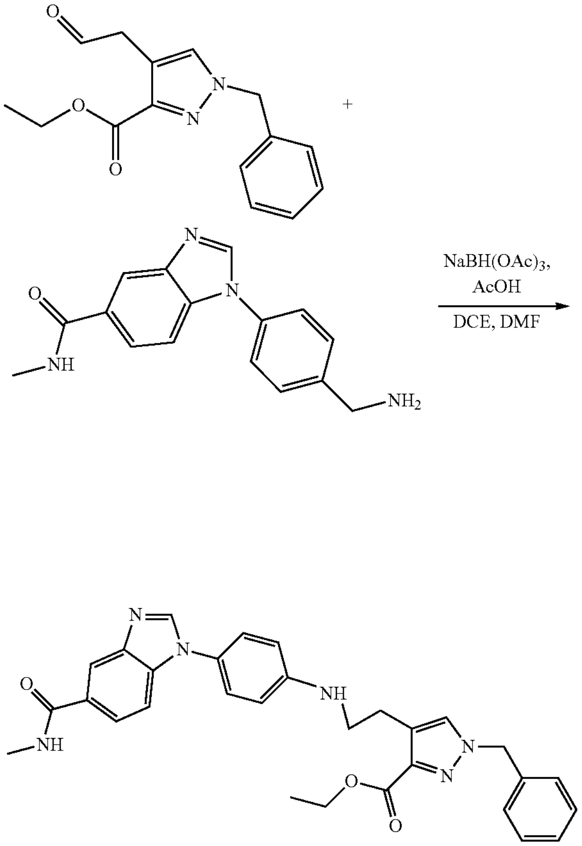

Ethyl 1-Benzyl-4-(2-(4-(5-(methylcarbamoyl)-1H-benzo[d]imidazol-1-yl)benzyl) amino)ethyl)-1H-pyrazol-3-carboxylate (QY-7-98): QY-9-28 (316 mg, 1.2 mmol) was well-mixed in 6 ml of 1,2-dichloroethane, and added into a 30 ml pressure bottle. QY-6-6 (270 mg, 0.96 mmol) and glacial acetic acid (279 mg, 4.6 mmol) were added and stirred for 20 min before the addition of sodium triacetoxyborohydride (492 mg, 2.3 mmol). The mixture was stirred overnight at room temperature and the raw materials were completely consumed. The reaction was quenched by adding distilled water dropwise under ice bath condition, filtered by filter membrane, and then separated and purified by C18 reversed-phase chromatographic column (water:acetonitrile=0 to 80%) to obtain 128 mg light yellow solid with a yield of 25%. ESI-MS m/z 537.1 (M+H)$^+$.

Synthesis of Compound QY-8-7:

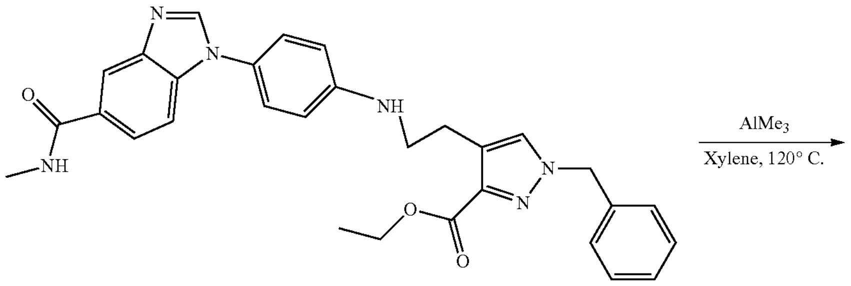

-continued

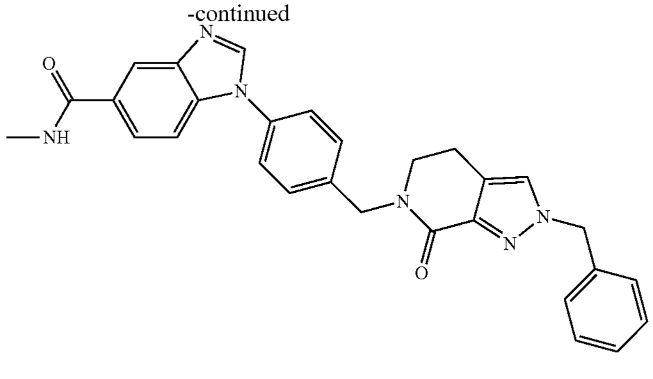

(4-((2-benzyl-7-oxo-2,4,5,7-tetrahydrotetrahydro-6H-pyrazolo[3,4-c]pyridin-6-yl) methyl)phenyl)-N-methyl-1H-benzo[d]imidazol-5-carboxamide (QY-8-7): QY-7-98 (64 mg, 0.12 mmol) was well mixed in 7 ml of xylene, transferred to a 15 ml pressure bottle and stirred. Trimethylaluminum (0.36 mmol) was added into the reaction solution dropwise at room temperature. After nitrogen protection, the mixture was gradually heated to 120° C., and the reaction was stopped after stirring overnight. The reaction was quenched with distilled water after slowly returning to room temperature. Roche salt solution was added before stirring for 30 min. The reaction system was diluted with 10 ml ethyl acetate, transferred to a separatory funnel, and extracted with ethyl acetate (10 ml*3). The organic phases were combined, washed with saturated sodium chloride (10 ml*2), dried over anhydrous sodium sulfate, filtered and spin-evaporated to remove organic solvent. After membrane filtration, the mixture was separated and purified by high performance liquid chromatography HPLC (water:acetonitrile=10 to 60%) to obtain 8 mg white solid with a yield of 14%. ESI-MS n/z 491.1 $(M+H)^+$.

Method 10:

Synthesis of Compound QY-8-15:

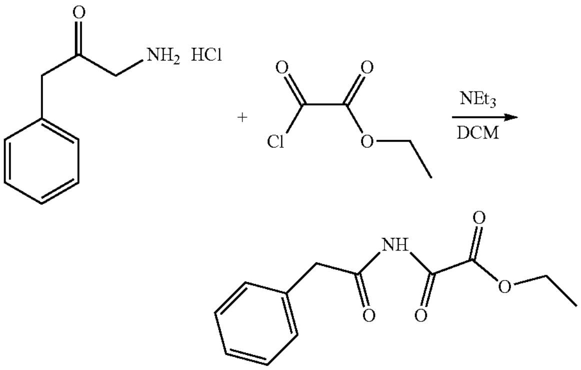

Ethyl 2-oxo-2-((2-oxo-3-phenylpropyl)amino)acetate (QY-8-15): in a 30 ml pressure bottle, 1-amino-3-phenylpropyl-2-ketone hydrochloride (500 mg, 2.7 mmol) was well-mixed in 15 ml of dichloromethane. Triethylamine (817 mg, 8.1 mmol) was added dropwise into the reaction system under ice bath condition. After stirring for 10 min, After stirring for 10 min, Monoethyl oxalyl chloride (734 mg, 5.4 mmol) was added slowly dropwise, and the mixture was allowed to return to room temperature and stirred overnight. The reaction was stopped after the raw material was completely consumed which is monitored by LC-MS. The reaction solution was transferred to a separatory funnel, washed with distilled water (10 ml*2), extracted with dichloromethane (15 ml*3). The organic phases were combined, and washed with saturated sodium chloride (5 ml*2). The post-treated organic phase was dried over anhydrous sodium sulfate, filtered and spin-dried to remove dichloromethane. The residue was separated and purified with silica gel column chromatography (petroleum ether:ethyl acetate=0 to 50%) to obtain 206 mg yellow brown solid with a yield of 31%. ESI-MS m/z 250.2 $(M+H)^+$.

Synthesis of Compound QY-8-25:

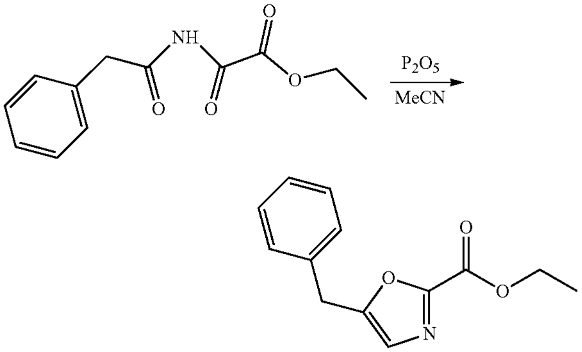

Ethyl 5-benzyloxazole-2-carboxylate (QY-8-25): in a 15 ml pressure bottle, QY-8-15 (206 mg, 0.83 mmol) was dissolved in 4 ml acetonitrile. Phosphorus pentoxide (587 mg, 4.1 mmol) was evenly mixed in 4 ml acetonitrile, and then the mixture was added dropwise to the reaction solution. The resulting mixture was vigorously stirred and slowly heated to 70° C. The reaction was monitored in real time by LC-MS. No peak of raw material was found after reacting for 3 h, and the reaction was stopped. After reducing to room temperature, and the reaction system was slowly dropped into saturated salt water at zero degree Celsius. The mixture was stirred for 5 min, and extracted with ethyl acetate (10 ml*3). The organic phases were combined, washed saturated $NaHCO_3$ (5 ml*1), washed with saturated salt water (5 ml*1), dried over inorganic salt desiccant, spin-evaporated to remove organic solvent. The residue was separated and purified by silica gel column chromatography (petroleum ether:ethyl acetate=0 to 30%) to obtain 90 mg light yellow transparent liquid with a yield of 47%. ESI-MS m/z 232.0 $(M+H)^+$.

Synthesis of Compound QY-8-28:

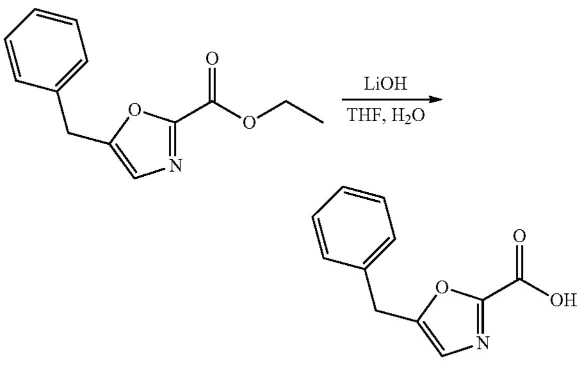

5-Benzyloxazole-2-carboxylic acid (QY-8-28): QY-8-25 (90 mg, 0.34 mmol) was dissolved in 2 ml of tetrahydrofuran, and transferred to an 8 ml pressure bottle. Lithium hydroxide monohydrate (33 mg, 0.78 mmol) was dissolved in 0.5 ml distilled water, and the resulting solution was added dropwise to the reaction solution under ice bath condition. After mixing and stirring evenly, the mixture was allowed to gradually return to room temperature. The reaction was monitored in real time by LC-MS, and stopped after 6 h. All solvents in the reaction system were removed by rotary evaporation, and the crude product can be directly subjected to the subsequent synthesis. ESI-MS n/z 202.1 $(M+H)^-$.

Synthesis of Compound QY-8-20:

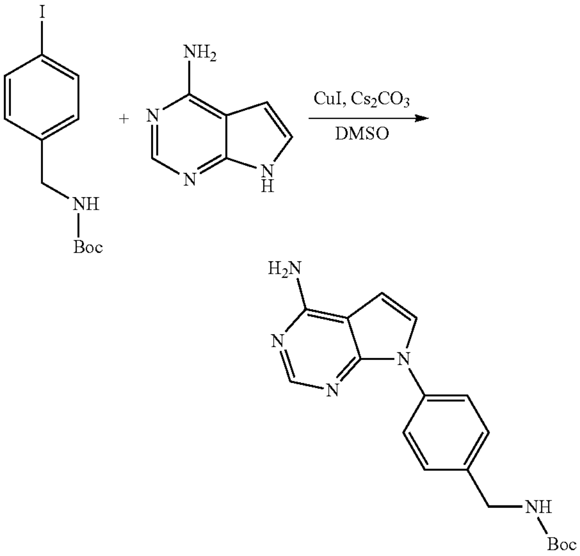

Tert-butyl (4-(4-amino-7H-pyrrolo[2,3-d]pyrimidin-7-yl) benzyl)carbamate (QY-8-20): To a 30 ml pressure bottle, N-Boc-4-iodobenzylamine (2.48 g, 7.5 mmol) was added. After dissolving with 15 ml dimethyl sulfoxide, 4-amino-7H-pyrrole(2,3-d)pyrimidine (1.0 g, 7.5 mmol), cuprous iodide (711 mg, 3.7 mmol), cesium carbonate (4.86 g, 14.9 mmol), and 4,7-dimethoxy-1,10phenanthroline (358 mg, 1.5 mmol) were added and then heated to 100° C. and reacted overnight under nitrogen protection. After the reactant was completely consumed, the reaction solution was filtered by filter membrane to remove solid insoluble matters, and separated and purified by the C18 reversed-phase chromatographic column (water:acetonitrile=0 to 80%) to obtain 1.94 g of light green oily liquid with a yield of 77%.

ESI-MS n/z 340.1 $(M+H)^+$.

Synthesis of Compound QY-8-22:

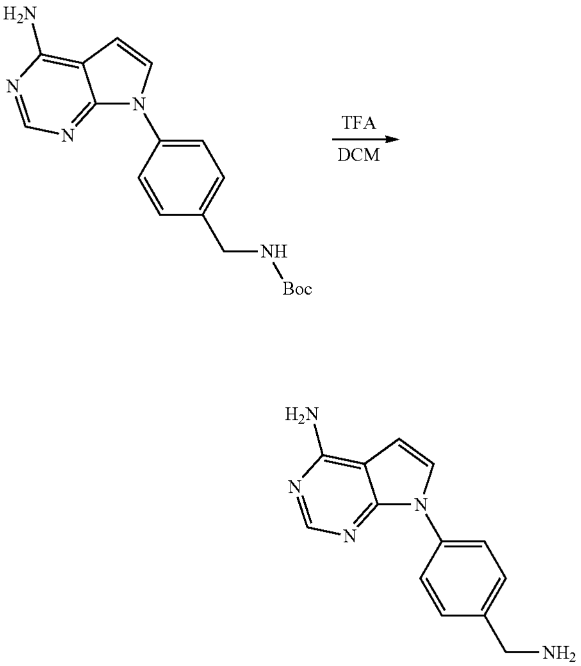

7-(4-(aminomethyl)phenyl)-7H-pyrrolo[2,3-d]pyrimidine-4-amine (QY-8-22): QY-8-20 (1.94 g, 5.7 mmol) was well-mixed in 20 ml dichloromethane, and transferred to a 100 ml round bottom flask. Trifluoroacetic acid 2.0 ml was added to the reaction solution at room temperature and mixed evenly. The reaction was monitored in real time by LC-MS and the raw materials are completely consumed after stirring overnight. The reaction solution was added with 20 ml dichloromethane each time, and spin-evaporated to remove the organic solvent mixture, repeating for 4-6 times. The crude product of this step can be directly subjected to subsequent synthesis without separation and purification. ESI-MS m/z 240.1 $(M+H)^+$.

Synthesis of Compound QY-8-30:

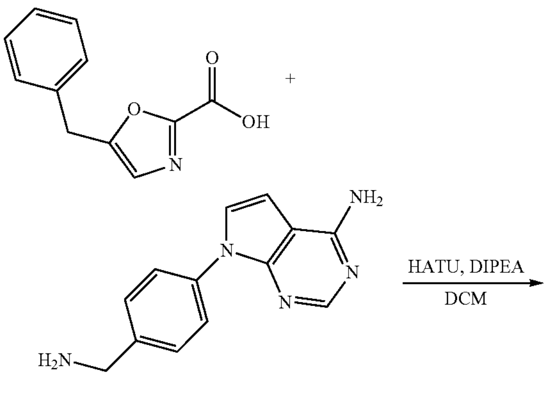

-continued

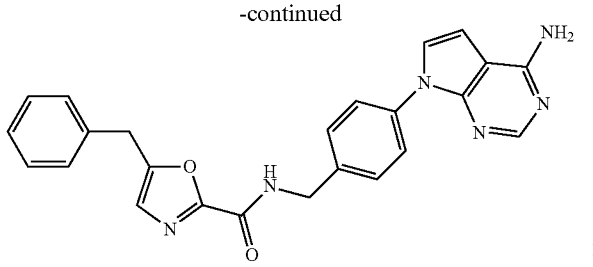

N-(4-(4-amino-7H-pyrrolo[2,3-d]pyrimidine-7-yl)benzyl)-5-benzyloxazol-2-carboxamide (QY-8-30): QY-8-28 (0.39 mmol) was dissolved in 4 ml dichloromethane contained in an 8 ml pressure bottle, followed by the addition of HATU (177 mg, 0.47 mmol). QY-8-22 (220 mg, 0.62 mmol) was added into well-mixed reaction solution. N,N-diisopropylethylamine (200 mg, 1.6 mmol) was added dropwise at room temperature and continued to react under stirring for 6 h. The reaction was monitored in real time by LC-MS. After the reaction was completed, the reaction system was transferred to a separatory funnel, washed with 10 ml of distilled water, and extracted with dichloromethane (15 ml*2). The organic phases were combined, washed with saturated sodium chloride (5 ml*2), dried over anhydrous sodium sulfate, spin-evaporated to remove dichloromethane. The residue was filtered through filter membrane, and separated and purified by C18 reversed-phase chromatographic column (water:acetonitrile=0 to 80%) to obtain 38 mg yellow brown oily liquid with a yield of 23%. ESI-MS m/z 425.2 $(M+H)^+$.

Method 11:

Synthesis of Compound QY-8-33:

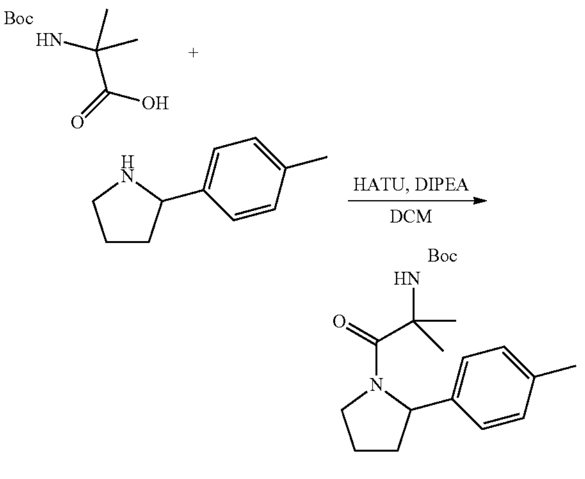

Tert-butyl (2-methyl-1-oxo-1-(2-(p-tolyl)pyrrolidin-1-yl)prop-2-yl)carbamate (QY-8-33): N-Boc-2-methylalanine (320 mg, 1.6 mmol) was dissolved in 8 ml dichloromethane contained in 15 ml pressure bottle, followed by the addition of HATU (652 mg, 1.7 mmol). QY-7-64 (230 mg, 1.4 mmol) was added into the well-mixed reaction solution. N,N-diisopropylethylamine (810 mg, 6.3 mmol) was added dropwise at room temperature and continued to stir at room temperature. The reaction was monitored in real time by LC-MS. The raw material was completely consumed after 5 h. The reaction system was transferred to a separatory funnel, washed with distilled water (10 ml*3) and extracted with dichloromethane (15 ml*3). The organic phases were combined, washed with saturated sodium chloride (10 ml*2), dried over anhydrous sodium sulfate, spin-evaporated to remove dichloromethane. The residue was separated and purified with silica gel column chromatography (petroleum ether:ethyl acetate=0 to 70%) to obtain 202 mg light yellow solid with a yield of 41%. ESI-MS m/z 247.1 $(M+H)^+$.

Synthesis of Compound QY-8-39:

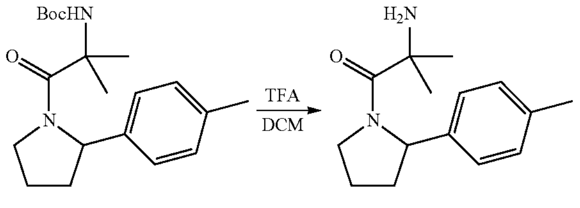 [SMILES: Cc1ccc(C2CCCN2C(=O)C(C)(C)NC(=O)OC(C)(C)C)cc1 ; Cc1ccc(C2CCCN2C(=O)C(C)(C)N)cc1]

3-Amino-2-methyl-1-(2-(p-tolyl)pyrrolidine-1-yl)prop-1-one (QY-8-39): QY-8-33 (202 mg, 0.58 mmol) was dissolved in 4 ml dichloromethane and transferred to a 15 ml pressure bottle. 0.4 ml trifluoroacetic was added dropwise into the reaction solution at room temperature and mixed evenly. The reaction was monitored in real time by LC-MS and the raw materials were completely consumed after 3 h. The reaction system was transferred to a 100 ml round bottom flask, added with 10 ml dichloromethane each time, spin-evaporated to remove the organic solvent mixture, repeating for 3-4 times. The crude product can be directly used in subsequent synthesis without separation and purification. ESI-MS m/z 247.1 $(M+H)^+$.

Synthesis of Compound QY-8-42:

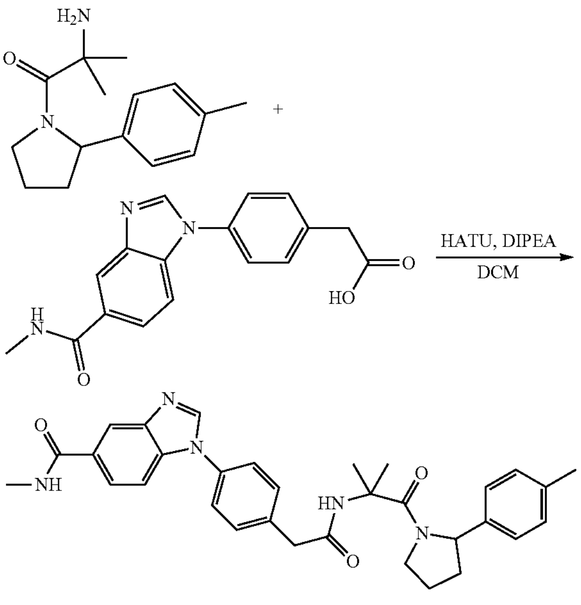

N-methyl-1-(4-(2-(2-methyl-1-oxo-1-(2-(p-tolyl)pyrrolidin-1-yl)prop-2-yl)amino)-2-oxoethyl)phen yl)-1H-benzo[d]imidazol-5-carboxamide (QY-8-42): in an 8 ml pressure bottle, QY-8-39 (0.29 mmol) was dissolved in 3 ml dichloromethane, and HATU (221 mg, 0.58 mmol) and QY-5-34 (90 mg, 0.29 mmol) were added. N,N-diisopropylethylamine (150 mg, 1.2 mmol) was added dropwise at room temperature and the mixture was continued to react under stirring for 5 h. The reaction was monitored in real time by LC-MS. After the reactants were completely consumed, the reaction solution was diluted with 5 ml of dichloromethane, transferred to a separatory funnel, washed with 10 ml distilled water, and extracted with dichloromethane (10 ml*3). The organic phases were combined, washed with saturated sodium chloride (10 ml*2), dried over anhydrous sodium sulfate, filtered and spin-evaporated to remove dichloromethane. After filter membrane filtration, the mixture was separated and purified by C18 reversed-phase chromatography column (water:acetonitrile=0 to 80%) to obtain 48 mg of yellow-brown oily liquid with a yield of 31%. ESI-MS m/z 538.1 $(M+H)^+$.

Method 12:

Synthesis of Compound ZSQ-13-19:

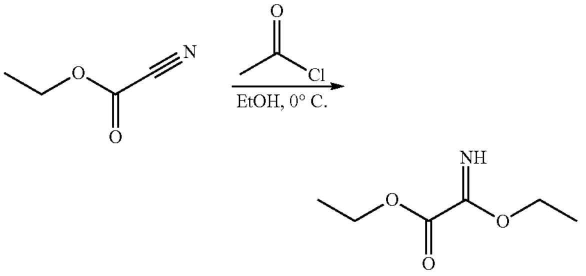

Ethyl 2-ethoxy-2-iminoacetate (ZSQ-13-19): To a 250 ml round bottom flask, ethyl cyanoformate (9.9 ml, 100 mmol) was added. After mixing and dissolving with ethanol (23.0 ml, 400 mmol), the reaction system was cooled to 0° C. Acetyl chloride (14.2 ml, 200 mmol) was added dropwise into the reaction solution. After addition, the reaction solution was kept at 0° C. and continued to stir overnight. After the reaction was completed, white bulk solid was obtained. The crude product obtained by suction filtration can be directly subjected to the next reaction without separation and purification. ESI-MS n/z 146.0 $(M+H)^+$.

Synthesis of compound ZSQ-13-20:

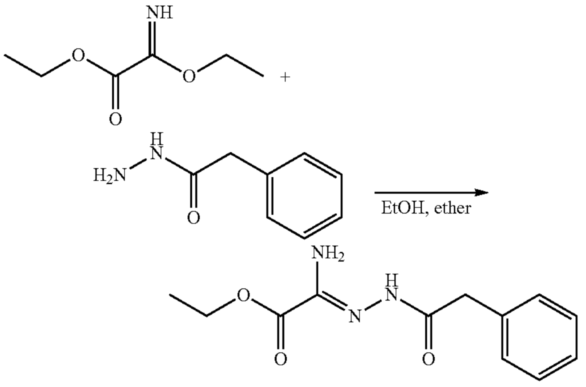

Ethyl (Z)-2-amino-2-(2-(2-phenylacetyl)hydrazono)acetate (ZSQ-13-20) To a 250 round bottom flask, ZSQ-13-19 (7.26 g, 50 mmol) was added. 50 ml of ethanol was added and the mixture was stirred and dissolved evenly, followed by the addition of phenylacetylhydrazine (7.51 g, 50 mmol) and 40 ml of ether was added under continuous stirring. The reaction was stopped after stirring overnight at room temperature. The crude product obtained by suction filtration, which was directly subjected to the next reaction without separation and purification. ESI-MS n/z 250.1 $(M+H)^+$.

Synthesis of Compound QY-8-49:

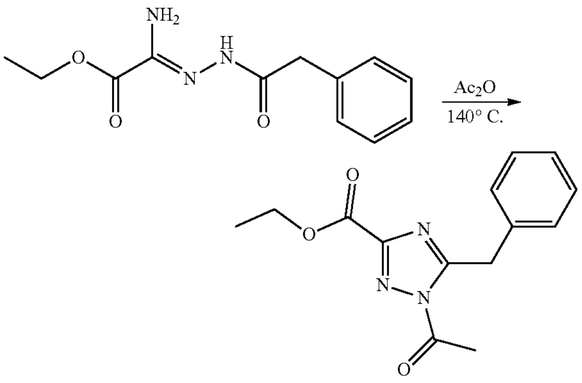

Ethyl 1-acetyl-5-benzyl-1H-1,2,4-triazol-3-carboxylate (QY-8-49): compound ZSQ (1.0 g, 4.0 mmol) was dissolved in 5 ml acetic anhydride. After being well mixed in a 15 ml pressure bottle, the mixture was slowly heated to 140° C. and stirred vigorously for 3 h. The reaction was monitored in real time by LC-MS until the reactants were completely consumed. After reducing to room temperature, the reaction system was quenched by slowly adding saturated sodium bicarbonate aqueous solution, transferred to a separatory funnel after stirring for 15 min, and extracted with ethyl acetate (20 ml*3). The organic phases were combined, washed with saturated sodium chloride (10 ml*2), dried over anhydrous sodium sulfate, filtered and evaporated to remove ethyl acetate. The residue was separated and purified by silica gel column chromatography (petroleum ether:ethyl acetate=0 to 40%) to afford 280 mg of pale yellow transparent oily liquid, with a yield of 26%. ESI-MS m/z 274.1 $(M+H)^+$.

Synthesis of Compound QY-8-52:

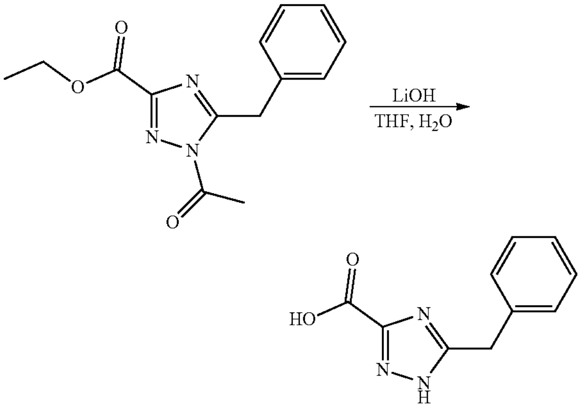

5-benzyl-1H-1,2,4-triazol-3-carboxylic acid (QY-8-52): QY-8-52 (280 mg, 1.0 mmol) was dissolved in 4 ml tetrahydrofuran, and transferred to an 8 ml pressure bottle. Lithium hydroxide monohydrate (147 mg, 3.5 mmol) was dissolved in 1 ml distilled water, and the resulting solution was added into the reaction solution dropwise under ice bath condition. The mixture was mixed and stirred evenly, then allowed to gradually return to room temperature. After stirring overnight, LC-MS monitoring showed that the raw material was complete consumed. All solvents in the reaction system were removed by rotary evaporation, and the crude product can be directly subjected to subsequent synthesis without purification. ESI-MS m/z 203.9 $(M+H)^+$.

Synthesis of Compound QY-8-60:

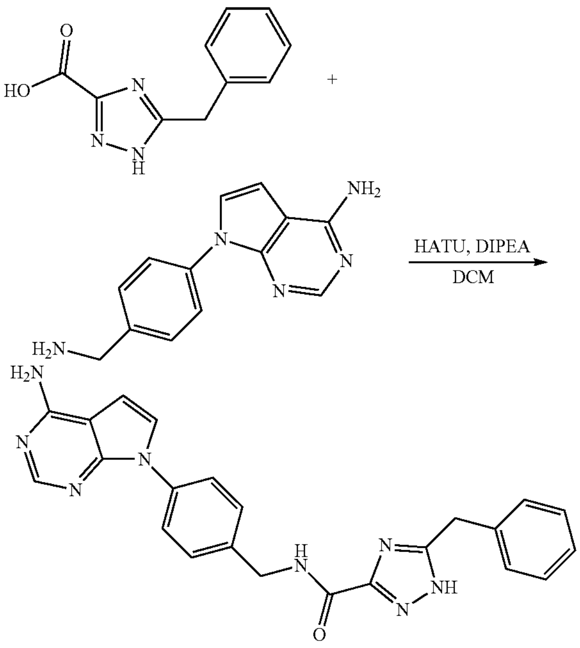

N-(4-(4-amino-7H-pyrrolo[2,3-d]pyrimidine-7-yl)benzyl)-5-benzyl-1H-1,2,4-triazol-3-carboxamide (QY-8-60): in an 8 ml pressure bottle, QY-8-52 (0.40 mmol) was dissolved in 3 ml dichloromethane, HATU (182 mg, 0.48 mmol) and QY-8-22 (155 mg, 0.44 mmol) were added into the reaction system. N,N-diisopropylethylamine (258 mg, 2.0 mmol) was added dropwise slowly at room temperature, and stirred for another 4 h. The reaction was monitored by LC-MS until the reactants were completely consumed, and then stopped. The reaction solution was diluted by adding 5 ml of dichloromethane, transferred to a separatory funnel, washed with 10 ml of distilled water, and extracted with dichloromethane (10 ml*3). The organic phases were combined, washed with saturated sodium chloride (10 ml*2), dried over anhydrous sodium sulfate, filtered and evaporated to remove dichloromethane, The residue was filtered through filter membrane, and then separated and purified by C18 reversed-phase chromatography column (water:acetonitrile=0 to 80%) to get 66 mg of yellowish brown liquid with a yield of 39%. ESI-MS m/z 425.2 $(M+H)^+$.

Method 13:

Synthesis of Compound QY-8-50:

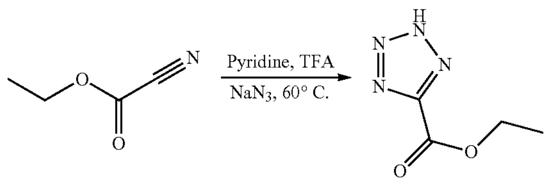

Ethyl 2H-tetrazol-5-carboxylate (QY-8-50): compound ethyl cyanoformate (1.0 g, 10.0 mmol) was dissolved in 12 ml of pyridine, well-mixed in a 75 ml sealed tube. Trifluoroacetic acid was added dropwise slowly at room temperature. After stirring for 10 min, the reaction solution was added with sodium azide (700 mg, 10.8 mmol) and then slowly heated to 60° C. The reaction was stopped after 24 h. Sodium azide was removed by suction filtration through celite, the celite was flushed with ethyl acetate (10 ml*3), to obtain the organic phase, which was evaporated to remove. The resulting crude product was directly subjected to the next step without purification. ESI-MS m/z 143.0 $(M+H)^+$.

Synthesis of Compound QY-8-55:

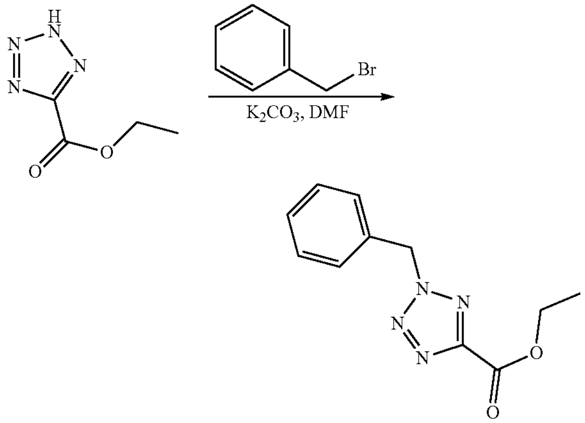

Ethyl 2-benzyl-2H-tetrazol-5-carboxylate (QY-8-55): QY-8-50 (10.0 mmol) was well mixed in 10 ml of N,N-dimethylformamide. Potassium carbonate (4.2 g, 30.0 mmol) was added to reaction solution and benzyl bromide (1.7 g, 10.0 mmol) was added to the reaction system under vigorous stirring at room temperature. The reaction was stopped after stirring overnight. The reaction system was filtered through celite to remove potassium carbonate, evaporated to dry to remove the organic solvent. The residue was filtered through filter membrane, separated and purified through C18 reversed-phase column (water:acetonitrile=0 to 100%) to obtain 550 mg yellow-brown oily liquid, with a yield of 24% for 2 steps. ESI-MS n/z 233.1 $(M+H)^+$.

Synthesis of Compound-QY-8-56:

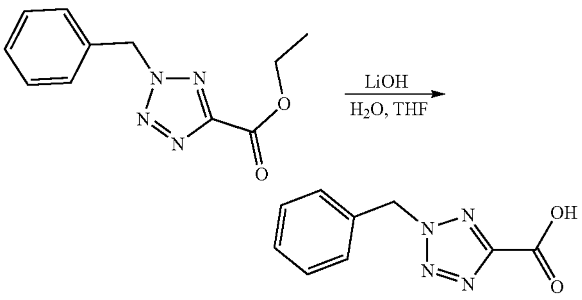

2-benzyl-2H-tetrazol-5-carboxylic acid (QY-8-56): QY-8-55 (100 mg, 0.43 mmol) was dissolved in 3 ml of tetrahydrofuran, and transferred to 8 ml pressure bottle. Lithium hydroxide monohydrate (27 mg, 0.65 mmol) was dissolved in 0.8 ml of distilled water, and then added dropwise into the reaction solution at room temperature. Reaction process was monitored by LC-MS in real-time. The raw material was completely consumed after 2 h. All solvents in the reaction system were removed by rotary evaporation, and the crude product can be directly subjected to the next reaction without purification. ESI-MS m/z 205.1 $(M+H)^+$.

Synthesis of Compound QY-8-58:

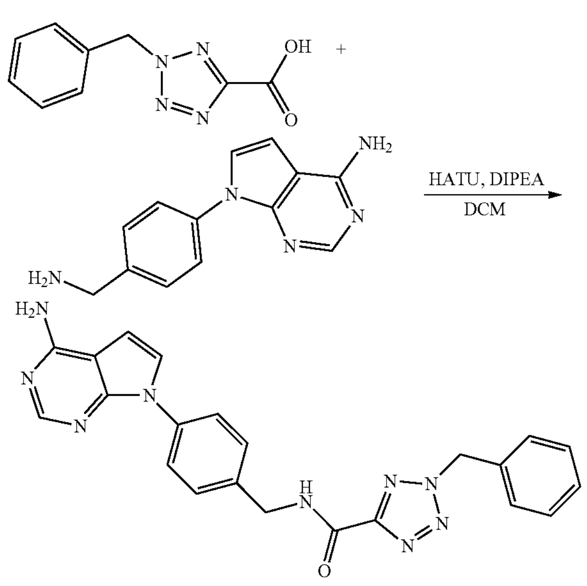

N-(4-(4-amino-7H-pyrrolo[2,3-d]pyrimidin-7-yl)benzyl)-2-benzyl-2H-tetrazol-5-carboxamide (QY-8-58): in an 8 ml pressure bottle, QY-8-56 (0.40 mmol) was dissolved in 3 ml dichloromethane, HATU (182 mg, 0.48 mmol) and QY-8-22 (141 mg, 0.40 mmol) were added. N,N-diisopropylethylamine (259 mg, 2.0 mmol) was added dropwise at room temperature, and continued to react under stirring. The reaction was monitored by LC-MS in real time and the reactants were completely consumed after 4 h. The reaction solution was diluted with 5 ml of dichloromethane, transferred to a separatory funnel, washed with 10 ml of distilled water, and extracted with dichloromethane (10 ml*3). The organic phases were combined, washed with saturated sodium chloride (10 ml*2), dried over anhydrous sodium sulfate, filtered and spin-evaporated to remove dichloromethane. The residue was filtered through filter membrane, separated and purified by C18 reversed-phase chromatographic column (water:acetonitrile=0 to 60%) to get 140 mg yellowish brown solid with a yield of 82%. ESI-MS n/z 426.1 $(M+H)^+$.

Method 14:

Synthesis of Compound QY-8-29:

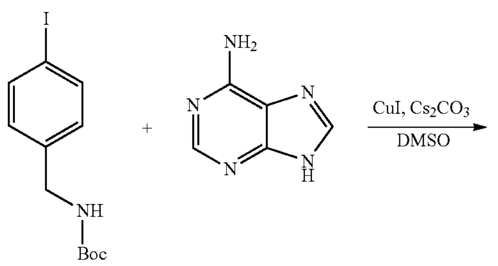

-continued

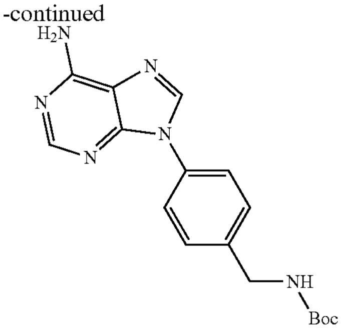

Tert-butyl (4-(6-amino-9H-purin-9-yl)benzyl)carbamate (QY-8-29): N-Boc-4-iodobenzylamine (330 mg, 1.0 mmol) was added into a 15 ml pressure bottle, dissolved with 3 ml dimethyl sulfoxide, adenine (135 mg, 1.0 mmol), cuprous iodide (95 mg, 0.5 mmol), cesium carbonate (652 mg, 2.0 mmol) and 4,7-dimethoxy-1,10 phenanthroline (48 mg, 0.2 mmol) were added. The reaction solution was heated to 100° C. and reacted overnight under nitrogen protection. After the reactant was completely consumed, the reaction solution was filtered by filter membrane to remove the solid insoluble matters, and separated and purified by the C18 reversed-phase chromatographic column (water:acetonitrile=0 to 80%) to obtain 287 mg green-white solid with a yield of 84%. ESI-MS n/z 341.2 $(M+H)^+$.

Synthesis of Compound QY-8-36:

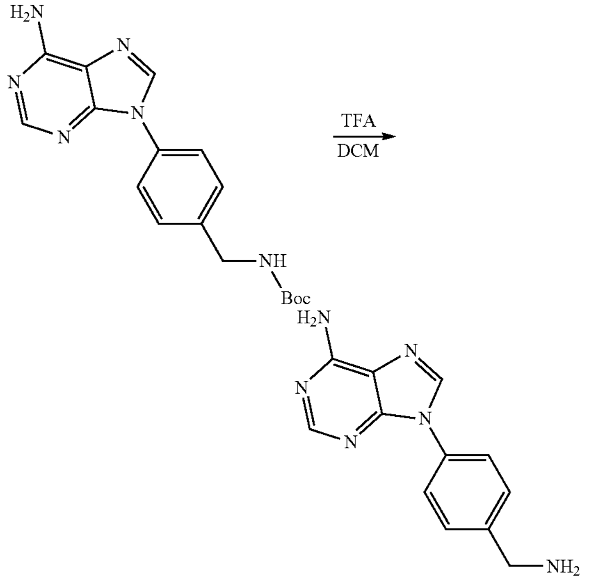

9-(4-(aminomethyl)phenyl)-9H-purin-6 amine (QY-8-36): QY-8-29 (286 g, 0.84 mmol) was well mixed in 3 ml of dichloromethane in a 15 ml pressure bottle. Trifluoroacetic acid 0.5 ml was added dropwise into the reaction solution at room temperature, and mixed and stirred evenly. The reaction was monitored in real time by LC-MS and the raw materials were completely consumed after stirring overnight. The reaction solution was added with 20 ml dichloromethane each time, and evaporated to remove the organic solvent mixture, repeating for 3-4 times. The crude product of this step can be directly subjected to the subsequent synthesis without separation and purification. ESI-MS m/z 241.2 $(M+H)^+$.

Synthesis of Compound QY-8-43:

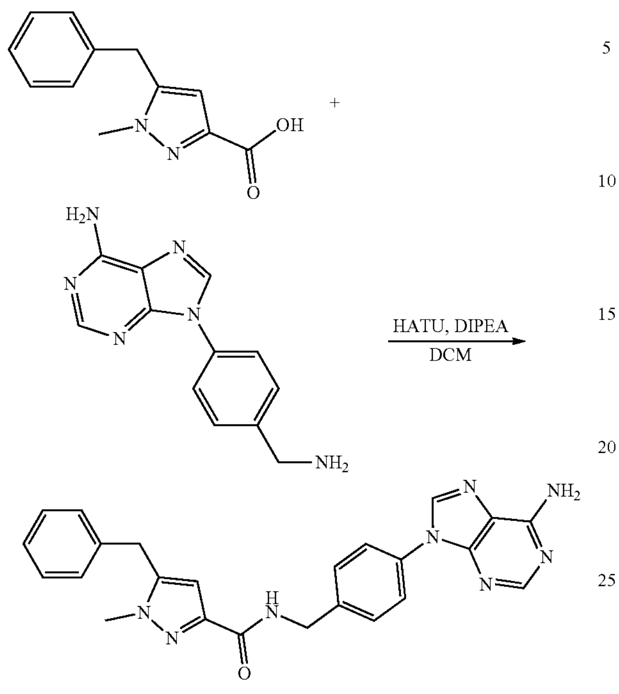

N-(4-(6-amino-9H-purin-9-yl)benzyl)-5-benzyl-1-methyl-1H-pyrazole-3-carboxamide (QY-8-43): QY-6-103B (150 mg, 0.69 mmol) was dissolved in 8 ml dichloromethane in an 8 ml pressure bottle, and HATU (316 mg, 0.83 mmol) was added. QY-8-36 (166 mg, 0.69 mmol) was added to well-mixed reaction solution. N,N-diisopropylethylamine (313 mg, 2.43 mmol) was added dropwise into the reaction solution at room temperature, and continued to react under stirring for 4 h. The reaction was monitored in real time by LC-MS. After the raw materials were completely consumed, the reaction solution was transferred to a separatory funnel, washed with 10 ml distilled water, and extracted with dichloromethane extraction (15 ml*3). The organic phases were combined, washed with saturated sodium chloride (10 ml*2), dried over anhydrous sodium sulfate, filtered and spin-evaporated to remove dichloromethane, separated and purified with silica gel column chromatography (dichloromethane:methanol=0 to 25%) to obtain 142 mg white solid with a yield of 47%. ESI-MS m/z 439.1 $(M+H)^+$.

Method 15:

Synthesis of Compound Y-9-69:

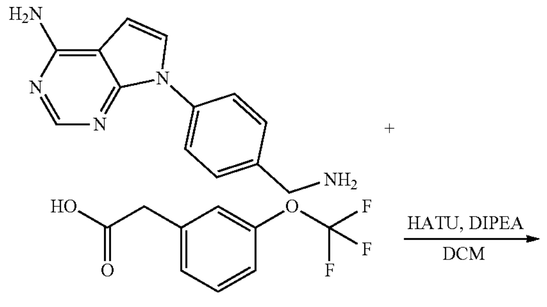

-continued

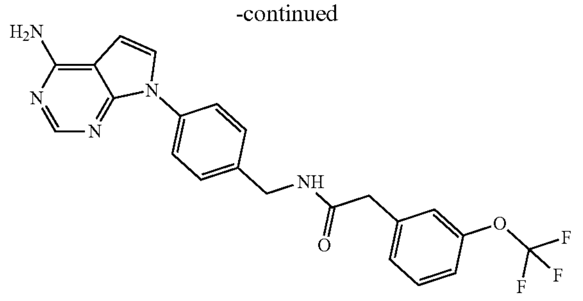

O—N-(4-(4-amino-7H-pyrrolo[2,3-d]pyrimidine-7-yl) benzyl)-2-(3-(trifluoromethoxy) phenyl)acetamide (QY-9-69): QY-8-22 (59 mg, 0.25 mmol) was dissolved in 3 ml of dichloromethane in an 8 ml pressure bottle, HATU (125 mg, 0.33 mmol) was added. 3-Trifluoromethoxyphenylacetic acid (60 mg, 0.25 mmol) was added to the well mixed reaction solution. N,N-diisopropylethylamine (129 mg, 1.0 mmol) was added dropwise at room temperature, and the reaction was continued to react under stirring for 3.5 h. The reaction was monitored in real time by LC-MS. After the reactants were completely consumed, the reaction solution was transferred to a separatory funnel, washed with 5 ml of distilled water, and extracted with dichloromethane (5 ml*3). The organic phases were combined, washed with saturated sodium chloride (5 ml*2), dried over anhydrous sodium sulfate, filtered and spin-evaporated to remove dichloromethane, the residue was separated and purified by silica gel column chromatography (dichloromethane:methanol=0 to 30%) to obtain 88 mg of light yellow oily liquid with a yield of 80.0%. ESI-MS n/z 442.0 $(M+H)^+$.

Method 16:

Synthesis of Compound QY-9-10:

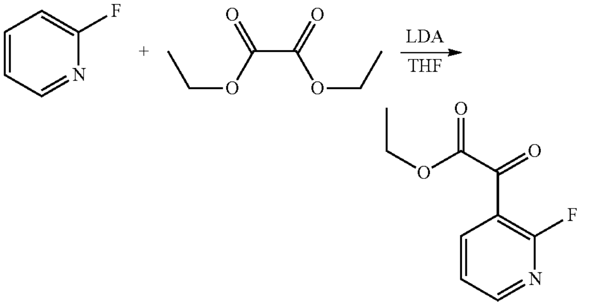

Ethyl 2-(2-fluoropyridine-3-yl)-2-oxoacetate (QY-9-10): 2-fluoropyridine (5.0 g, 51.5 mmol) was added into a 250 ml round bottom flask, and dissolved and mixed evenly after adding 120 ml tetrahydrofuran. After nitrogen replacement protection, the reaction system was transferred to −78° C. Lithium diisopropylamide (30.4 ml, 61.8 mmol) was slowly added dropwise into the reaction solution. After addition, diethyl oxalate (9.0 g, 61.8 mmol) was added. The reaction solution was allowed to gradually return to room temperature and continued to react under stirring for 2 h. The reaction was monitored in real time by LC-MS until the reactants were completely consumed. The reaction was quenched by adding saturated ammonium chloride, the reaction system was transferred to a separatory funnel, and extracted with ethyl acetate (20 ml*3). The organic phases were combined, washed with saturated sodium chloride (15 ml*2), dried over anhydrous sodium sulfate, filtered and spin evaporated to remove ethyl acetate. The residue was separated and purified with silica gel column chromatography (petroleum ether:ethyl acetate=0 to 40%) to obtain 3.54 g of bright yellow oily liquid with a yield of 34.9%. ESI-MS m/z 198.0 $(M+H)^+$.

Synthesis of Compound QY-9-18:

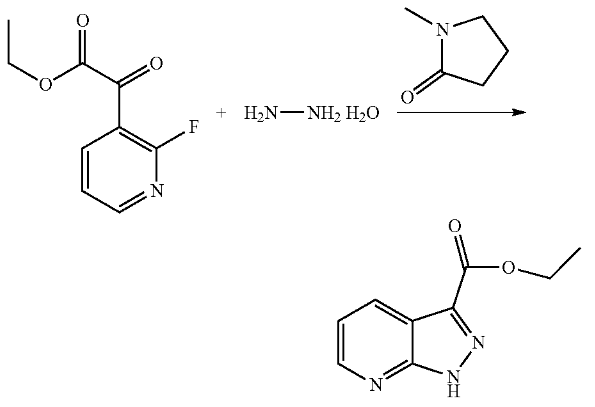

Ethyl 1H-pyrazolo[3,4-b]pyridin-3-carboxylate (QY-9-18): QY-9-10 (2.87 g, 14.6 mmol) was added into a 100 ml round bottom flask and dissolved and mixed evenly after adding in 25 ml N-methylpyrrolidone. Hydrazine hydrate (0.87 g, 17.5 mmol) was added slowly dropwise to the reaction solution under ice bath condition, and stirred at 0° C. for 20 min. After gradually return to room temperature, the mixture was heated to 80° C. and stirred overnight. LC-MS monitoring showed that the reactants were completely consumed. The reaction was add with distilled water, filtered through filter membrane, separated and purified by C18 reversed-phase chromatographic column (water:acetonitrile=0 to 80%) to obtain 1.37 g yellow-red solid with a yield of 49%. ESI-MS n/z 192.0 $(M+H)^+$.

Synthesis of Compound QY-9-21:

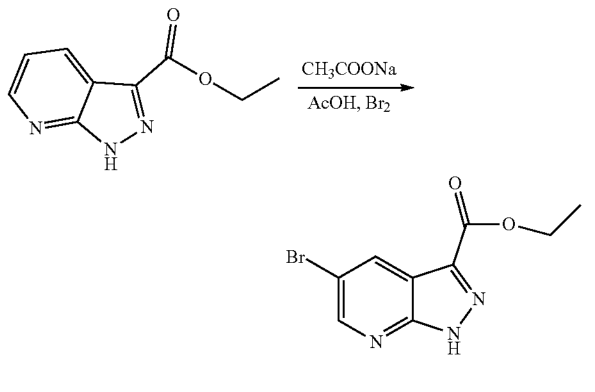

Ethyl 5-bromo-1H-pyrazolo[3,4-b]pyridin-3-carboxylate (QY-9-21): QY-9-18 (1.37 g, 7.17 mmol) and sodium acetate (3.53 g, 43.0 mmol) were well-mixed in 25 ml glacial acetic acid and added into a 100 ml round-bottom flask and stirred evenly. The mixture was added dropwise with liquid bromine (3.43 g, 21.5 mmol) at room temperature, and stirred for 8 h after being heated to 100° C. LC-MS monitoring showed the reactants were completely consumed, after gradually returning to room temperature, the reaction was stopped. The reaction was quenched with 3M sodium thiosulfate solution, transferred to a separatory funnel, and extracted with ethyl acetate (15 ml*3). The organic phases were combined, washed with distilled water (10 ml*2), washed with saturated salt water (10 ml*2), dried over anhydrous sodium sulfate, filtered and spin dried to remove ethyl acetate. The residue was separated and purified by silica gel column chromatography (petroleum ether:ethyl acetate=0 to 25%) to obtain 0.26 g white solid with a yield of 13.4%. ESI-MS m/z 269.9 $(M+H)^+$.

Synthesis of Compound QY-9-29:

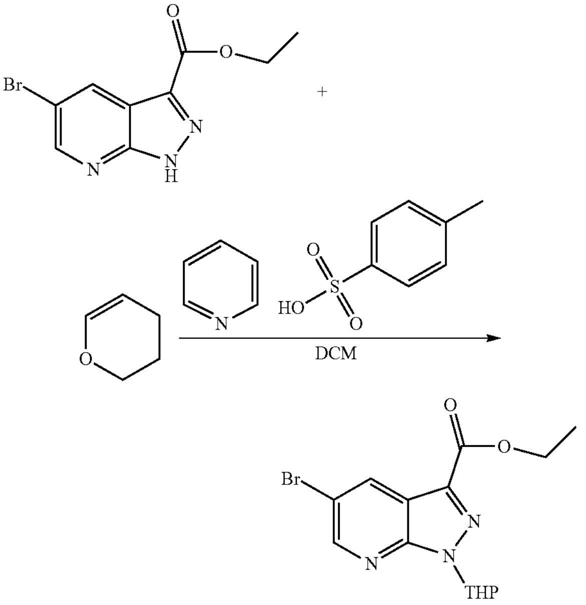

Ethyl 5-Bromo-1-(tetrahydro-2H-pyran-2-yl)-1H-pyrazolo[3,4-b]pyridin-3-carboxylate (QY-9-29): QY-9-21 (255 mg, 0.94 mmol) was dissolved in 7 ml dichloromethane and transferred to a 15 ml pressure bottle. 3,4-Dihydro-2H-pyran (159 mg, 1.89 mmol) was added. Pyridine p-toluenesulfonate (48 mg, 0.19 mmol) was added to stirred evenly reaction solution The mixture was heated to 60° C. and continued to stir for 5 h. The reaction was monitored in real time by LC-MS until the reactants were completely consumed. The reaction was directly spin dried to remove dichloromethane, separated and purified by silica gel column chromatography (petroleum ether:ethyl acetate=0 to 15%) to obtain 269 mg white solid with a yield of 80.8%. ESI-MS m/z 354.0 $(M+H)^+$.

Synthesis of Compound QY-9-51:

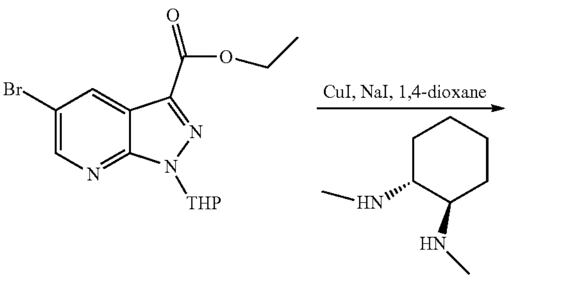

-continued

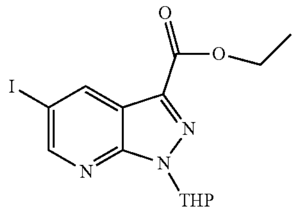

Ethyl 5-Iodine-1-(tetrahydro-2H-pyran-2-yl)-1H-pyrazolo[3,4-b]pyridine-3-carboxylate (QY-9-51): QY-9-29 (390 mg, 1.10 mmol) was added to a 15 ml pressure bottle, dissolved with 5 ml dimethyl sulfoxide, then sodium iodide (436 mg, 2.91 mmol), cuprous iodide (34 mg, 0.18 mmol), and (1S,2S)-(+)-N,N'-dimethyl-1,2-cyclohexanediamine (38 mg, 0.27 mmol) were added. The reaction solution was heated to 130° C. and reacted for 3 h under microwave. LC-MS monitored the complete consumption of reaction materials. After membrane filtration to remove solid insoluble matters, the reaction was separated and purified by C18 reversed-phase chromatographic column (water:acetonitrile=5 to 100%) to obtain 359 mg yellow brown solid with a yield of 81.3%. ESI-MS m/z 402.0 (M+H)$^+$.

Synthesis of Compound QY-9-57:

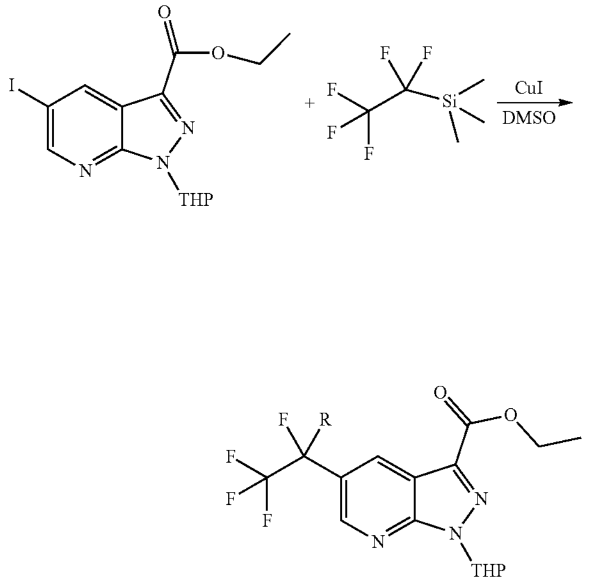

Ethyl 5-(perfluoroethyl)-1-(tetrahydro-2H-pyran-2-yl)-1H-pyrazolo[3,4-b]pyridine-3-carboxylate (QY-9-57): QY-9-51 (316 mg, 0.79 mmol) was added into a 15 ml pressure bottle, dissolved with 4 ml dimethyl sulfoxide, (pentafluoroethyl)trimethylsilane (604 mg, 3.14 mmol), and cuprous iodide (600 mg, 3.15 mmol) were added. The mixture was heated to 80° C. and reacted overnight after being well mixed. LC-MS monitored the complete consumption of reaction materials. After filter membrane filtration to remove solid insoluble matters, the reaction was separated and purified by C18 reversed-phase chromatographic column (water:acetonitrile=5 to 100%) to obtain 106 mg colorless transparent oily liquid with a yield of 34.1%. ESI-MS m/z 394.1 (M+H)$^+$.

Synthesis of Compound QY-9-74:

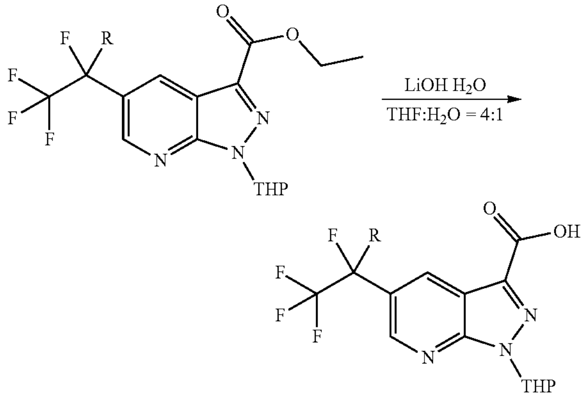

5-(Perfluoroethyl)-1-(tetrahydro-2H-pyran-2-yl)-1H-pyrazolo[3,4-b]pyridine-3-carboxylic acid (QY-9-74): QY-9-57 (46 mg, 0.12 mmol) was dissolved in 2 ml tetrahydrofuran, and transferred to an 8 ml pressure bottle. lithium hydroxide monohydrate (24 mg, 0.47 mmol) was dissolved in 0.5 ml distilled water, and then dropped to the reaction solution under ice bath condition. After mixing and stirring evenly, the mixture was allowed to gradually return to room temperature. LC-MS monitored the reaction was complete after being stirred overnight. The reaction was spin-evaporated to remove tetrahydrofuran and water, and dried with the oil pump. The residue was directly subjected to the next reaction without purification.

ESI-MS m/z 364.1 (M+H)$^-$.

Synthesis of Compound QV-9-76:

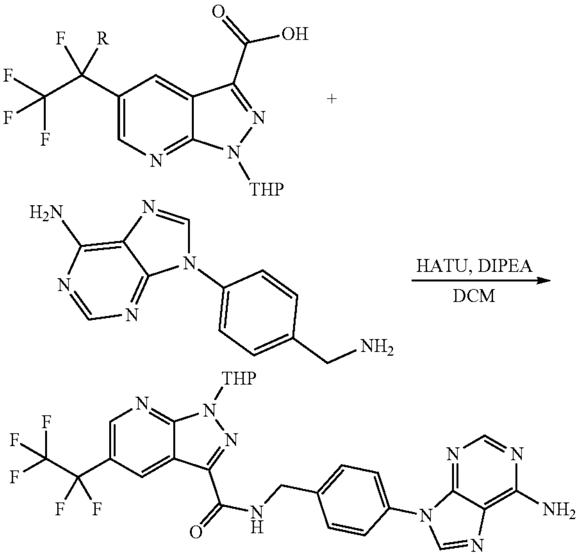

N-(4-(6-amino-9H-purin-9-yl)benzyl)-5-(perfluoroethyl)-1-(tetrahydro-2H-pyran-2-yl)-1H-pyrazolo[3,4-b]pyridine-3-carboxamide (QY-9-76): QY-9-74 (0.12 mmol) was dissolved in 3 ml dichloromethane in an 8 ml pressure bottle, HATU (54 mg, 0.14 mmol) and QY-8-36 (31 mg, 0.13 mmol) was added. N,N-diisopropylethylamine (60 mg, 0.47 mmol) was added dropwise at room temperature and the mixture was stirred continuously at room temperature.

The reaction was monitored in real time by LC-MS. After the reaction was complete, the reaction solution was diluted by adding 5 ml of dichloromethane, transferred to a separatory funnel, washed with 5 ml of distilled water and extracted with dichloromethane (5 ml*3). The organic phases were combined, and washed with saturated sodium chloride (5 ml*2). The post-processed organic phase was dried by anhydrous sodium sulfate, filtered and spin-dried to remove dichloromethane, and the residue was separated and purified by silica gel column chromatography (dichloromethane:methanol (ammonia)=0 to 20%) to get 52 mg yellowish brown solid, the yield is 76%. ESI-MS m/z 588.2 $(M+H)^+$.

Synthesis of Compound QY-9-77:

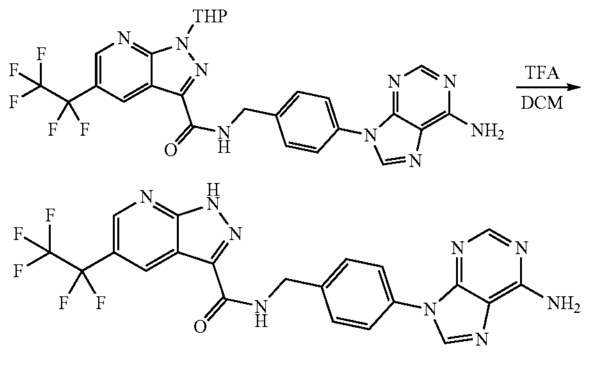

N-(4-(6-amino-9H-purin-9-yl)benzyl)-5-(perfluoroethyl)-1H-pyrazolo[3,4-b]pyridine-3-carboxamide (QY-9-77): QY-9-76 (52 mg, 0.09 mmol) was mixed in 2 ml of dichloromethane, and transferred to an 8 ml pressure flask. The reaction solution was dropped with 0.4 ml of trifluoroacetic acid at room temperature, mixed and stirred well. The reaction was monitored in real time by LC-MS. The raw materials was completely consumed after 1.5 h, and the reaction was transferred to a round bottom flask. 10 ml of dichloromethane was added and the organic solvent mixture was removed by spin-drying, this step was repeated for 3-4 times. The resulting residue was separated and purified by HPLC to afford 38 mg of white solid with a yield of 87%. ESI-MS m/z 504.1 $(M+H)^+$.

Method 17:

Synthesis of Compound QY-10-21:

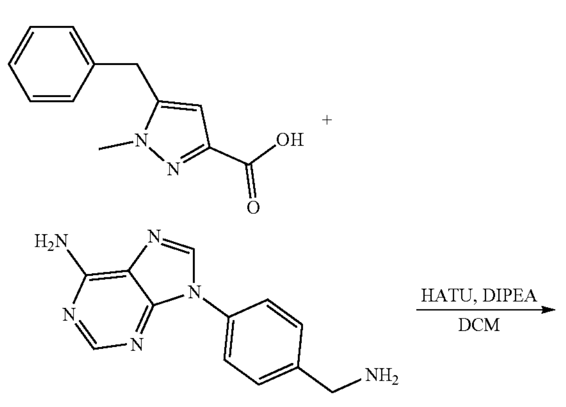

-continued

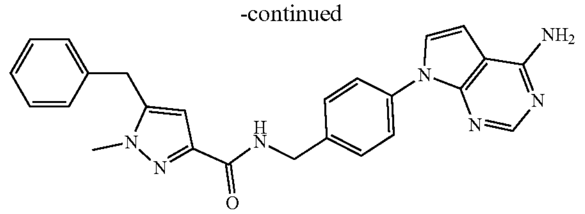

N-(4-(4-amino-7H-pyrrolo[2,3-d]pyrimidin-7-yl)benzyl)-5-benzyl-1-methyl-1H-pyrazol-3-carboxamide (QY-10-21): in a 100 ml round bottom flask, QY-6-103B (271 mg, 1.25 mmol) was dissolved in 15 ml dichloromethane, HATU (570 mg, 1.50 mmol) was added. QY-8-22 (300 mg, 1.25 mmol) was added to well-mixed reaction solution. N,N-diisopropylethylamine (645 mg, 5.0 mmol) was added dropwise at room temperature. The reaction was continued to react under stirring for 3.5 h. The reaction was monitored in real time by LC-MS until the substrate was completely consumed, and then transferred to a separatory funnel, washed with 10 ml distilled water, and extracted with dichloromethane (15 ml*3). The organic phases were combined, washed with saturated sodium chloride (10 ml*2), dried over anhydrous sodium sulfate, filtered and spin-evaporated to remove dichloromethane, the residue was separated and purified by silica gel column chromatography (dichloromethane:methanol (ammonia)=0 to 25%) to obtain 344 mg light yellow oily liquid with a yield of 63%. ESI-MS n/z 438.2 $(M+H)^+$.

Method 18:

Synthesis of Compound QY-10-47:

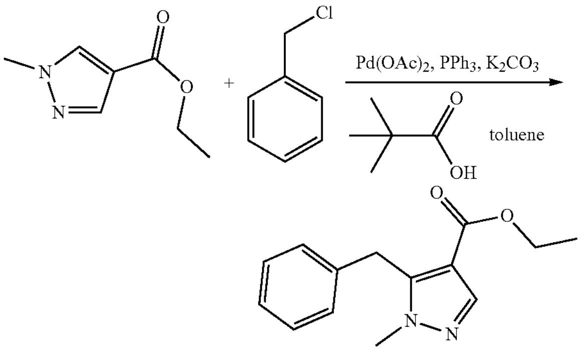

Ethyl 5-benzyl-1-methyl-1H-pyrazole-4-carboxylate (QY-10-47): to a 75 ml sealed tube was added with 15 ml toluene, Ethyl 1-methyl pyrazole-4-carboxylate (960 mg, 6.23 mmol), sequentially. After stirring well, palladium acetate (139 mg, 0.62 mmol), triphenylphosphine (327 mg, 1.25 mmol), potassium carbonate (2.15 g, 15.6 mmol), and pivalic acid (191 mg, 1.87 mmol) were added, benzyl chloride (946 mg, 7.47 mmol) was added dropwise. The mixture was heated to 100° C. and reacted overnight under nitrogen protection. The reaction was monitored by LC-MS and the raw materials was completely consumed. The reaction solution was diluted with ethyl acetate, transferred to a separatory funnel, then washed with distilled water, and extracted with ethyl acetate (10 ml*3). The organic phases were combined, washed with saturated sodium chloride (10 ml*2). The organic phase was dried over anhydrous sodium sulfate, filtered and evaporated to remove the organic solvent. The residue was separated and purified with silica gel column chromatography (petroleum ether:ethyl acetate=0 to 40%) to obtain 190 mg of light yellow oily liquid with a yield of 12.5%. ESI-MS n/z 245.1 $(M+H)^+$.

Synthesis of Compound QY-10-56:

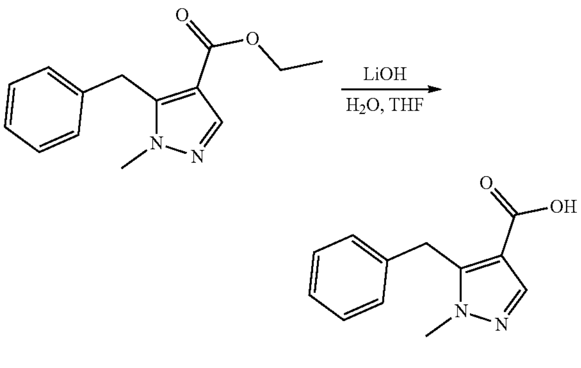

5-benzyl-1-methyl-1H-pyrazole-4-carboxylic acid (QY-10-56): QY-10-47 (190 mg, 0.78 mmol) was dissolved in 5 ml tetrahydrofuran, and transferred to a 15 ml pressure bottle. Lithium hydroxide monohydrate (130 mg, 3.11 mmol) was dissolved in 2 ml distilled water, and then added dropwise into the reaction solution under ice bath condition. The mixture was allowed to gradually return to room temperature after being mixed and stirred well. The reaction was monitored in real time by LC-MS and the reaction was complete after being stirred overnight, transferred to a 100 ml round bottom flask, spin-evaporated to remove the organic solvent and water, and dried with oil pump. The resulting residue was directly subjected to the next reaction without separation and purification. ESI-MS m/z 215.1 $(M+H)^-$.

Synthesis of Compound QY-10-39:

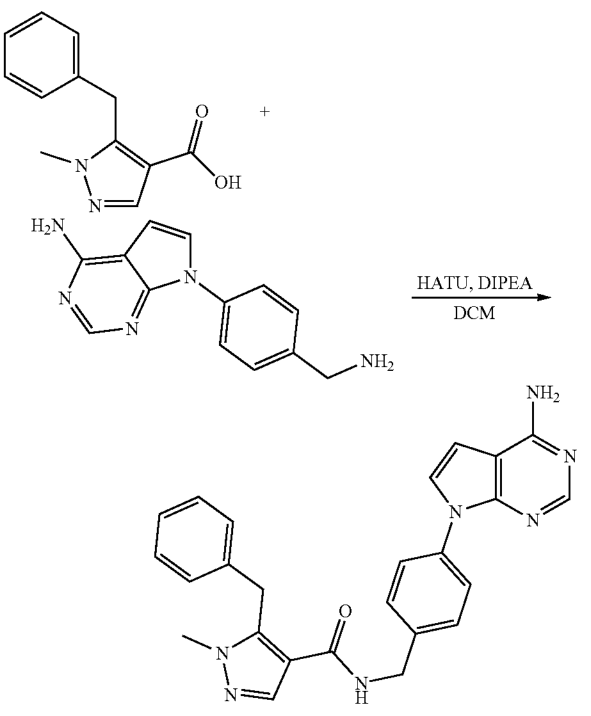

N-(4-(4-amino-7H-pyrrolo[2,3-d]pyrimidine-7-yl)benzyl)-5-benzyl-1-methyl-1H-pyrazole-4-carboxamide (QY-10-39): QY-10-56 (0.31 mmol) was dissolved in 3 ml dichloromethane in an 8 ml pressure bottle, HATU (141 mg, 0.37 mmol) and QY-8-22 (74 mg, 0.31 mmol) was added to the reaction solution. N,N-diisopropylethylamine (160 mg, 1.24 mmol) was added dropwise at room temperature. The reaction was monitored in real time by LC-MS and the raw materials were completely consumed after 4 h. The reaction solution was diluted by adding 10 ml of dichloromethane, transferred to a separatory funnel, washed with 5 ml of distilled water, and extracted with dichloromethane (10 ml*3). The organic phases were combined, and washed with saturated sodium chloride (5 ml*2). The post-processed organic phase was dried by anhydrous sodium sulfate, filtered and spin-dried to remove dichloromethane, and the residue was separated and purified by silica gel column chromatography (dichloromethane:methanol (ammonia)=0 to −20%) to afford 89 mg white solid with a yield of 66%. ESI-MS n/z 438.2 $(M+H)^+$.

Method 19:

Synthesis of Compound QY-12-88:

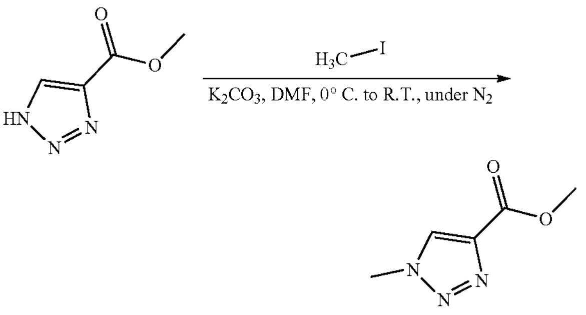

Methyl 1-methyl-1H-1,2,3-triazole-4-carboxylate (QY-12-88): Methyl 1,2,3-triazole-4-formate (1.27 g, 10.0 mmol) was dissolved in 20 ml N,N-dimethylformamide in a 100 ml round bottom flask. Potassium carbonate (0.83 g, 6.0 mmol) was added at room temperature, methyl iodide (1.50 g, 10.5 mmol) was added dropwise to the reaction solution under ice bath condition. The reaction solution was stirred for 1 h and then allowed to gradually return to room temperature and reacted for 16 h. The reaction was monitored in real time by LC-MS until the raw materials were completely consumed and then stopped. After the organic solvent was removed by evaporation, the reaction solution was diluted with dichloromethane, transferred to a separatory funnel, washed with distilled water (10 ml*3), and extracted with dichloromethane (15 ml*3). The organic phases were combined, washed with saturated sodium chloride (10 ml*2), dried over anhydrous sodium sulfate, filtered and spin-evaporated to remove dichloromethane, the residue was separated and purified with silica gel column chromatography (petroleum ether: ethyl acetate=10 to 90%) to obtain 305 mg white powder solid with a yield of 22%. ESI-MS m/z 142.1 $(M+H)^+$.

Synthesis of Compound QY-12-95:

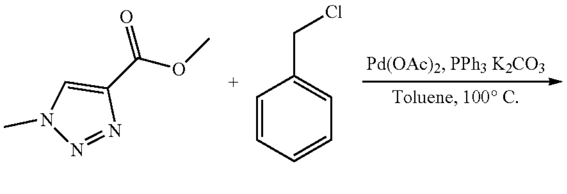

-continued

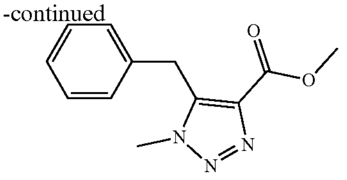

Methyl 5-benzyl-1-methyl-1H-1,2,3-triazole-4-carboxylate (QY-12-95): to a 15 ml pressure bottle was added 5 ml toluene, QY-12-88 (305 mg, 2.16 mmol). After mixing well, palladium acetate (24 mg, 0.11 mmol), triphenylphosphine (113 mg, 0.43 mmol), potassium carbonate (746 mg, 5.40 mmol), and pivalic acid (66 mg, 0.65 mmol) were add, and benzyl chloride (274 mg, 2.16 mmol) was added dropwise. The mixture was heated to 100° C. and reacted overnight after nitrogen protection. After the raw materials were completely completely consumed, the reaction solution was spin-evaporated to remove toluene, diluted with ethyl acetate. After suction filtration through celite, the organic solvent was removed by evaporation, and the residue was separated and purified with silica gel column chromatography (petroleum ether:ethyl acetate=0 to 80%) to obtain 173 mg of light yellow transparent oily liquid with a yield of 35%. ESI-MS m/z 232.1 $(M+H)^+$.

Synthesis of Compound QY-13-15:

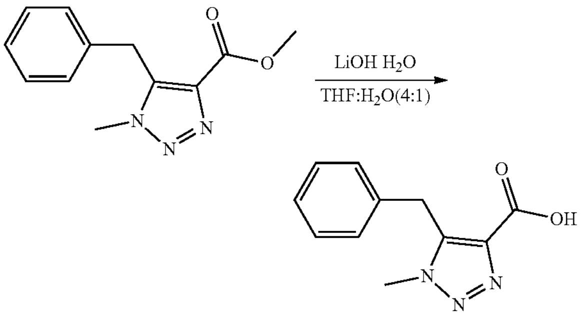

5-benzyl-1-methyl-1H-1,2,3-triazole-4-carboxylic acid (QY-13-15): QY-12-95 (173 mg, 0.75 mmol) was dissolved in 3 ml tetrahydrofuran, and transferred to an 8 ml pressure bottle. Lithium hydroxide monohydrate (63 mg, 1.50 mmol) was dissolved in 0.8 ml distilled water, and then added dropwise into the reaction solution at room temperature. The reaction progress was monitored in real time by LC-MS, and 5 h later, the raw material was completely consumed. All solvents in the reaction system were removed by spin-evaporation. The crude product can be directly subjected to the next reaction without separation and purification. ESI-MS m/z 218.1 $(M+H)^+$.

Synthesis of Compound QY-13-17:

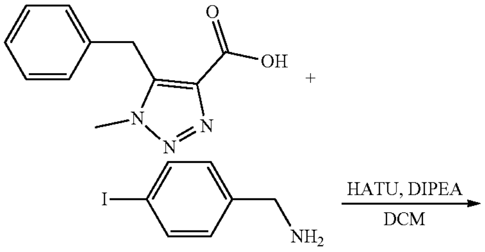

-continued

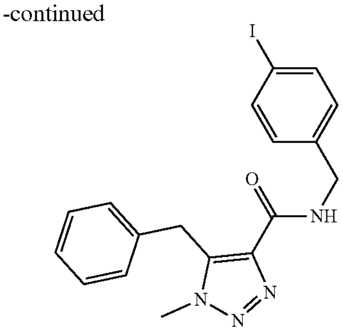

Benzyl-N-(4-iodobenzyl)-1-methyl-1H-1,2,3-triazol-4-carboxamide (QY-13-17): QY-13-15 (0.75 mmol) was dissolved in 5 ml dichloromethane in a 15 ml round bottom flask, HATU (341 mg, 0.90 mmol) and 4-iodobenzylamine (174 mg, 0.75 mmol) were added. N,N-diisopropylethylamine (289 mg, 2.24 mmol) was added dropwise at room temperature. The mixture was stirred continuously at room temperature. The reaction was monitored in real time by LC-MS. After the reaction was complete, the reaction solution was diluted by adding 15 ml of dichloromethane, transferred to a separatory funnel, washed with 10 ml of distilled water and extracted with dichloromethane (10 ml*3). The organic phases were combined, and washed with saturated sodium chloride (10 ml*2). The post-processed organic phase was dried by anhydrous sodium sulfate, filtered and spin-dried to remove dichloromethane, and the residue was separated and purified by silica gel column chromatography (petroleum ether:ethyl acetate=10 to 100%) to get 153 mg white foam solid with a yield of 47%. ESI-MS m/z 433.1 $(M+H)^+$.

Synthesis of Compound QY-13-19:

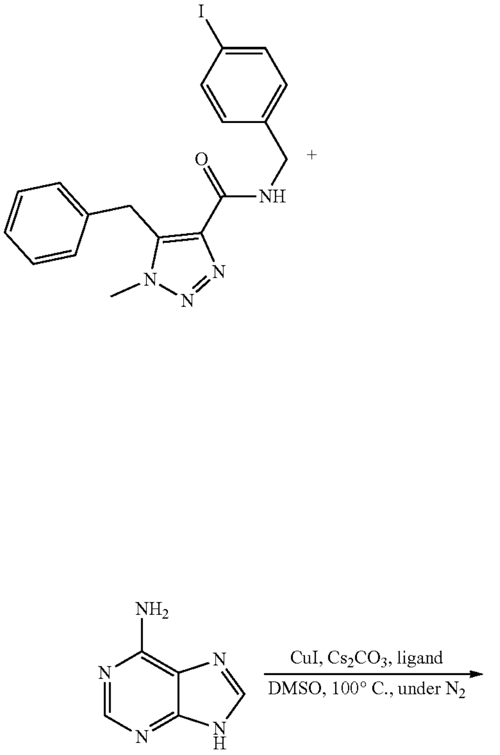

-continued

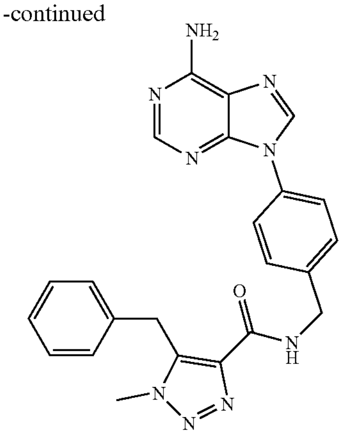

N-(4-(6-amino-9H-purin-9-yl)benzyl)-5-benzyl-1-methyl-1H-1,2,3-triazole-4-carboxamide (QY-13-19): QY-13-17 (153 mg, 0.35 mmol) was added to an 8 ml pressure resistant bottle. After dissolving it with 3 ml of dimethyl sulfoxide, adenine (57 mg, 0.42 mmol), cuprous iodide (34 mg, 0.18 mmol), cesium carbonate (346 mg, 1.1 mmol), and 4,7-dimethoxy-1,10 phenanthroline (17 mg, 0.07 mmol) were added. The mixture was heated to 100° C. and reacted overnight after nitrogen protection. After complete consumption of the reactants, and membrane filtration to remove the solid insoluble matters, the reaction was separated and purified by C18 reversed-phase chromatographic column (water:acetonitrile=10 to 100%) to obtain 55 mg white solid with a yield of 35%. ESI-MS m/z 440.1 $(M+H)^+$.

Method 20:

Synthesis of Compound QY-13-10:

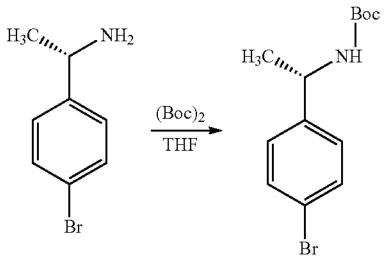

Tert-butyl (S)-(1-(4-bromophenyl)ethyl)carbamate (QY-13-10): (S)-1-(4-bromobenzene)ethylamine (2.20 g, 11.0 mmol) was dissolved in 50 ml tetrahydrofuran, and transferred to a 200 ml round bottom flask. Ditert-butyl dicarbonate (2.18 g, 10.0 mmol) was slowly added dropwise into the reaction solution. The reaction solution was stirred overnight at room temperature. monitoring showed the reaction was complete finished. The reaction system was spin-dried together and the residue was separated and purified by silica gel column chromatography (petroleum ether: ethyl acetate=0 to 40%) to afford 2.50 g white solid with a yield of 83%. ESI-MS m/z 300.1 $(M+H)^+$.

Synthesis of Compound QY-13-22:

Tert-butyl (S)-(1-(4-iodophenyl)ethyl)carbamate (QY-13-22): in a 30 ml pressure resistant bottle, 10 ml 1,4-dioxane, *Dioxane*, 110° C., *under* $N_2$ mol) were added sequentially. After mixing and dissolving well, sodium iodide (1.50 g, 10.0 mmol), cuprous iodide (48 mg, 0.25 mmol), and (1S,2S)-(+)-N,N'-dimethyl-1,2-cyclohexanediamine (71 mg, 0.50 mmol) were added. After nitrogen protection, the reaction was heated to 100° C. and stirred for 24 h. After complete consumption of the reactants and then membrane filtration to remove the solid insoluble matters, the reaction was evaporated to remove the organic solvent, and separated and purified by the silica gel column chromatography (dichloromethane:ethyl acetate=0 to 30%) to obtain 1.62 g yellow-white solid with a yield of 93%. ESI-MS m/z 348.2 $(M+H)^+$ Synthesis of Compound QY-13-23:

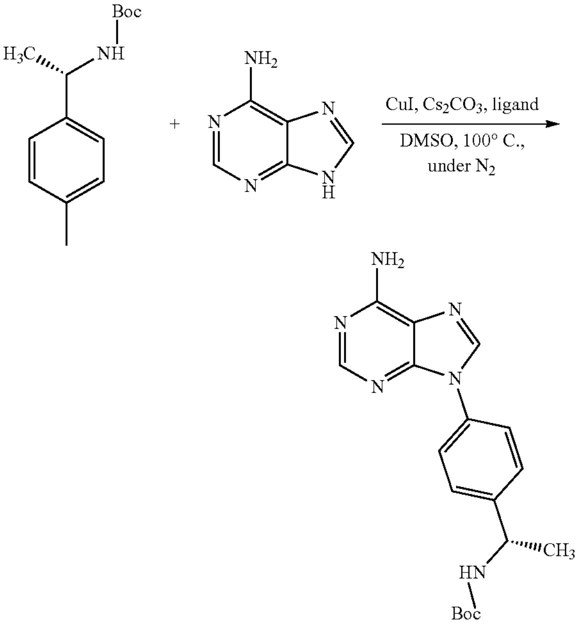

Tert-butyl (S)-(1-(4-(6-amino-9H-purin-9-yl)phenyl)ethyl)carbamate (QY-13-23): QY-13-22 (1.62 g, 4.66 mmol) was added to a 40 ml pressure resistant bottle. After dissolving with 25 ml of dimethyl sulfoxide, adenine (755 mg, 5.59 mmol), cuprous iodide (444 mg, 2.33 mmol), cesium carbonate (2.39 g, 7.34 mmol) and 4,7-dimethoxy-1,10 phenanthroline (112 mg, 0.47 mmol) were added. After nitrogen protection, the mixture was heated to 100° C. and reacted overnight. After complete consumption of the reactants and then membrane filtration to remove the solid insoluble matters, the reaction was separated and purified by the C18 reversed-phase chromatographic column (water: acetonitrile=10 to 100%) to obtain 646 mg yellow-white solid with a yield of 39%. ESI-MS n/z 355.1 $(M+H)^+$.

Synthesis of Compound QY-13-28:

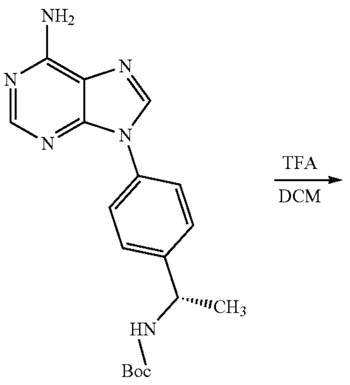

-continued

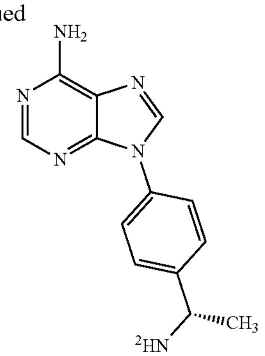

(S)-9-(4-(1-aminoethyl)phenyl)-9H-purin-6-amine (QY-13-28): QY-13-23 (1.45 g, 4.08 mmol) was well-mixed in 20 ml of dichloromethane, and transferred to a 100 ml round-bottom flask. 2.0 ml trifluoroacetic acid was added dropwise into the reaction solution at room temperature and the mixture was mixed and stirred evenly. The reaction was monitored in real time by LC-MS and the raw materials were completely consumed after 4 h. The reaction solution was added with 20 ml of dichloromethane, and evaporated to remove the organic solvent mixture, repeating for 3-4 times. The obtained product can be directly subjected into the next reaction without purification. ESI-MS n/z 255.2 $(M+H)^+$.

Synthesis of Compound QY-12-67:

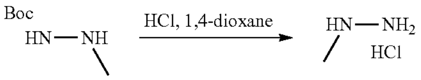

Methyl hydrazine hydrochloride (QY-12-67):1-BOC-2-methylhydrazine (7.31 g, 50.0 mmol) was weighed and transferred into a 100 ml round bottom flask, and 30 ml of hydrogen chloride solution of dioxane was slowly added into the flask under ice bath condition. The mixture was stirred in the ice bath for 30 min, and continued to stir at room temperature overnight. The reaction was stopped after the raw materials were completely consumed. The reaction solution was diluted by adding 30 ml dichloromethane, spin-evaporated to remove all organic solvents to afford milk white solid powder, which can be directly subjected to the next reaction without purification.

Synthesis of Compound QY-12-69:

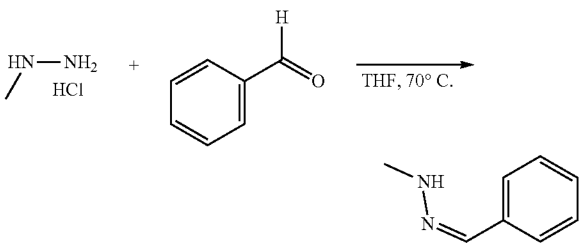

1-benzylidene-2-methylhydrazine (QY-12-69): Benzaldehyde (1.38 g, 13.0 mmol) was added into a 100 ml round bottom flask, and was dissolved and stirred evenly after adding 24 ml tetrahydrofuran. QY-12-67 (1.60 g, 19.5 mmol) was added at room temperature, heated to 70° C. and stirred for 4 hours. Thin layer chromatography monitoring showed that raw materials were completely consumed and the reaction was stopped. The reaction was filtered by filter membrane and the filter residue was removed, and the obtained crude product was directly subjected to the next reaction. ESI-MS n/z 135.1 $(M+H)^+$.

Synthesis of Compound QY-12-66:

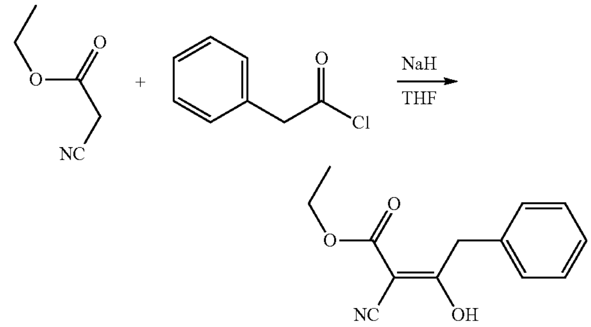

Ethyl (E)-2-cyano-3-hydroxy-4-phenylbut-2-enoate (QY-12-66): ethyl cyanoacetate (5.65 g, 50.0 mmol) was dissolved in 100 ml tetrahydrofuran in a 250 ml round bottom flask. Sodium hydride (60% wt) (2.0 g, 50.0 mmol) was added in batches under ice bath condition. After the reaction system was allowed to gradually return to room temperature and stirred for 10 min, phenylacetyl chloride (6.44 g, 42.0 mmol) was mixed well in 20 ml tetrahydrofuran and added dropwise into the above reaction solution. The reaction was monitored by thin layer chromatography and no raw material left completely consumed after 4.5 h, and then the reaction was stopped. The reaction was quenched by adding distilled water, spin evaporated to remove tetrahydrofuran, and then the reaction solution was diluted with 50 ml of dichloromethane, washed with 20 ml of distilled water, and extracted with dichloromethane (20 ml*3). The organic phases were combined, washed with saturated salt water (10 ml*1), dried over anhydrous sodium sulfate. After the organic solvent was removed using rotary evaporator, the residue was separated and purified by silica gel column chromatography (petroleum ether:ethyl acetate=10 to 30%) to obtain 4.16 g of orange-yellow oily liquid with a yield of 43%.

Synthesis of Compound QY-12-70:

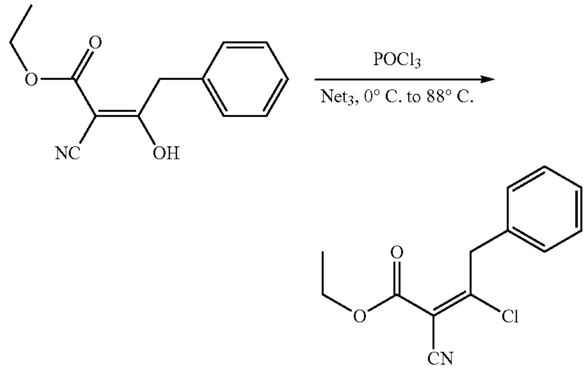

Ethyl (E)-3-chloro-2-cyano-4-phenylbut-2-enoate (QY-12-70): QY-12-66 (2.08 g, 9.0 mmol) was well dissolved in 10 ml of phosphorus oxychloride. Triethylamine (1.37 g, 13.5 mmol) was slowly added dropwise into the reaction solution under ice bath condition. After the reaction system was gradually brought back to room temperature and stirred for 5 min, it was heated to 88° C. The reaction was monitored by thin layer chromatography and no raw material left after 1 h, and then the reaction was stopped. The reaction system was slowly added dropwise into ice water to quench the reaction, and after transfer to a separatory funnel, and the reaction was extracted by adding ethyl acetate (40 ml*3). The organic phases were combined, washed with 1N dilute hydrochloric acid (10 ml*2), washed with saturated salt water (10 ml*1), and dried over anhydrous sodium sulfate. After the organic solvent was removed using rotary evaporator, the residue was separated and purified by silica gel column chromatography (petroleum ether:ethyl acetate=0 to 35%) to obtain 950 mg light yellow oily liquid with a yield of 42%. ESI-MS n/z 250.2 $(M+H)^+$.

Synthesis of Compound QY-12-73:

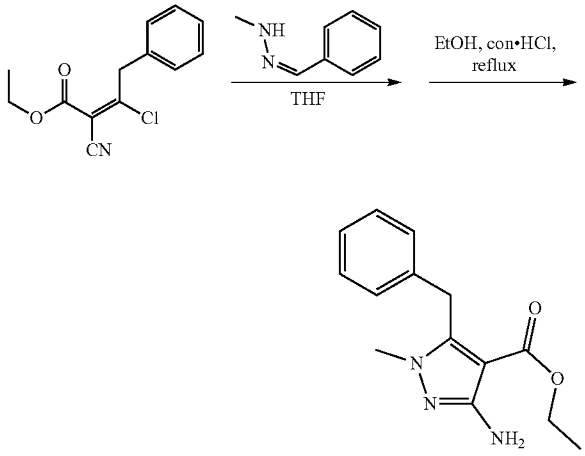

Ethyl 3-amino-5-benzyl-1-methyl-1H-pyrazole-4-carboxylate (QY-12-73): QY-12-69 (1.41 g, 10.5 mmol) and QY-12-70 (1.86 g, 7.5 mmol) were dissolved well in 21 ml tetrahydrofuran. After stirring for 4 h at room temperature, the organic solvent was removed by rotary evaporator. The reaction system was added with 21 ml of ethanol and mixed well, followed by the addition of 2.4 ml of 12N concentrated hydrochloric acid, and the reaction was heated to reflux and stirred overnight. LC-MS monitoring showed that the reaction was complete, and the reaction was stopped. All solvents were removed by rotary evaporation and the residue was purified by silica gel column chromatography (dichloromethane:methanol (ammonia)=0 to 20%) to obtain 1.05 g of yellow-brown foam solid with a yield of 54%. ESI-MS n/z 260.2 $(M+H)^+$.

Synthesis of Compound QY-12-78:

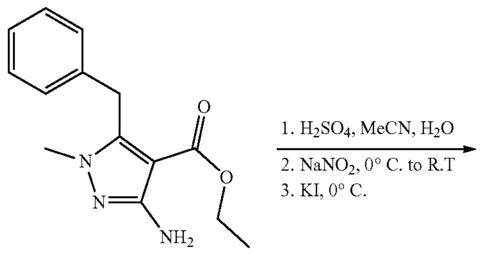

-continued

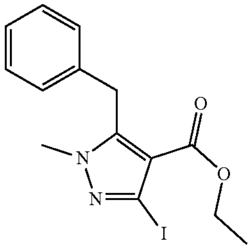

Ethyl 5-benzyl-3-iodo-1-methyl-1H-pyrazole-4-carboxylate (QY-12-78): QY-12-73 (350 mg, 1.35 mmol) was dissolved in 3 ml of acetonitrile and 6 ml of distilled water. Concentrated sulfuric acid (265 mg, 2.7 mmol) was added dropwise under ice bath condition. After stirring for 10 min, sodium nitrite (102 mg, 1.48 mmol) was dissolved in 3 ml of distilled water and slowly added dropwise into the above reaction system. The reaction system was stirred for 5 min under ice bath condition and then allowed to slowly return to room temperature and stirred for 1 h. Potassium iodide (672 mg, 4.05 mmol) was dissolved in 3 ml distilled water, and the reaction solution was added dropwise with the aqueous solution of potassium iodide under ice bath condition and stirred at 0° C. for 1 h. LC-MS monitoring showed that the reaction was complete and the reaction was stopped. The reaction was quenched by adding sodium thiosulfate solution, then transferred to a separatory funnel, and extracted with ethyl acetate (20 ml*3). The organic phases were combined, washed with distilled water (10 ml*1), washed with saturated salt water (10 ml*2), and dried over anhydrous sodium sulfate. After the organic solvent was removed via rotary evaporation, the residue was separated and purified by silica gel column chromatography (petroleum ether:ethyl acetate=0 to 50%) to obtain 150 mg yellow solid with a yield of 30%. ESI-MS n/z 371.1 $(M+H)^+$.

Synthesis of Compound QY-12-79:

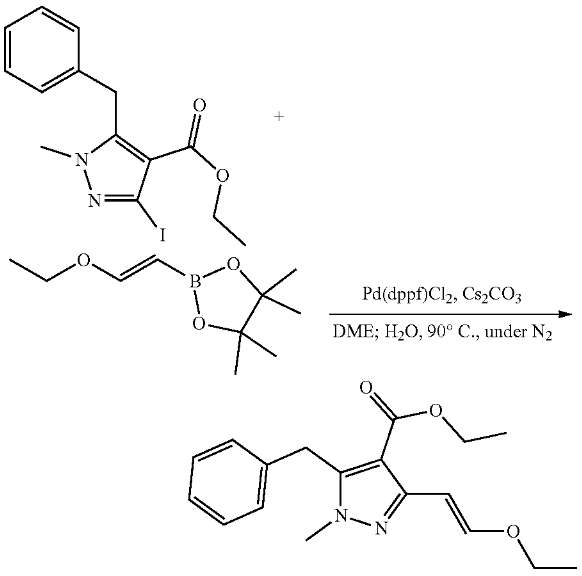

Ethyl (E)-5-benzyl-3-(2-ethoxyvinyl)-1-methyl-1H-pyrazole-4-carboxylic acid (QY-12-79): QY-12-78 (150 mg, 0.41 mmol) was dissolved in 2 ml of ethylene glycol dimethyl ether and 0.4 ml distilled water and then added to an 8 ml pressure bottle. Pd(dppf)$Cl_2$ (30 mg, 0.04 mmol), cesium carbonate (294 mg, 0.90 mmol), and (E)-1-ethoxyvinyl-2-borate pinanol ester (161 mg, 0.81 mmol) were added and mixed well. Then the reaction system was protected with nitrogen, gradually heated to 90° C. and reacted overnight. LC-MS monitoring showed that the reaction was complete, and the reaction was stopped. After filter membrane filtration, the reaction solution was separated and purified by C18 reversed-phase chromatographic column (water:acetonitrile=10 to 100%) to obtain 112 mg yellow-brown solid with a yield of 87%. ESI-MS n/z 315.2 $(M+H)^+$.

Synthesis of Compound QY-12-84:

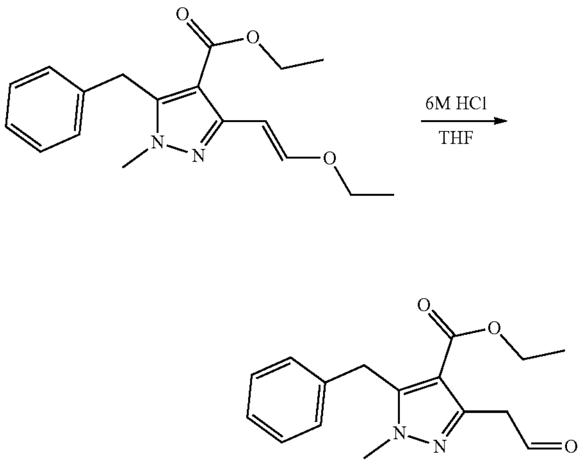

Ethyl 5-benzyl-1-methyl-3-(2-oxyethyl)-1H-pyrazol-4-carboxylate (QY-12-84): QY-12-79 (112 g, 0.36 mmol) was dissolved in 2.0 ml of tetrahydrofuran and then transferred into an 8 ml pressure bottle. The reaction solution was added dropwise with 1.5 ml of 6M hydrochloric acid aqueous solution under ice bath condition, and stirred overnight at room temperature. The reaction was monitored by LC-MS until the reaction was complete. Then the pH was adjusted by adding saturated sodium bicarbonate solution to alkalescence. The reaction system was transferred to a separatory funnel, and extracted with ethyl acetate (5 ml*3). The organic phases were combined, washed with saturated sodium chloride washing (5 ml*2). The organic phase was dried over anhydrous sodium sulfate, and spin-evaporated to remove the organic solvent to obtain the crude product which was directly subjected to the next reaction. ESI-MS n/z 287.1 $(M+H)^+$.

Synthesis of Compound QY-13-32:

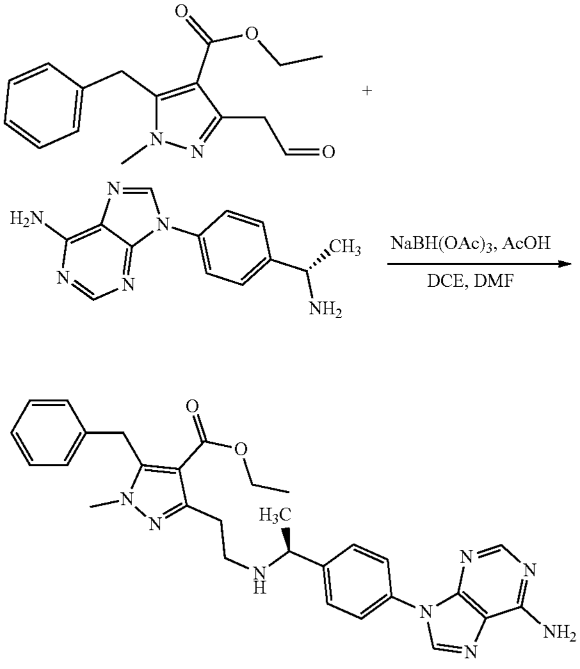

Ethyl (S)-3-(2-((1-(4-(6-amino-9H-purin-9-yl)phenyl)ethyl)amino)ethyl)-5-benzyl-1-methyl-1H-pyrazole-4-carboxylate (QY-13-32): QY-12-84 (1.7 mmol) was well mixed in 10 ml of 1,2-dichloroethane and added into a 30 ml pressure flask. The reaction solution was added with QY-13-28 (1.08 g, 4.24 mmol) and glacial acetic acid (306 mg, 5.1 mmol), and stirred for 20 min, followed by the addition of sodium triacetoxyborohydride (899 mg, 4.24 mmol). The resulting solution was stirred overnight at room temperature. LC-MS monitoring showed the reaction was complete and the reaction was stopped. The organic solvent was removed by rotary evaporation. The reaction system was mixed uniformly with dimethyl sulfoxide, and then filtered by the filter membrane. The residue was separated and purified by C18 reversed-phase chromatographic column (water:acetonitrile=10 to 100%) to afford 586 mg yellow-green foam solid with a yield of 66%. ESI-MS m/z 525.3 $(M+H)^+$.

Synthesis of Compound QY-13-33:

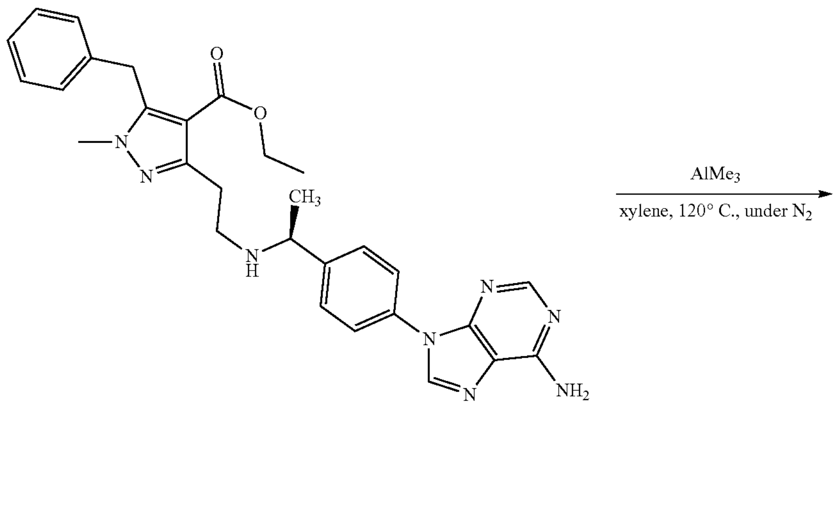

-continued

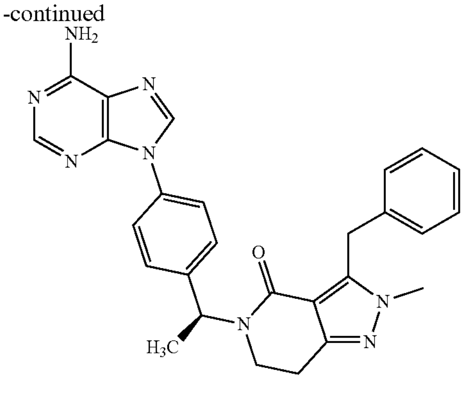

(5-(S)-5-(1-(4-(6-amino-9H-purine-9-yl)phenyl)ethyl)-3-benzyl-2-methyl-2,5,6,7-tetrahydro-4H-pyrazolo[4,3-c]pyridine-4-one (QY-13-33): QY-13-32 (262 mg, 0.50 mmol) was well mixed in 20 ml xylene, transferred to a 40 ml pressure bottle and stirred. Trimethylaluminum (1.50 mmol) was added slowly dropwise to the reaction solution at room temperature. After nitrogen protection, the reaction solution was gradually heated to 120° C., stirred overnight and stopped. After slowly returning to room temperature, the reaction solution was quenched by adding distilled water dropwise, added with Roche salt solution and stirred for 30 min. The reaction system was diluted by adding 20 ml of ethyl acetate, transferred to a separatory funnel, and extracted with ethyl acetate (60 ml*3). The organic phases were combined, washed with saturated sodium chloride (20 ml*2), dried over anhydrous sodium sulfate, filtered and evaporated to remove the organic solvent, and the residue was separated and purified by silica gel column chromatography (dichloromethane:methanol (ammonia)=0 to 20%) to get 105 mg orange-yellow oily liquid with a yield of 44%. ESI-MS n/z 479.2 $(M+H)^+$.

According to the above method, by replacing different synthetic substrates, the compounds shown in Table A were obtained:

TABLE A

| | |
|---|---|
| QY-5-35 | 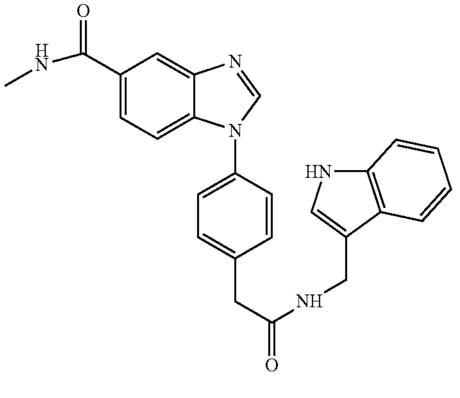 [SMILES: CNC(=O)c1ccc2c(c1)ncn2-c1ccc(CC(=O)NCc2c[nH]c3ccccc23)cc1] |
| QY-5-40 | 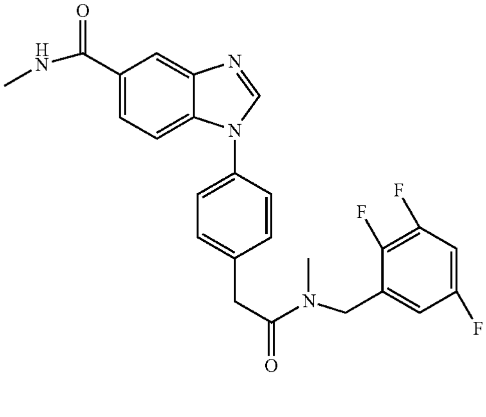 [SMILES: CNC(=O)c1ccc2c(c1)ncn2-c1ccc(CC(=O)N(C)Cc2cc(F)cc(F)c2F)cc1] |

TABLE A-continued
QY-5-62
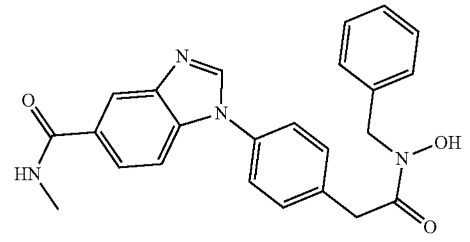 [SMILES: CNC(=O)c1ccc2c(c1)ncn2-c1ccc(CC(=O)N(O)Cc2ccccc2)cc1]
QY-6-15
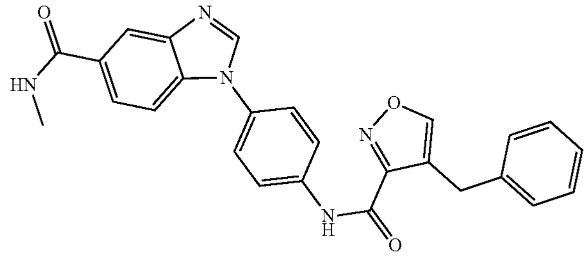 [SMILES: CNC(=O)c1ccc2c(c1)ncn2-c1ccc(NC(=O)c2nocc2Cc2ccccc2)cc1]
QY-6-16
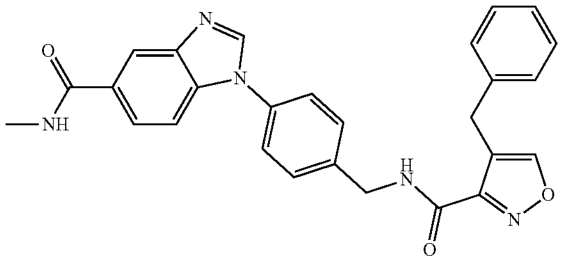 [SMILES: CNC(=O)c1ccc2c(c1)ncn2-c1ccc(CNC(=O)c2nocc2Cc2ccccc2)cc1]
QY-7-2A
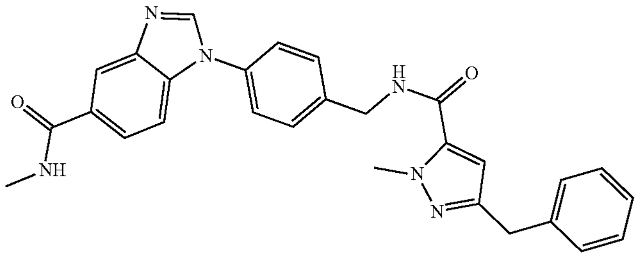 [SMILES: CNC(=O)c1ccc2c(c1)ncn2-c1ccc(CNC(=O)c2cc(Cc3ccccc3)nn2C)cc1]
QY-7-2B
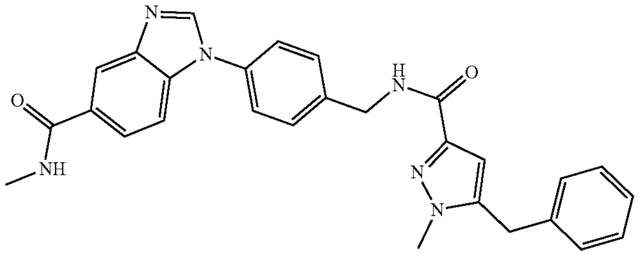 [SMILES: CNC(=O)c1ccc2c(c1)ncn2-c1ccc(CNC(=O)c2cc(Cc3ccccc3)n(C)n2)cc1]
QY-7-14
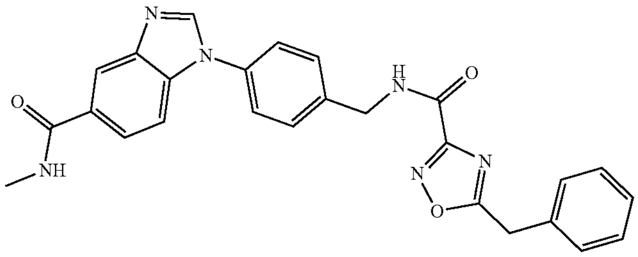 [SMILES: CNC(=O)c1ccc2c(c1)ncn2-c1ccc(CNC(=O)c2noc(Cc3ccccc3)n2)cc1]

TABLE A-continued
QY-7-32
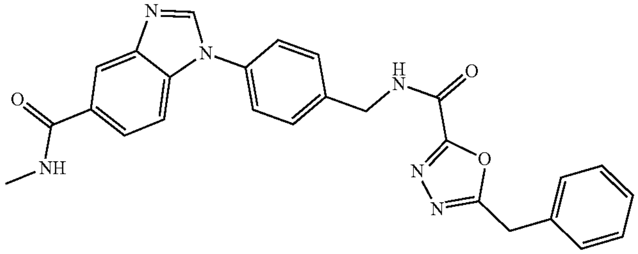 [SMILES: CNC(=O)c1ccc2c(c1)ncn2-c1ccc(CNC(=O)c2nnc(Cc3ccccc3)o2)cc1]
QY-7-65
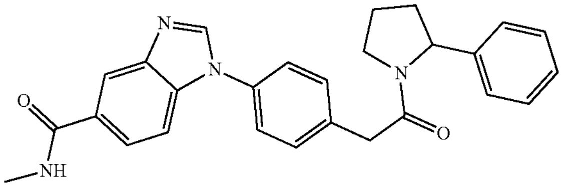 [SMILES: CNC(=O)c1ccc2c(c1)ncn2-c1ccc(CC(=O)N2CCCC2c2ccccc2)cc1]
QY-8-7
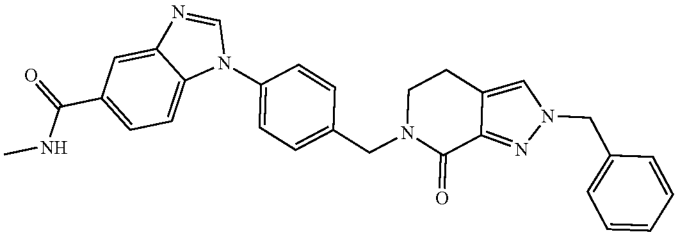 [SMILES: CNC(=O)c1ccc2c(c1)ncn2-c1ccc(CN2CCc3cn(Cc4ccccc4)nc3C2=O)cc1]
QY-8-30
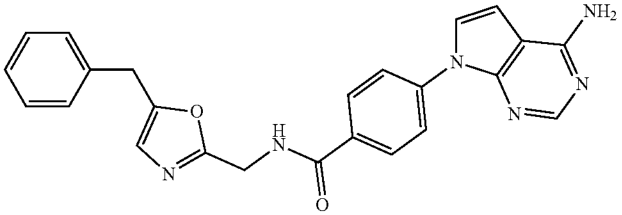 [SMILES: Nc1ncnc2c1ccn2-c1ccc(C(=O)NCc2ncc(Cc3ccccc3)o2)cc1]
QY-8-31
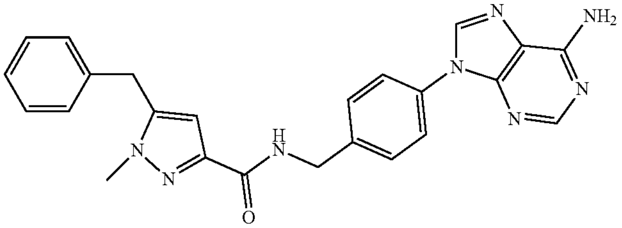 [SMILES: Cn1nc(C(=O)NCc2ccc(-n3cnc4c(N)ncnc43)cc2)cc1Cc1ccccc1]
QY-8-42
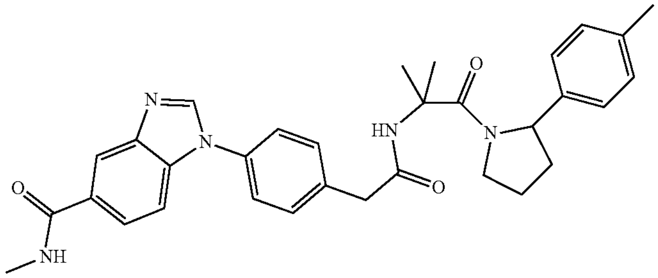

TABLE A-continued
QY-8-43
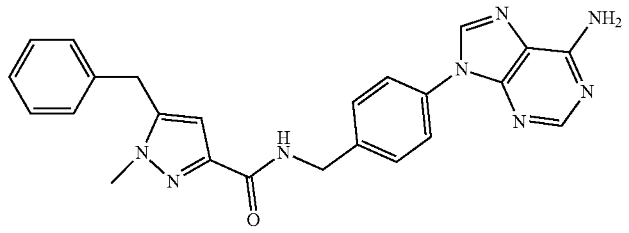 [SMILES: Cn1nc(C(=O)NCc2ccc(-n3cnc4c(N)ncnc43)cc2)cc1Cc1ccccc1]
QY-8-48
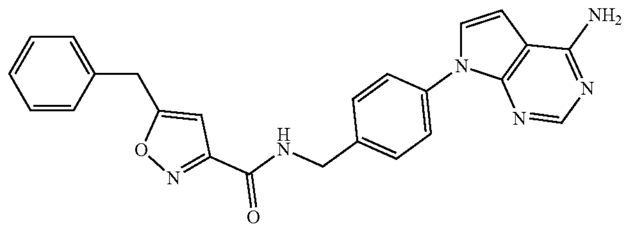 [SMILES: Nc1ncnc2c1ccn2-c1ccc(CNC(=O)c2cc(Cc3ccccc3)on2)cc1]
QY-8-58
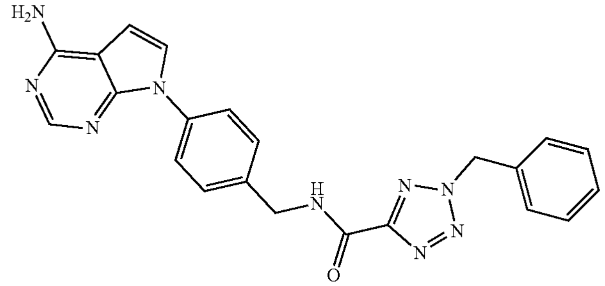 [SMILES: Nc1ncnc2c1ccn2-c1ccc(CNC(=O)c2nnn(Cc3ccccc3)n2)cc1]
QY-8-60
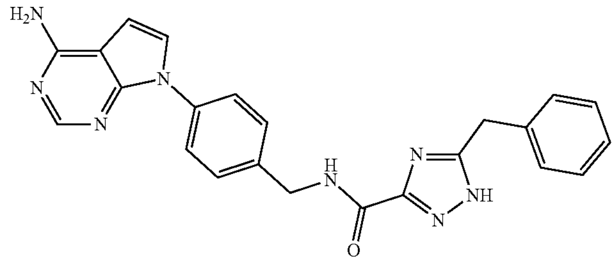 [SMILES: Nc1ncnc2c1ccn2-c1ccc(CNC(=O)c2n[nH]c(Cc3ccccc3)n2)cc1]
QY-9-33
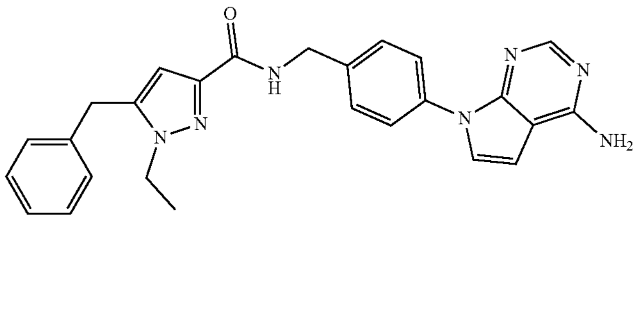 [SMILES: CCn1nc(C(=O)NCc2ccc(-n3ccc4c(N)ncnc43)cc2)cc1Cc1ccccc1]
QY-9-34
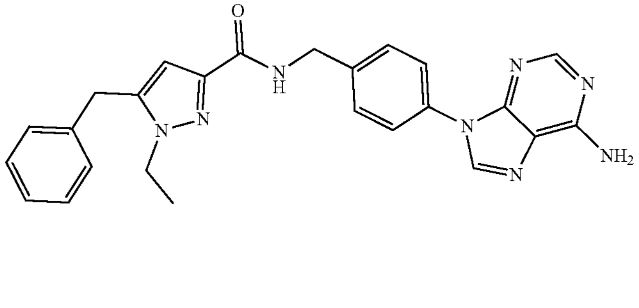 [SMILES: CCn1nc(C(=O)NCc2ccc(-n3cnc4c(N)ncnc43)cc2)cc1Cc1ccccc1]

TABLE A-continued
QY-9-41
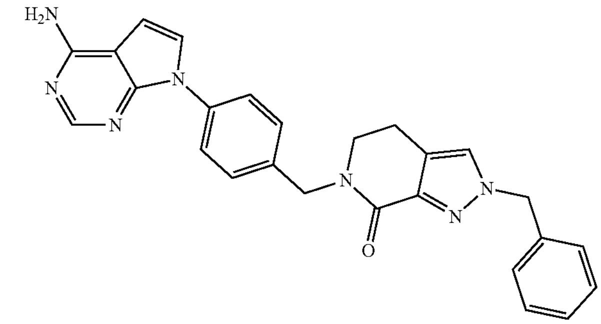
QY-9-50
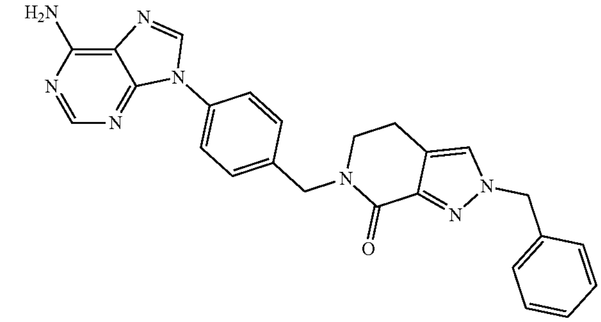 [SMILES: Nc1ncnc2c1ncn2-c1ccc(CN2CCc3cn(Cc4ccccc4)nc3C2=O)cc1]
QY-9-69
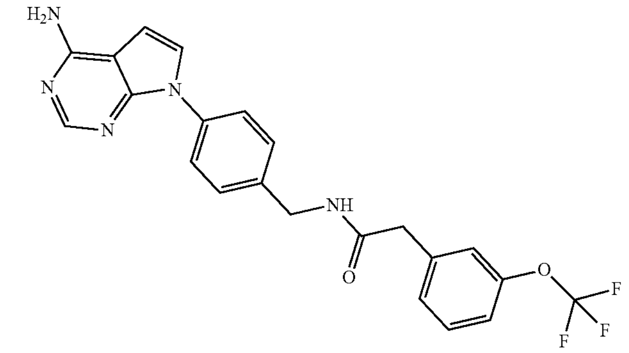 [SMILES: Nc1ncnc2c1ccn2-c1ccc(CNC(=O)Cc2cccc(OC(F)(F)F)c2)cc1]
QY-9-70
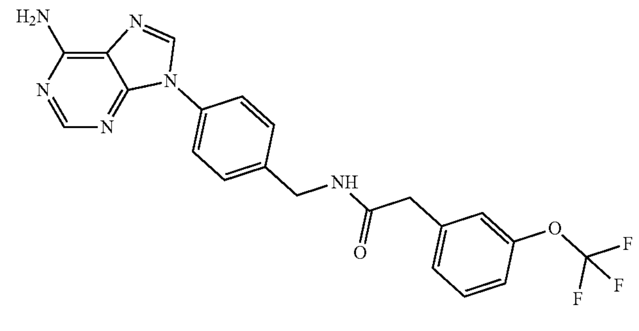 [SMILES: Nc1ncnc2c1ncn2-c1ccc(CNC(=O)Cc2cccc(OC(F)(F)F)c2)cc1]
QY-9-77
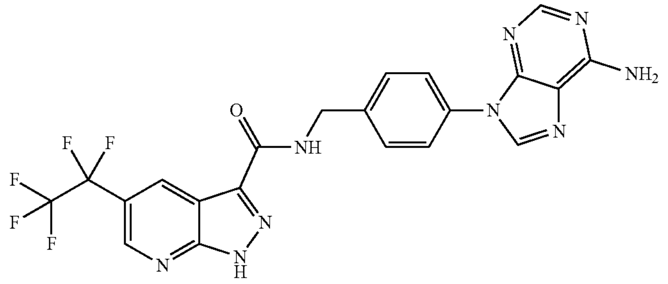 [SMILES: Nc1ncnc2c1ncn2-c1ccc(CNC(=O)c2n[nH]c3ncc(C(F)(F)C(F)(F)F)cc23)cc1]

TABLE A-continued
QY-10-21
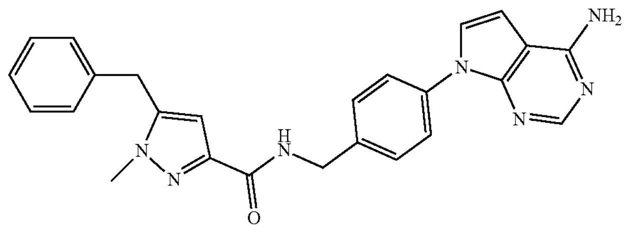 [SMILES: Cn1nc(C(=O)NCc2ccc(-n3ccc4c(N)ncnc43)cc2)cc1Cc1ccccc1]
QY-10-39
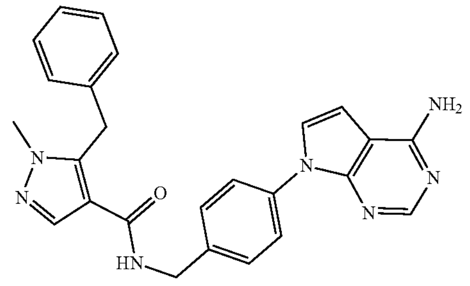 [SMILES: Cn1ncc(C(=O)NCc2ccc(-n3ccc4c(N)ncnc43)cc2)c1Cc1ccccc1]
QY-10-40
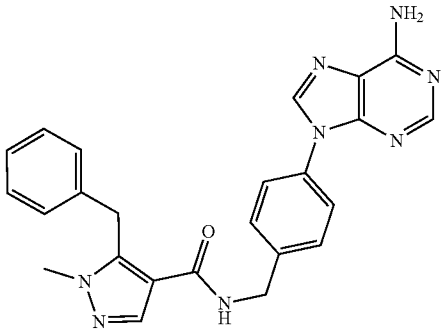 [SMILES: Cn1ncc(C(=O)NCc2ccc(-n3cnc4c(N)ncnc43)cc2)c1Cc1ccccc1]
QY-10-65
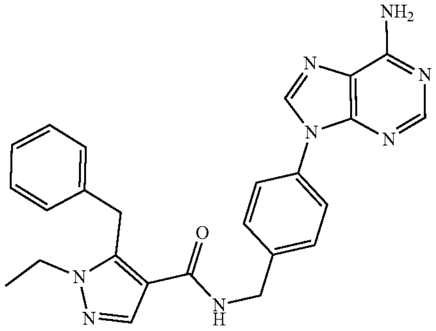 [SMILES: CCn1ncc(C(=O)NCc2ccc(-n3cnc4c(N)ncnc43)cc2)c1Cc1ccccc1]
QY-10-73
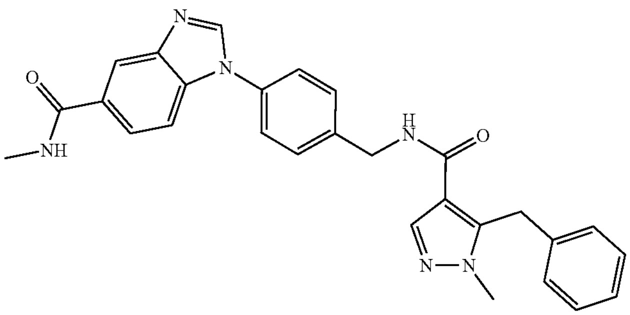 [SMILES: CNC(=O)c1ccc2c(c1)ncn2-c1ccc(CNC(=O)c2cnn(C)c2Cc2ccccc2)cc1]

TABLE A-continued
ZSQ-13-35
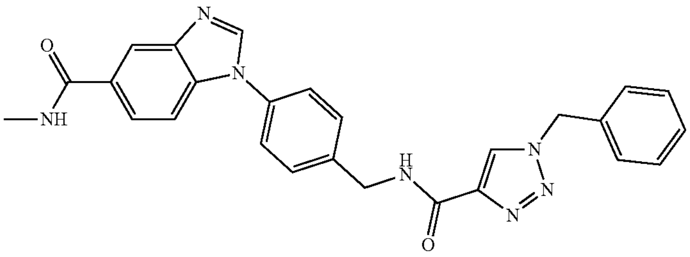 [SMILES: CNC(=O)c1ccc2c(c1)ncn2-c1ccc(CNC(=O)c2cn(Cc3ccccc3)nn2)cc1]
ZSQ-13-36
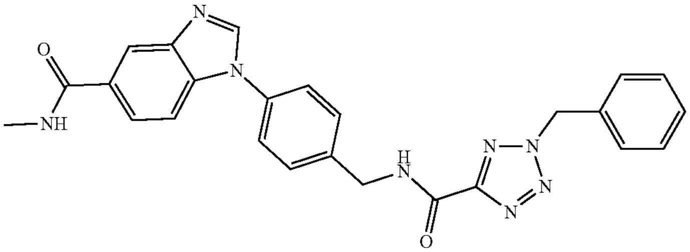 [SMILES: CNC(=O)c1ccc2c(c1)ncn2-c1ccc(CNC(=O)c2nnn(Cc3ccccc3)n2)cc1]
ZSQ-13-46
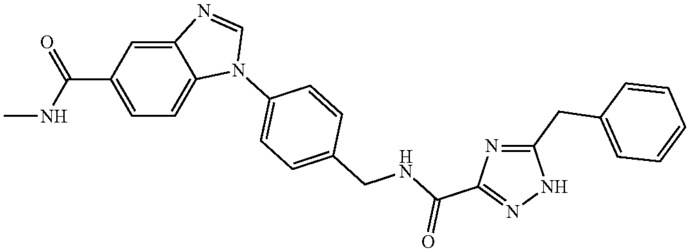 [SMILES: CNC(=O)c1ccc2c(c1)ncn2-c1ccc(CNC(=O)c2n[nH]c(Cc3ccccc3)n2)cc1]
ZSQ-15-48
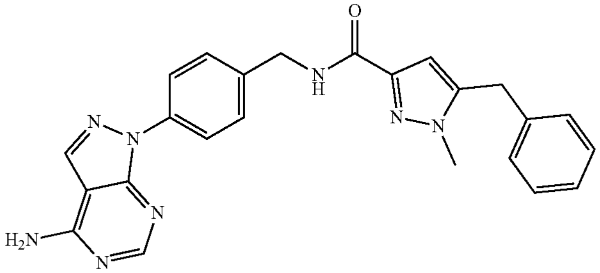 [SMILES: Cn1nc(C(=O)NCc2ccc(-n3ncc4c(N)ncnc43)cc2)cc1Cc1ccccc1]
ZSQ-15-68
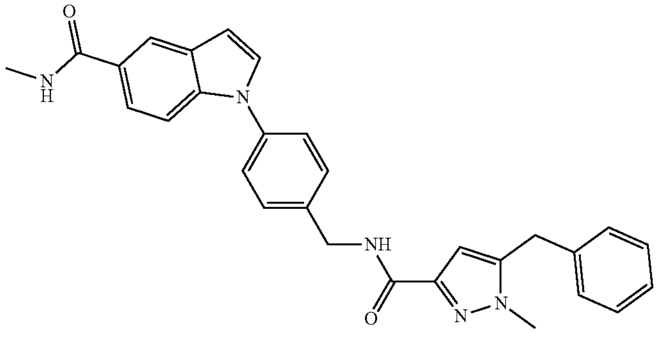 [SMILES: CNC(=O)c1ccc2c(ccn2-c2ccc(CNC(=O)c3cc(Cc4ccccc4)n(C)n3)cc2)c1]

TABLE A-continued
ZSQ-15-67
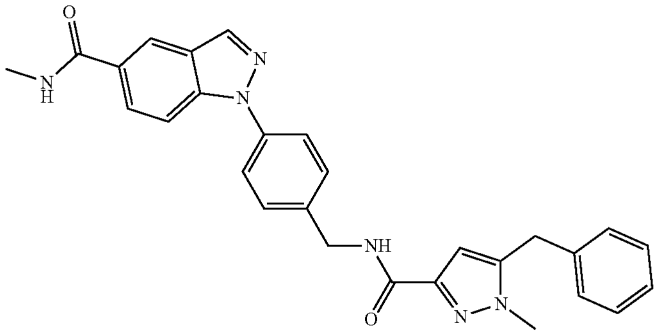 [SMILES: CNC(=O)c1ccc2c(cnn2-c2ccc(CNC(=O)c3cc(Cc4ccccc4)n(C)n3)cc2)c1]
XHJ-2-88
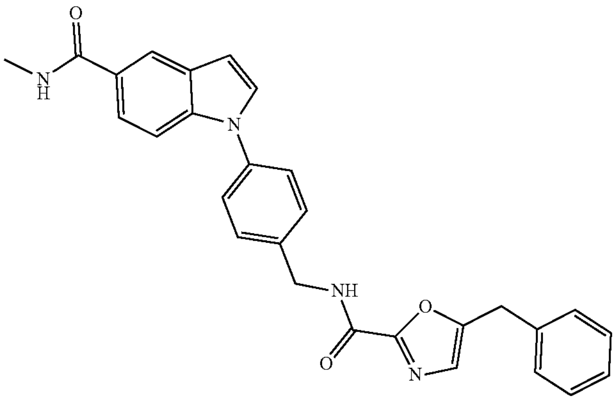 [SMILES: CNC(=O)c1ccc2c(ccn2-c2ccc(CNC(=O)c3ncc(Cc4ccccc4)o3)cc2)c1]
ZSQ-16-3
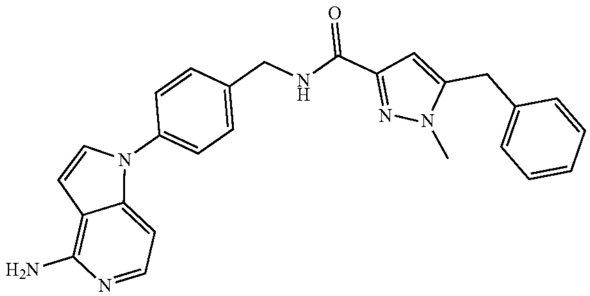 [SMILES: Cn1nc(C(=O)NCc2ccc(-n3ccc4c(N)nccc43)cc2)cc1Cc1ccccc1]
XHJ-4-48
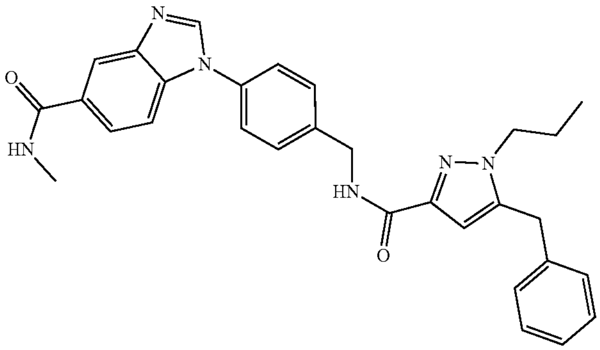 [SMILES: CCCn1nc(C(=O)NCc2ccc(-n3cnc4cc(C(=O)NC)ccc43)cc2)cc1Cc1ccccc1]

TABLE A-continued
| | |
|---|---|
| XHJ-4-36 | 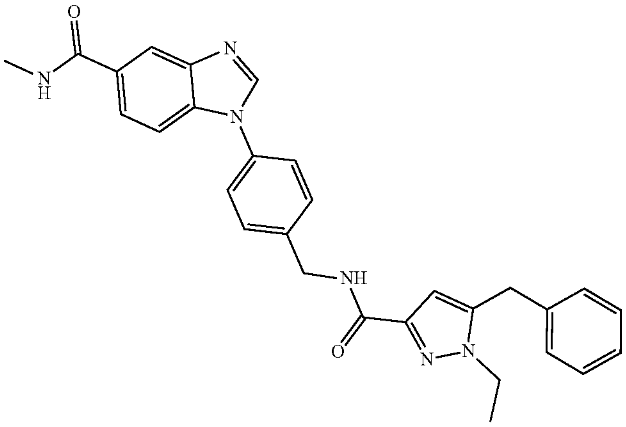 [SMILES: CCn1nc(C(=O)NCc2ccc(-n3cnc4cc(C(=O)NC)ccc43)cc2)cc1Cc1ccccc1] |
| ZSQ-20-106 | 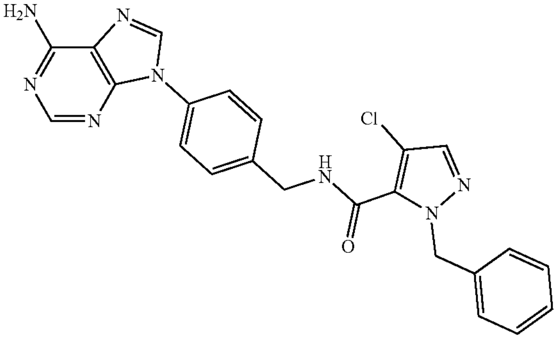 [SMILES: Nc1ncnc2c1ncn2-c1ccc(CNC(=O)c2c(Cl)cnn2Cc2ccccc2)cc1] |
| ZSQ-20-94 | 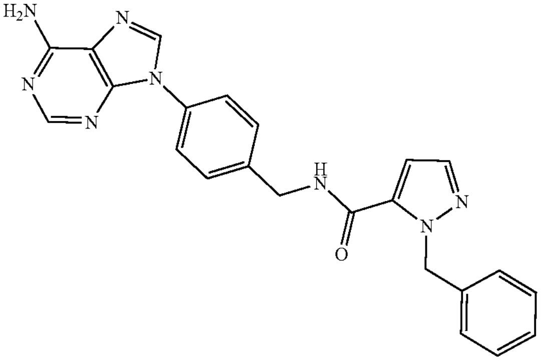 [SMILES: Nc1ncnc2c1ncn2-c1ccc(CNC(=O)c2ccnn2Cc2ccccc2)cc1] |
| ZSQ-21-2 | 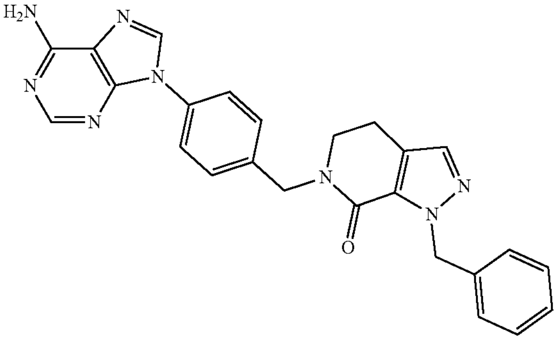 [SMILES: Nc1ncnc2c1ncn2-c1ccc(CN2CCc3cnn(Cc4ccccc4)c3C2=O)cc1] |

TABLE A-continued
ZSQ-21-1
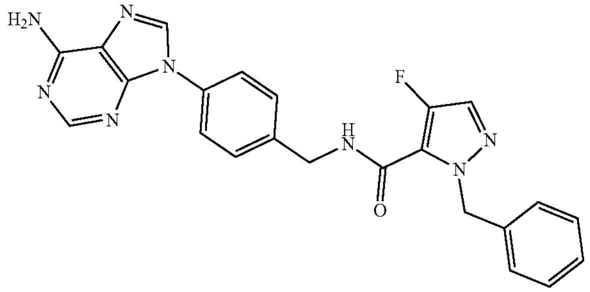 [SMILES: Nc1ncnc2c1ncn2-c1ccc(CNC(=O)c2c(F)cnn2Cc2ccccc2)cc1]
ZSQ-21-13
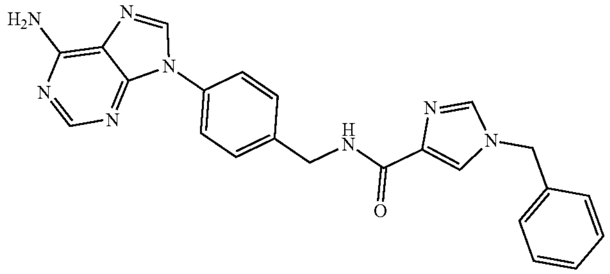 [SMILES: Nc1ncnc2c1ncn2-c1ccc(CNC(=O)c2cn(Cc3ccccc3)cn2)cc1]
ZSQ-21-8
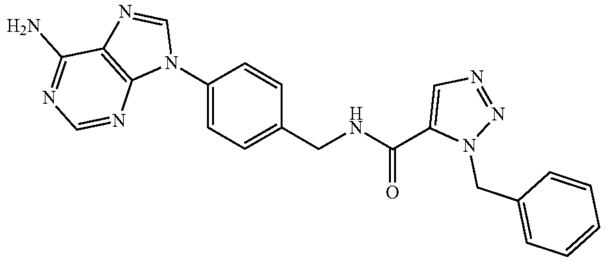 [SMILES: Nc1ncnc2c1ncn2-c1ccc(CNC(=O)c2cnnn2Cc2ccccc2)cc1]
ZSQ-21-18
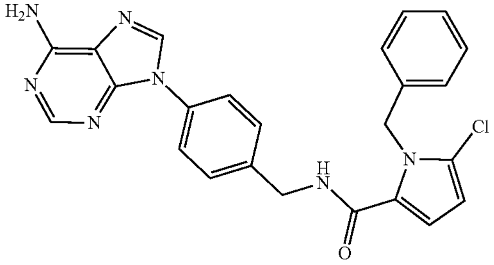 [SMILES: Nc1ncnc2c1ncn2-c1ccc(CNC(=O)c2ccc(Cl)n2Cc2ccccc2)cc1]
ZSQ-21-14
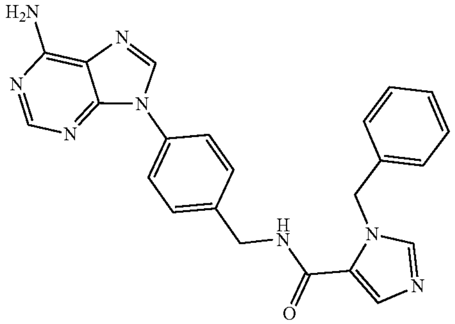 [SMILES: Nc1ncnc2c1ncn2-c1ccc(CNC(=O)c2cncn2Cc2ccccc2)cc1]

TABLE A-continued
ZSQ-21-30
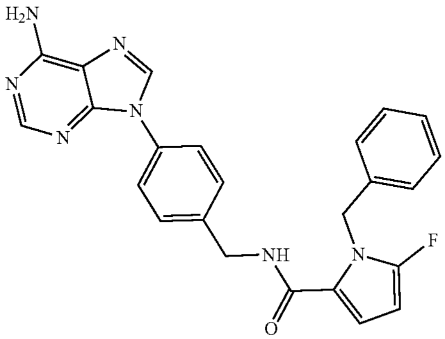 [SMILES: Nc1ncnc2c1ncn2-c1ccc(CNC(=O)c2ccc(F)n2Cc2ccccc2)cc1]
QY-11-75
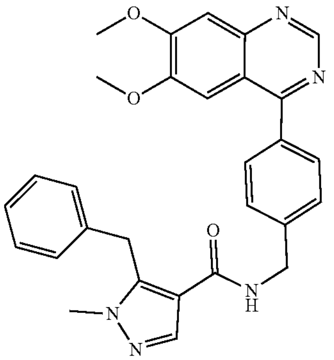 [SMILES: COc1cc2ncnc(-c3ccc(CNC(=O)c4cnn(C)c4Cc4ccccc4)cc3)c2cc1OC]
QY-11-76
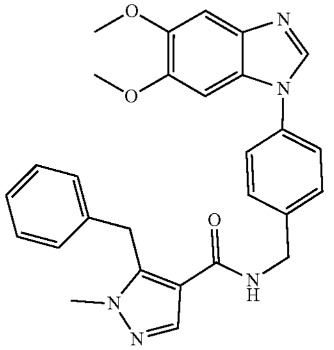 [SMILES: COc1cc2ncn(-c3ccc(CNC(=O)c4cnn(C)c4Cc4ccccc4)cc3)c2cc1OC]
QY-11-77
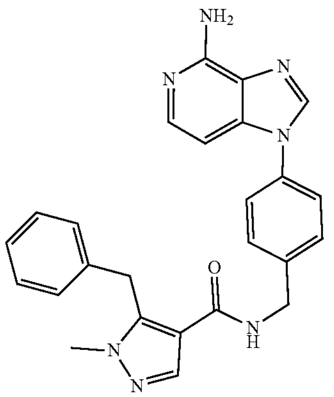 [SMILES: Cn1ncc(C(=O)NCc2ccc(-n3cnc4c(N)nccc43)cc2)c1Cc1ccccc1]

TABLE A-continued
QY-11-78
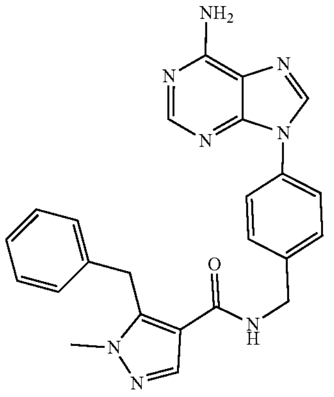 [SMILES: Cn1ncc(C(=O)NCc2ccc(-n3cnc4c(N)ncnc43)cc2)c1Cc1ccccc1]
QY-11-79
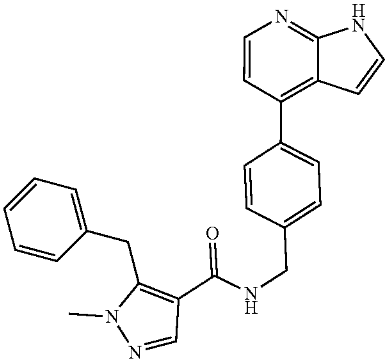 [SMILES: Cn1ncc(C(=O)NCc2ccc(-c3ccnc4[nH]ccc34)cc2)c1Cc1ccccc1]
QY-11-80
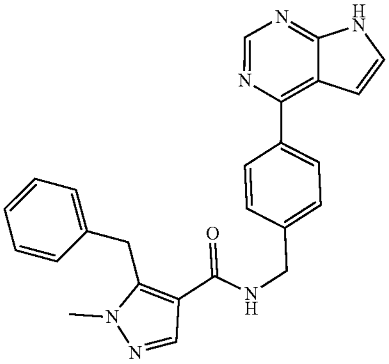
QY-11-68A
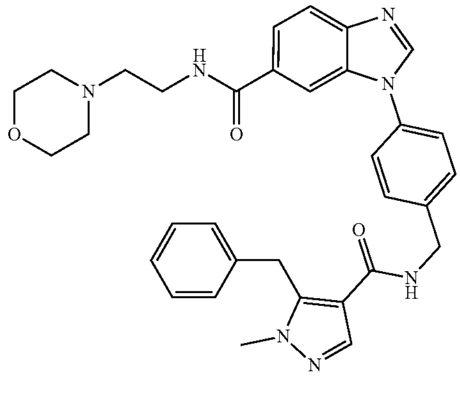 [SMILES: Cn1ncc(C(=O)NCc2ccc(-n3cnc4ccc(C(=O)NCCN5CCOCC5)cc43)cc2)c1Cc1ccccc1]

TABLE A-continued
QY-11-68B
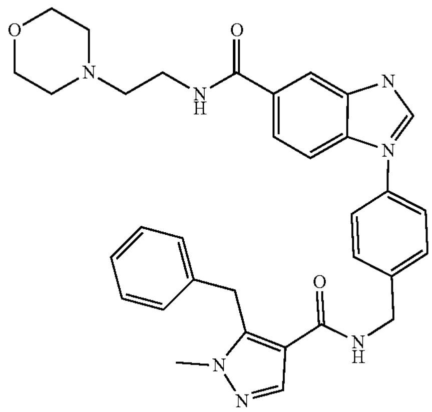
QY-11-69A
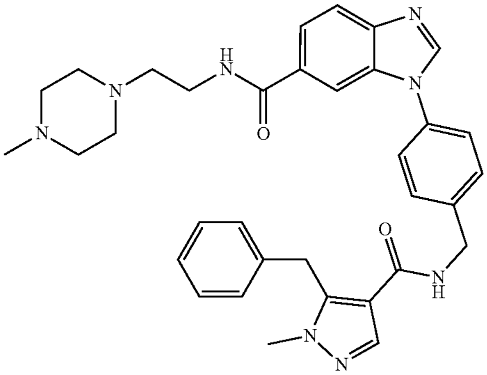 [SMILES: CN1CCN(CCNC(=O)c2ccc3ncn(-c4ccc(CNC(=O)c5cnn(C)c5Cc5ccccc5)cc4)c3c2)CC1]
QY-11-69B
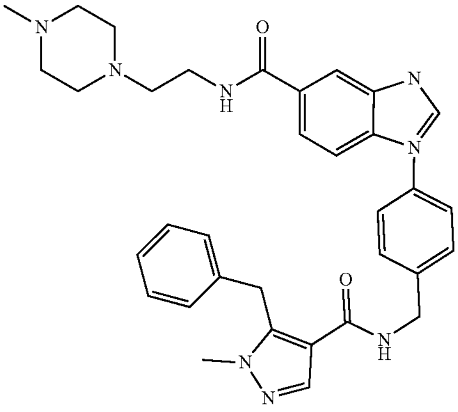
QY-11-74A
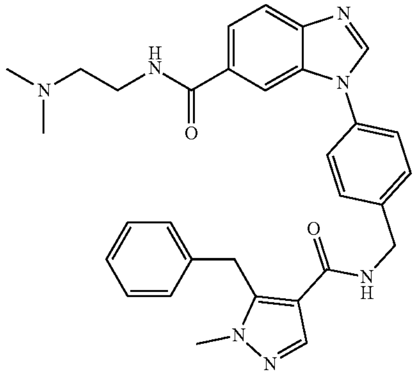 [SMILES: CN(C)CCNC(=O)c1ccc2ncn(-c3ccc(CNC(=O)c4cnn(C)c4Cc4ccccc4)cc3)c2c1]

TABLE A-continued
QY-11-74B
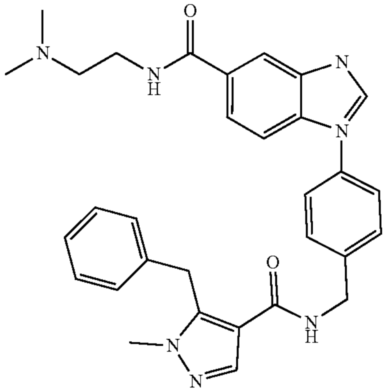
QY-11-102A
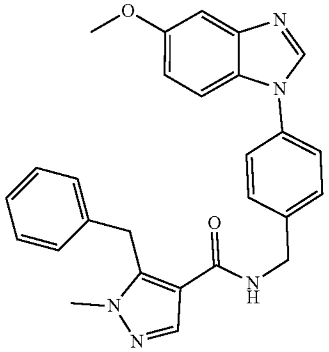 [SMILES: COc1ccc2c(c1)ncn2-c1ccc(CNC(=O)c2cnn(C)c2Cc2ccccc2)cc1]
QY-11-102B
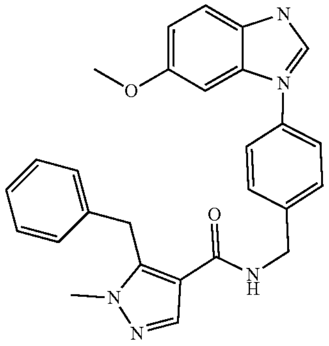
QY-11-104
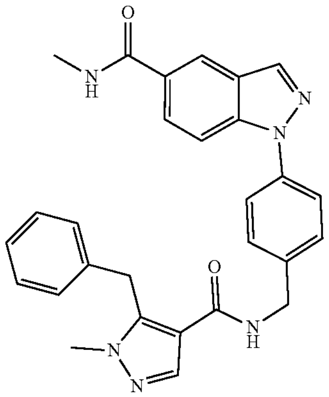 [SMILES: CNC(=O)c1ccc2c(cnn2-c2ccc(CNC(=O)c3cnn(C)c3Cc3ccccc3)cc2)c1]

TABLE A-continued
QY-12-4
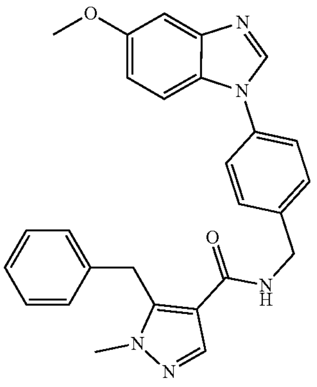 [SMILES: COc1ccc2c(c1)ncn2-c1ccc(CNC(=O)c2cnn(C)c2Cc2ccccc2)cc1]
QY-12-31
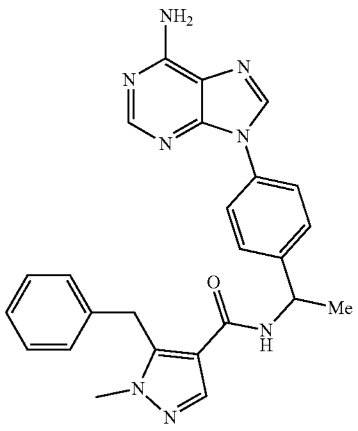 [SMILES: CC(NC(=O)c1cnn(C)c1Cc1ccccc1)c1ccc(-n2cnc3c(N)ncnc32)cc1]
QY-12-35
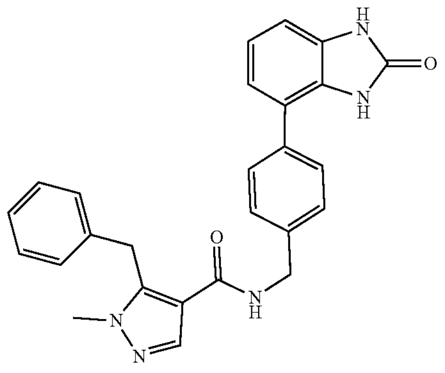 [SMILES: Cn1ncc(C(=O)NCc2ccc(-c3cccc4[nH]c(=O)[nH]c34)cc2)c1Cc1ccccc1]
QY-12-39
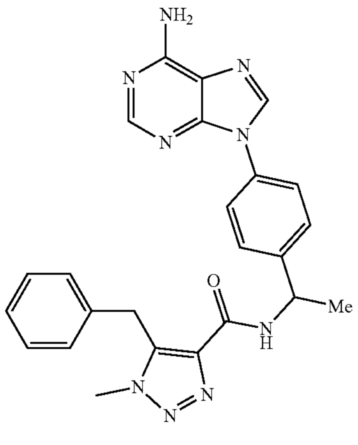 [SMILES: CC(NC(=O)c1nnn(C)c1Cc1ccccc1)c1ccc(-n2cnc3c(N)ncnc32)cc1]

TABLE A-continued
QY-12-47
(QY-12-40)
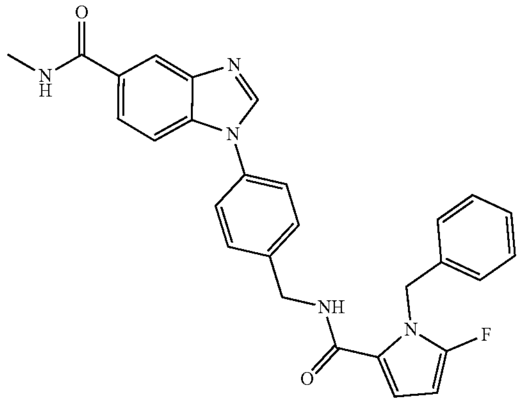 [SMILES: CNC(=O)c1ccc2c(c1)ncn2-c1ccc(CNC(=O)c2ccc(F)n2Cc2ccccc2)cc1]
QY-12-51
(QY-12-58)
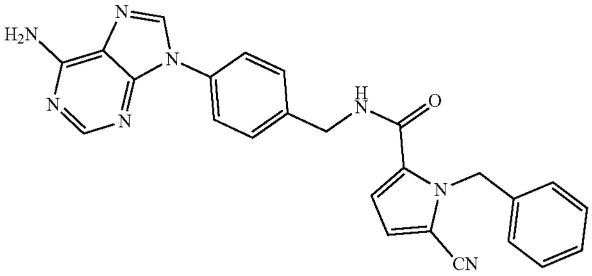 [SMILES: N#Cc1ccc(C(=O)NCc2ccc(-n3cnc4c(N)ncnc43)cc2)n1Cc1ccccc1]
ZSQ-22-96
(ZSQ-22-88)
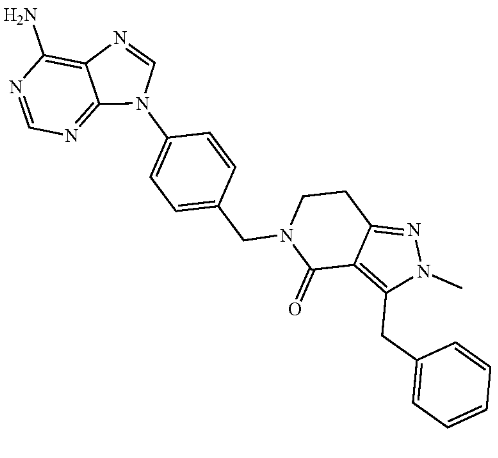 [SMILES: Cn1nc2c(c1Cc1ccccc1)C(=O)N(Cc1ccc(-n3cnc4c(N)ncnc43)cc1)CC2]
QY-12-66
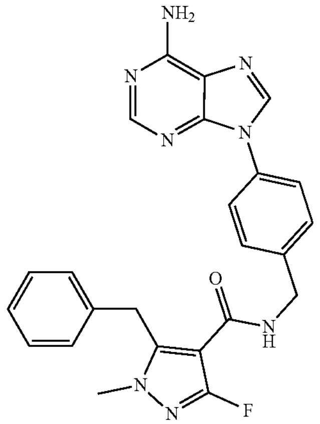 [SMILES: Cn1nc(F)c(C(=O)NCc2ccc(-n3cnc4c(N)ncnc43)cc2)c1Cc1ccccc1]

TABLE A-continued
QY-12-90
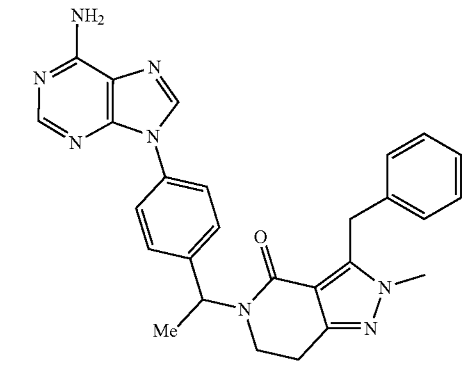 [SMILES: CC(c1ccc(-n2cnc3c(N)ncnc32)cc1)N1CCc2nn(C)c(Cc3ccccc3)c2C1=O]
QY-12-97
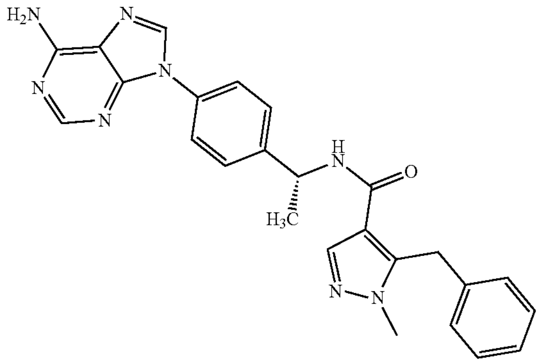 [SMILES: C[C@@H](NC(=O)c1cnn(C)c1Cc1ccccc1)c1ccc(-n2cnc3c(N)ncnc32)cc1]
QY-12-100
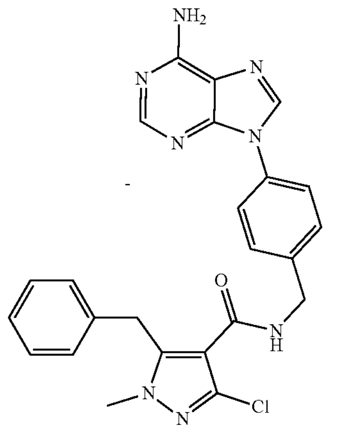 [SMILES: Cn1nc(Cl)c(C(=O)NCc2ccc(-n3cnc4c(N)ncnc43)cc2)c1Cc1ccccc1]
QY-12-102
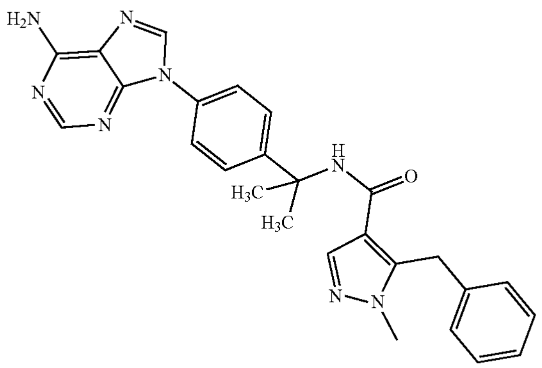 [SMILES: Cn1ncc(C(=O)NC(C)(C)c2ccc(-n3cnc4c(N)ncnc43)cc2)c1Cc1ccccc1]

TABLE A-continued
QY-13-19
(QY-12-59)
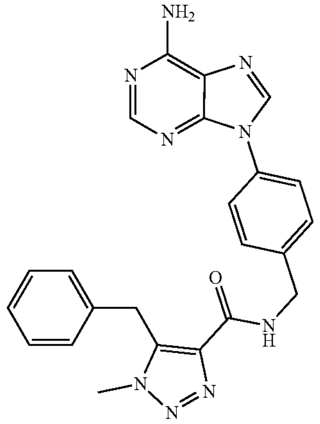 [SMILES: Cn1nnc(C(=O)NCc2ccc(-n3cnc4c(N)ncnc43)cc2)c1Cc1ccccc1]
QY-13-29
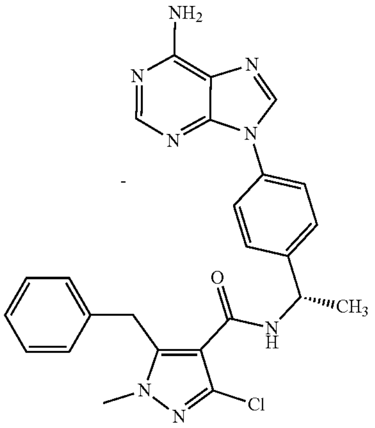 [SMILES: C[C@H](NC(=O)c1c(Cl)nn(C)c1Cc1ccccc1)c1ccc(-n2cnc3c(N)ncnc32)cc1]
QY-13-31
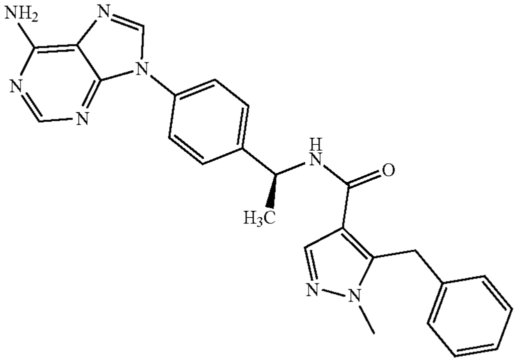 [SMILES: C[C@H](NC(=O)c1cnn(C)c1Cc1ccccc1)c1ccc(-n2cnc3c(N)ncnc32)cc1]
QY-13-33
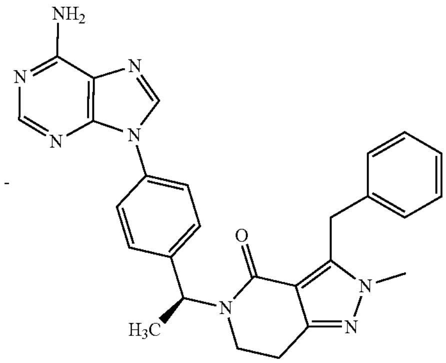 [SMILES: C[C@@H](c1ccc(-n2cnc3c(N)ncnc32)cc1)N1CCc2nn(C)c(Cc3ccccc3)c2C1=O]

TABLE A-continued
QY-13-50
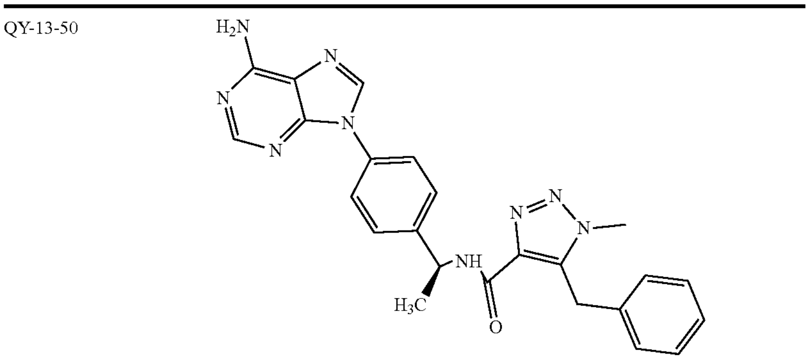
QY-15-22
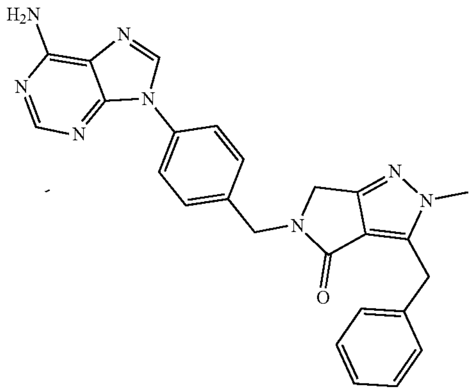 [SMILES: Cn1nc2c(c1Cc1ccccc1)C(=O)N(Cc1ccc(-n3cnc4c(N)ncnc43)cc1)C2]
QY-15-59
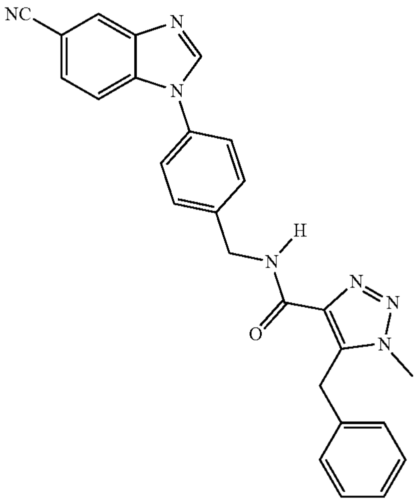 [SMILES: Cn1nnc(C(=O)NCc2ccc(-n3cnc4cc(C#N)ccc43)cc2)c1Cc1ccccc1]

TABLE A-continued
QY-15-81
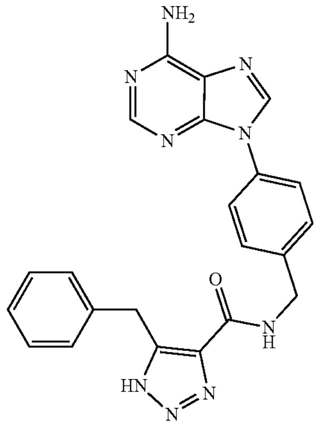 [SMILES: Nc1ncnc2c1ncn2-c1ccc(CNC(=O)c2nn[nH]c2Cc2ccccc2)cc1]
QY-15-84
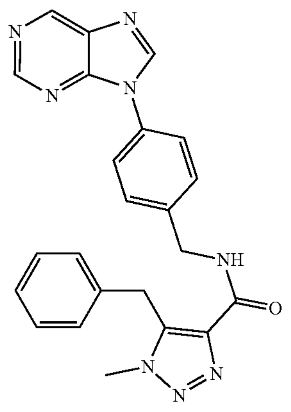 [SMILES: Cn1nnc(C(=O)NCc2ccc(-n3cnc4cncnc43)cc2)c1Cc1ccccc1]
QY-15-85
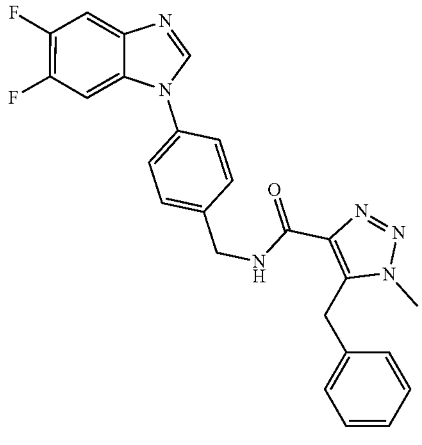 [SMILES: Cn1nnc(C(=O)NCc2ccc(-n3cnc4cc(F)c(F)cc43)cc2)c1Cc1ccccc1]

TABLE A-continued
| | |
|---|---|
| QY-15-86 | 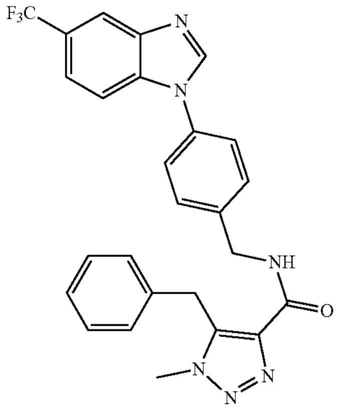 [SMILES: Cn1nnc(C(=O)NCc2ccc(-n3cnc4cc(C(F)(F)F)ccc43)cc2)c1Cc1ccccc1] |
| QY-15-87 | 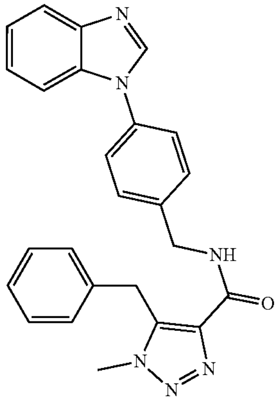 [SMILES: Cn1nnc(C(=O)NCc2ccc(-n3cnc4ccccc43)cc2)c1Cc1ccccc1] |
| ET-0934 | 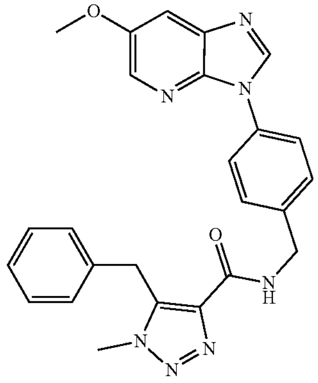 [SMILES: COc1cnc2c(c1)ncn2-c1ccc(CNC(=O)c2nnn(C)c2Cc2ccccc2)cc1] |
| ET-0935 | 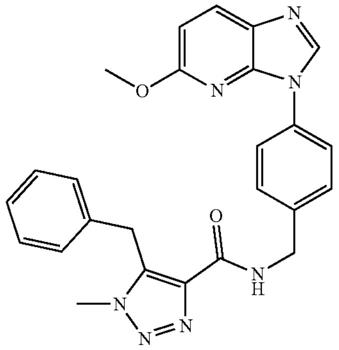 [SMILES: COc1ccc2ncn(-c3ccc(CNC(=O)c4nnn(C)c4Cc4ccccc4)cc3)c2n1] |

The NMR data for the compounds shown in Table A were as follows:

QY-5-35: $^1$H NMR (400 MH-z, DMSO-d6) δ 10.93 (s, 1H), 8.83 (s, 1H), 8.55 (dd, J=7.2, 4.5 Hz, 1H), 8.42 (m, 1H), 8.31 (d, J=1.1 Hz, 0.5H), 8.10 (s, 0.5H), 7.88-7.84 (m, 1H), 7.69-7.63 (m, 2H), 7.54 (m, 3H), 7.36 (d, J=8.1 Hz, 1H), 7.27 (t, J=2.2 Hz, 1H), 7.12-7.05 (m, 1H), 7.01-6.95 (m, 1H), 4.45-4.43 (m, 2H), 3.57 (d, J=5.9 Hz, 2H), 2.81 (dd, J=12.4, 4.5 Hz, 3H); ESI-MS m/z 438.0 $(M+H)^+$.

QY-5-40: $^1$H NMR (400 MHz, DMSO-d6) δ 8.79 (s, 1H), 8.53 (d, J=4.6 Hz, 1H), 8.31 (s, 1H), 7.90 (dd, J=8.6, 1.6 Hz, 1H), 7.70-7.62 (m, 4H), 7.51 (d, J=8.5 Hz, 3H), 4.63 (s, 2H), 3.96 (s, 2H), 3.13 (s, 3H), 2.83 (d, J=4.5 Hz, 3H); ESI-MS m/z 466.2 $(M+H)^+$.

QY-5-621 $^1$H NMR. (400 MHz, DMSO-d6) δ 10.13 (s, 1H), 8.79 (d, J=4.6 Hz, 1H), 8.58-8.51 (m, 1H), 8.31 (d, J=1.1 Hz, 1H), 7.90 (m, 1H), 7.66 (dd, J=11.9, 5.2 Hz, 3H), 7.54 (m, 2H), 7.32 (m, 5H), 4.74 (s, 2H), 3.92 (s, 2H), 2.81 (dci, J=11.6, 4.5 Hz, 3H); ESI-MS m/z 415.2 $(M+H)^+$.

QY-6-15: $^1$H NMR (400 MHz, DMSO-d6) δ 10.97 (d, J=9.0 Hz, 1H), 8.76 (m, 1H), 8.59-8.50 (m, 1H), 8.30 (d, J=1.1 Hz, 1H), 8.06 (m, 3H), 7.85-7.83 (m, 1H), 7.72 (dd, J=8.8, 6.7 Hz, 2H), 7.41-7.27 (m, 5H), 6.73 (d, J=2.1 Hz, 1H), 4.28 (s, 2H), 2.81 (m, 3H); ESI-MS m/z 452.1 $(M+H)^+$.

QY-6-16: $^1$H NMR (400 MHz, DMSO-d6) δ 9.43 (q, J=6.1 Hz, 1H), 8.82 (m, 1H), 8.54 (d, J=4.6 Hz, 1H), 8.30 (d, J=1.1 Hz, 1H), 8.08 (s, 1H), 7.90-7.84 (m, 1H), 7.67 (dd, J=8.1, 2.0 Hz, 2H), 7.57 (t, J=9.1 Hz, 2H), 7.40-7.24 (m, 5H), 6.59 (d, J=2.4 Hz, 1H), 4.53 (t, J=5.6 Hz, 2H), 4.23 (s, 2H), 2.80 (m, 3H); ESI-MS m/z 466.2 $(M+H)^+$.

QY-7-2A: 1H NMR (400 MHz, DMSO-d6) δ 9.06 (t, J=4.9 Hz, 1H), 8.90 (m, 1H), 8.56 (d, J=4.5 Hz, 1H), 8.31 (d, J=1.1 Hz, 1H), 7.91-7.86 (m, 1H), 7.69 (t, J=8.1 Hz, 3H), 7.56 (t, J=9.1 Hz, 2H), 7.26 (m, 5H), 6.68 (d, J=3.1 Hz, 1H), 4.50 (t, J=5.5 Hz, 2H), 4.03 (d, J=1.5 Hz, 3H), 3.89 (s, 2H), 2.80 (dd, J=13.9, 4.5 Hz, 3H); ESI-MS m/z 479.1 $(M+H)^+$.

QY-7-2B: $^1$H NMR (400 MHz, DMSO-d6) δ 8.85 (s, 1H), 8.77 (t, J=6.4 Hz, 1H), 8.55 (d, J=4.5 Hz, 1H), 8.31 (d, J=1.1 Hz, 1H), 7.91-7.86 (m, 1H), 7.72-7.63 (m, 3H), 7.56 (t, J=9.3 Hz, 2H), 7.34 (t, J=7.3 Hz, 2H), 7.26 (m, 3H), 6.37 (d, J=1.7 Hz, 1H), 4.49 (t, J=5.7 Hz, 2H), 4.07 (s, 2H), 3.78 (s, 3H), 2.80 (m, 3H); ESI-MS m/z 479.1 $(M+H)^+$.

QY-7-14: $^1$H NMR (400 MHz, DMSO-d6) δ 9.67 (t, J=6.1 Hz, 1H), 8.81 (m, 1H), 8.54 (d, J=4.5 Hz, 1H), 8.30 (d, J=1.1 Hz, 1H), 7.90-7.84 (m, 1H), 7.73-7.65 (m, 3H), 7.59 (t, J=9.1 Hz, 2H), 7.41-7.32 (m, 5H), 4.55 (t, J=5.6 Hz, 2H), 4.46 (s, 2H), 2.80 (dd, J=13.9, 4.5 Hz, 3H); ESI-MS m/z 467.0 $(M+H)^+$.

QY-7-32: $^1$H NMR (400 MHz, DMSO-d6) δ 9.96 (d, J=6.0 Hz, 1H), 8.75 (d, J=12.2 Hz, 1H), 8.51 (s, 1H), 8.08 (d, J 12.0 Hz, 1H), 7.84 (d, J=12.0 Hz, 2H), 7.74-7.54 (m, 41), 7.42-7.28 (m, 4H), 4.57 (s, 2H), 4.39 (d, J=12.1 Hz, 2H), 2.80 (d, J=7.7 Hz, 3H); ESI-MS m/z 467.1 $(M+H)^+$.

QY-7-65: $^1$H NMR (400 MHz, DMSO-d6) δ 8.78 (s, 1H), 8.57-8.51 (m, 1H), 8.07 (d, J=14.7 Hz, 1H), 7.86-7.81 (m, 2H), 7.67 (d, J=8.4 Hz, 1H), 7.54 (dd, J=12.0, 8.5 Hz, 2H), 7.41 (t, J=7.4 Hz, 1H), 7.23 (m, 5H), 5.27 (d, J=6.4 Hz, 0.5H), 5.09 (dd, J=7.9, 2.3 Hz, 0.5H), 3.90 (m, 2H), 3.72-3.58 (m, 2H), 2.79 (d, J=4.1 Hz, 3H), 2.44-2.20 (m, 2H), 1.83 (dd, J=7.5, 2.9 Hz, 2H); ESI-MS m/z 439.1 $(M+H)^+$.

QY-8-7: $^1$H NMR (400 MHz, DMSO-d6) δ 8.73 (d, J=13.6 Hz, 1H), 8.51 (d, J=4.5 Hz, 1H), 8.30 (d, J=1.1 Hz, 1H), 7.85 (m, 1H), 7.77 (s, 1H), 7.68 (dt, J=8.4, 6.6 Hz, 3H), 7.57 (t, J=8.6 Hz, 2H), 7.39-7.29 (m, 5H), 5.37 (s, 2H), 4.76 (d, J=5.0 Hz, 2H), 3.56 (m, 2H), 2.84-2.76 (m, 5H); ESI-MS m/z 491.1 $(M+H)^+$.

QY-8-30: $^1$H NMR (400 MHz, DMSO-d6) δ 9.49 (t, J=6.3 Hz, 1H), 8.60 (s, 2H), 8.34 (s, 1H), 7.75 (d, J=3.6 Hz, 1H), 7.66 (d, J=8.5 Hz, 2H), 7.48 (d, J=8.5 Hz, 2H), 7.31 (m, 5H), 7.16 (s, 1H), 7.05 (d, J=3.6 Hz, 1H), 4.47 (d, J=6.2 Hz, 2H), 4.14 (s, 2H); ESI-MS m/z 425.2 $(M+H)^+$.

QY-8-31: $^1$H NMR (400 MHz, DMSO-d6) δ 9.62 (t, J=6.2 Hz, 1H), 8.60 (s, 2H), 8.34 (s, 1H), 7.77 (d, J=3.6 Hz, 1H), 7.71-7.65 (m, 2H), 7.50 (d, J=8.5 Hz, 2H), 7.42-7.27 (m, 5H), 7.05 (d, J=3.6 Hz, 1H), 4.51 (d, J=6.2 Hz, 2H), 4.45 (s, 2H); ESI-MS m/z 426.1 $(M+H)^+$.

QY-8-42: $^1$H NMR (400 MHz, DMSO-d6) δ 8.81 (s, 1H), 8.53 (d, J=8.6 Hz, 2H), 8.30 (d, J=1.2 Hz, 1H), 7.85 (s, 1H), 7.64 (m, 5H), 7.07-6.90 (m, 4H), 4.95 (d, J=5.7 Hz, 1H), 3.64 (d, J=7.2 Hz, 2H), 3.51 (m, 2H), 2.80 (dd, J=12.2, 4.5 Hz, 3H), 2.23 (d, J=3.2 Hz, 3H), 2.00 (m, 1H), 1.66 (m, 2H), 1.47 (d, J=5.5 Hz, 1H), 1.40 (s, 3H), 1.33 (s, 3H); ESI-MS m/z 538.1 $(M+H)^+$.

QY-8-43: $^1$H NMR (400 MHz, DMSO-d6) δ 8.72 (t, J=6.3 Hz, 1H), 8.67 (s, 1H), 8.33 (s, 1H), 7.76 (d, J=8.5 Hz, 2H), 7.49 (d, J=8.5 Hz, 2H), 7.34 (t, J=7.3 Hz, 2H), 7.28-7.19 (m, 3H), 6.36 (s, 1H), 4.46 (d, J=6.3 Hz, 2H), 4.06 (s, 2H), 3.77 (s, 3H); ESI-MS m/z 439.1 $(M+H)^+$.

QY-8-48: $^1$H NMR (400 MHz, DMSO-d6) δ 9.38 (t, J=6.2 Hz, 1H), 8.60 (s, 2H), 8.34 (s, 1H), 7.76 (d, J=3.6 Hz, 1H), 7.70-7.64 (m, 2H), 7.49 (d, J=8.5 Hz, 2H), 7.38-7.26 (m, 5H), 7.05 (d, J=3.6 Hz, 1H), 6.57 (s, 1H), 4.49 (d, J=6.2 Hz, 2H), 4.22 (s, 2H); ESI-MS m/z 425.2 $(M+H)^+$.

QY-8-58: $^1$H NMR (400 MHz, DMSO-d6) δ 9.69 (t, J=6.2 Hz, 1H), 8.77 (s, 2H), 8.34 (s, 1H), 7.76 (d, J=3.6 Hz, 1H), 7.67 (d, J=8.5 Hz, 2H), 7.51 (d, J=8.5 Hz, 2H), 7.44-7.38 (m, 5H), 7.05 (d, J=3.6 Hz, 1H), 6.03 (s, 2H), 4.54 (d, J=6.2 Hz, 2H); ESI-MS m/z 426.1 $(M+H)^+$.

QY-8-60: $^1$H NMR (400 MHz, DMSO-d6) δ 8.33 (s, 1H), 7.74 (d, J=3.6 Hz, 1H), 7.66 (d, J=8.4 Hz, 2H), 7.49 (d, J=8.4 Hz, 2H), 7.34-7.20 (m, 6H), 7.03 (d, J=3.6 Hz, 1H), 4.48 (d, J=6.2 Hz, 2H), 4.11 (s, 2H); ESI-MS m/z 425.2 $(M+H)^+$.

QY-9-33: $^1$H NMR (400 MHz, DMSO-d6) δ 8.70 (t, J=6.3 Hz, 1H), 8.36 (s, 1H), 7.78 (d, J=3.6 Hz, 1H), 7.64 (d, J=8.3 Hz, 2H), 7.48 (d, J=8.3 Hz, 2H), 7.33 (d, J=6.9 Hz, 2H), 7.25 (t, J=6.8 Hz, 3H), 7.07 (d, J=3.6 Hz, 1H), 6.37 (s, 1H), 4.46 (d, J=6.2 Hz, 2H), 4.13-4.06 (m, 4H), 1.23 (d, J=7.2 Hz, 3H); ESI-MS m/z 452.1 $(M+H)^+$.

QY-9-34: $^1$H NMR (400 MHz, DMSO-d6) δ 8.74-8.67 (m, 2H), 8.35 (s, 1H), 7.78-7.72 (m, 2H), 7.51 (d, J=8.5 Hz, 2H), 7.36-7.31 (m, 2H), 7.25 (dd, J=7.2, 5.4 Hz, 3H), 6.37 (s, 1H), 4.46 (d, J=6.2 Hz, 2H), 4.10 (m, 4H), 1.23 (d, J=7.1 Hz, 3H); ESI-MS m/z 453.1 $(M+H)^+$.

QY-9-41: $^1$H NMR (400 MHz, DMSO-d6) δ 8.36 (s, 1H), 7.81-7.76 (m, 2H), 7.69 (d, J=8.5 Hz, 2H), 7.50 (d, J=8.5 Hz, 2H), 7.38-7.28 (m, 5H), 7.07 (d, J=3.6 Hz, 1H), 5.37 (s, 2H), 4.72 (s, 2H), 3.52 (t, J=6.6 Hz, 2H), 2.77 (t, J=6.6 Hz, 2H); ESI-MS m/z 450.1 $(M+H)^+$.

QY-9-50: $^1$H NMR (400 MHz, DMSO-d6) δ 8.71 (s, 1H), 8.35 (s, 1H), 7.84-7.76 (m, 3H), 7.53 (d, J=8.5 Hz, 2H), 7.39-7.28 (m, 5H), 5.37 (s, 2H), 4.73 (s, 2H), 3.52 (t, J=6.6 Hz, 2H), 2.77 (t, J=6.6 Hz, 2H); ESI-MS m/z 451.2 $(M+H)^+$.

QY-9-69: $^1$H NMR (400 MHz, DMSO-d6) δ 8.74 (t, J=5.9 Hz, 1H), 8.36 (s, 1H), 7.78 (d, J=3.6 Hz, 1H), 7.69-7.60 (m, 2H), 7.44 (m, 3H), 7.35-7.27 (m, 2H), 7.25 (dd, J=8.2, 1.0 Hz, 1H), 7.07 (d, J=3.6 Hz, 1H), 4.35 (d, J=5.9 Hz, 2H), 3.59 (s, 2H); ESI-MS m/z 442.1 $(M+H)^+$.

QY-9-70: $^1$H NMR (400 MHz, DMSO-d6) δ 8.75 (t, J=5.9 Hz, 1H), 8.71 (s, 1H), 8.35 (s, 1H), 7.78 (d, J=8.5 Hz, 2H), 7.49-7.42 (m, 3H), 7.35-7.29 (m, 2H), 7.25 (dd, J=8.2, 1.0 Hz, 1H), 4.36 (d, J=5.9 Hz, 2H), 3.59 (s, 2H); ESI-MS m/z 443.1 $(M+H^+$.

QY-9-77: $^1$H NMR (400 MHz, DMSO-d6) δ 14.82 (s, 1H), 9.51 (t, J=6.3 Hz, 1H), 8.93 (d, J=2.1 Hz, 1H), 8.80 (d, J=2.0 Hz, 1H), 8.68 (s, 1H), 8.32 (s, 1H), 7.80 (d, J=8.5 Hz, 2H), 7.59 (d, J=8.5 Hz, 2H), 4.59 (d, J=6.2 Hz, 2H); ESI-MS m/z 504.1 $(M+H)^+$.

QY-10-21: $^1$H NMR (400 MHz, DMSO-d6) δ 8.75 (s, 1H), 8.35 (s, 1H), 7.77 (d, J=3.6 Hz, 1H), 7.64 (d, J=8.5 Hz, 2H), 7.47 (d, J=8.5 Hz, 2H), 7.34 (t, J=7.3 Hz, 2H), 7.27-7.21 (m, 3H), 7.06 (d, J=3.6 Hz, 1H), 6.36 (s, 1H), 4.44 (d, J=6.0 Hz, 2H), 4.06 (s, 2H), 3.77 (s, 3H); ESI-MS m/z 438.1 $(M+H)^+$.

QY-10-39: $^1$H NMR (400 MHz, DMSO-d6) δ 8.71 (t, J=6.0 Hz, 1H), 8.35 (s, 1H), 7.99 (s, 1H), 7.78 (d, J=3.6 Hz, 1H), 7.70-7.65 (m, 2H), 7.49 (d, J=8.5 Hz, 2H), 7.31-7.26 (m, 2H), 7.19 (m, 3H), 7.07 (d, J=3.6 Hz, 1H), 4.50 (d, J=5.8 Hz, 2H), 4.46 (s, 2H), 3.66 (s, 3H); ESI-MS m/z 438.1 $(M+H)^+$.

QY-10-40: $^1$H NMR (400 MHz, DMSO-d6) δ 8.76-8.66 (m, 2H), 8.35 (s, 1H), 7.99 (s, 1H), 7.82-7.77 (m, 2H), 7.52 (d, J=8.6 Hz, 2H), 7.31-7.25 (m, 2H), 7.21-7.17 (m, 3H), 4.51 (d, J=5.8 Hz, 2H), 4.46 (s, 2H), 3.66 (s, 3H); ESI-MS m/z 439.1 $(M+H)^+$.

QY-10-65: $^1$H NMR (400 MHz, DMSO-d6) δ 8.76-8.68 (m, 2H), 8.36 (s, 1H), 8.04 (s, 1H), 7.82-7.77 (m, 2H), 7.53 (d, J=8.5 Hz, 2H), 7.31-7.25 (m, 2H), 7.19 (dd, J=7.3, 3.5 Hz, 3H), 4.51 (d, J=5.7 Hz, 2H), 4.48 (s, 2H), 3.98 (q, J=7.2 Hz, 2H), 1.07 (t, J=7.2 Hz, 3H); ESI-MS m/z 453.2 $(M+H)^+$.

QY-10-73: $^1$H NMR (400 MHz, DMSO-d6) δ 8.85-8.72 (m, 2H), 8.52 (d, J=4.5 Hz, 1H), 8.31 (d, J=1.2 Hz, 1H), 8.01 (d, J=3.3 Hz, 1H), 7.90-7.84 (m, 1H), 7.68 (q, J=7.5 Hz, 3H), 7.58 (m, 2H), 7.32-7.26 (m, 2H), 7.22-7.17 (m, 3H), 4.54 (t, J=5.2 Hz, 2H), 4.47 (s, 2H), 3.66 (s, 3H), 2.81 (m, 3H); ESI-MS m/z 479.1 $(M+H)^+$.

QY-11-68A: $^1$H NMR (400 MHz, DMSO-d6) δ 8.79 (m, 2H), 8.73 (s, 1H), 8.08 (s, 1H), 8.01 (s, 1H), 7.87 (s, 2H), 7.68 (d, J=8.4 Hz, 2H), 7.59 (d, J=8.4 Hz, 2H), 7.32-7.26 (m, 2H), 7.20 (dd, J=5.1, 2.8 Hz, 3H), 4.55 (d, J=5.9 Hz, 2H), 4.47 (s, 2H), 3.66 (s, 3H), 3.66-3.46 (m, 8H), 3.32 (d, J=5.7 Hz, 2H), 3.13 (s, 2H); ESI-MS m/z 578.2 $(M+H)^+$.

QY-11-68B: $^1$H NMR (400 MHz, DMSO-d6) δ 8.78 (m, 2H), 8.70 (s, 1H), 8.36 (d, J=1.2 Hz, 1H), 8.01 (s, 1H), 7.89 (dd, J=8.6, 1.5 Hz, 1H), 7.72-7.65 (m, 3H), 7.57 (d, J=8.4 Hz, 2H), 7.32-7.26 (m, 2H), 7.21-7.16 (m, 3H), 4.54 (d, J=6.0 Hz, 2H), 4.47 (s, 2H), 4.02 (m, 2H), 3.68 (s, 2H), 3.66 (s, 3H), 3.58 (m, 4H), 3.37 (d, J=5.6 Hz, 2H), 3.17 (s, 2H); ESI-MS m/z 578.2 $(M+H)^+$.

QY-11-69A: $^1$H NMR (400 MHz, DMSO-d6) δ 8.77 (t, J=6.1 Hz, 1H), 8.73 (s, 1H), 8.66 (s, 1H), 8.07 (s, 1H), 8.01 (s, 1H), 7.85 (d, J=0.8 Hz, 2H), 7.68 (d, J=8.4 Hz, 2H), 7.59 (d, J=8.4 Hz, 2H), 7.32-7.26 (m, 2H), 7.22-7.17 (m, 3H), 4.55 (d, J=5.9 Hz, 2H), 4.47 (s, 2H), 3.84 (s, 8H), 3.66 (s, 3H), 3.50 (d, J=5.4 Hz, 2H), 2.90 (s, 2H), 2.78 (s, 3H); ESI-MS m/z 591.2 $(M+H)^+$.

QY-11-69B: $^1$H NMR (400 MHz, DMSO-d6) δ 8.76 (t, J=6.1 Hz, 1H), 8.71 (s, 1H), 8.67 (s, 1H), 8.34 (d, J=1.2 Hz, 1H), 8.01 (s, 1H), 7.89 (m, 1H), 7.70-7.65 (m, 3H), 7.57 (m, 2H), 7.29 (m, 2H), 7.19 (dd, J=5.0, 2.8 Hz, 3H), 4.54 (d, J=5.9 Hz, 2H), 4.47 (s, 2H), 4.06 (s, 8H), 3.66 (s, 3H), 3.56 (d, J=5.7 Hz, 2H), 3.01 (s, 2H), 2.81 (s, 3H); ESI-MS m/z 591.2 $(M+H)^+$.

QY-11-74A: $^1$H NMR (400 MHz, DMSO-d6) δ 8.77 (t, J=5.9 Hz, 2H), 8.72 (s, 1H), 8.08 (s, 1H), 8.01 (s, 1H), 7.87 (s, 2H), 7.67 (d, J=8.5 Hz, 2H), 7.59 (d, J=8.5 Hz, 2H), 7.31-7.25 (m, 2H), 7.20 (m, 3H), 4.55 (d, J=6.0 Hz, 2H), 4.47 (s, 2H), 3.66 (s, 3H), 3.61 (d, J=5.8 Hz, 2H), 3.26 (m, 2H), 2.84 (d, J=4.8 Hz, 6H); ESI-MS m/z 536.2 $(M+H)^+$.

QY-11-74B: $^1$H NMR (400 MHz, DMSO-d6) δ 8.76 (t, J=5.8 Hz, 2H), 8.70 (s, 1H), 8.36 (d, J=1.2 Hz, 1H), 8.01 (s, 1H), 7.89 (dd, J=8.6, 1.5 Hz, 1H), 7.71-7.65 (m, 3H), 7.57 (d, J=8.5 Hz, 2H), 7.29 (dd, J=10.4, 4.4 Hz, 2H), 7.19 (dd, J=5.0, 2.8 Hz, 3H), 4.54 (d, J=6.0 Hz, 2H), 4.47 (s, 2H), 3.66 (s, 3H), 3.64 (s, 2H), 3.31 (dd, J=11.5, 5.8 Hz, 2H), 2.88 (d, J=4.8 Hz, 6H); ESI-MS m/z 536.2 $(M+H)^+$.

QY-11-75: $^1$H NMR (400 MHz, DMSO-d6) δ 9.13 (s, 1H), 8.75 (t, J=6.1 Hz, 1H), 8.02 (s, 1H), 7.83 (d, J=8.2 Hz, 2H), 7.53 (d, J=8.2 Hz, 2H), 7.44 (s, 1H), 7.34 (s, 1H), 7.28 (m, 2H), 7.20 (d, J=7.4 Hz, 3H), 4.58 (d, J=6.0 Hz, 2H), 4.48 (s, 21H), 4.01 (s, 3H), 3.83 (s, 3H), 3.67 (s, 3H); ESI-MS m/z 494.1 $(M+H)^+$.

QY-11-76

$^1$H NMR (400 MHz, DMSO-d6) δ 8.92 (s, 1H), 8.76 (t, J=6.1 Hz, 1H), 8.01 (s, 1H), 7.71 (d, J=8.5 Hz, 2H), 7.58 (d, J=8.5 Hz, 2H), 7.35 (s, 1H), 7.32-7.25 (m, 2H), 7.22-7.16 (m, 3H), 7.10 (s, 1H), 4.54 (d, J=6.0 Hz, 2H), 4.47 (s, 2H), 3.86 (s, 3H), 3.81 (s, 3H), 3.66 (s, 3H); ESI-MS m/z 482.1 $(M+H)^+$.

QY-11-77: $^1$H NMR (400 MHz, DMSO-d6) (400 MHz, DMSO) δ 8.80-8.74 (m, 2H), 8.61 (s, 2H), 8.00 (s, 1H), 7.75 (d, J=7.1 Hz, 1H), 7.65 (d, J=8.5 Hz, 2H), 7.58 (d, J=8.5 Hz, 2H), 7.31-7.25 (m, 2H), 7.19 (t, J=6.3 Hz, 3H), 7.08 (d, J=7.1 Hz, 1H), 4.54 (d, J=6.0 Hz, 2H), 4.46 (s, 2H), 3.66 (s, 3H); ESI-MS m/z 438.1 $(M+H)^+$.

QY-11-78: $^1$H NMR (400 MHz, DMSO-d6) δ 8.69 (t, J=6.1 Hz, 1H), 8.45 (s, 1H), 8.39 (s, 1H), 8.07 (d, J=8.6 Hz, 2H), 7.99 (s, 1H), 7.48 (d, J=8.6 Hz, 2H), 7.28 (m, 2H), 7.19 (m, 3H), 4.49 (d, J=5.9 Hz, 2H), 4.46 (s, 2H), 3.66 (s, 3H); ESI-MS m/z 439.1 $(M+H)^+$.

QY-11-79: $^1$H NMR (400 MHz, DMSO-d6) δ 11.99 (s, 1H), 8.71 (t, J=6.0 Hz, 1H), 8.33 (d, J=5.1 Hz, 1H), 8.00 (s, 1H), 7.77 (d, J=8.2 Hz, 2H), 7.62-7.57 (m, 1H), 7.49 (d, J=8.2 Hz, 2H), 7.33-7.24 (m, 3H), 7.23-7.16 (m, 3H), 6.67 (dd, J=3.5, 1.8 Hz, 1H), 4.53 (d, J=6.0 Hz, 2H), 4.47 (s, 2H), 3.66 (s, 3H); ESI-MS m/z 422.1 $(M+H)^+$.

QY-11-80: $^1$H NMR (400 MHz, DMSO-d6) δ 12.55 (s, 1H), 8.91 (s, 1H), 8.74 (t, J=6.0 Hz, 1H), 8.13 (d, J=8.3 Hz, 2H), 8.01 (s, 1H), 7.79-7.73 (m, 1H), 7.54 (d, J=8.3 Hz, 2H), 7.28 (m, 2H), 7.23-7.17 (m, 3H), 6.96 (m, 1H), 4.55 (d, J=5.9 Hz, 2H), 4.47 (s, 2H), 3.66 (s, 3H); ESI-MS m/z 423.2 $(M+H)^+$.

QY-11-102A: $^1$H NMR (400 MHz, DMSO-d6) δ 9.02 (s, 1H), 8.75 (t, J=6.0 Hz, 1H), 8.00 (d, J=2.3 Hz, 1H), 7.71-7.67 (m, 2H), 7.57 (dd, J=8.6, 2.1 Hz, 3H), 7.34 (d, J=2.3 Hz, 1H), 7.30-7.26 (m, 2H), 7.21-7.17 (m, 3H), 7.08-7.05 (m, 1H), 4.54 (d, J=5.9 Hz, 2H), 4.47 (s, 2H), 3.85 (s, 3H), 3.80 (s, 3H); ESI-MS m/z 452.1 $(M+H)^+$.

QY-11-102B: 1H NMR (400 MHz, DMSO-d6) δ 8.82 (s, 1H), 8.75 (t, J=6.0 Hz, 1H), 8.01 (s, 1H), 7.75-7.66 (m, 3H), 7.57 (d, J=8.5 Hz, 2H), 7.28 (m, 2H), 7.22-7.16 (m, 3H), 7.09-7.00 (m, 2H), 4.54 (d, J=6.0 Hz, 2H), 4.47 (s, 2H), 3.80 (s, 3H), 3.66 (s, 3H); ESI-MS m/z 452.1 $(M+H)^+$.

QY-11-104: $^1$H NMR (400 MHz, DMSO-d6) δ 9.26 (s, 1H), 8.72 (t, J=6.0 Hz, 1H), 8.47 (q, J=4.3 Hz, 1H), 8.33 (s, 1H), 8.07 (d, J=8.6 Hz, 2H), 8.00 (s, 1H), 7.79-7.72 (m, 2H), 7.52 (d, J=8.6 Hz, 2H), 7.29 (m, 2H), 7.20 (m, 3H), 4.52 (d, J=6.0 Hz, 2H), 4.47 (s, 2H), 3.66 (s, 3H), 2.82 (d, J=4.5 Hz, 3H); ESI-MS m/z 479.1 $(M+H)^+$.

QY-12-4: $^1$H NMR (400 MHz, DMSO-d6) δ 8.87 (s, 1H), 8.70 (t, J=6.0 Hz, 1H), 8.00 (t, J=4.3 Hz, 3H), 7.63 (m, 1H), 7.48 (m, 2H), 7.27 (d, J=7.2 Hz, 2H), 7.20 (m, 3H), 7.04-6.97 (m, 2H), 4.50 (d, J=6.0 Hz, 2H), 4.47 (s, 2H), 3.80 (s, 3H), 3.66 (s, 3H); ESI-MS m/z 452.1 $(M+H)^+$.

QY-12-31: $^1$H NMR (400 MHz, DMSO-d6) δ 8.54 (s, 1H), 8.46 (d, J=7.9 Hz, 1H), 8.19 (s, 1H), 8.08 (s, 1H), 7.87-7.76 (m, 2H), 7.60-7.50 (m, 2H), 7.39 (s, 2H), 7.32-7.22 (m, 2H), 7.22-7.10 (m, 3H), 5.20 (p, J=7.2 Hz, 1H), 4.50-4.24 (m, 2H), 3.64 (s, 3H), 1.50 (d, J=7.1 Hz, 3H); ESI-MS m/z 453.1 $(M+H)^+$.

QY-12-47: $^1$H NMR (400 MHz, DMSO-d6) δ 8.81-8.67 (m, 2H), 8.53 (q, J=4.5 Hz, 1H), 8.31 (d, J=1.5 Hz, 1H), 7.89 (dd, J=8.6, 1.7 Hz, 1H), 7.70-7.58 (m, 3H), 7.54-7.44 (m, 2H), 7.32 (dd, J=8.1, 6.5 Hz, 2H), 7.29-7.20 (m, 1H), 7.14-7.04 (m, 2H), 6.90 (dd, J=6.0, 4.3 Hz, 1H), 5.77 (t, J=4.1 Hz, 1H), 5.59 (s, 2H), 4.48 (d, J=6.0 Hz, 2H), 2.82 (d, J=4.5 Hz, 3H); ESI-MS m/z 482.2 $(M+H)^+$.

QY-12-51: $^1$H NMR (400 MHz, DMSO-d6) δ 9.19 (t, J=6.1 Hz, 1H), 8.56 (s, 1H), 8.20 (s, 1H), 7.87-7.67 (m, 2H), 7.47-7.38 (m, 4H), 7.38-7.23 (m, 3H), 7.14-7.05 (m, 3H), 7.01 (d, J=4.3 Hz, 1H), 5.76 (s, 2H), 4.48 (d, J=6.0 Hz, 2H); ESI-MS m/z 449.1 $(M+H)^+$.

QY-12-90: $^1$H NMR (400 MHz, DMSO-d6) δ 8.72 (s, 1H), 8.35 (s, 1H), 7.93-7.73 (m, 2H), 7.64-7.50 (m, 2H), 7.37-7.26 (m, 4H), 7.26-7.16 (m, 1H), 6.01 (q, J=7.0 Hz, 1H), 4.40 (d, J=3.3 Hz, 2H), 3.64 (s, 3H), 3.14 (m, 2H), 2.74 (m, 2H), 1.59 (d, J=7.1 Hz, 3H); ESI-MS m/z 479.2 $(M+H)^+$.

QY-12-97: $^1$H NMR (400 MHz, DMSO-d6) δ 8.70 (s, 1H), 8.48 (d, J=7.9 Hz, 1H), 8.35 (s, 1H), 8.08 (s, 1H), 7.84-7.69 (m, 2H), 7.64-7.53 (m, 2H), 7.31-7.22 (m, 2H), 7.21-7.08 (m, 3H), 5.20 (p, J=7.1 Hz, 1H), 4.57-4.20 (m, 2H), 3.65 (s, 3H), 1.51 (d, J=7.1 Hz, 3H); ESI-MS m/z 453.1 $(M+H)^+$.

QY-12-100: $^1$H NMR (400 MHz, DMSO-d6) δ 8.50 (s, 1H), 8.45 (t, J=6.0 Hz, 1H), 8.14 (s, 1H), 7.83-7.69 (m, 2H), 7.49-7.38 (m, 2H), 7.35 (s, 2H), 7.23 (dd, J=8.0, 6.6 Hz, 2H), 7.18-7.07 (m, 3H), 4.44 (d, J=6.0 Hz, 2H), 4.22 (s, 2H), 3.59 (s, 3H); ESI-MS m/z 473.2 $(M+H)^+$.

QY-12-102: $^1$H NMR (400 MHz, DMSO-d6) δ 8.70 (s, 1H), 8.35 (s, 1H), 8.10 (d, J=6.6 Hz, 2H), 7.78-7.64 (m, 2H), 7.62-7.48 (m, 2H), 7.26 (dd, J=8.0, 6.8 Hz, 2H), 7.20-7.14 (m, 1H), 7.14-7.08 (m, 2H), 4.33 (s, 21), 3.65 (s, 3H), 1.70 (s, 6H); ESI-MS m/z 467.2 $(M+H)^+$.

QY-13-19: $^1$H NMR (400 MHz, DMSO-d6) δ 9.30 (t, J=6.3 Hz, 1H), 8.71 (s, 1H), 8.35 (s, 1H), 7.83-7.70 (m, 2H), 7.55 (d, J=8.3 Hz, 2H), 7.37-7.26 (m, 2H), 7.27-7.14 (m, 3H), 4.54 (d, J=6.3 Hz, 2H), 4.47 (s, 2H), 3.90 (s, 3H); ESI-MS m/z 440.2 $(M+H)^+$.

QY-13-29: $^1$H NMR (400 MHz, DMSO-d6) δ 8.56 (s, 1H), 8.46 (d, J=7.8 Hz, 1H), 8.20 (s, 1H), 7.89-7.77 (m, 2H), 7.58 (d, J=8.5 Hz, 2H), 7.42 (s, 2H), 7.28 (m, 2H), 7.24-7.19 (m, 1H), 7.19-7.12 (m, 2H), 5.14 (p, J=7.1 Hz, 1H), 4.37-4.06 (m, 2H), 3.67 (s, 3H), 1.47 (d, J=7.0 Hz, 3H); ESI-MS m/z 487.1 $(M+H)^+$.

QY-13-31: $^1$H NMR (400 MHz, DMSO-d6) δ 8.55 (s, 1H), 8.48 (d, J=7.9 Hz, 1H), 8.19 (s, 1H), 8.08 (s, 1H), 7.86-7.74 (m, 2H), 7.60-7.51 (m, 2H), 7.41 (s, 2H), 7.27 (dd, J=8.0, 6.8 Hz, 2H), 7.20-7.12 (m, 3H), 5.20 (p, J=7.2 Hz, 1H), 4.56-4.22 (m, 2H), 3.65 (s, 3H), 1.50 (d, J=7.1 Hz, 3H); ESI-MS m/z 453.2 $(M+H)^+$.

QY-13-33: $^1$H NMR (400 MHz, DMSO-d6) δ 8.59 (s, 1H), 8.21 (s, 1H), 7.98-7.76 (m, 2H), 7.55 (d, J=8.4 Hz, 2H), 7.43 (s, 2H), 7.37-7.27 (m, 4H), 7.26-7.16 (m, 1H), 6.01 (q, J=7.0 Hz, 1H), 4.48-4.32 (m, 2H), 3.64 (s, 3H), 3.51 (m, 1H), 3.14 (m, 1H), 2.86-2.62 (m, 2H), 1.58 (d, J=7.1 Hz, 3H); ESI-MS m/z 479.1 $(M+H)^+$.

QY-13-50: $^1$H NMR (400 MHz, DMSO-d6) δ 9.09 (d, J=8.3 Hz, 1H), 8.71 (s, 1H), 8.35 (s, 1H), 7.82-7.71 (m, 2H), 7.70-7.55 (m, 2H), 7.32-7.25 (m, 2H), 7.23-7.13 (m, 3H), 5.26 (p, J=7.2 Hz, 1H), 4.57-4.29 (m, 2H), 3.89 (s, 3H), 1.56 (d, J=7.1 Hz, 3H); ESI-MS m/z 454.2 $(M+H)^+$.

QY-15-59: $^1$H NMR (400 MHz, DMSO-d6) δ 9.27 (t, J=6.3 Hz, 1H), 8.85 (s, 0.35H), 8.80 (s, 0.65H), 8.36 (s, 0.65H), 8.16 (s, 0.35H), 7.96 (d, J=8.4 Hz, 0.35H), 7.77 (d, J=8.5 Hz, 0.65H), 7.74-7.64 (m, 3H), 7.60 (d, J=8.2 Hz, 2H), 7.30 (t, J=7.5 Hz, 2H), 7.22 (m, 3H), 4.57 (d, J=6.3 Hz, 2H), 4.47 (s, 2H), 3.90 (s, 3H); ESI-MS m/z 448.1 $(M+H)^+$.

ET-0934: $^1$H NMR (400 MHz, DMSO-d6) δ 9.27 (t, J=6.4 Hz, 1H), 8.65 (s, 1H), 8.35-8.15 (m, 1H), 7.68 (d, J=8.2 Hz, 2H), 7.63-7.51 (m, 3H), 7.30 (t, J=7.4 Hz, 2H), 7.22 (d, J=8.2 Hz, 3H), 4.56 (d, J=6.3 Hz, 2H), 4.47 (s, 2H), 3.90 (s, 3H), 3.87 (s, 3H); ESI-MS m/z 454.1 $(M+H)^+$.

ET-0935: $^1$H NMR (400 MHz, DMSO-d6) δ 9.23 (t, J=6.4 Hz, 1H), 8.81 (s, 1H), 8.18 (d, J=2.6 Hz, 1H), 7.98-7.78 (m, 3H), 7.54 (d, J=8.1 Hz, 2H), 7.30 (t, J=7.5 Hz, 2H), 7.23 (d, J=6.3 Hz, 3H), 4.54 (d, J=6.3 Hz, 2H), 4.47 (s, 2H), 3.89 (d, J=2.8 Hz, 6H); ESI-MS m/z 454.1 $(M+H)^+$.

ZSQ-13-35: $^1$H NMR (400 MHz, DMSO-d6) δ 9.24 (t, J=6.2 Hz, 1H), 8.68 (d, J=3.6 Hz, 2H), 8.50 (d, J=4.5 Hz, 1H), 8.29 (d, J=1.1 Hz, 1H), 7.86 (dd, J=8.6, 1.6 Hz, 1H), 7.67-7.62 (m, 3H), 7.56 (d, J=8.5 Hz, 2H), 7.41-7.32 (m, 5H), 5.66 (s, 2H), 4.54 (d, J=6.2 Hz, 2H), 2.82 (d, J=4.5 Hz, 3H); ESI-MS m/z 466.1 $(M+H)^+$.

ZSQ-13-36: $^1$H NMR (400 MHz, DMSO-d6) δ 9.72 (t, J=6.2 Hz, 1H), 8.76 (s, 1H), 8.54-8.49 (m, 1H), 8.30 (d, J=1.1 Hz, 1H), 7.88 (dd, J=8.6, 1.6 Hz, 1H), 7.70-7.65 (m, 3H), 7.59 (d, J=8.5 Hz, 2H), 7.42-7.39 (m, 5H), 6.03 (d, J=4.5 Hz, 2H), 4.57 (d, J=6.2 Hz, 2H), 2.82 (d, J=4.5 Hz, 3H); ESI-MS m/z 467.2 $(M+H)^+$.

ZSQ-13-46: $^1$H NMR (400 MHz, DMSO-d6) δ 9.20 (s, 1H), 8.73-8.59 (m, 2H), 8.34 (d, J=1.0 Hz, 1H), 7.97 (dd, J=8.6, 1.5 Hz, 1H), 7.76-7.65 (m, 3H), 7.53 (t, J=9.5 Hz, 2H), 7.35-7.20 (m, 6H), 4.41 (t, J=5.8 Hz, 2H), 3.53 (d, J=2.8 Hz, 2H), 2.82 (m, 3H); ESI-MS m/z 466.1 $(M+H)^+$.

ZSQ-15-48: $^1$H NMR (400 MHz, DMSO-d6) δ 8.69 (t, J=6.3 Hz, 1H), 8.45 (s, 1H), 8.39 (s, 1H), 8.06-8.00 (m, 2H), 7.46 (d, J=8.6 Hz, 2H), 7.34 (dd, J=8.2, 6.4 Hz, 2H), 7.27-7.21 (m, 3H), 6.36 (s, 1H), 4.44 (d, J=6.3 Hz, 2H), 4.06 (s, 2H), 3.77 (s, 3H); ESI-MS m/z 439.2 $(M+H)^+$.

ZSQ-15-67: $^1$H NMR (400 MHz, DMSO-d6) δ 8.73 (t, J=6.3 Hz, 1H), 8.55 (d, J=4.6 Hz, 1H), 8.49 (s, 1H), 8.41 (s, 1H), 7.96 (dd, J=8.9, 1.5 Hz, 1H), 7.85 (d, J=8.9 Hz, 1H), 7.72 (d, J=8.4 Hz, 2H), 7.50 (d, J=8.5 Hz, 2H), 7.34 (t, J=7.3 Hz, 2H), 7.25 (dd, J=8.8, 7.3 Hz, 3H), 6.37 (s, 1H), 4.47 (d, J=6.3 Hz, 2H), 4.07 (s, 2H), 3.78 (s, 3H), 2.82 (d, J=4.5 Hz, 3H); ESI-MS m/z 479.1 $(M+H)^+$.

ZSQ-15-68: $^1$H NMR (400 MHz, DMSO-d6) δ 8.73 (t, J=6.0 Hz, 1H), 8.38 (d, J=4.5 Hz, 1H), 8.20 (d, J=1.3 Hz, 1H), 8.00 (s, 1H), 7.75-7.68 (m, 2H), 7.60-7.49 (m, 5H), 7.28 (dd, J=9.3, 5.6 Hz, 2H), 7.20 (d, J=6.6 Hz, 3H), 6.80 (d, J=3.3 Hz, 1H), 4.52 (d, J=6.0 Hz, 2H), 4.48 (s, 2H), 3.66 (s, 3H), 2.80 (d, J=4.4 Hz, 3H); ESI-MS m/z 478.2 $(M+H)^+$.

ZSQ-16-3: $^1$H NMR (400 MHz, DMSO-d6) δ 8.77 (t, J=6.3 Hz, 1H), 8.37 (s, 2H), 7.74 (d, J=3.4 Hz, 1H), 7.59 (d, J=6.8 Hz, 1H), 7.52 (s, 4H), 7.37-7.31 (m, 2H), 7.25 (m, 4H), 6.97 (d, J=7.2 Hz, 1H), 6.36 (s, 1H), 4.47 (d, J=6.3 Hz, 2H), 4.07 (s, 2H), 3.77 (s, 3H); ESI-MS m/z 437.1 $(M+H)^+$.

XHJ-2-88: $^1$H NMR (400 MHz, DMSO-d6) δ 9.56 (q, J=6.3 Hz, 1H), 9.09 (m, 1H), 8.66-8.56 (m, 1H), 8.34 (s, 1H), 7.93 (t, J=8.4 Hz, 1H), 7.75-7.55 (m, 5H), 7.32 (m, 5H), 7.18 (s, 1H), 4.53 (t, J=5.8 Hz, 2H), 4.15 (s, 2H), 2.81 (m, 3H); ESI-MS m/z 466.1 $(M+H)^+$.

XHJ-4-36: $^1$H NMR (400 MHz, DMSO-d6) δ 8.72 (q, J=6.1 Hz, 1H), 8.63 (d, J=6.9 Hz, 1H), 8.50 (d, J=4.5 Hz, 1H), 8.29 (d, J=1.2 Hz, 1H), 7.85 (dd, J=8.6, 1.5 Hz, 1H), 7.81 (s, 1H), 7.65-7.63 (m, 2H), 7.55 (t, J=8.6 Hz, 2H), 7.34 (dd, J=9.4, 5.5 Hz, 2H), 7.25 (dd, J=7.1, 5.2 Hz, 3H), 6.38 (d, J=1.8 Hz, 1H), 4.49 (t, J=5.4 Hz, 2H), 4.10 (m, 4H), 2.80 (m, 3H), 1.25-1.22 (m, 3H); ESI-MS m/z 493.1 $(M+H)^+$.

XHJ-4-48: $^1$H NMR (400 MHz, DMSO-d6) δ 8.85-8.70 (m, 2H), 8.54 (d, J=4.4 Hz, 1H), 8.07 (s, 1H), 7.91-7.80 (m, 2H), 7.70-7.64 (m, 2H), 7.61-7.51 (m, 2H), 7.34 (m, 2H), 7.30-7.19 (m, 3H), 6.37 (d, J=1.9 Hz, 1H), 4.49 (t, J=5.6 Hz, 2H), 4.03 (m, 4H), 2.80 (dd, J=14.7, 4.5 Hz, 3H), 1.67 (dd, J=14.6, 7.4 Hz, 2H), 0.80 (t, J=7.4 Hz, 3H); ESI-MS m/z 507.1 $(M+H)^+$.

ZSQ-20-94: $^1$H NMR (400 MHz, DMSO-d6) δ 9.15 (t, J=6.1 Hz, 1H), 8.69 (s, 1H), 8.34 (s, 1H), 8.20 (s, 2H), 7.82-7.76 (m, 2H), 7.57 (d, J=2.0 Hz, 1H), 7.50-7.43 (m, 2H), 7.34-7.22 (m, 3H), 7.17-7.11 (m, 2H), 6.97 (d, J=2.1 Hz, 1H), 5.75 (s, 2H), 4.50 (d, J=6.1 Hz, 2H); ESI-MS m/z 425.1 $(M+H)^+$.

ZSQ-20-106: $^1$H NMR (400 MHz, DMSO-d6) δ 9.14 (t, J=6.0 Hz, 1H), 8.74 (s, 1H), 8.38 (s, 3H), 7.84-7.76 (m, 2H), 7.72 (s, 1H), 7.51-7.43 (m, 2H), 7.35-7.25 (m, 3H), 7.14 (dd, J=7.6, 1.9 Hz, 2H), 5.50 (s, 2H), 4.53 (d, J=6.0 Hz, 2H); ESI-MS m/z 459.0 $(M+H)^+$.

ZSQ-21-1: $^1$H NMR (400 MHz, DMSO-d6) δ 8.96-8.87 (m, 1H), 8.70 (s, 1H), 8.35 (s, 1H), 8.23 (s, 2H), 7.82-7.75 (m, 2H), 7.69 (d, J=4.4 Hz, 1H), 7.48-7.40 (m, 2H), 7.35-7.23 (m, 3H), 7.17-7.09 (m, 2H), 5.57 (s, 2H), 4.51 (d, J=6.1 Hz, 2H); ESI-MS m/z 443.1 $(M+H)^+$.

ZSQ-21-2: $^1$H NMR (400 MHz, DMSO-d6) δ 8.70 (s, 1H), 8.34 (s, 1H), 8.21 (s, 2H), 7.82 (d, J=8.4 Hz, 2H), 7.52 (d, J=8.3 Hz, 2H), 7.47 (s, 1H), 7.33 (dd, J=7.9, 6.4 Hz, 2H), 7.29-7.21 (m, 3H), 5.72 (s, 2H), 4.75 (s, 2H), 3.58 (t, J=6.8 Hz, 2H), 2.80 (t, J=6.8 Hz, 2H); ESI-MS m/z 451.1 $(M+H)^+$.

ZSQ-21-8: $^1$H NMR (400 MHz, DMSO-d6) δ 9.42 (t, J=6.0 Hz, 1H), 8.61 (s, 1H), 8.31 (s, 1H), 8.25 (s, 1H), 7.86-7.79 (m, 2H), 7.66 (s, 2H), 7.49-7.44 (m, 2H), 7.38-7.28 (m, 3H), 7.25-7.18 (m, 2H), 5.93 (s, 2H), 4.51 (s, 2H); ESI-MS m/z 426.1 $(M+H)^+$.

ZSQ-21-13: $^1$H NMR (400 MHz, DMSO-d6) δ 8.77 (s, 1H), 8.66 (s, 1H), 8.32 (s, 1H), 8.17 (s, 2H), 7.85 (s, 1H), 7.77 (d, J=8.0 Hz, 2H), 7.50 (d, J=8.1 Hz, 2H), 7.43-7.31 (m, 4H), 5.28 (s, 2H), 4.48 (d, J=5.4 Hz, 2H); ESI-MS m/z 425.2 $(M+H)^+$.

ZSQ-21-14: $^1$H NMR (400 MHz, DMSO-d6) δ 9.21 (t, J=6.0 Hz, 1H), 8.78 (s, 1H), 8.68 (s, 1H), 8.34 (s, 1H), 8.18 (s, 2H), 7.99 (d, J=1.2 Hz, 1H), 7.82-7.72 (m, 2H), 7.47-7.40 (m, 2H), 7.39-7.29 (m, 3H), 7.28-7.20 (m, 2H), 5.68 (s, 2H), 4.48 (d, J=6.0 Hz, 2H); ESI-MS m/z 425.2 $(M+H)^+$.

ZSQ-21-18: $^1$H NMR (400 MHz, DMSO-d6) δ 8.83 (t, J=6.1 Hz, 1H), 8.68 (s, 1H), 8.34 (s, 1H), 8.20 (s, 2H), 7.81-7.73 (m, 2H), 7.47-7.40 (m, 2H), 7.35-7.27 (m, 2H), 7.27-7.20 (m, 1H), 7.10-6.92 (m, 3H), 6.29 (d, J=4.1 Hz, 1H), 5.72 (s, 2H), 4.45 (d, J=6.0 Hz, 2H); ESI-MS m/z 458.1 $(M+H)^+$.

ZSQ-21-30: $^1$H NMR (400 MHz, DMSO-d6) δ 8.72 (t, J=6.1 Hz, 1H), 8.60 (s, 1H), 8.25 (s, 1H), 7.82-7.77 (m, 2H), 7.69 (s, 2H), 7.44 (m, 2H), 7.35-7.30 (m, 2H), 7.28-7.23 (m, 1H), 7.11 (d, J=7.2 Hz, 2H), 6.88 (dd, J=5.9, 4.3 Hz, 1H), 5.75 (t, J=4.1 Hz, 1H), 5.58 (s, 2H), 4.45 (d, J=6.1 Hz, 2H); ESI-MS m/z 442.1 $(M+H)^+$.

ZSQ-22-96: $^1$H NMR (400 MHz, DMSO-d6) δ 8.71 (s, 1H), 8.35 (s, 1H), 7.87-7.73 (m, 2H), 7.60-7.46 (m, 2H), 7.37-7.26 (m, 4H), 7.25-7.17 (m, 1H), 4.74 (s, 2H), 4.39 (s, 2H), 3.65 (s, 3H), 3.57 (d, J=6.7 Hz, 2H), 2.83 (t, J=6.7 Hz, 2H); ESI-MS m/z 465.2 $(M+H)^+$.

BIOLOGICAL TEST EXAMPLE

The structures of the control compounds used in the test example are as follows

Nec-1s

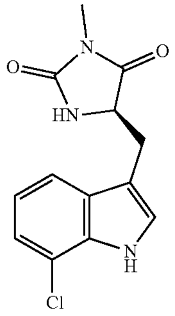

GSK2982772

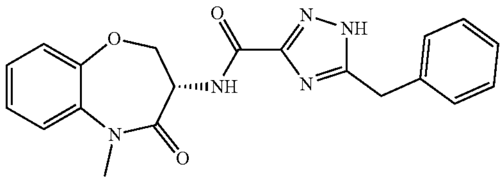 [SMILES: CN1C(=O)[C@@H](NC(=O)c2n[nH]c(Cc3ccccc3)n2)COc2ccccc21]

SM164

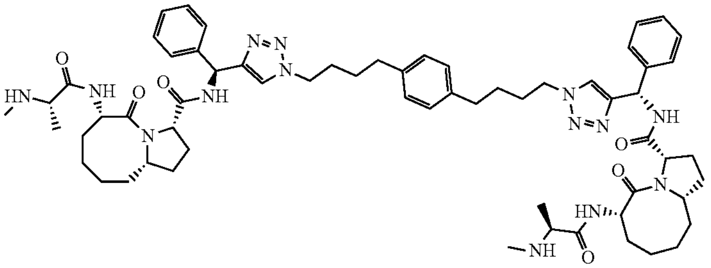 [SMILES: CN[C@@H](C)C(=O)N[C@H]1CCCC[C@H]2CC[C@@H](C(=O)N[C@@H](c3ccccc3)c3cn(CCCCc4ccc(CCCCn5cc([C@@H](NC(=O)[C@@H]6CC[C@@H]7CCCC[C@H](NC(=O)[C@H](C)NC)C(=O)N76)c6ccccc6)nn5)cc4)nn3)N2C1=O]

-continued zVAD

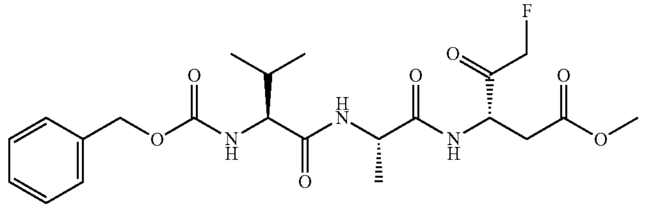 [SMILES: COC(=O)C[C@H](NC(=O)[C@H](C)NC(=O)[C@@H](NC(=O)OCc1ccccc1)C(C)C)C(=O)CF]

Biological Test Example 1 the Inhibitory Activity Test of RIPK1 Inhibitor on Programmed Cell Necrosis The adopted biological assay protocol was: the effect of compounds on programmed necroptosis of TNF-induced FADD (Fas-Associated Death Domain) deficient Jurkat cells and L929 cells.

In order to verify the inhibitory effect of the compounds of the present invention on programmed cell necrosis at the cellular level, cell types that is closely related to the RIP1 pathway, namely FADD deficient Jurkat cells (human peripheral blood leukemia T cell strain) and L929 cells, were selected. Two different stimulation methods were used: tumor necrosis factor (TNFα) was used alone, or TNFα was used in combination with mitochondria-derived cysteine aspartate activator (SMAC) SM164. Cells viability was calculated by detecting chemiluminescence values, thereby obtaining the biological activity of the compound on the inhibition of programmed cell necrosis.

Methods: FADD deficient Jurkat cells: FADD deficient Jurkat cells (human peripheral blood leukemia T cell line) were cultured in vitro. After growing to the logarithmic growth phase, the cells were collected, centrifuged at 1000 rpm for 5 min, the supernatant was discarded, and the cell concentration was adjusted to $2.5\times10^5$/mL. Cells were seeded into 384-well plates, 40 μl per well. 5 μL of SM164 (50 nM) diluted in cell culture medium and 5 μL of each compound were added to the corresponding wells. After pretreatment at 37° C. for 1 h, 5 μL of TNFα (50 ng/mL) diluted in cell culture medium was added to each well of the stimulation group, and 5 μL of the culture medium was added to the control group. The plate was cultured in a cell incubator (37° C., 5% $CO_2$) for 14 h, and 15 g of Cell Titer-Glo solution was added to each well, then incubated for 30 min at room temperature, and intracellular ATP level was measured by detecting luminescence. The unstimulated DMSO control wells were taken as 100% cell viability. L929 cells: The L929 cells (mouse fibroblasts) were cultured in vitro, digested and diluted to $6.25\times10^4$/ml, and the cells were seeded into 384-well plates, 40 μl per well. The plate was placed in a cell incubator (37° C., 5% $CO_2$) for 12 hours. 5 μL of SM164 (500 nM) diluted in cell culture medium and 5 μL of each compound were added to the corresponding wells. After pretreatment at 37° C. for 1 h, 5 μL of TNFα (500 ng/mL) diluted in cell culture medium was added to each well of the stimulation group, and 5 μL of the culture medium was added to the control group. After the plate was cultured for 14 h in a cell incubator (37° C., 5% $CO_2$), 15 μl of Cell Titer-Glo solution was added to each well. The plate was incubated at room temperature for 30 min, and intracellular ATP level was measured by detecting luminescence. The unstimulated DMSO control wells were taken as 100% cell viability. $EC_{50}$ values of the compounds were calculated using Prism Graphpad statistical software. The results were shown in FIG. 1 and Table 1.

TABLE 1

Inhibitory Activity Test Results of RIPK1 Inhibitor on Programmed Cell Necrosis

| | $EC_{50}$ (μM) | | | |
|---|---|---|---|---|
| | FADD−/− Jurkat cells (human) | | L929 cells (mouse) | |
| Compound No. | TNFα | TNFα + SM164 | TNFα | TNFα + SM164 |
| 7-Cl-O-Nec-1(Nec-1s) | 0.2281 | 0.9001 | 0.4428 | 1.896 |
| GSK2982772 | 0.00068 | 0.004 | 2.51 | >10 |
| QY-5-35 | 2.493 | >10 | >10 | >10 |
| QY-5-40 | 2.5 | >10 | 5.0 | >10 |
| QY-5-62 | 0.00498 | 0.09802 | 3.805 | >10 |
| QY-6-15 | 1.368 | >10 | >10 | >10 |
| QY-6-16 | 0.008097 | 0.113 | 2.138 | 3.348 |
| QY-7-2B | 0.005122 | 0.04393 | 0.3124 | 2.022 |
| QY-7-14 | 0.02431 | 0.1795 | 0.9615 | 4.735 |
| QY-7-32 | 0.1854 | 1.516 | >10 | >10 |
| QY-7-65 | >10 | >10 | >10 | >10 |
| QY-8-7 | 0.01075 | 0.03776 | 3 | >10 |
| QY-8-30 | 0.01123 | 0.013 | 0.8291 | 6.3 |
| QY-8-31 | 1.3 | 7.4 | >10 | >10 |
| QY-8-42 | >10 | >10 | >10 | >10 |
| QY-8-43 | 0.00285 | 0.01773 | 0.01106 | 0.1521 |
| QY-8-48 | 0.9724 | >10 | >10 | >10 |
| QY-8-58 | 0.1965 | 0.5771 | >10 | >10 |
| QY-8-60 | >10 | >10 | >10 | >10 |
| QY-9-33 | 0.00377 | 1.04 | >10 | >10 |

TABLE 1-continued

Inhibitory Activity Test Results of RIPK1 Inhibitor on Programmed Cell Necrosis

| | $EC_{50}$ (μM) | | | |
|---|---|---|---|---|
| | FADD−/− Jurkat cells (human) | | L929 cells (mouse) | |
| Compound No. | TNFα | TNFα + SM164 | TNFα | TNFα + SM164 |
| QY-9-34 | 0.000416 | 0.003522 | 8.36 | >10 |
| QY-9-41 | 0.0215 | 0.2345 | >10 | >10 |
| QY-9-50 | 0.000191 | 0.0121 | 1.39 | 2.729 |
| QY-9-69 | >10 | >10 | 0.5669 | >10 |
| QY-9-70 | 2.96 | >10 | 0.3499 | 6.3 |
| QY-9-77 | 0.009036 | 0.1706 | 0.3439 | 5 |
| QY-10-21 | 0.049 | 0.2992 | >10 | >10 |
| QY-10-39 | 0.00007 | 0.00295 | 0.01004 | 0.09611 |
| QY-10-40 | 0.000001 | 0.00006 | 0.00048 | 0.00145 |
| QY-10-65 | 0.001203 | 0.0346 | 0.02213 | 0.07378 |
| QY-10-73 | 0.00006974 | 0.005197 | 0.01997 | 0.07672 |
| ZSQ-13-35 | 0.2334 | 1.594 | >10 | >10 |
| ZSQ-13-36 | 0.02401 | 0.15 | 1.106 | 4.31 |
| ZSQ-13-46 | >10 | >10 | >10 | >10 |
| ZSQ-15-48 | 0.07089 | 0.4513 | 6.548 | >10 |
| ZSQ-15-68 | 0.1147 | 0.6704 | 0.6096 | 1.804 |
| ZSQ-16-3 | 0.3611 | >10 | 2.316 | >10 |
| XHJ-2-88 | 0.07009 | 0.3803 | 0.8311 | 3.975 |
| XHJ-4-36 | 0.00591 | 0.04276 | 0.0107 | >10 |
| XHJ-4-48 | 0.1093 | 0.738 | 3.007 | >10 |
| ZSQ-21-13 | 0.04268 | 0.03896 | — | — |
| ZSQ-21-14 | 0.2902 | >10 | — | — |
| ZSQ-21-18 | 0.006568 | 0.08059 | — | — |
| ZSQ-21-30 | 0.00008533 | 0.001603 | 0.0009157 | 0.007409 |
| QY-11-75 | 0.2333 | 1.503 | >10 | >10 |
| QY-11-76 | 0.00002426 | 0.00004997 | 0.00005977 | 0.0004325 |
| QY-11-77 | 0.000012 | 0.0008383 | 0.001166 | 0.0006301 |
| QY-11-78 | 0.000036 | 0.0006887 | 0.009872 | 0.02321 |
| QY-11-79 | 0.1523 | 0.747 | >10 | >10 |
| QY-11-80 | 0.03496 | 0.4823 | 1.967 | 3.462 |
| QY-11-68A | 0.0005809 | 0.003792 | 0.1606 | 0.001582 |
| QY-11-68B | 0.0006958 | 0.002955 | 0.02054 | 0.08343 |
| QY-11-69A | 0.002997 | 0.1938 | >10 | >10 |
| QY-11-69B | 0.0009841 | 0.006325 | 0.0005632 | 0.001076 |
| QY-11-74A | 0.05298 | 0.3685 | >10 | >10 |
| QY-11-74B | 0.0002931 | 0.003726 | 0.0003858 | 0.0006869 |
| QY-11-102A | 0.000001684 | 0.00006494 | 0.000005128 | 0.00007929 |
| QY-11-102B | 0.00001328 | 0.0003062 | 0.00002777 | 0.0004239 |
| QY-11-104 | 0.004426 | 0.04838 | — | — |
| QY-12-4 | 0.01756 | 0.1276 | — | — |
| QY-12-31 | 0.00009672 | 0.0002542 | 0.0003561 | 0.0005689 |
| QY-12-47 | 0.001743 | 0.01741 | 0.006003 | 0.03437 |
| QY-12-51 | 0.2145 | 1.86 | 0.875 | 3.77 |
| ZSQ-22-96 | 0.0002033 | 0.002256 | 0.008385 | 0.03865 |
| QY-12-90 | 0.00013 | 0.0008127 | 0.002409 | 0.04266 |
| QY-12-97 | 0.0361 | 0.132 | 0.05185 | 0.2192 |
| QY-12-100 | 0.0001721 | 0.0007339 | 0.0004576 | 0.004634 |
| QY-12-102 | 0.00752 | 0.02849 | 0.5501 | 6.964 |
| QY-13-19 | 0.00005569 | 0.0005161 | 0.001459 | 0.003088 |
| QY-13-29 | 0.00009161 | 0.0003177 | 0.0003172 | 0.0004624 |
| QY-13-31 | 0.000084 | 0.0003053 | 0.0004374 | 0.0005527 |
| QY-13-33 | 0.0002961 | 0.002854 | 0.001319 | 0.003018 |
| QY-13-50 | 0.000001 | 0.000001 | — | — |
| QY-15-59 | 0.000007669 | 0.0000009699 | 0.000001 | 0.000001 |
| ET-0934 | 0.0004893 | 0.01546 | 0.0166 | 0.558 |
| ET-0935 | 0.00002354 | 0.0002435 | 0.000001 | 0.000001 |

The experimental results of FIG. 1 and Table 1 suggested that: whether stimulated with TNFα alone or in combination with SM164, the preferred compounds of the present invention, compounds such as QY-10-40, QY-11-76, QY-11-102A/B, QY-12-100, QY-13-19, QY-13-31, QY-13-33, QY-15-59 and ET-0935, show a stronger activity of inhibition of programmed necrosis than clinical inhibitor GSK2982772 on both human FADD-deficient Jurkat cells; while on mouse-derived L929 cells, wherein GSK2982772 is almost inactive, the preferred compounds of the present invention, many compounds including QY10-40, QY-11-76 and QY-11-102A/B and the like, are still able to excellently inhibit the occurrence of programmed necrosis. QY10-40 essentially completely inhibits TNFα-induced programmed necrosis in FADD-deficient Jurkat cells or L929 cells with a concentration of above 1 nM, and does not exhibit any cytotoxicity at a 1000-fold effective inhibitory concentration (1 μM).

Biological Test Example 2 Liver Microsomal Stability Test of RIPK1 Inhibitor

The adopted biological test protocol was: testing the half-life of the compound in human- or mouse-derived liver microsomes.

Liver microsomes contain many enzymes involved in drug metabolism, especially cytochrome P-450, and therefore it is one of the major tissues involved in drug metabolism in living organisms. There are some correlations between the stability of the compound in liver microsomes and the pharmacogenetic stability thereof in vivo. Therefore, the relative stability of compounds in vivo can be roughly predicted by testing the half-life of different compounds in human- or mouse-derived liver microsomes. The test results were shown in Table 2. The specific methods were as follows:

Methods: 0.75 μL of 0.5 mM samples (compounds to be tested and control verapamil), 9.38 μL of 20 mg/mL liver microsomes (Human and Mouse) were taken and added to 239.88 μL PBS (on ice), and divided into 30 μL/tube samples respectively. The samples were incubated at 37° C. in a constant temperature water bath for 5 min, and then all samples were taken out. At zero-time, control group was added with 90 μL of ice acetonitrile first, and then added with 15 μL of 3 mM NADPH solution sequentially, and incubated at 37° C. in a constant temperature water bath. The corresponding samples were taken out after 5 min, 10 min, 20 min, 30 min and 60 min, respectively, and quenched by adding 90 μL of ice acetonitrile. All samples were centrifuged at 10000 rpm for 10 min, and the supernatants were taken and placed in a liquid phase vial waiting for LC-MS analysis.

TABLE 2

Liver Microsomal Stability Test Results of RIPK1 inhibitors

| | $T_{1/2}$ (min) | |
|---|---|---|
| | Human | Mouse |
| Verapamil | 11.0 | 4.6 |
| QY-6-16 | 21.66 | 24.75 |
| QY-7-2B | 40.8 | 34.7 |
| QY-7-14 | 13.9 | 77.0 |
| ZSQ-13-36 | 99 | 99.0 |
| XHJ-4-36 | 46.2 | 10.7 |
| QY-8-7 | 46.2 | 12.2 |
| QY-8-43 | 38.5 | 23.9 |
| QY-9-33 | 9.6 | 11.2 |
| QY-9-34 | 14.7 | 13.9 |
| QY-9-41 | 38.5 | 36.5 |
| QY-9-50 | 86.6 | 115.5 |
| QY-10-39 | 21.7 | 25.7 |
| QY-10-40 | 40.8 | 69.3 |
| QY-10-73 | 36.5 | 40.8 |
| ZSQ-21-13 | 577 | 99 |
| ZSQ-21-18 | 8.6 | 30.1 |
| ZSQ-21-30 | 14.4 | 14.4 |
| QY-11-68B | — | 34.7 |
| QY-11-69B | 43.3 | 46.2 |
| QY-11-76 | 13.1 | — |
| QY-11-77 | 16.5 | 11.4 |
| QY-11-78 | 12.6 | 23.9 |
| QY-11-102A | 15.8 | |

The experimental results suggested that multiple representative RIPK1 inhibitors such as QY-10-40 show good stability in human or mouse derived liver microsomes.

Biological Test Example 3: Testing the Effect of Representative Compound QY-10-40 on the Kinase Activity of RIPK1 Protein The adopted biological test protocol was: testing the effect of compound QY-10-40 on the kinase activity of RIPK1(1-330) protein. RIPK1(1-330) protein purified in vitro retains the whole kinase activity domain and maintains good kinase activity. Through the $IC_{50}$ of the compounds of the present invention inhibiting RIPK1 kinase activity in the cases of different concentrations of ATP, the binding mode of the compounds to was obtained, Nec-1s, a known RIPK1 ATP-non-competitive inhibitor, was used as control.

The process of in vitro kinase reaction is related to the substrate concentration. The effect of substrate-competitive inhibitors will change drastically with the change of substrate concentration, while the effect of substrate-non-competitive inhibitors will not change with the change of substrate concentration. Kinase ATP-competitive inhibitors inhibit kinase activity by competing the binding sites with ATP, and ATP-competitive kinase inhibitors are generally less specific due to the conservation of ATP binding sites. In contrast, ATP-non-competitive kinase inhibitors generally have higher specificity.

Figure 2:
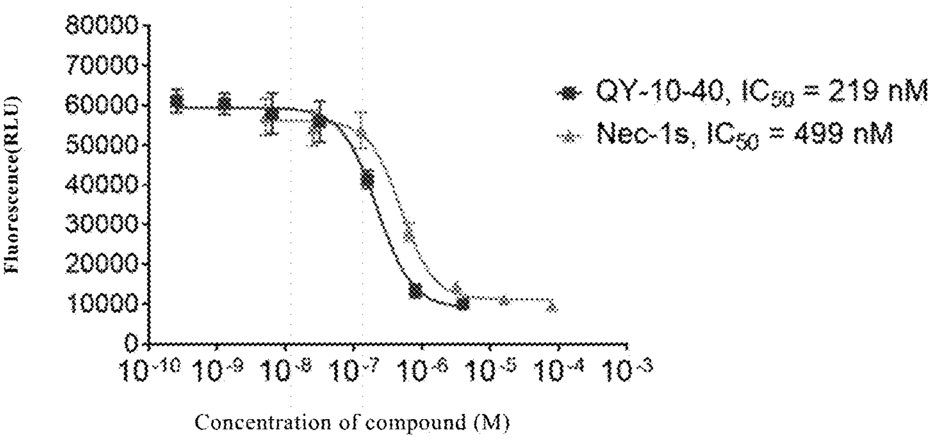
FIG. 2 is the concentration-inhibitory effect curves of representative compound QY-10-40 on the kinase activity of RIPK1(1-330) protein.

Methods: RIPK1 (1-330) protein with a final concentration of 2 μM and ATP (IX kinase buffer) with a corresponding concentration, final concentration of 5 μL, were added to the 384-well plate, respectively. Each group at least set up triplicate wells and reacted for 2 h at 37° C. 5 μL ADP-Glo reagent was added, which was used to stop kinase reaction and remove residual ATP in reaction system. The plates was placed at room temperature for 40 min. 10 μL kinase detection reagent was added, which was used to convert ADP into ATP and introduce luciferase and luciferin for ATP detection into the system. The reaction was carried out at room temperature for 1 h. 7500 Fast Real-Time PCR System was used to detect luminescence. The $IC_{50}$ of the compounds inhibiting the kinase reaction was calculated using Prism Graphpad statistical software. The experimental results were shown in FIG. 2.

The experimental results suggested that the representative compound QY-10-40 display a concentration-dependent effective inhibitory effect on RIPK1 kinase, and its effective semi-inhibitory concentration is 219 nM, which is better than the control Nec-1s (effective semi-inhibitory concentration is 499 nM).

Biological Test Example 4: Effects of Representative Inhibitors on Programmed Cell Necrosis Pathway The adopted biological test protocol was: testing the effect of the compound on key signals in the TNFα-induced programmed necrosis pathway in FADD-deficient Jurkat or L929 cells, and the known RIPK1 ATP non-competitive inhibitor Nec-1s and clinical inhibitor GSK2982772 were used as controls.

Signaling of TNFα-induced Necroptosis is mediated by a complex called Necrosome (Complex IIb), which includes TRADD, FADD, Caspase-8, RIPK1, RIPK3 and MLKL. The kinase activity of RIPK1 has been proved to play a critical role in the regulation of programmed cell necrosis. During programmed cell necrosis, RIPK1 underwent autophosphorylation activation, within serine 166 was one of the main phosphorylation sites. After programmed cell necrosis occurred, oligomeric MLKL translocated to cell membrane and mediated cell death by calcium influx.

In order to verify whether the compounds of the present invention can inhibit programmed cell necrosis by inhibiting the activity of RIPK1, and to detect the changes in the signal of the programmed necrosis pathway. FADD-deficient Jurkat or L929 cells treated with the compound of the present invention were used, and TNFα was added to induce programmed necrosis. Then the cells were collected and phosphorylation of RIPK1 and oligomerization of MLKL were detected using western blot.

Figure 3:
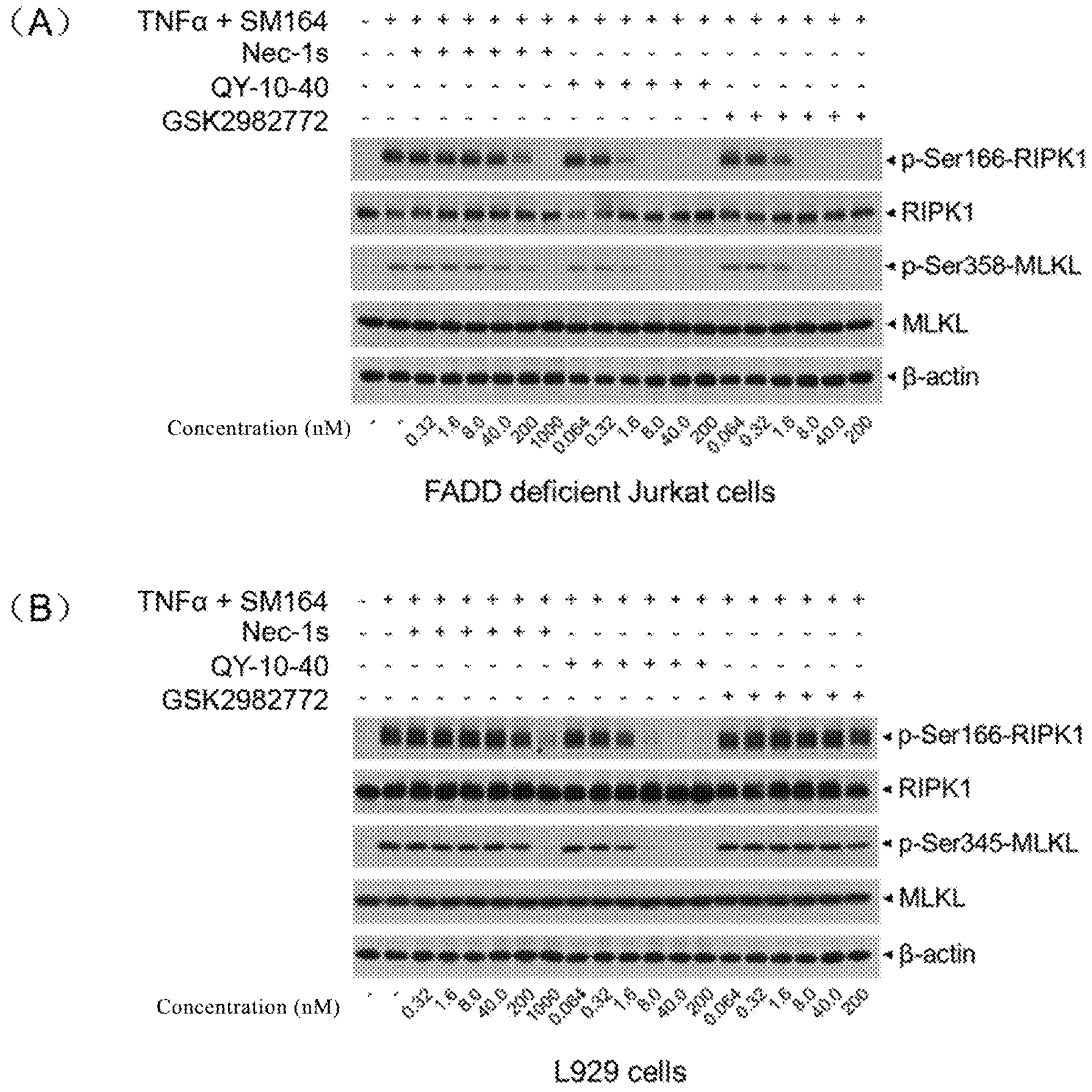
FIG. 3 shows the effects of QY-10-40, Nec-1s and GSK2982772 on TNF pathway signals activated by TNFα combined with SM164 in human or mouse cell lines at different concentrations.

Methods: FADD-deficient Jurkat cells or L929 cells were cultured in vitro. After growing to the logarithmic growth phase, the cells were collected, centrifuged at 1000 rpm for 5 min, the supernatant was discarded, and the cell concentration was adjusted to $1\times10^6$/mL. In the 12-well cell culture plate, each well was added with 1 ml of cells, and 0.2 μL of DMSO solution with a concentration of 50 mM drug or pure DMSO control, and pretreated for 1 h. 0.5 μL of TNF α (PBS solution) with a concentration of 100 μg/ml was added to each stimulated group. After cultured in a cell incubator (37° C., 5% $CO_2$) for 4 h, the cells were collected by centrifugation at 3000 rpm for 3 min and washed twice with pre-cooled PBS solution. The supernatant was tried to remove, and 200 μL RIPA cell lysate was added to the cell precipitation. Then it was placed in a shaker at 4° C. and lysed for 30 min, centrifuged at 15000 rpm at 4° C. for 15 min, and the supernatant cell lysate was taken. The BCA protein quantification kit was used to detect the protein content of each group, and PIPA lysis buffer was used to adjust the protein amount to make the final volume being 100 μL. The samples were identified by western-blot. Western-blot: 25 μL of 5× protein loading buffer was added to 100 μL of cell lysate, and the mixture was heated at 95° C. for 10 min. After the samples were cooled, electrophoresis was carried out using SDS-PAGE (9%) gel at 60V, and 30 min later, switched to 120V until the leading band was electrophoresed to the bottom of the gel. Using a turbo semi-dry transfer system with a constant current of 0.2 A to transfer for 80 minutes. The proteins in the gel were transferred to a PC membrane with a pore size of 0.2 μL. The transferred PC membrane was placed in 5% skim milk powder (TBST solution) for blocking for 2 h, and incubated with the corresponding primary antibody at 4° C. for 12 h, and washed with TBST for 3 times, 10 min each time. The sample was incubated with the corresponding secondary antibody for 2 h at room temperature, washed with TBST three times, 10 min each time. The resulting sample was incubated with ECL luminescent solution and the luminescent signal was detected. The results were shown in FIG. 3.

The experimental results suggested that the representative compound QY-10-40 effectively inhibit the phosphorylation of RIPK1 and the phosphorylation of downstream protein MLKL in Jurkat cells at 1.6 nM, and the inhibitory effect thereof is slightly better than that of GSK2982772, is far superior to that of Nec-1s; in L929 cells, QY-10-40 is far superior to the other two.

Biological Test Example 5: The Inhibitory Activity Test of RIPK1 Inhibitor on Programmed Cell Necrosis The adopted biological test protocol was: the effect of compounds on programmed necrosis in MEFs cells (mouse embryonic fibroblasts) with RIPK1 S161E mutation.

In the severe period of the development of related inflammation, the intracellular RIPK1 has been highly activated, and the reported RIPK1 inhibitors are more likely to inhibit the newly synthesized inactivated RIPK1 kinase protein, and the inhibition on the highly activated RIPK1 is weak. Therefore, the intervention effect on related inflammation is weaker and slower. In order to verify the inhibitory effect of the compound of the present invention on the highly activated RIPK1 kinase at the cellular level, MEFs cells stably expressing RIPK1 S161E (simulating the activation state of RIPK1 after phosphorylation) were selected, TNFα-SM164-zVAD (Caspase inhibitor for inhibiting apoptosis) (TSZ) was used in combination to induce programmed cell necrosis, and cell viability was calculated by detecting chemiluminescence values, thereby obtaining the biological activity of the compound in inhibiting programmed necrosis.

Figure 4:
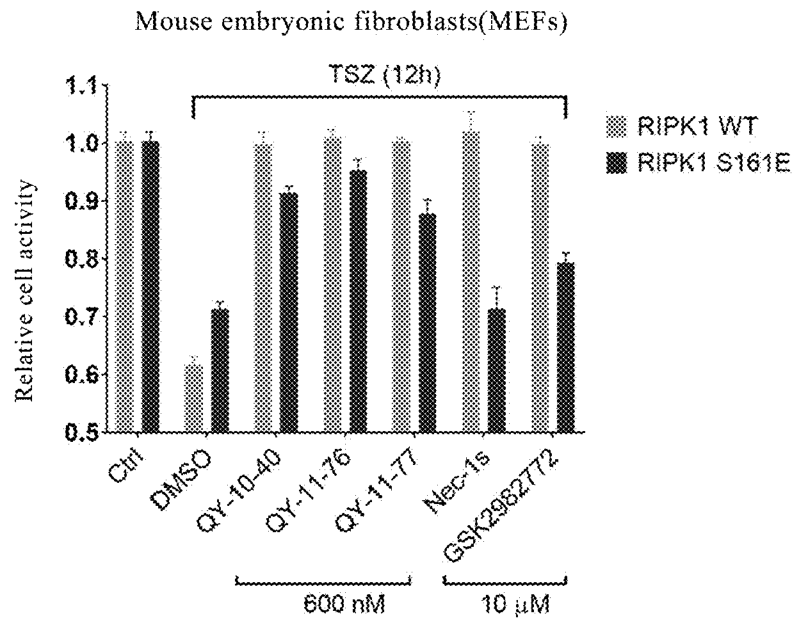
FIG. 4 shows the results of the inhibitory activity test of RIPK1 inhibitor on programmed necrosis of RIPK1 continuously activated cells.

Methods: MEFs cells replenished by RIPK1: WT-RIPK1, S161A-RIPK1 and S161E-RIPK1 were replenished in RIPK1 stable knockout cells respectively. After stable expression and being cultured to logarithmic growth phase, the cells were collected, and centrifuged at 1000 rpm for 5 min. The supernatant was discarded. Cell concentration was adjusted to $5\times10^4$/mL, and cells were inoculated into 384-well plates with 40 μL per well. Cell culture medium diluted SM164 (100 nM), zVAD (50 μM) and compound, each 5 $R^L$, were added to the corresponding wells. After pretreatment at 37° C. for 1 h, 5 μL of cell culture medium diluted TNF (50 ng/mL) was added to each well in the stimulated group and 5 μL of culture medium was added to the control group. After being cultured in a cell incubator (37° C., 5% $CO_2$) for 12 h, each well was added with 15 μL Cell Titer-Glo solution, incubated at room temperature for 30 min, and the chemiluminescence value (luminescence) was detected to measure the intracellular ATP level. The unstimulated DMSO control wells (Ctrl) were taken as 100% cell viability. $EC_{50}$ values of the compounds were calculated using Prism Graphpad statistical software. The results were shown in FIG. 4.

The experimental results suggested that in MEFs cells expressing RIPK1 WT, the representative compounds, QY-10-40, QY-11-76 and QY11-77 (all 600 nM), and Nec-1s and GSK2982772 (both 10 μM) can effectively inhibit the occurrence of programmed necrosis. In MEFs cells expressing RIPK1 S161E mutant, representative compounds, QY-10-40, QY-11-76 and QY11-77 (at 600 nM), can significantly inhibit occurrence of programmed necrosis under stimulation. In contrast, Nec-1s does not exhibit inhibition at 10 μM concentration, and GSK2982772 only shows weak inhibition. Therefore, the inhibitory effect of the representative compounds on the highly activated RIPK1 are far the other two.

Biological Test Example 6: Pharmacokinetic Properties of Representative Compound QY-10-40

The adopted biological test protocol was: drug metabolism test of the compound on the mouse in vivo.

Figure 5:
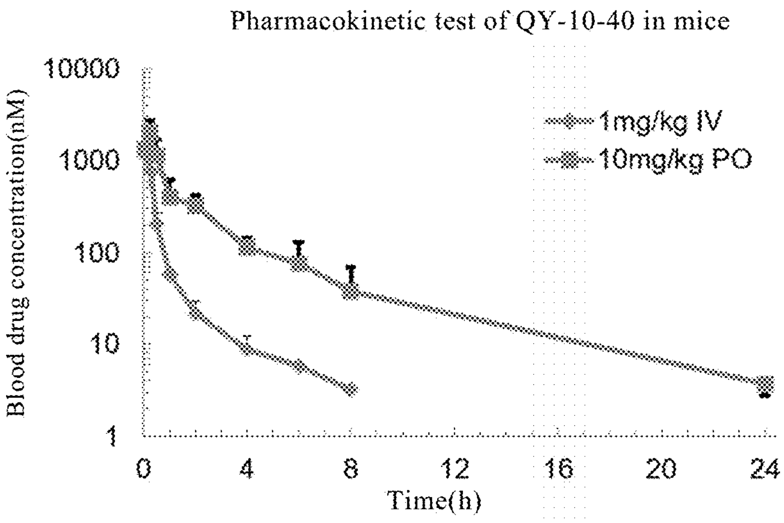
FIG. 5 shows the concentration-time curve of representative compound QY-10-40 in plasma and pharmacokinetic parameters.

In order to verify the selectivity of the compound of the present invention on the kinase group in vivo, a representative compound QY-10-40 was selected and the pharmacokinetic properties of the compound in mice (n=3) were tested using single administration by gavage (PO, 10 mg/kg) or intravenous injection (IV, 1 mg/kg). The results were shown in FIG. 5.

The results suggested that QY-10-40 rapidly reach the peak in mice after a single dose and show better bioavailability (F) and half-life ($T_{1/2}$), with blood concentrations remaining stable above the effective inhibitory concentration (10 nM) for most of the time within 24 h after gavage administration of 10 mg/kg.

Biological Test Example 7: The Effect of Representative Compound QY-10-40 on TNFα-Induced Systematic Inflammatory Response Syndrome The adopted biological test scheme was: Tail vein injection of tumor necrosis factor TNFα would lead to the occurrence of systemic inflammatory response syndrome in mice, resulting in decreased body temperature and death. The effect of representative compound QY-10-40 on TNFα-induced systemic inflammatory response syndrome was tested, and the change in body temperature and death of mice were monitored. Using known RIPK1 inhibitor Nec-1s as control, clinical inhibitor GSK2982772 was not used due its poor inhibitory activity on mouse RIPK1.

Systemic inflammatory response syndrome, also known as inflammatory storm, refers to a systemic non-specific inflammatory response caused by infectious or non-infectious injuries such as severe infection, multiple trauma, burns, ischemia reperfusion, and acute pancreatitis. Under this condition, large amounts of inflammatory factors will release, in severe cases organism will loss the control of inflammatory response, resulting in multi-organ failure and even death.

Figure 6:
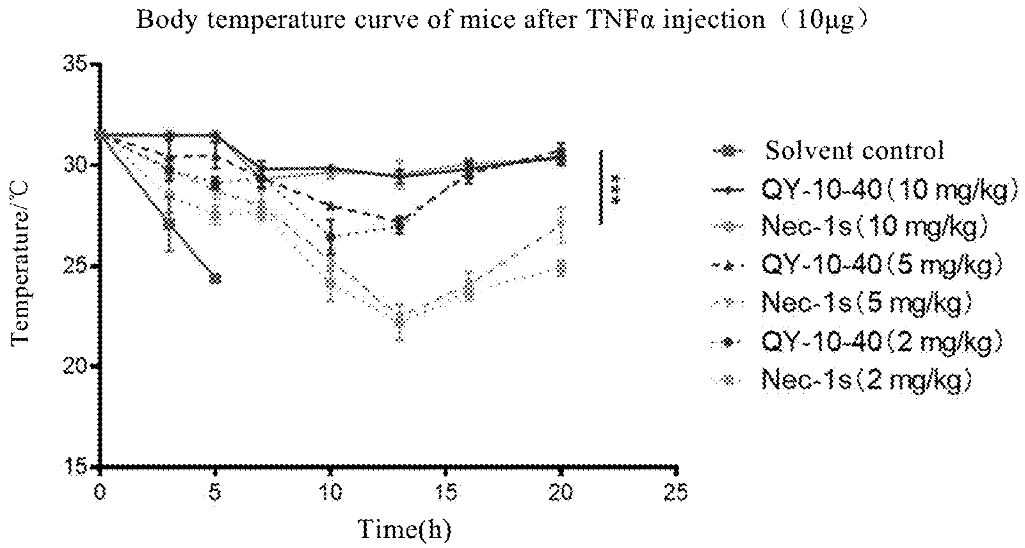
FIG. 6 shows the effects of representative compound QY-10-40 and control compound Nec-1s on body temperature changes in mice.

Methods: The compounds to be tested were dissolved in 0.5% carboxymethyl cellulose according to the required concentration one day in advance, and sonicated overnight. Each mouse was gavaged with 200 μl. 20 min later, 10 mg TNFα (dissolved in 125 ml PBS) was injected through the tail vein. Body temperature changes of mice were monitored by infrared thermometer after injection. The effects of the compounds were calculated using Prism Graphpad statistical software. The results were shown in FIG. 6.

Experimental results suggested that in the absence of inhibitors, all mice died within 6 h of TNFα injection. The compound QY-10-40 effectively resists against TNFα-induced hypothermia, inflammation response and death at a low dose (2 mg/kg) and is more effective than Nec-1s at the same dose.

Biological Test Example 8: Effects of Representative Compounds on Digestive Systematic Inflammation Induced by RIPK1$^{K612R/K612R}$ Mutation in Mice The adopted biological test scheme was: RIPK1$^{K612R/K612R}$ mutant mice were used as model mice to test the effect of representative compound QY-10-40 or QY-13-19 on spontaneous intestinal inflammation. The known RIPK1 inhibitor Nec-1s was used as control.

K612R mutation leads to decreased in intracellular RIPK1 level but abnormal activation, making it sensitive to programmed necrosis and caspase-1 activation, and responding to TLRs signaling. RIPK1$^{K612R/K612R}$ mice will appear responses such as age-dependent reduced RIPK1 expression and abnormal activation, spontaneous intestinal inflammation and splenomegaly.

Methods: The compounds to be tested were dissolved in 0.5% carboxymethyl cellulose according to the required concentration one day in advance, and sonicated overnight. Mice were gavaged in a volume of 0.1 ml/10 g body weight. Body weight was measured three times a week, and samples were collected at the end of the experiment. The effect of the compounds was calculated using Prism Graphpad statistical software.

Figure 7:
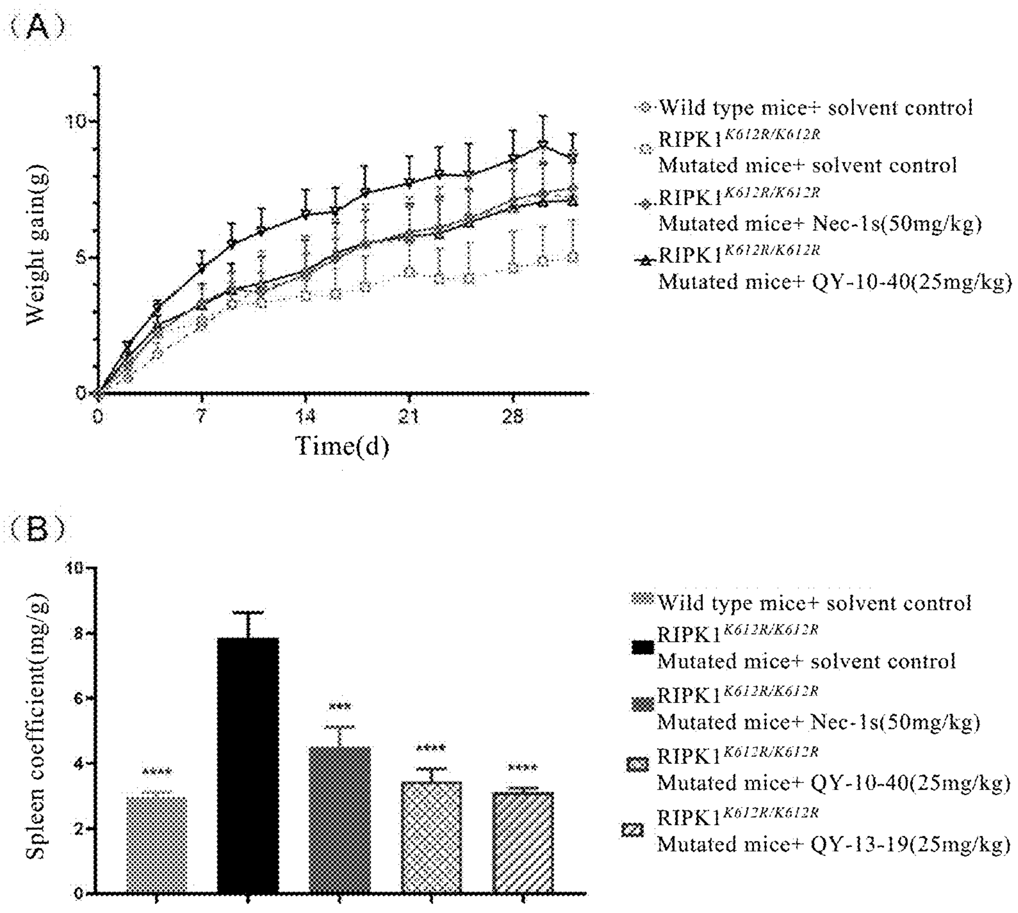
FIGS. 7A and B show the effects of representative compound QY-10-40, QY-13-19 and control compound Nec-1s on body weight changes and organ coefficient (organ weight/body weight) in mice, respectively.

FIGS. 7A and B showed the results of effects of representative compound QY-10-40, QY-13-19 and control compound Nec-1s on body weight changes and organ coefficient (organ weight/body weight) in mice, respectively.

The experimental results suggested that compounds QY-10-40 or QY-13-19 can inhibit the effect of the digestive system inflammation caused by K612R mutation on body weight and spleen coefficient of mice, and the efficacies thereof at lower doses (25 mg/kg) are better than that of the control compound Nec-1s (50 mg/kg).

Biological Test Example 9: Co-Crystallization of Representative Compound QY-7-2B with Human-Derived Recombinant RIPK1 Protein and Structural Analysis Thereof Methods: The recombinant human RIPK1 catalytic domain truncated protein (including amino acid residue 1-294 and four mutations of C23A, C127A, C233A and C240A) was expressed by insect cell Sf9 and purified, and concentrated to about 9 mg/mL. QY-7-2B (final concentration 2.5 mM) was added, and co-crystallization was induced by suspension drop method and vapor diffusion method at 18° C. The crystal diffraction data of the RIPK1 and QY-7-2B eutectic crystal was collected by X-ray diffraction method, and the electron cloud distribution structure inside the eutectic crystal with a resolution of 3.1 A was determined through data analysis. The three-dimensional binding model of RIPK1 recombinant protein molecule and small molecule QY-7-2B at the atomic level was simulated by software such as COOT and PHENIX.

Figure 8:
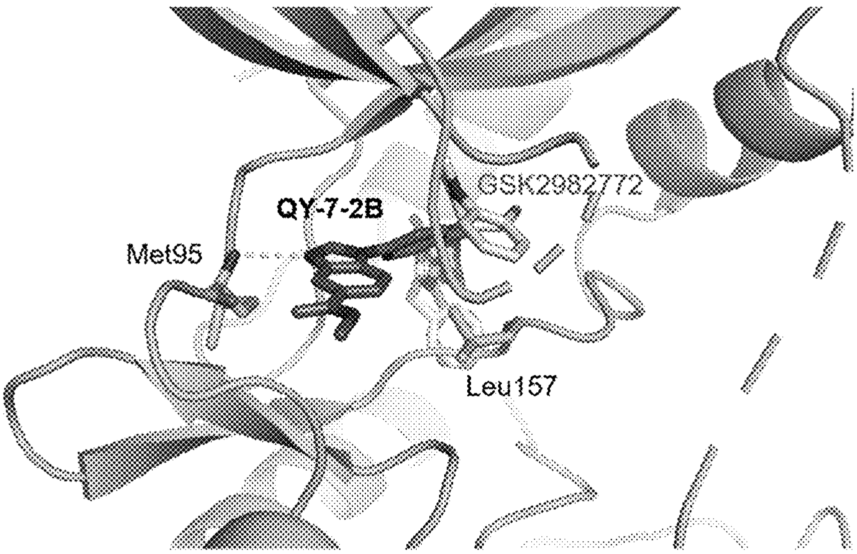
FIG. 8 shows the co-crystalline structure of the representative QY-7-2B and the human RIPK1 protein kinase domain, and shows the difference between the series of compounds of the present invention and the control compound GSK2982772 in the binding mode to the RIPK1 protein.

FIG. 8 showed the co-crystalline structure of the representative QY-7-2B and the human-derived RIPK1 protein kinase domain, and displayed the differences in the binding mode to the RIPK1 protein between the series of compounds of the present invention and the control compound GSK2982772. Specifically, both QY-7-2B and GSK2982772 occupy the hydrophobic allosteric pocket near the ATP binding pocket of the RIPK1 kinase domain, and cause the Leu157 configuration near the pocket to remain outward, so that RIPK1 is stabilized in an inactive state. Unlike GSK2982772, a part of QY-7-2B extends to the hinge area of the ATP binding pocket and forms a hydrogen bond with the Met95 residue, which further stabilizes the mutual binding with RIPK1, thereby enhancing the inhibitory effect on the latter.

All documents mentioned in the present invention are cited as references in this application, just as each document is individually cited as a reference. In addition, it should be understood that, after reading the above teaching content of the present invention, those skilled in the art can make various changes or modifications to the present invention, and these equivalent forms also fall within the scope defined by the appended claims of the present application.

The invention claimed is:

1. A compound or a pharmaceutically acceptable salt thereof, a hydrate thereof, or a solvate thereof, wherein the compound has a structure of Formula III;

(III)

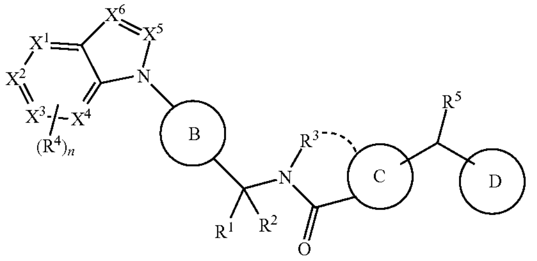

wherein, $X^1$, $X^3$, and $X^5$ are $C(R^a)$, and $X^2$, $X^4$, and $X^6$ are N, $R^a$ is each independently selected from the group consisting of null, H, substituted $C_{1-6}$alkyl, and unsubstituted $C_{1-6}$alkyl, n=0, 1, or 2, $R^4$ are each independently selected from the group consisting of: H, CN, halogen, substituted or unsubstituted $C_{1-6}$alkyl, —O—$R^b$, —S—$R^b$, —$N(R^b)_2$, —C(O)—$NR^6$—$R^b$, —C(O)—$NR^6$—$C_{1-4}$alkylene-$N(R^b)_2$, and —$NR^6$—C(O)—$R^b$, each $R^b$ is independently selected from the group consisting of: H, and substituted or unsubstituted $C_{1-6}$alkyl; or two $R^b$ together with the nitrogen atom to which they are attached form a substituted or unsubstituted 5, 6, or 7 membered saturated heterocyclyl, wherein, in addition to the nitrogen atom connected to $R^b$, the saturated heterocyclyl further contains 0, 1, or 2 additional heteroatoms selected from N, O, and S as ring atoms, $R^6$ is selected from the group consisting of: H, OH, substituted or unsubstituted $C_{1-4}$alkyl, and substituted or unsubstituted $C_{1-4}$alkoxy, ring B is selected from the group consisting of: substituted or unsubstituted $C_{6-10}$aryl, and substituted or unsubstituted 5-10 membered heteroaryl containing 1 to 5 heteroatoms selected from the group consisting of N, O, and S, $R^1$ and $R^2$ are each independently selected from the group consisting of: H, substituted or unsubstituted $C_{1-4}$alkyl, ring C is

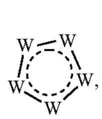

wherein W are each independently selected from the group consisting of: O, S, C, N, $C(R^c)$, and $N(R^d)$, wherein $R^c$ is each independently selected from the group consisting of: H, CN, halogen, and substituted or unsubstituted $C_{1-6}$alkyl, and $R^d$ is each independently selected from the group consisting of: H, CN, and substituted or unsubstituted $C_{1-6}$alkyl, $R^3$ is selected from the group consisting of: H, OH, substituted or unsubstituted $C_{1-4}$alkyl, and substituted or unsubstituted $C_{1-4}$alkoxy; or $R^3$ together with the ring atom W that is located at the ortho position of attachment position of —C(O)— and ring C, and said —C(O)— forms a substituted or unsubstituted 5, 6, or 7 membered saturated heterocyclic ring, wherein in addition to N that is attached to $R^3$, the saturated heterocyclic ring further contains 0, 1, or 2 additional heteroatoms selected from N, O, and S as ring atoms, $R^5$ is selected from the group consisting of: H, OH, substituted or unsubstituted $C_{1-4}$alkyl, and substituted or unsubstituted $C_{1-4}$alkoxy, ring D is selected from the group consisting of: substituted or unsubstituted $C_{6-10}$aromatic rings, and substituted or unsubstituted 5-10-membered heteroaryl; wherein the 5-10-membered heteroaryl contains 1 to 5 heteroatoms selected from N, O, and S, unless otherwise specified, the substituted refers to the hydrogen atom on the group being substituted with one or more substituents selected from the group consisting of: oxo (═O), —CN, halogen, nitro, $C_{1-6}$alkyl, halogenated $C_{1-6}$alkyl, —OR, —SR, —$S(O)_2R$, —$S(═O)_2NR_2$, —$NR_2$, —COOR, $C_{6-10}$aryl that is optionally substituted with R, 5-10-membered heteroaryl containing 1-3 heteroatoms selected from N, S, and O that is optionally substituted by R, $C_{3-8}$ cycloalkyl that is optionally substituted with R, 5-12-membered saturated heterocyclyl containing 1-3 heteroatoms selected from N, S, and O that is optionally substituted with R, —$C_{1-4}$alkylene-$C_{6-10}$aryl optionally substituted with R, —$C_{1-4}$alkylene-5-10 membered heteroaryl containing 1-3 heteroatoms selected from N, S, and O that is optionally substituted with R, —$C_{1-4}$alkylene-$C_{3-8}$cycloalkyl optionally substituted with R, and —$C_{1-4}$alkylene-5-12 membered saturated heterocyclyl containing 1-3 heteroatoms selected from N, S, and O optionally substituted with R, and R is independently selected from the group consisting of: H, $C_{1-6}$alkyl, halogenated $C_{1-6}$alkyl, and $C_{1-6}$hydroxyalkyl.

2. The compound of claim 1, wherein $R^4$ is each independently selected from the group consisting of: H, substituted or unsubstituted $C_{1-6}$alkyl, —O—$R^b$, —S—$R^b$, —$N(R^b)_2$, —C(O)—$NR^6$—$R^b$, —C(O)—$NR^6$—$C_{1-4}$alkylene-$N(R^b)_2$, and —$NR^6$—C(O)—$R^b$.

3. The compound according to claim 1, wherein the compound has a structure of formula IV-1 or IV-2;

(IV-1)

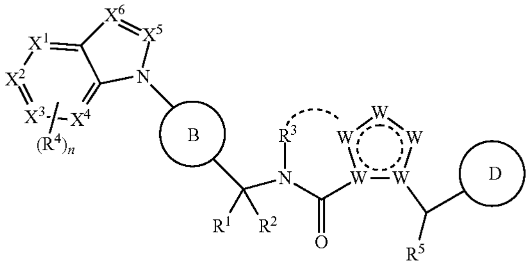

(IV-2)

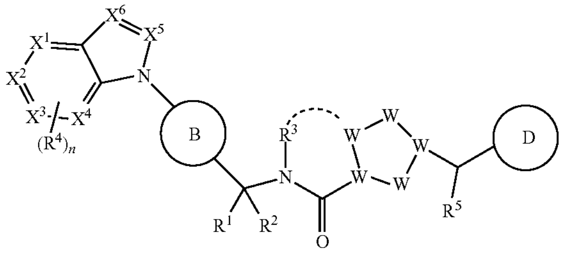

wherein, $X^1$, $X^3$, and $X^5$ are $C(R^a)$; and $X^2$, $X^4$, and $X^6$ are N, $R^a$ is each independently selected from the group consisting of: null, H, and substituted or unsubstituted $C_{1-6}$alkyl, $R^3$ is selected from the group consisting of: H, OH, and substituted or unsubstituted $C_{1-4}$alkyl, or $R^3$ together with the ring W and the —C(O)— forms a substituted or unsubstituted 5, 6, or 7 membered saturated heterocyclic ring; wherein in addition to N that is attached to $R^3$, the saturated heterocyclic ring further contains 0, 1, or 2 additional heteroatoms selected from N, O, and S as ring atoms; and $R^5$ is selected from the group consisting of: H, OH, and substituted or unsubstituted $C_{1-4}$alkyl.

4. The compound of claim 1, wherein the compound is selected from the compounds shown in the following Table:

QY-8-43

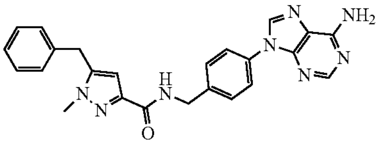 [SMILES: Cn1nc(C(=O)NCc2ccc(-n3cnc4c(N)ncnc43)cc2)cc1Cc1ccccc1]

QY-9-34

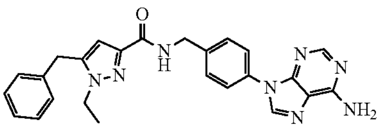 [SMILES: CCn1nc(C(=O)NCc2ccc(-n3cnc4c(N)ncnc43)cc2)cc1Cc1ccccc1]

QY-9-50

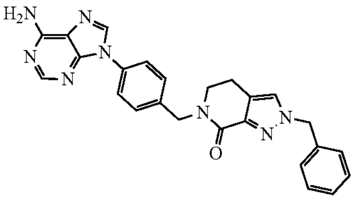 [SMILES: Nc1ncnc2c1ncn2-c1ccc(CN2CCc3cn(Cc4ccccc4)nc3C2=O)cc1]

QY-10-40

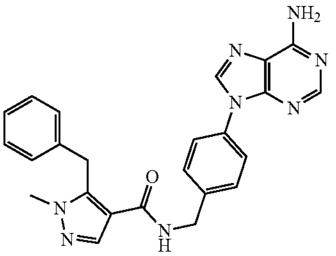 [SMILES: Cn1ncc(C(=O)NCc2ccc(-n3cnc4c(N)ncnc43)cc2)c1Cc1ccccc1]

QY-10-65

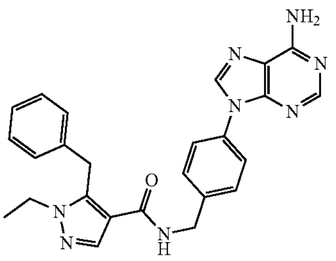 [SMILES: CCn1ncc(C(=O)NCc2ccc(-n3cnc4c(N)ncnc43)cc2)c1Cc1ccccc1]

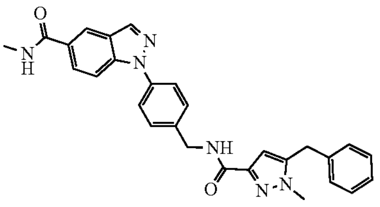 [SMILES: CNC(=O)c1ccc2c(cnn2-c2ccc(CNC(=O)c3cc(Cc4ccccc4)n(C)n3)cc2)c1]

-continued

ZSQ-20-106

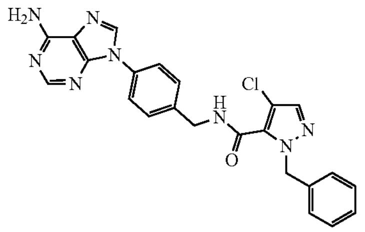 [SMILES: Nc1ncnc2c1ncn2-c1ccc(CNC(=O)c2c(Cl)cnn2Cc2ccccc2)cc1]

ZSQ-20-94

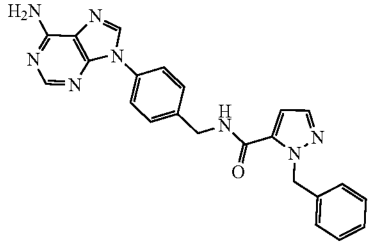 [SMILES: Nc1ncnc2c1ncn2-c1ccc(CNC(=O)c2ccnn2Cc2ccccc2)cc1]

ZSQ-21-1

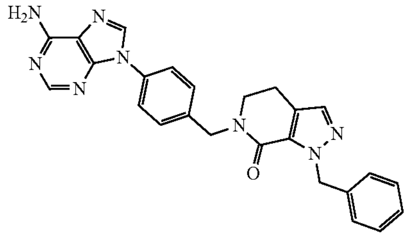 [SMILES: Nc1ncnc2c1ncn2-c1ccc(CN2CCc3cnn(Cc4ccccc4)c3C2=O)cc1]

ZSQ-21-1

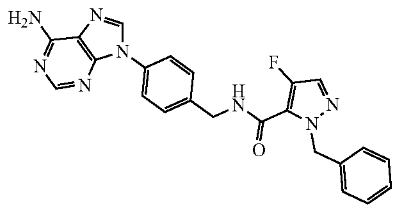 [SMILES: Nc1ncnc2c1ncn2-c1ccc(CNC(=O)c2c(F)cnn2Cc2ccccc2)cc1]

ZSQ-21-13

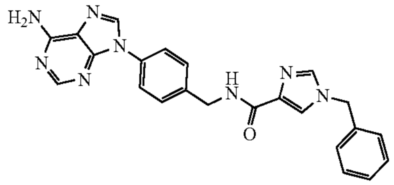 [SMILES: Nc1ncnc2c1ncn2-c1ccc(CNC(=O)c2cn(Cc3ccccc3)cn2)cc1]

ZSQ-21-8

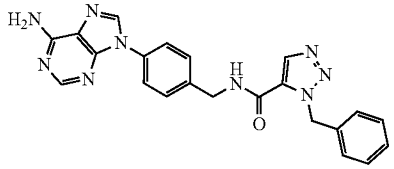 [SMILES: Nc1ncnc2c1ncn2-c1ccc(CNC(=O)c2cnnn2Cc2ccccc2)cc1]

ZSQ-21-18

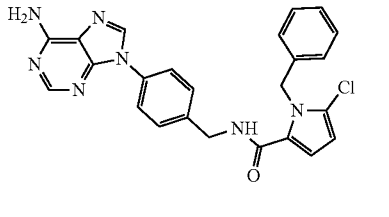 [SMILES: Nc1ncnc2c1ncn2-c1ccc(CNC(=O)c2ccc(Cl)n2Cc2ccccc2)cc1]

ZSQ-21-14
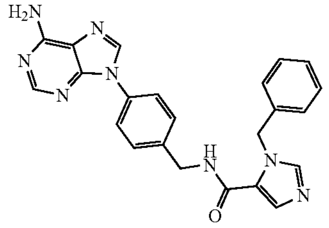 [SMILES: Nc1ncnc2c1ncn2-c1ccc(CNC(=O)c2cncn2Cc2ccccc2)cc1]
ZSQ-21-30
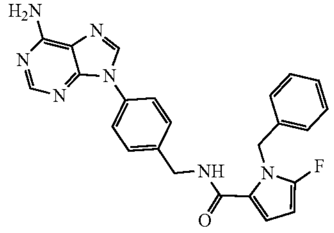 [SMILES: Nc1ncnc2c1ncn2-c1ccc(CNC(=O)c2ccc(F)n2Cc2ccccc2)cc1]
QY-11-78
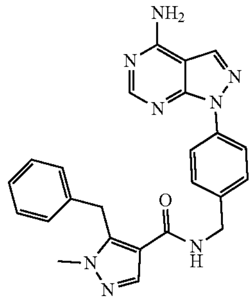 [SMILES: Cn1ncc(C(=O)NCc2ccc(-n3ncc4c(N)ncnc43)cc2)c1Cc1ccccc1]
QY-12-31
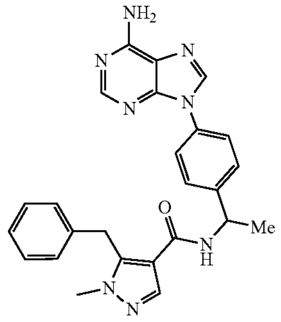 [SMILES: CC(NC(=O)c1cnn(C)c1Cc1ccccc1)c1ccc(-n2cnc3c(N)ncnc32)cc1]
QY-12-39
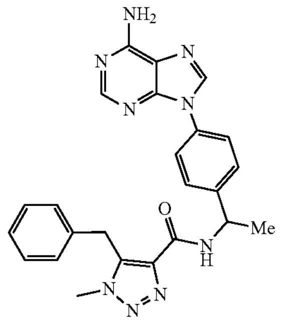 [SMILES: CC(NC(=O)c1nnn(C)c1Cc1ccccc1)c1ccc(-n2cnc3c(N)ncnc32)cc1]
QY-12-51
(QY-12-58)
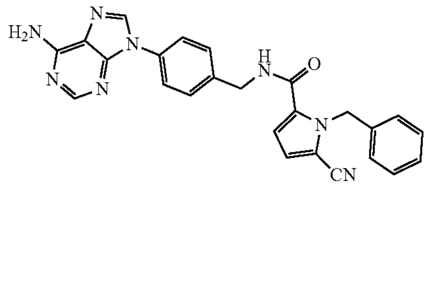 [SMILES: N#Cc1ccc(C(=O)NCc2ccc(-n3cnc4c(N)ncnc43)cc2)n1Cc1ccccc1]
ZSQ-22-96
(ZSQ-22-88)
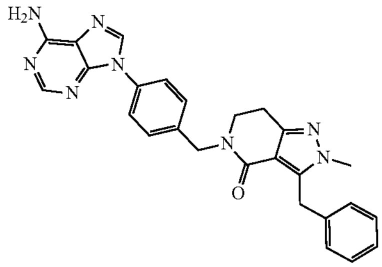 [SMILES: Cn1nc2c(c1Cc1ccccc1)C(=O)N(Cc1ccc(-n3cnc4c(N)ncnc43)cc1)CC2]
QY-12-66
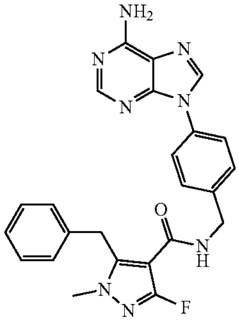 [SMILES: Cn1nc(F)c(C(=O)NCc2ccc(-n3cnc4c(N)ncnc43)cc2)c1Cc1ccccc1]
QY-12-90
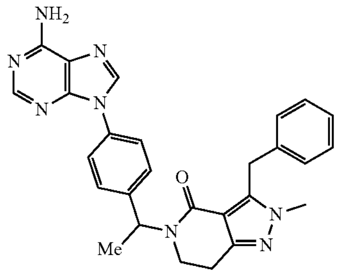 [SMILES: CC(c1ccc(-n2cnc3c(N)ncnc32)cc1)N1CCc2nn(C)c(Cc3ccccc3)c2C1=O]
QY-12-97
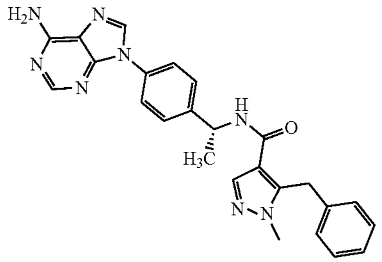 [SMILES: C[C@@H](NC(=O)c1cnn(C)c1Cc1ccccc1)c1ccc(-n2cnc3c(N)ncnc32)cc1]
QY-12-100
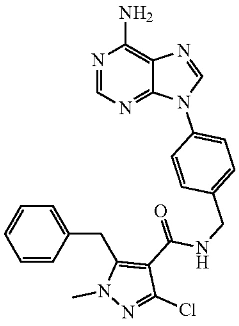 [SMILES: Cn1nc(Cl)c(C(=O)NCc2ccc(-n3cnc4c(N)ncnc43)cc2)c1Cc1ccccc1]

-continued

QY-12-102

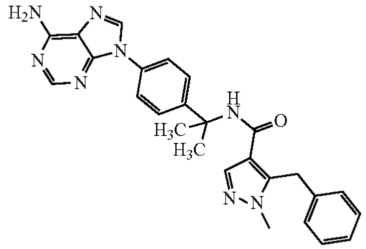 [SMILES: Cn1ncc(C(=O)NC(C)(C)c2ccc(-n3cnc4c(N)ncnc43)cc2)c1Cc1ccccc1]

QY-13-19
(QY-12-59)

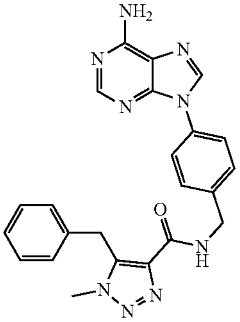 [SMILES: Cn1nnc(C(=O)NCc2ccc(-n3cnc4c(N)ncnc43)cc2)c1Cc1ccccc1]

QY-12-29

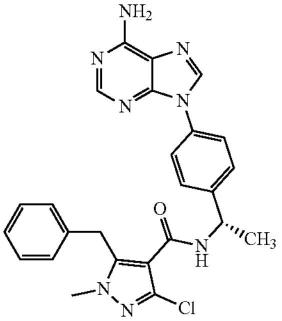 [SMILES: C[C@H](NC(=O)c1c(Cl)nn(C)c1Cc1ccccc1)c1ccc(-n2cnc3c(N)ncnc32)cc1]

QY-13-31

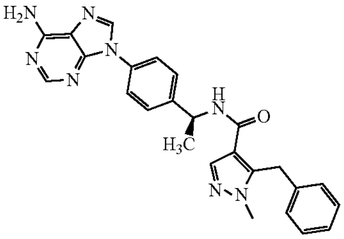 [SMILES: C[C@H](NC(=O)c1cnn(C)c1Cc1ccccc1)c1ccc(-n2cnc3c(N)ncnc32)cc1]

QY-13-33

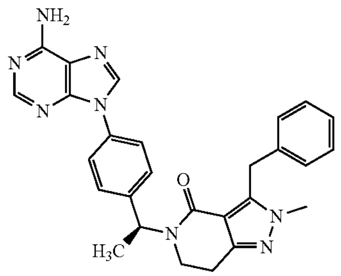 [SMILES: C[C@@H](c1ccc(-n2cnc3c(N)ncnc32)cc1)N1CCc2nn(C)c(Cc3ccccc3)c2C1=O]

-continued

QY-13-50

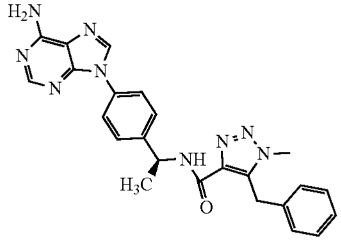 [SMILES: C[C@H](NC(=O)c1nnn(C)c1Cc1ccccc1)c1ccc(-n2cnc3c(N)ncnc32)cc1]

QY-15-22

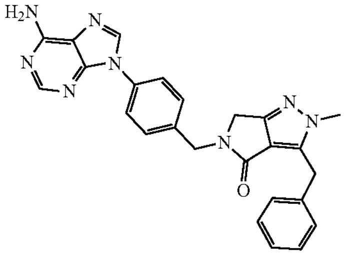 [SMILES: Cn1nc2c(c1Cc1ccccc1)C(=O)N(Cc1ccc(-n3cnc4c(N)ncnc43)cc1)C2]

QY-15-81

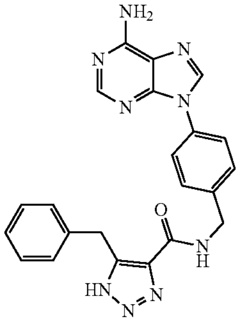 [SMILES: Nc1ncnc2c1ncn2-c1ccc(CNC(=O)c2nn[nH]c2Cc2ccccc2)cc1]

QY-15-84

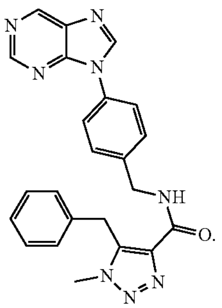 [SMILES: Cn1nnc(C(=O)NCc2ccc(-n3cnc4cncnc43)cc2)c1Cc1ccccc1]

5. A preparation method of the compound according to claim 1, wherein i) the preparation method is Method-One, and the Method-One comprises a step of:

in an inert solvent, reacting a compound having a structure of formula II-2A with a compound having a structure of formula II-2B, thereby obtaining the compound having the structure of formula II:

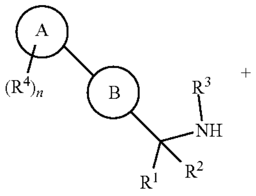

(II-1A)

-continued

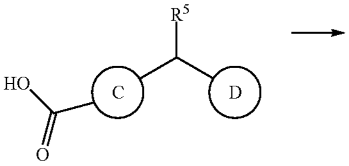

(II-1B)

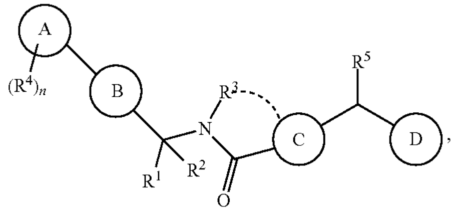

(II)

wherein

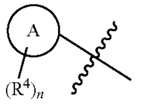

is

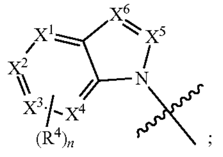

;

and $R^3$ is selected from the group consisting of: H, OH, substituted or unsubstituted $C_{1-4}$alkyl;

or ii) the method is Method-Two, and the Method-Two comprises the steps of:

a) in an inert solvent, reacting a compound having a structure of formula II-2A with a compound having a structure of II-2B, thereby obtaining a compound having the structure of formula II-2C:

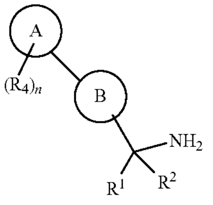

(II-2A)

+

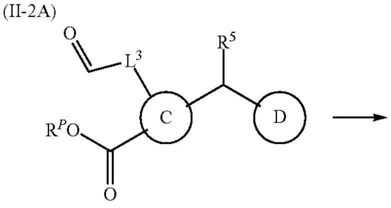

(II-2B)

-continued

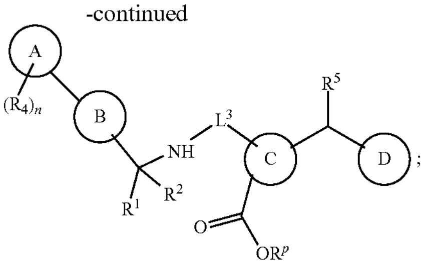

(II-2C)

and b) in an inert solvent, reacting the compound having a structure of formula II-2C, thereby forming the compound having the structure of formula II:

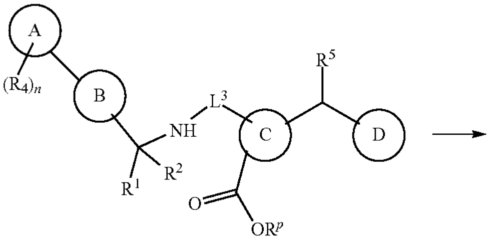

(II-2C)

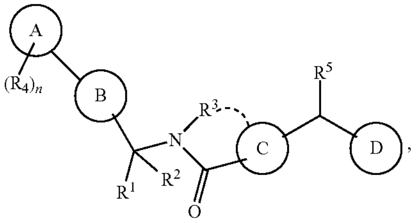

(II)

wherein

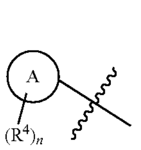

is

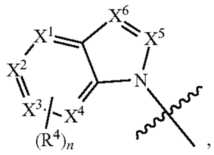

, $R^3$ together with the ring atom W, that is located at the ortho position of the attachment position of —C(O)— and ring C, and the —C(O)— in L1 forms a substituted or unsubstituted 5, 6, or 7 membered saturated heterocyclic ring, and the saturated heterocyclic ring further contains 0, 1 or 2 additional heteroatoms selected from N, O, and S as ring atoms, and $L^3$ is a single bond, substituted or unsubstituted $C_{1-2}$alkylene.

6. A pharmaceutical composition, wherein the pharmaceutical composition comprises: (a) a therapeutically effective amount of the compound according to claim 1, or the pharmaceutically acceptable salt thereof, the hydrate thereof, or the solvate thereof; and (b) a pharmaceutically acceptable carrier.

7. The compound according to claim 1, where the ring B is selected from the group consisting of: substituted or unsubstituted phenyl and substituted or unsubstituted 6 membered heteroaryl containing 1, 2, or 3 heteroatoms of N.

8. The compound according to claim 1, where the ring B is

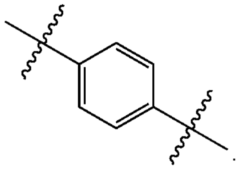 [SMILES: *c1ccc(*)cc1]

.

9. The compound according to claim 1, wherein the ring C is selected from the group consisting of:

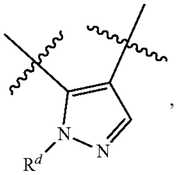
,
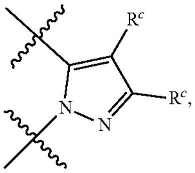
,
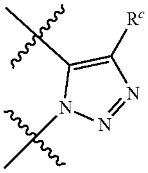
,
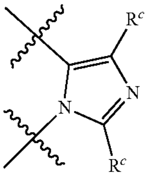
,
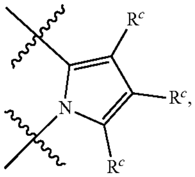
,
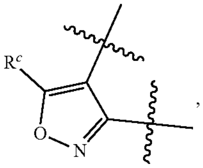
,
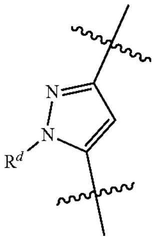
,
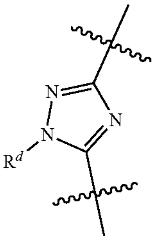
,
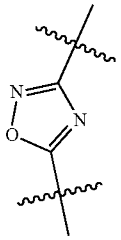
,
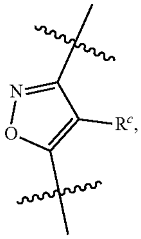
,
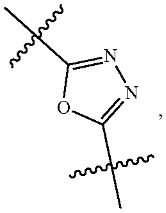
,
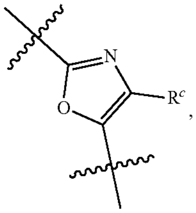
,
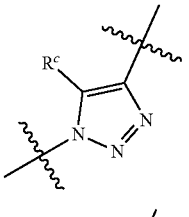
,
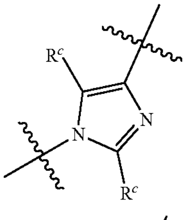
,
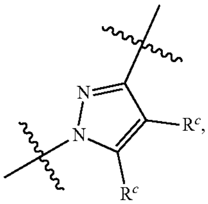
,
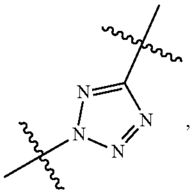
, -continued

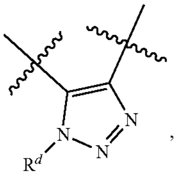
,
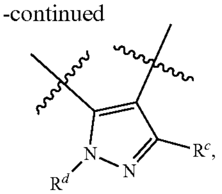
, and
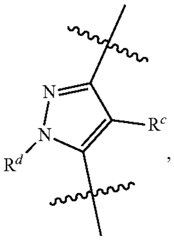
, wherein $R^c$ is each independently selected from the group consisting of H, CN, halogen, substituted $C_{1-6}$alkyl, and unsubstituted $C_{1-6}$alkyl, and $R^d$ is each independently selected from the group consisting of H, substituted $C_{1-6}$alkyl, and unsubstituted $C_{1-6}$alkyl.

10. The compound according to claim 1, where the ring D is an unsubstituted phenyl, or a phenyl substituted with 1 or 2 substituents selected from the group consisting of halogen, $C_{1-4}$alkyl, and halogenated $C_{1-4}$alkyl.

11. The compound according to claim 1, wherein the ring B is selected from the group consisting of substituted or unsubstituted phenyl and substituted or unsubstituted 5 or 6 membered heteroaryl;

the ring C is selected from the group consisting of

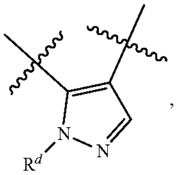
,
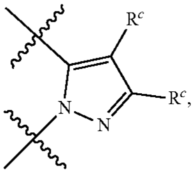
,
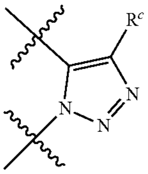
,
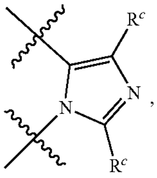
,
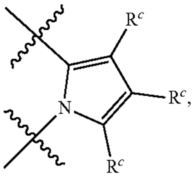
,
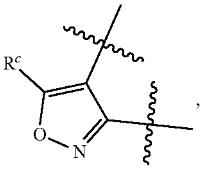
,
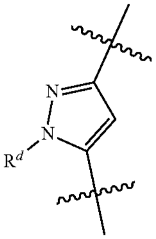
,
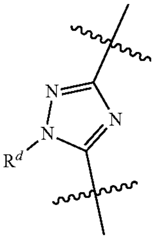
,
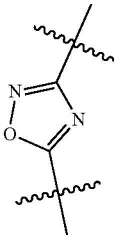
,
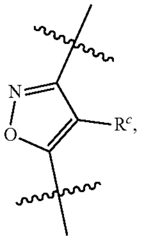
,
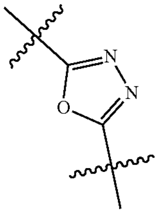
,
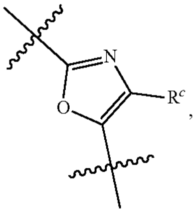
, -continued

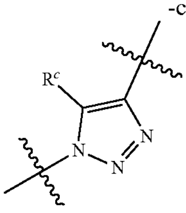,
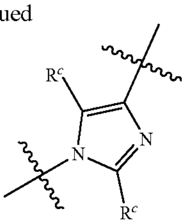,
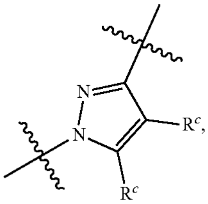
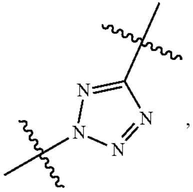,
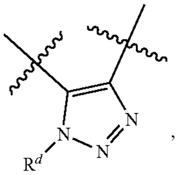,
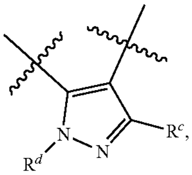
and
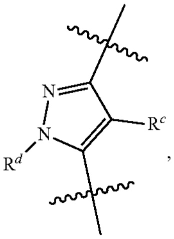, wherein $R^c$ is each independently selected from the group consisting of H, CN, halogen, substituted $C_{1-6}$alkyl, and unsubstituted $C_{1-6}$alkyl, $R^d$ is each independently selected from the group consisting of H, substituted $C_{1-6}$alkyl, and unsubstituted $C_{1-6}$alkyl, and the ring D is unsubstituted phenyl, or phenyl substituted with 1 or 2 substituents selected from the group consisting of halogen, $C_{1-4}$alkyl, and halogenated $C_{1-4}$alkyl.

12. The compound according to claim 1, wherein the ring B is

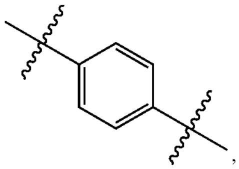 [SMILES: *c1ccc(*)cc1], the ring C is selected from the group consisting of

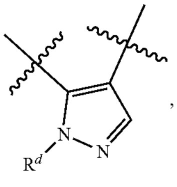,
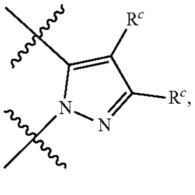
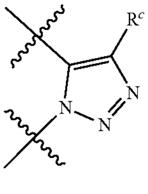,

-continued

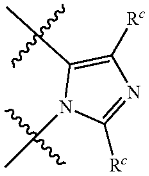,
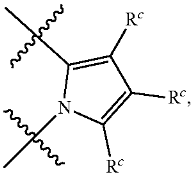
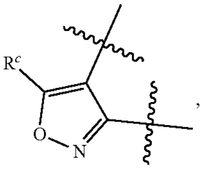,
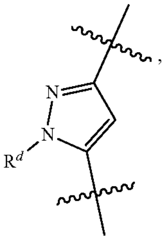,
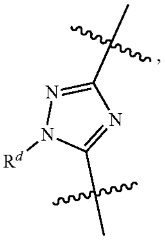,
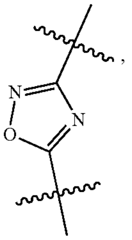,
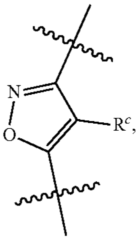
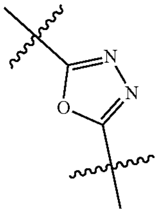,
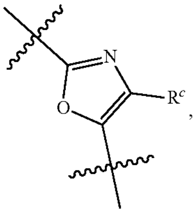
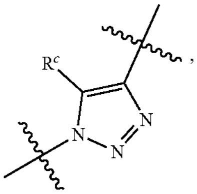,
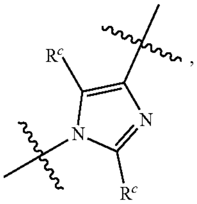
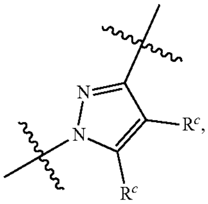,
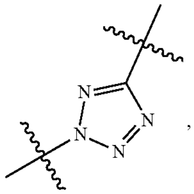
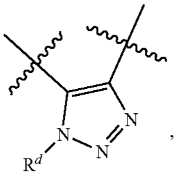,
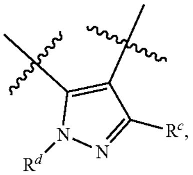
and
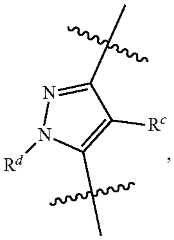, wherein $R^c$ is each independently selected from the group consisting of H, CN, halogen, substituted $C_{1-6}$alkyl, and unsubstituted $C_{1-6}$alkyl, $R^d$ is each independently selected from the group consisting of H, substituted $C_{1-6}$alkyl, and unsubstituted $C_{1-6}$alkyl and the ring D is unsubstituted phenyl, or phenyl substituted with 1 or 2 substituents selected from the group consisting of halogen, $C_{1-4}$alkyl, and halogenated $C_{1-4}$alkyl.

* * * * *